US 11,833,156 B2

United States Patent
Hallur et al.

(10) Patent No.: US 11,833,156 B2
(45) Date of Patent: Dec. 5, 2023

(54) HETEROCYCLIC COMPOUNDS AS PAD INHIBITORS

(71) Applicant: JUBILANT EPIPAD LLC, Yardley, PA (US)

(72) Inventors: Gurulingappa Hallur, Bangalore (IN); Athisayamani Jeyaraj Duraiswamy, Bangalore (IN); Buchi Reddy Purra, Bangalore (IN); N. V. S. K. Rao, Bangalore (IN); Sridharan Rajagopal, Bangalore (IN)

(73) Assignee: JUBILANT EPIPAD LLC, Yardley, PA (US)

( * ) Notice: Subject to any disclaimer, the term of this patent is extended or adjusted under 35 U.S.C. 154(b) by 0 days.

(21) Appl. No.: 16/649,597

(22) PCT Filed: Sep. 20, 2018

(86) PCT No.: PCT/IN2018/050614
§ 371 (c)(1),
(2) Date: Mar. 20, 2020

(87) PCT Pub. No.: WO2019/058393
PCT Pub. Date: Mar. 28, 2019

(65) Prior Publication Data
US 2020/0276206 A1  Sep. 3, 2020

(30) Foreign Application Priority Data

Sep. 22, 2017  (IN) ............................ 201741033768

(51) Int. Cl.
*C07D 498/06*  (2006.01)
*C07D 498/16*  (2006.01)
(Continued)

(52) U.S. Cl.
CPC ...... *A61K 31/5383* (2013.01); *A61K 31/4985* (2013.01); *A61K 31/553* (2013.01);
(Continued)

(58) Field of Classification Search
CPC ........ A61K 31/5365; A61P 1/00; A61P 11/06; A61P 17/06; A61P 19/02; A61P 29/00; A61P 35/00; C07D 498/06; C07D 498/16
See application file for complete search history.

(56) References Cited

U.S. PATENT DOCUMENTS 3,565,896 A  2/1971 Ghielmetti et al.
3,970,753 A  7/1976 Durant
(Continued)

FOREIGN PATENT DOCUMENTS

CN  101838264  9/2010
CN  105461693 A  4/2016
(Continued)

OTHER PUBLICATIONS

Acharya et al., "Neuronal PAD4 expression and protein citrullination: Possible role in production of autoantibodies associated with neurodegenerative disease", J. Autoimmun., vol. 38, pp. 369-380, 2012.
(Continued)

*Primary Examiner* — Brenda L Coleman
(74) *Attorney, Agent, or Firm* — Knobbe, Martens, Olson & Bear LLP

(57) ABSTRACT

Heterocyclic compounds of Formula (I), (II), and (III) are described herein along with their polymorphs, stereoisomers, prodrugs, solvates, co-crystals, intermediates, pharmaceutically acceptable salts, and metabolites thereof. The compounds described herein, their polymorphs, stereoisomers, prodrugs, solvates, co-crystals, intermediates, pharmaceutically acceptable salts, and metabolites thereof are PAD4 inhibitors and may be useful in the treatment of various disorders, for example rheumatoid arthritis, vasculitis, systemic lupus erythematosis, cutaneous lupus erythematosis, ulcerative colitis, cancer, cystic fibrosis, asthma, multiple sclerosis and psoriasis.

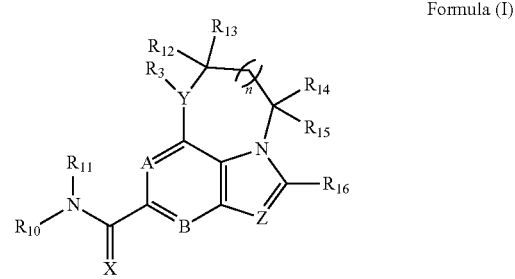

Formula (I)

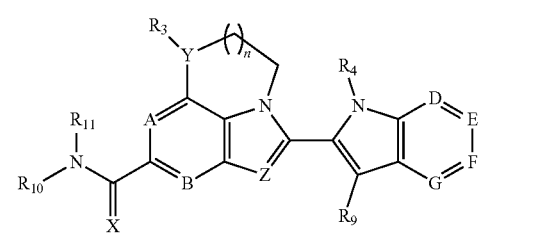

Formula (II)

(Continued)

-continued

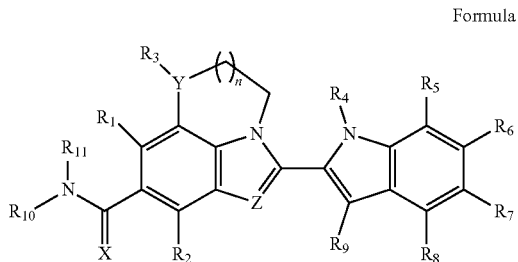

Formula (III)

12 Claims, No Drawings

(51) Int. Cl.
| | |
|---|---|
| A61K 31/5365 | (2006.01) |
| A61P 1/00 | (2006.01) |
| A61P 11/06 | (2006.01) |
| A61P 17/06 | (2006.01) |
| A61P 19/02 | (2006.01) |
| A61P 29/00 | (2006.01) |
| A61P 35/00 | (2006.01) |
| A61K 31/5383 | (2006.01) |
| A61K 31/4985 | (2006.01) |
| A61K 31/553 | (2006.01) |
| A61K 45/06 | (2006.01) |
| C07D 487/06 | (2006.01) |

(52) U.S. Cl.
CPC ............ A61K 45/06 (2013.01); C07D 487/06 (2013.01); C07D 498/06 (2013.01)

(56) References Cited

U.S. PATENT DOCUMENTS

| | | | |
|---|---|---|---|
| 3,985,881 A | 10/1976 | Mehrhof et al. | |
| 4,246,274 A | 1/1981 | Regel et al. | |
| 4,315,855 A | 2/1982 | Schefczik | |
| 4,495,191 A | 1/1985 | Ehrhardt et al. | |
| 4,703,056 A | 10/1987 | Hideg et al. | |
| 4,757,081 A | 7/1988 | Yonekura et al. | |
| 4,871,735 A | 10/1989 | Heider et al. | |
| 4,871,751 A | 10/1989 | Yonekura et al. | |
| 4,962,113 A | 10/1990 | Tsushima et al. | |
| 5,001,132 A | 3/1991 | Manoury et al. | |
| 5,010,094 A | 4/1991 | Schade et al. | |
| 5,047,411 A | 9/1991 | Takasugi et al. | |
| 5,100,890 A | 3/1992 | Siegal et al. | |
| 5,179,125 A | 1/1993 | Mimura et al. | |
| 5,210,266 A | 5/1993 | Mimura et al. | |
| 5,229,516 A | 7/1993 | Messer et al. | |
| 5,244,908 A | 9/1993 | Takatani et al. | |
| 5,273,980 A | 12/1993 | Frenette et al. | |
| 5,330,989 A | 7/1994 | Soll et al. | |
| 5,420,289 A | 5/1995 | Musser et al. | |
| 5,541,033 A | 7/1996 | Blakeney et al. | |
| 5,547,814 A | 8/1996 | Blakeney et al. | |
| 5,550,162 A | 8/1996 | Frost et al. | |
| 5,554,621 A | 9/1996 | Poindexter et al. | |
| 5,663,183 A | 9/1997 | Frost et al. | |
| 6,844,445 B2 | 1/2005 | Wierzbicki et al. | |
| 6,887,868 B2* | 5/2005 | Fu .................... | A61P 25/00 514/230.2 |
| 8,148,408 B2 | 4/2012 | Bunnelle et al. | |
| 8,642,660 B2 | 2/2014 | Goldfarb | |
| 9,067,898 B1 | 6/2015 | Illig | |
| 2002/0094989 A1 | 7/2002 | Hale et al. | |
| 2002/0173531 A1 | 11/2002 | Wierzbicki et al. | |

| | | |
|---|---|---|
| 2003/0018025 A1 | 1/2003 | Thurkauf et al. |
| 2004/0229160 A1 | 11/2004 | Nalini et al. |
| 2005/0159334 A1 | 7/2005 | Gluck |
| 2005/0228014 A1 | 10/2005 | Marquess et al. |
| 2006/0270686 A1 | 11/2006 | Kelly et al. |
| 2007/0191371 A1 | 8/2007 | Bennett et al. |
| 2007/0219218 A1 | 9/2007 | Yu et al. |
| 2008/0280891 A1 | 11/2008 | Kelly et al. |
| 2010/0249127 A1 | 9/2010 | Namdev |
| 2017/0105971 A1 | 4/2017 | Catrina |
| 2017/0174672 A1 | 6/2017 | Amberg et al. |
| 2021/0015810 A1 | 1/2021 | Venkateshappa et al. |
| 2021/0371431 A1 | 12/2021 | Vadivelu et al. |

FOREIGN PATENT DOCUMENTS

| | | |
|---|---|---|
| CN | 107056630 A | 8/2017 |
| CN | 107163044 A | 9/2017 |
| CN | 108358917 A | 8/2018 |
| CN | 110105299 A | 8/2019 |
| CN | 110963997 A | 9/2019 |
| CN | 107056630 B | 1/2020 |
| CN | 111606904 A | 9/2020 |
| DE | 1961595 A | 6/1970 |
| DE | 2832677 A1 | 2/1980 |
| DE | 3210570 A1 | 10/1983 |
| DE | 3628545 A1 | 4/1987 |
| DE | 3901723 A1 | 7/1990 |
| DE | 4227522 A1 | 2/1994 |
| DE | 19717371 A1 | 10/1998 |
| DE | 19834751 | 2/2000 |
| EP | 0090269 A1 | 10/1983 |
| EP | 0218118 A1 | 4/1987 |
| EP | 0239391 A2 | 9/1987 |
| EP | 0259793 A1 | 3/1988 |
| EP | 0301751 A1 | 2/1989 |
| EP | 0370852 A1 | 5/1990 |
| EP | 0218118 B1 | 9/1991 |
| EP | 0471236 A1 | 2/1992 |
| EP | 0259793 B1 | 7/1992 |
| EP | 0301751 B1 | 3/1993 |
| EP | 0533056 A2 | 3/1993 |
| EP | 0535924 A1 | 4/1993 |
| EP | 0533056 A3 | 6/1993 |
| EP | 0666250 A1 | 8/1995 |
| EP | 0747378 A1 | 12/1996 |
| EP | 0764640 A1 | 3/1997 |
| EP | 0819977 A1 | 1/1998 |
| EP | 0666250 B1 | 2/1998 |
| EP | 1245565 A1 | 10/2002 |
| EP | 1245565 B1 | 9/2003 |
| EP | 1388342 A1 | 2/2004 |
| EP | 2194035 A2 | 6/2010 |
| EP | 2194035 A3 | 6/2010 |
| EP | 2194035 B1 | 11/2011 |
| EP | 3 112 362 A1 | 1/2017 |
| FR | 2102082 A2 | 4/1972 |
| FR | 2102082 B2 | 10/1974 |
| FR | 2706895 A1 | 12/1994 |
| FR | 2706895 B1 | 8/1995 |
| GB | 1230663 A | 5/1971 |
| GB | 1356789 A | 6/1974 |
| JP | 62187452 A | 8/1987 |
| JP | H 02215809 A | 8/1990 |
| JP | 06184076 | 12/1992 |
| JP | 07304770 | 5/1994 |
| JP | 11119379 A1 | 4/1999 |
| JP | 2001233712 A | 8/2001 |
| JP | 2005060247 A | 3/2005 |
| JP | 2008280344 A | 11/2008 |
| JP | 2009209090 A | 9/2009 |
| JP | 2009274984 | 11/2009 |
| JP | 2011063589 A | 3/2011 |
| JP | 2011207765 | 10/2011 |
| JP | 2019156770 A | 9/2019 |
| JP | 2021054909 | 4/2021 |
| RU | 2371444 C1 | 10/2009 |
| WO | WO 86/05519 | 9/1986 |
| WO | WO 9106537 A2 | 5/1991 |

(56) References Cited

FOREIGN PATENT DOCUMENTS

| | | |
|---|---|---|
| WO | WO 9106537 A3 | 10/1991 |
| WO | WO 9301157 A1 | 1/1993 |
| WO | WO 9312094 A1 | 6/1993 |
| WO | WO 9320099 A2 | 10/1993 |
| WO | WO 9320099 A3 | 11/1993 |
| WO | WO 9401407 A2 | 1/1994 |
| WO | WO 9401407 A3 | 3/1994 |
| WO | WO 9422829 A2 | 10/1994 |
| WO | WO 9422834 A1 | 10/1994 |
| WO | WO 9427971 A1 | 12/1994 |
| WO | WO 9422829 A3 | 1/1995 |
| WO | WO 9509843 A1 | 4/1995 |
| WO | WO 9511226 A1 | 4/1995 |
| WO | WO 9521164 A1 | 8/1995 |
| WO | WO 9521832 A1 | 8/1995 |
| WO | WO 9610012 A1 | 4/1996 |
| WO | WO 9616040 A1 | 5/1996 |
| WO | WO 9709066 A1 | 3/1997 |
| WO | WO 9724119 A1 | 7/1997 |
| WO | WO 9740051 A1 | 10/1997 |
| WO | WO 9817648 A1 | 4/1998 |
| WO | WO 9824766 A1 | 6/1998 |
| WO | WO 9834609 A1 | 8/1998 |
| WO | WO 9836749 A1 | 8/1998 |
| WO | WO 9838156 A1 | 9/1998 |
| WO | WO 9906387 A2 | 2/1999 |
| WO | WO 9906387 A3 | 4/1999 |
| WO | WO 9932447 A2 | 7/1999 |
| WO | WO 9932447 A3 | 10/1999 |
| WO | WO 2000007978 A1 | 2/2000 |
| WO | WO 2000023420 A1 | 4/2000 |
| WO | WO 2000026203 A1 | 5/2000 |
| WO | WO 2001070731 A1 | 9/2001 |
| WO | WO 2001077075 A2 | 10/2001 |
| WO | WO 2001087293 A1 | 11/2001 |
| WO | WO 2002002518 A2 | 1/2002 |
| WO | WO 2002002520 A2 | 1/2002 |
| WO | WO 2002083673 A1 | 1/2002 |
| WO | WO 2001077075 A3 | 3/2002 |
| WO | WO 2002002518 A3 | 8/2002 |
| WO | WO 2002002520 A3 | 8/2002 |
| WO | WO 2002066478 A1 | 8/2002 |
| WO | WO 2002070510 A2 | 9/2002 |
| WO | WO 2002076964 A1 | 10/2002 |
| WO | WO 2002076979 A1 | 10/2002 |
| WO | WO 2002088089 A1 | 11/2002 |
| WO | WO 2002098869 A2 | 12/2002 |
| WO | WO 2002100813 A2 | 12/2002 |
| WO | WO 2002070510 A3 | 1/2003 |
| WO | WO 2008000408 A1 | 1/2003 |
| WO | WO 2003035076 A1 | 5/2003 |
| WO | WO 2003037887 A1 | 5/2003 |
| WO | WO 2003044016 A1 | 5/2003 |
| WO | WO 2003044017 A1 | 5/2003 |
| WO | WO 2003066613 A1 | 8/2003 |
| WO | WO 2003084916 A2 | 10/2003 |
| WO | WO 2002100813 A3 | 11/2003 |
| WO | WO 2003084916 A3 | 12/2003 |
| WO | WO 2002098869 A3 | 2/2004 |
| WO | WO 2004011430 A1 | 2/2004 |
| WO | WO 2004014372 A1 | 2/2004 |
| WO | WO 2004022558 A2 | 3/2004 |
| WO | WO 2004035579 A1 | 4/2004 |
| WO | WO 2004022558 A3 | 5/2004 |
| WO | WO 2004/052846 A1 | 6/2004 |
| WO | WO 2004048363 A1 | 6/2004 |
| WO | WO 2004058679 A2 | 7/2004 |
| WO | WO 2004058679 A3 | 8/2004 |
| WO | WO 2004078731 A1 | 9/2004 |
| WO | WO 2004109400 A2 | 12/2004 |
| WO | WO 2002034716 A2 | 5/2005 |
| WO | WO 2005058823 A1 | 6/2005 |
| WO | WO 2005092899 A1 | 10/2005 |
| WO | WO 2005100350 A1 | 10/2005 |
| WO | WO 2005105805 A1 | 11/2005 |
| WO | WO 2005105805 A9 | 1/2006 |
| WO | WO 2006048330 A1 | 5/2006 |
| WO | WO 2006062224 A1 | 6/2006 |
| WO | WO 2006069125 A1 | 6/2006 |
| WO | WO 2006102588 A1 | 9/2006 |
| WO | WO 2006105971 A1 | 10/2006 |
| WO | WO 2004109400 A3 | 11/2006 |
| WO | WO 2006125119 A1 | 11/2006 |
| WO | WO 2006130707 A2 | 12/2006 |
| WO | WO 2006133104 A2 | 12/2006 |
| WO | WO 2006130707 A3 | 1/2007 |
| WO | WO 2006133104 A3 | 4/2007 |
| WO | WO 2007073503 A2 | 6/2007 |
| WO | WO 2007087548 A2 | 8/2007 |
| WO | WO 2007105989 A2 | 9/2007 |
| WO | WO 2007106469 A2 | 9/2007 |
| WO | WO 2007073503 A3 | 11/2007 |
| WO | WO 2007105989 A3 | 11/2007 |
| WO | WO 2007133108 A1 | 11/2007 |
| WO | WO 2007106469 A3 | 12/2007 |
| WO | WO 2008008059 A1 | 1/2008 |
| WO | WO 20082022945 A1 | 2/2008 |
| WO | WO 2008051757 A1 | 5/2008 |
| WO | WO 2008064320 A2 | 5/2008 |
| WO | WO 2008065500 A2 | 6/2008 |
| WO | WO 2008065500 A3 | 6/2008 |
| WO | WO 2008066789 A2 | 6/2008 |
| WO | WO 2008079988 A2 | 7/2008 |
| WO | WO 2008104077 A1 | 9/2008 |
| WO | WO 2008112715 A2 | 9/2008 |
| WO | WO 2008064320 A3 | 10/2008 |
| WO | WO 2008121687 A2 | 10/2008 |
| WO | WO 2008123582 A1 | 10/2008 |
| WO | WO 2008112715 A3 | 11/2008 |
| WO | WO 2008135526 A1 | 11/2008 |
| WO | WO 2008156142 A1 | 12/2008 |
| WO | WO 2009010925 A2 | 1/2009 |
| WO | WO 2009023179 A2 | 2/2009 |
| WO | WO 2009038842 A2 | 3/2009 |
| WO | WO 2009048152 A2 | 4/2009 |
| WO | WO 2009054914 A1 | 4/2009 |
| WO | WO 2009010925 A3 | 7/2009 |
| WO | WO 2009080351 A1 | 7/2009 |
| WO | WO 2009104819 A1 | 8/2009 |
| WO | WO 2009048152 A3 | 9/2009 |
| WO | WO 2009112651 A1 | 9/2009 |
| WO | WO 2009137309 A2 | 11/2009 |
| WO | WO 2009140101 A2 | 11/2009 |
| WO | WO 2005123703 A2 | 12/2009 |
| WO | WO 2009038842 A3 | 12/2009 |
| WO | WO 2009153313 A1 | 12/2009 |
| WO | WO 2010048207 A2 | 4/2010 |
| WO | WO 2010075973 A1 | 7/2010 |
| WO | WO 2010077680 A2 | 7/2010 |
| WO | WO 2010091409 A1 | 8/2010 |
| WO | WO 2010098495 A1 | 9/2010 |
| WO | WO 2010151799 A2 | 12/2010 |
| WO | WO 2011023989 A1 | 3/2011 |
| WO | WO 2011086178 A1 | 7/2011 |
| WO | WO 2011100380 A1 | 8/2011 |
| WO | WO 2011123751 A2 | 10/2011 |
| WO | WO 2012006202 A1 | 1/2012 |
| WO | WO 2012006203 A1 | 1/2012 |
| WO | WO 2012022045 A1 | 2/2012 |
| WO | WO 2012022265 A1 | 2/2012 |
| WO | WO 2021028810 A1 | 2/2012 |
| WO | WO 2012058133 A1 | 5/2012 |
| WO | WO 2012087833 A1 | 6/2012 |
| WO | WO 2013000994 A1 | 1/2013 |
| WO | WO 2013002879 A1 | 1/2013 |
| WO | WO 2013002880 A1 | 1/2013 |
| WO | WO 2013018371 A1 | 2/2013 |
| WO | WO 2013025733 A1 | 2/2013 |
| WO | WO 2013068470 A1 | 5/2013 |
| WO | WO 2013096049 A1 | 6/2013 |
| WO | WO 2013096055 A1 | 6/2013 |
| WO | WO 2013096059 A1 | 6/2013 |
| WO | WO 2013096060 A1 | 6/2013 |
| WO | WO 2013096681 A1 | 6/2013 |

(56) References Cited

FOREIGN PATENT DOCUMENTS

| | | |
|---|---|---|
| WO | WO 2013120464 A1 | 8/2013 |
| WO | WO 2013127729 A1 | 9/2013 |
| WO | WO 2010077680 A3 | 10/2013 |
| WO | WO 2013174895 A1 | 11/2013 |
| WO | WO 2013178810 A1 | 12/2013 |
| WO | WO 2013192430 A2 | 12/2013 |
| WO | WO 2014/015905 A1 | 1/2014 |
| WO | WO 2014013182 A1 | 1/2014 |
| WO | WO 2014031872 A2 | 2/2014 |
| WO | WO 2014031986 A1 | 2/2014 |
| WO | WO 2014031872 A3 | 4/2014 |
| WO | WO 2014077321 A1 | 5/2014 |
| WO | WO 2014/100719 A2 | 6/2014 |
| WO | WO 2014100764 A2 | 6/2014 |
| WO | WO 2014100764 A3 | 9/2014 |
| WO | WO 2014152018 A1 | 9/2014 |
| WO | WO 2015011397 A1 | 1/2015 |
| WO | WO 2015031295 A1 | 3/2015 |
| WO | WO 2015034820 A1 | 3/2015 |
| WO | WO 2015086512 A1 | 6/2015 |
| WO | WO 2015086527 A1 | 6/2015 |
| WO | WO 2015108038 A1 | 7/2015 |
| WO | WO 2015140051 A1 | 9/2015 |
| WO | WO 2015197028 A1 | 12/2015 |
| WO | WO 2016008433 A1 | 1/2016 |
| WO | WO 2016031815 A1 | 3/2016 |
| WO | WO 2016034675 A1 | 3/2016 |
| WO | WO 2016036636 A1 | 3/2016 |
| WO | WO 2016051306 A2 | 4/2016 |
| WO | WO 2016102727 A1 | 6/2016 |
| WO | WO 2016/185279 A1 | 11/2016 |
| WO | WO 2006126939 A1 | 11/2016 |
| WO | WO 2017024180 A1 | 2/2017 |
| WO | WO 2017025510 A1 | 2/2017 |
| WO | WO 2017/042182 A1 | 3/2017 |
| WO | WO 2017068412 A1 | 4/2017 |
| WO | WO 2017106634 A1 | 6/2017 |
| WO | WO 2017109095 A1 | 6/2017 |
| WO | WO 2017/118762 | 7/2017 |
| WO | WO 2017/147102 A1 | 8/2017 |
| WO | WO 2017216281 A1 | 12/2017 |
| WO | WO 2018002848 A1 | 1/2018 |
| WO | WO 2018019204 A1 | 2/2018 |
| WO | WO 2018026971 A1 | 2/2018 |
| WO | WO 2018112843 A1 | 6/2018 |
| WO | WO 2018119036 A1 | 6/2018 |
| WO | WO 2018121610 A1 | 7/2018 |
| WO | WO 2018183411 A1 | 10/2018 |
| WO | WO 2018208985 A2 | 11/2018 |
| WO | WO 2018234342 A1 | 12/2018 |
| WO | WO 2019007696 A1 | 1/2019 |
| WO | WO 2019/058393 A1 | 3/2019 |
| WO | WO 2019/077631 A1 | 4/2019 |
| WO | WO 2019079783 A1 | 4/2019 |
| WO | WO 2019/087214 A1 | 5/2019 |
| WO | WO 2019/102494 A1 | 5/2019 |
| WO | WO 2019126081 A1 | 6/2019 |
| WO | WO 2019154047 A1 | 8/2019 |
| WO | WO 2019160014 A1 | 8/2019 |
| WO | WO 2019175897 A1 | 9/2019 |
| WO | WO 2019205147 A1 | 10/2019 |
| WO | WO 2019213234 A1 | 11/2019 |
| WO | WO 2020028723 A1 | 2/2020 |
| WO | WO 2020029980 A1 | 2/2020 |
| WO | WO 2020045216 A1 | 3/2020 |
| WO | WO 2020083971 A2 | 4/2020 |
| WO | WO 2020092394 A1 | 5/2020 |
| WO | WO 2020201773 A1 | 10/2020 |
| WO | WO 2020246910 A1 | 12/2020 |
| WO | WO 2021014949 A1 | 1/2021 |
| WO | WO 2021018858 A1 | 2/2021 |
| WO | WO 2021060432 A1 | 4/2021 |
| WO | WO 2021096238 A1 | 5/2021 |
| WO | WO 2021096241 A1 | 5/2021 |

OTHER PUBLICATIONS

Candi et al., "The Cornified Envelope: A Model of Cell Death in the Skin", Nat. Rev. Mol. Cell Biol., vol. 6, pp. 328-340, 2005.
Cedervall et al., NETosis in Cancer, Oncoscience, vol. 2, No. 11, pp. 900-901, 2015.
Chang et al., "Increased PADI4 expression in blood and tissues of patients with malignant tumors", BMC Cancer, vol. 9, pp. 40, 2009.
Christophorou et al., Citrullination regulated pluripotency and histone H1 binding to chromatin, Nature, vol. 507, pp. 104-108, 2014.
Chumanevich et al., "Suppression of colitis in mice by C1-amidine: a novel peptidylarginine deiminase inhibitor", Am. J. Physiol. Gastrointest. Liver Physiol., vol. 300, No. 6, pp. G929-G938, 2011.
Gyorgy et al., "Citrullination: A posttranslational modification in health and disease", Int. J. Biochem. Cell Biol., vol. 38, pp. 1662-1677, 2006.
Lewis et al., "Inhibition of PAD4 activity is sufficient to disrupt mouse and human NET formation", Nature Chemical Biology 11(3), 189-191. 10.1038/nchembio.1735, 2015.
Ireland et al., "Autophagy in antigen-presenting cells results in presentation of citrullinated peptides to CD4 T cells", J. Exp. Med., vol. 208, pp. 2625-2632, 2011.
Jones et al., "Protein arginine deiminase 4 (PAD4): current understanding and future therapeutic potential", Curr. Opin. Drug Discov. Devel., vol. 12, pp. 616-627, 2009.
Knight et al., "Peptidylarginine Deiminase Inhibition Reduces Vascular Damage and Modulates Innate Immune Responses in Murine Models of Atherosclerosis", Circ. Res., vol. 114, No. 6, pp. 947-956, 2014.
Kochi et al., "PADI4 polymorphism predisposes male smokers to rheumatoid arthritis", Ann. Rheum. Dis., vol. 70, pp. 512-515, 2011.
Lange et al., "Protein deiminases: New players in the developmentally regulated loss of neural regenerative ability", Dev. Biol., vol. 355, No. 2, pp. 205-214, 2011.
Li et al., "Regulation of p53 Target Gene Expression by Peptidylarginine Deiminase 4", Mol. Cell Biol., vol. 28, pp. 4745-4758, 2008.
Liu, G.-Y, et al., "Overexpression of peptidylarginine deiminase IV features in apoptosis of haematopoietic cells", Apoptosis, vol. 11, pp. 183-196, 2006.
Loos et al., "Citrullination of CXCL10 and CXCL11 by peptidylarginine deiminase: a naturally occurring posttranslational modification of chemokines and new dimension of immunoregulation", Blood, vol. 112, pp. 2648-2656, 2008.
Makrygiannakis et al., "Citrullination is an inflammation-dependent process", Ann. Rheum. Dis., vol. 65, pp. 1219-1222, 2006.
Mastronardi et al., "Increased Citrullination of Histone H3 in Multiple Sclerosis Brain and Animal Models of Demyelination: A Role for Tumor Necrosis Factor-Induced Peptidylarginine Deiminase 4 Translocation", The Journal of Neurosciences, vol. 26, pp. 11387-11396, 2006.
Nakashima et al., "Molecular Characterization of Peptidylarginine Deiminase in HL-60 Cells Induced by Retinoic Acid and 1α, 25-Dihydroxyvitamin $D_3$", J. Biol. Chem., vol. 274, pp. 27786-27792, 1999.
Neeli et al., "Histone Deimination As a Response to Inflammatory Stimuli in Neutrophils", J. Immunol., vol. 180, pp. 1895-1902, 2008.
Slack et al., "Protein arginine deiminase 4: a target for an epigenetic cancer therapy", Cellular And Molecular Life Sciences, vol. 68, No. 4, pp. 709-720, 2011.
Wang et al., "Histone hypercitrullination mediates chromatin decondensation and neutrophil extracellular trap formation", J. Cell Biol., vol. 184, pp. 205-213, 2009.
Willis et al., N-α-Benzoyl-N5-(2-Chloro-1-Iminoethyl)-1-Ornithine Amine, a Protein Arginine Deiminase Inhibitor, Reduces the Severity of Murine Collagen-Induced Arthritis, J. Immunol., vol. 186, No. 7, pp. 4396-4404, 2011.
Fuhrmann, Jakob, et al., "Chemical Biology of Protein Arginine Modifications in Epigenetic Regulation," Chemical Reviews, 2015, 115, 5413-5461.
Jones, Justin, et al., "Protein arginine deiminase 4 (PAD4): current understanding and future therapeutic potential," Curr Opin Drug Discov Devel. Sep. 2009; 12(5).

(56) References Cited

OTHER PUBLICATIONS

Mohanan, Sunish, et al., "Potential Role of Peptidylarginine Deiminase Enzymes and Protein Citrullination in Cancer Pathogenesis," Biochemistry Research International, vol. 2012, article ID 895343.
Wang, Shu, et al., "Peptidylarginine deiminases in citrullination, gene regulation, health and pathogenesis," Biochim Biophys Acta, Oct. 2013; 1829 (10): 1126-1135.
Wei, Lianhu, et al., "Novel Inhibitors of Protein Arginine Deiminase with Potential Activity in Multiple Sclerosis Animal Model," Journal of Medicinal Chemistry, 2013, 56, 1715-1722.
First Examination Report dated Sep. 8, 2021 received in Indian Patent Application No. 201741033768.
Arisan, et al., "Putative Roles for Peptidylarginine Deiminases in COVID-19", International Journal of Molecular Sciences, vol. 21, No. 13, in 29 pages, 2020.
Barber, et al., "Restoring function in exhausted CD8 T cells during chronic viral infection", Nature, vol. 439, No. 7077, pp. 682-687, 2005.
Bardhan, et al., "The PD1:PD-L1/2 Pathway from Discovery to Clinical Implementation", Frontiers In Immunology, vol. 7, No. 550, pp. 1-17, 2016.
Barnes, et al., "Targeting potential drivers of COVID-19: Neutrophil extracellular traps", Journal of Experimental Medicine, vol. 217, No. 6, in 7 pages, 2020.
Bertini, et al., "Carbazole-containing arylcarboxamides as BACE1 inhibitors," Bioorganic & Medicinal Chemistry Letters (2011), 21 (22), 6657-6661.
Borregaard, "Neutrophils, from Marrow to Microbes", Immunity, vol. 33, No. 5, pp. 657-670, 2010.
Brinkmann, et al., "Neutrophil Extracellular Traps Kill Bacteria", Science, vol. 303, No. 5663, pp. 1532-1535, 2004.
Chemical Abstracts, STN Registry Database, Record for RN 1648388-87-7, Entered into STN Feb. 16, 2015.
Chen, et al., "Anti-PD-1/PD-L1 therapy of human cancer: past, present, and future", Journal of Clinical Investigation, vol. 125, No. 9, pp. 3384-3391, 2015.
Chiummiento, et a;., "New indolic non-peptidic HIV protease inhibitors from (S)-glycidol: synthesis and preliminary biological activity," Tetrahedron (2009), 65(31), 5984-5989.
Cromwell, et al., "Amino ketones. III. B-Tetrahydroisoquinolino ketones and derivatives. Reaction with Grignard reagents," Journal of the American Chemical Society (1944), 66, 872-3.
Curiel, et al., "Blockade of B7-H1 improves myeloid dendritic cell-mediated antitumor or immunity", Nature Medicine, vol. 9, No. 5, pp. 562-567, 2003.
Dimauro et al., Discovery of Aminoquinazolines as Potent, Orally Bioavailable Inhibitor of Lck: Synthesis, SAR, and in Vivo Antiinflammatory Activity, Journal of Medical Chemistry, vol. 49, No. 19, pp. 5671-5686, 2006.
Dong, et al., "Tumor-associated B7-H1 promotes T-cell apoptosis: A potential mechanism of immune evasion", Nature Medicine, vol. 8, No. 8, pp. 793-800, 2002.
Dong, et al., "PD-1 and its ligands are important immune checkpoints in cancer", Oncotarget, vol. 8, No. 2, pp. 2171-2186, 2017.
Evans, et al. "Phenoxyacetic acids as PPAR☐ partial agonists: Synthesis, optimization, and in vivo efficacy," Bioorganic & Medicinal Chemistry Letters (2011), 21(8), 2345-2350.
Flies, et al., "The New B7S: Playing a Pivotal Rose in Tumor Immunity", Immunotherapy, vol. 30, No. 3, pp. 251-260, 2007.
Flies, et al., "Blockade of the B7-H1/PD-1 Pathway for Cancer Immunotherapy", Yale J. Biology Medicine, vol. 84, No. 4, pp. 409-421, 2011.
Francisco, et al., "PD-L1 regulates the development, maintenance, and function of induced regulatory T cells", Journal of Experimental Medicine, vol. 206, No. 13, pp. 3015-3029, 2009.
Fukagawa, Tomokichi, "The biuret reaction. VII. Primary-quaternary bases which give the biuret reaction," Z. physiol. Chem. (1931), 201, 40-6.

Goi, et al., "Synthesis and pharmacological properties of pyridinecarbonyl derivatives of 7-substituted theophyllines," Chimica Therapeutica (1973), 8(6), 634-7.
Guo, et al., "Development of Benzophenone-Alkyne Bifunctional Sigma Receptor Ligands," ChemBioChem (2012), 13(15), 2277-2289.
Hamanishi, et al., "PD-1/PD-L1 blockade in cancer treatment: perspectives and issues", Int. J. Clin. Oncol., vol. 21, pp. 462-473, 2016.
Hankovsky, et al., "New antiarrhythmic agents. 2,2,5,5-Tetramethyl-3-pyrroline-3-carboxamides and 2,2,5,5 tetramethylpyrrolidine-3-carboxamides," Journal of Medicinal Chemistry (1986), 29(7), 1138-52.
He, et al., "Development of PD-1/PD-L1 Pathway in Tumor Immune Microenvironment and Treatment for Non-Small Cell Lung Cancer", Scientific Reports, vol. 5, pp. 1-9, 2015.
Hwang, et al., "Synthesis and evaluation of methylsulfonylnitrobenzamides (MSNBAs) as inhibitors of the thyroid hormone receptor-coactivator interaction," Bioorganic & Medicinal Chemistry Letters (2013), 23(6), 1891-1895.
International Search Report and WritTen Opinion dated Nov. 12, 2018 for PCT/IN2018/050614.
International Search Report & written opinion, dated Feb. 14, 2019, in International Application No. PCT/IN2018/050671.
International Search Report & Written Opinion, dated Feb. 20, 2019, in International Application No. PCT/IN2018/50716.
International Search Report & Written Opinion, dated May 20, 2019 in International Application No. PCT/IN2019/050203.
Ivaschenko, et al., "Synthesis, biological evaluation and in silico modeling of novel integrase strand transfer inhibitors (INSTIs)," European Journal of Medicinal Chemistry (2020), 189, 112064.
Labrie, et al., "In vitro activity of novel dual action MDR anthranilamide modulators with inhibitory activity at CYP450," Bioorganic & Medicinal Chemistry (2006), 14(23), 7972-7987.
Lai, et al., "A Novel PD-L1-targeting Antagonistic DNA Aptamer With Antitumor Effects", Mol. Therapy—Nucl. Acids, vol. 5, pp. e397, 2016.
Lakshmann, et al.,"Synthesis and evaluation of novel N-substituted-6 methoxynaphthalene-2-carboxamides as potential chemosensitizing agents for cancer," Chemical & Pharmaceutical Bulletin (2008), 56(7), 894-896.
Lee, et al., Interferon regulatory factor-1 is prerequisite to the constitutive expression and IFN-y-induced upregulation of B7-H1 (CD274), FEBS Letters, vol. 580, pp. 755-762, 2006.
"Letter to the Editors-in-Chief", Thrombosis Research 191, pp. 26-27, 2020.
Leung, et al., "The CD28-B7 Family in Anti-Tumor Immunity: Emerging Concepts in Cancer Immunotherapy", Immune Network, vol. 14, No. 6, pp. 265-276, 2014.
Muenst, et al., "Expression of programmed death ligand 1 (PD-L1) is associated with poor prognosis in human breast cancer", Breast Cancer Res. Treat., vol. 146, No. 1, pp. 15-24, 2014.
Nathan, "Neutrophils and COVID-19: Nots, NETs, and knots", The Journal of Experimental Medicine, vol. 217, No. 9, in 3 pages, 2020.
Nicolaou, et al., "Synthesis of imides, N-acyl vinylogous carbamates and ureas, and nitriles by oxidation of amides and amines with Dess-Martin periodinane," Angewandte Chemie, International Edition (2005), 44(37), 5992-5997.
Omran, et al., "Synthesis and biological evaluation of new Donepezil-like Thiaindanones as AChE inhibitors," Journal of Enzyme Inhibition and Medicinal Chemistry (2008), 23(5), 696-703.
Patsoukis, et al., "PD-1 inhibits T cell proliferation by upregulating p27 and p15 and suppressing Cdc25A", Cell Cycle, vol. 11, No. 23, pp. 4305-4309, 2012.
Piper, et al., "Synthesis of potential inhibitors of hypoxanthine-guanine phosphoribosyltransferase for testing as antiprotozoal agents. 1. 7-Substituted 6-oxopurines," Journal of Medicinal Chemistry (1980), 23(4), 357-64.
Schönrich, et al., "Neutrophil Extracellular Traps Go Viral", Frontiers in Immunology, vol. 7, No. 366 in 7 pages, 2016.
Sheppard, et al., "PD-1 inhibits T-cell receptor induced phosphorylation of the ZAP70/CD3 signalosome and downstream signaling to PKC0", FEBS Letters, vol. 574, pp. 37-41, 2004.

(56) References Cited

OTHER PUBLICATIONS

Smahel, Michal, "PD-1/PD-L1 Blockade Therapy for Tumors with Downregulated MHC Class I Expression", Int. J. Mol. Sci., vol. 18, No. 6, pp. 1331, 2017.
Spassova, et al., "Synthesis of N-(3-azido-2 hydroxypropyl), N-(3-phthalimido-2-hydroxypropyl) and N-(3-amino-2 hydroxypropyl) derivatives of heterocyclic bases," Collection of Czechoslovak Chemical Communications (1994), 59(5), 1153-74.
Topalian, et al., "Targeting the PD-1/B7-H1 (PD-L1) pathway to activate anti-tumor immunity", Curr. Opin. Immunol., vol. 24, No. 2, pp. 207-212, 2012.
Uenishi, et al, "Structural effects of diazonaphthoquinone-photoactivecompound backbone on resist lithographic properties," Proceedings of SPIE—The International Society for Optical Engineering (1991), 1466(Adv. Resist Technol. Process. 8), 102-16.
Vinay, et al., "Immune evasion in cancer: Mechanistic basis and therapeutic strategies", Seminars In Cancer Biology, vol. 35, pp. S185-S198, 2015.
Vooturi, et al., "Solution-phase parallel synthesis of novel membrane-targeted antibiotics," Journal of Combinatorial Chemistry (2010), 12(1), 151-160.
Wang, et al., "Prognostic significance of PD-L1 in solid tumor", Medicine Baltimore, vol. 96, No. 18, pp. e6369, 2017.
Wang, et al., "PD-LI expression in human cancers and its association with clinical outcomes", Oncotargets and Therapy, vol. 9, pp. 5023-5039, 2016.
Zajdel, et al, "Solid-phase synthesis of aryl-alkylamine derivatives using protected aminoalcohol building blocks on SynPhase lanterns," QSAR & Combinatorial Science (2007), 26(2), 215-219.
Zamarron, et al., "Dual Roles of Immune Cells and Their Factors in Cancer Development and Progression", Intl. J. Biol. Sciences, vol. 7, No. 5, pp. 651-658, 2011.
Zawrotniak, et al., "Neutrophil extracellular traps (NETs)—formation and implications", ACTA Biochimica Polonica, vol. 60, No. 3, pp. 277-284, 2013.
Zhuravel, et al, "Solution-phase synthesis of a combinatorial library of 3-[4-(Coumarin-3-yl)-1,3-thiazol-2-ylcarbamoyl]propanoic acid amides," Molecules (2005), 10(2), 444-456.
Zou, et al., "Neutrophil extracellular traps in COVID-19", JCI Insight, vol. 5, No. 11, pp. 1-11, 2020.
Zou, et al., "PD-L1 (B7-H1) and PD-1 pathway blockade for cancer therapy: Mechanisms, response biomarkers, and combinations", Sci. Transl. Med., vol. 8, No. 328, pp. 328rv4, 2016.
RN: 1893826-27-1, 1892358-83-6, Database Registry [Online], Apr. 20, 2016, Retrieved from STN, Date of search: Jul. 15, 2021.
Hidalgo et al., Neutrophil extracellular traps: from physiology to pathology, Cardiovascular Research, 00, pp. 1-17, 2021.
Holmes et al., Insight into Neutrophil Extracellular Traps through Systematic Evaluation of Citrullination and Peptidylarginine Deiminases, Journal of Immunology Research, vol. 2019, Article ID 21160192, pp. 1-12, 2019.
Rohrbach et al., Activation of PAD4 in NET formation, frontiers in Immunology, vol. 3, Article 360, pp. 1-10, 2012.

* cited by examiner

HETEROCYCLIC COMPOUNDS AS PAD INHIBITORS

PRIORITY AND CROSS REFERENCE TO RELATED APPLICATIONS

This application is the U.S. National Stage Application under 35 U.S.C. § 371 of International Application No. PCT/IN2018/050614, filed Sep. 20, 2018, designating the U.S. and published in English as WO 2019/058393 A1 on Mar. 28, 2019, which claims the benefit of Indian Patent Application No. IN 201741033768, filed Sep. 22, 2017. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD OF THE INVENTION

The present disclosure is directed to novel heterocyclic compounds of Formula (I), (II), and (III) along with their polymorphs, stereoisomers, prodrugs, solvates, co-crystals, intermediates, pharmaceutically acceptable salts, and metabolites thereof which act as PAD4 inhibitors.

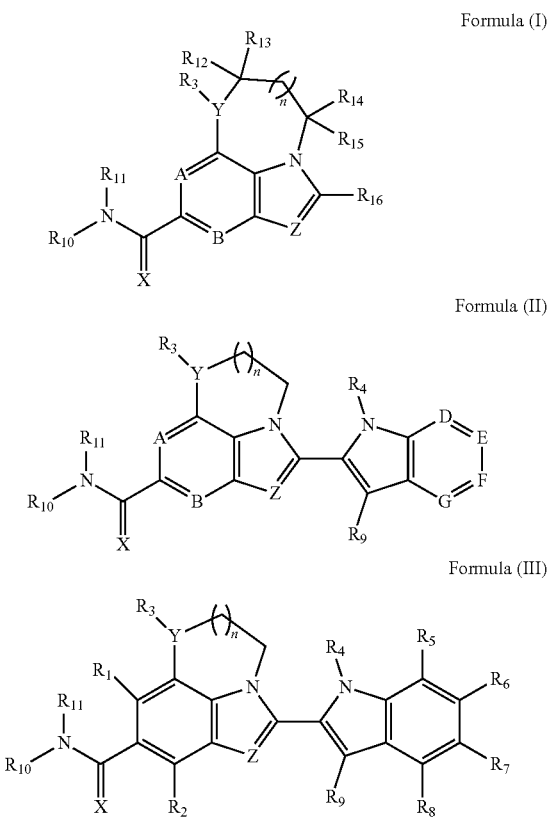

The process for the preparation of the above heterocyclic compounds of the Formula (I), (II), and (III), their polymorphs, stereoisomers, prodrugs, solvates, co-crystals, intermediates, pharmaceutically acceptable salts, pharmaceutical compositions, and metabolites, are also described herein which are useful in the preparation of such compounds.

The compounds described herein are PAD4 inhibitors and may be useful in the treatment of various disorders, for example rheumatoid arthritis, vasculitis, systemic lupus erythematosis, cutaneous lupus erythematosis, ulcerative colitis, cancer, cystic fibrosis, asthma, multiple sclerosis, and psoriasis.

BACKGROUND OF THE INVENTION

The PAD (protein arginine de-iminase) consists of a family of enzymes that convert peptidyl-arginine to peptidyl citrulline. The process for this conversion is known as citrullination (J. E. Jones, et al. Curr. Opin. Drug Discov. Devel., 2009, 12, 616-627). There are five isozymes of the PAD family found in mammals, viz. PAD1, PAD2, PAD3, PAD4, and PAD6. The amino acid sequence of these isozymes share a sequence similarity of 70-95% with mammals. Citrullination which is a post-translational modification of arginine to citrulline by the closely related enzymes of PAD family affect numerous physiological and pathological processes.

Citrullination has been implicated in various ailments, for example, cell differentiation (K. Nakashima et al., J. Biol. Chem., 1999, 274, 27786-27792), stem cell pluripotency (M. A. Christophorou et al., Nature, 2014, 507, 104-108), apoptosis (G. Y. Liu, Apoptosis, 2006, 11, 183-196), neutrophil extracellular trap (NET) formation (Y. Wang et al., J. Cell Biol., 2009, 184, 205-213), transcriptional regulation (P. Li et al., Mol. Cell Biol., 2008, 28, 4745-4758), antigen processing in autophagy (J. M. Ireland et al., J. Exp. Med., 2011, 208, 2625-2632), inflammation (D. Makrygiannakis et al., Ann. Rheum. Dis., 2006, 65, 1219-1222), the cornification of skin (E. Candi et al., *Nat. Rev. Mol. Cell Biol.,* 2005, 6, 328-340), demyelination in multiple sclerosis (F. G. Mastronardi et al., J. Neurosci., 2006, 26, 11387-11396), chemokine regulation (T. Loos et al., Blood, 2008, 112, 2648-2656), spinal cord injury repair (S. Lange et al., Dev. Biol., 2011, 355, 205-214), and various normal cellular processes.

The role of PAD in pathogenesis of many diseases has become increasingly evident as the enzymes that catalyze citrullination, also produce autoantibodies that recognize the citrullinated proteins. The introduction of citrulline, resultant of PAD activity, changes both the structure and function of proteins. At physiological activity levels, PADs regulate many cell-signaling pathways like cell differentiation, apoptosis, and gene transcription (György et al. Int. J. Biochem. Cell Biol., 2006, 38, 1662-1677). Over the past decade, it is becoming increasingly apparent that aberrant PAD activity is involved in many human inflammatory diseases such as, rheumatoid arthritis (RA), Alzheimer's disease, and multiple sclerosis (N. K. Acharya, J. Autoimmun., 2012, 38, 369-380).

PAD4 have also been known for the deamination or citrullination of a variety of proteins both in vitro and in vivo, with consequences of diverse functional response in a variety of diseases, such as, rheumatoid arthritis (RA), diseases with neutrophilic contributions to pathogenesis (for example, vasculitis, systemic lupus erythematosus, ulcerative colitis), along with oncology indications (J. E. Jones, et al. Curr. Opin. Drug Discov. Devel., 2009, 12, 616-627). PAD4 has been found to be involved in the formation of neutrophil extracellular traps (NETs) and more specifically in the histone citrullination that occurs during NETosis (J. Cedervall, A.-K. Olsson, *Oncoscience,* 2015, 2(11), 900-901). Thus, PAD4 enzyme is linked to diseases characterized by abnormal levels of neutrophil extracellular traps (NETs). The proposed role of PAD4 in NETosis is pertinent for rheumatoid arthritis (RA) as NETs are deficient in the absence of PAD4 and PAD4 is released extracellulary in RA joints, probably due to the pathological status of RA neutrophils.

Considering the fact that NETs are implicated in many diseases, the therapeutic potential of PAD inhibitor drugs would be significant. PAD4 inhibitors may also have wider applicability as tools and therapeutics for human disease through epigenetic mechanisms.

In literature, a number of PAD inhibitors that are selective for PAD4 are known (H. D. Lewis et al., Nature Chemical Biology, 2015, 11, 189-191). Some of these compounds are chloro-amidine, fluoro-chloridine and their related analogs act as mechanism-based inhibitors that irreversibly inactivate PAD4 and other PAD isozymes. The PAD4 inhibitor compounds have utility against rheumatoid arthritis (RA). PAD4, detected in synovial tissue, has been found to be responsible for citrullination of a variety of joint proteins. These citrullinated protein substrates produce anti-citrullinated antibodies which are responsible for disease pathogenesis (Y. Kochi et al., Ann. Rheum. Dis., 2011, 70, 512-515).

PAD4 inhibitors have also been known for alleviating pathological activity in a variety of diseases. Some specific studies show that the defence mechanism of neutrophils to eliminate pathogens, also known as NET formation is associated with histone citrullination (I. Neeli et al., J. Immunol., 2008, 180, 1895-1902). Therefore, PAD4 inhibitor compounds can be utilized in injuries and disease pathologies where NET formation in tissues occurs. In addition, PAD4 inhibitors have wider applicability to neutrophilic diseases.

US20170105971 discloses the alleviation, treatment and/or prevention of auto immune diseases like, rheumatoid arthritis, osteoarthritis and arthralgia by using amidines as PAD inhibitor compounds. Another application US20050159334 also discusses the treatment of rheumatoid arthritis (RA) with the administration of suitable PAD inhibitor.

The PAD inhibitor compound chloro-amidine, has been widely studied to demonstrate their efficacy in several animal disease models like, collagen-induced arthritis (V. C. Willis et al., J. Immunol., 2011, 186(7), 4396-4404), dextran sulfate sodium (DSS)-induced experimental colitis (A. A. Chumanevich et al., Am. J. Physiol. Gastrointest. Liver Physiol., 2011, 300(6), G929-G938), lupus-prone MRL/lpr mice atherosclerosis and arterial thrombosis (J. S. Knight et al., Circ. Res., 2014, 114(6), 947-956), spinal cord injury repair (S. Lange et al., Dev. Biol., 2011, 355(2), 205-214), and experimental autoimmune encephalomyelitis (EAE). The study on DSS colitis demonstrated that chloro-amidine drives in vitro and in vivo apoptosis of inflammatory cells, indicating the efficacy of PAD4 inhibitors in treating inflammatory diseases.

PAD4 is predominantly expressed in granulocytes and is strongly linked to diverse diseases. In multiple tumors, PAD4 is found to be overexpressed affecting the p53 function and downstream pathways. Calcium binding to PAD promotes the bioactive conformation, increasing PAD4 activity by ten thousand times.

Slack et al. demonstrated the use of PAD4 inhibitors in the treatment of cancers (J. L. Slack et al., Cellular and Molecular Life Sciences, 2011, 68(4), 709-720). Overexpression of PAD4 had already been demonstrated in numerous cancers (X. Chang et al., BMC Cancer, 2009, 9, 40). It is suggested that PAD4 inhibitors have an anti-proliferative role as well. PAD4 deiminases arginine residues in histones at the promoters of p53-target genes such as p21, which are involved in cell cycle arrest and induction of apoptosis (P. Li et al., Molecular & Cell Biology, 2008, 28(15), 4745-4758).

PAD inhibition is a viable strategy for the treatment of numerous diseases mentioned above. The use of PAD inhibitors in various other diseases where dysregulated PAD activity is implicated needs to be explored. Although a definitive role for dysregulated PAD activity in these diseases has not been established, a direct link is plausible. However, there remains an unmet need to identify and develop PAD4 inhibitors which may treat PAD4 mediated disorders with efficacy.

SUMMARY OF INVENTION

The present disclosure discloses a compound of Formula (I)

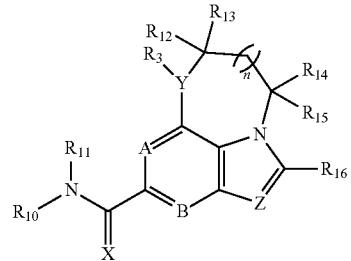

Formula (I)

their polymorphs, stereoisomers, prodrugs, solvates, co-crystals, intermediates, pharmaceutically acceptable salts, and metabolites thereof, wherein X is selected from O or S; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, (CO) $C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)$ $C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

The present disclosure also discloses compound of Formula (II)

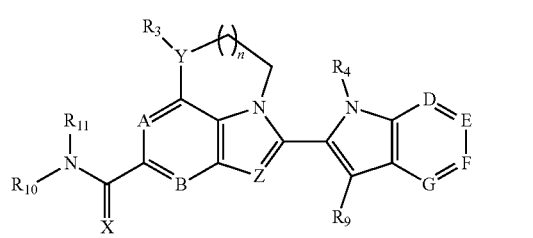

Formula (II)

their polymorphs, stereoisomers, prodrugs, solvates, co-crystals, intermediates, pharmaceutically acceptable salts, and metabolites thereof, wherein X is selected from O or S; Y is selected from O, N, S, S(O), SO$_2$ or C; Z is selected from N or CR$_{17}$; A is selected from N or CR$_1$; B is selected from N or CR$_2$; D is selected from N or CR$_5$; E is selected from N or CR$_6$; F is selected from N or CR$_7$; G is selected from N or CR$_8$; n is 0-2; $R_1$, $R_2$, $R_5$, $R_6$, $R_7$, $R_8$, and $R_9$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$$C_{1-6}$ alkyl, SO$_2$$C_{1-6}$ haloalkyl, SO$_2$$C_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$$C_{5-6}$ aryl, and SO$_2$$C_{1-6}$ heteroaryl, wherein $C_{1-6}$ alkyl, (CO)$C_{1-6}$ alkyl, C(O)$C_{1-6}$ haloalkyl, SO$_2$$C_{5-6}$ aryl, and SO$_2$$C_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, C(O)$C_{1-6}$ alkyl, C(O)$C_{1-6}$ haloalkyl, C(O)NR$_{18}$, C(O)$C_{1-6}$ alkylamino, SO$_2$$C_{1-6}$ alkyl, SO$_2$$C_{1-6}$ haloalkyl, SO$_2$NR$_{18}$, SO$_2$NC$_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, C(O)$C_{5-6}$ aryl, C(O)$C_{1-6}$ heteroaryl, SO$_2$$C_{5-6}$ aryl, and SO$_2$$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, (CO)$C_{1-6}$ alkyl, C(O)$C_{1-6}$ haloalkyl, and SO$_2$$C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, —CH$_2$OH, —COOH, and cyano; $R_{10}$ is hydrogen; $R_{11}$ is selected from the group consisting of $C_{1-6}$ alkylamino, and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

The present disclosure further discloses compound of Formula (III)

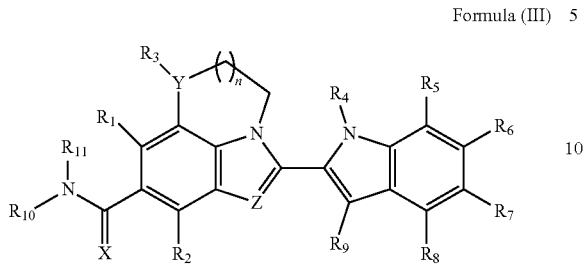

Formula (III)

their polymorphs, stereoisomers, prodrugs, solvates, co-crystals, intermediates, pharmaceutically acceptable salts, and metabolites thereof,
wherein
X is selected from O or S; Y is selected from O, N, S, S(O), SO$_2$ or C; Z is selected from N or CR$_{17}$; n is 0-2; R$_1$, R$_2$, R$_5$, R$_6$, R$_7$, R$_8$, and R$_9$ are independently selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, C$_{2-6}$ alkenyl-C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; R$_3$ is absent or is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{5-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; R$_4$ is selected from the group consisting of hydrogen, C$_{1-6}$ alkyl, C$_{1-6}$ haloalkyl, C$_{1-6}$ alkoxy, C$_{3-6}$ cycloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$NR$_{18}$, SO$_2$NC$_{1-6}$ alkylamino, C$_{5-6}$ aryl, C$_{1-6}$ alkyl-C$_{5-6}$ aryl, C$_{1-6}$ heterocyclyl, C$_{1-6}$ alkyl-C$_{1-6}$ heterocyclyl, C$_{1-6}$ heteroaryl, C$_{1-6}$ alkyl-C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, C$_{1-6}$ alkoxy, C$_{3-6}$ cycloalkyl, C$_{5-6}$ aryl, C$_{1-6}$ alkyl-C$_{5-6}$ aryl, C$_{1-6}$ heterocyclyl, C$_{1-6}$ alkyl-C$_{1-6}$ heterocyclyl, C$_{1-6}$ heteroaryl, C$_{1-6}$ alkyl-C$_{1-6}$ heteroaryl, (CO)C$_{1-6}$ alkyl, C(O)C$_{1-6}$ haloalkyl, and SO$_2$C$_{1-6}$ alkyl, is optionally substituted with one or more groups selected from hydrogen, C$_{1-6}$ alkyl, C$_{1-6}$ alkoxy, C$_{3-8}$ cycloalkyl, C$_{5-6}$ aryl, C$_{1-6}$ heteroaryl, halogen, hydroxyl, CH$_2$OH, COOH, and cyano; R$_{10}$ is hydrogen; R$_{11}$ is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cyclo alkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; and 5-10 membered monocyclic or bicyclic saturated heterocyclic ring with 1-3 heteroatoms selected from N, S or O, or R$_{10}$ and R$_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, C$_{1-6}$ alkylamino, C$_{1-6}$ acylamino, —NHC(NH)CH$_2$Cl, —NHC(O)CH=CHCH$_2$N(CH$_3$)$_2$, C$_{1-6}$ alkyl, halogen, C$_{1-6}$ alkoxy, and hydroxyl; R$_{17}$ is selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; and R$_{18}$ is independently selected from the group consisting of hydrogen, C$_{1-6}$ alkyl, and combinations thereof.

The present disclosure further describes the process of preparation of compounds of Formula (I), Formula (II), and Formula (III) or its polymorphs, stereoisomers, prodrugs, solvates, co-crystals, intermediates, pharmaceutically acceptable salts, and metabolites thereof.

The present disclosure further discloses a pharmaceutical composition comprising a compound of Formula (I), Formula (II), and Formula (III) or a pharmaceutically acceptable salt thereof, together with a pharmaceutically acceptable carrier, optionally in combination with one or more other pharmaceutical compositions.

The present disclosure further discloses a method for inhibiting one or more PAD family in a cell with an effective amount of the compound of the present disclosure.

The present disclosure further discloses a method of treating a condition mediated by one or more PAD's, the method comprising administering to a subject suffering from a condition mediated by one or more PAD family, a therapeutically effective amount of the compound of Formula (I), Formula (II), and Formula (III) or the pharmaceutical composition of the present disclosure with other clinically relevant agents or biological agents to a subject in need thereof.

The present disclosure further discloses a compound of Formula (I), Formula (II) and Formula (III) used for the treatment of rheumatoid arthritis, vasculitis, systemic lupus erythematosus, ulcerative colitis, cancer, cystic fibrosis, asthma, cutaneous lupus erythematosis, and psoriasis.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

Furthermore, the compound of Formula (I), Formula (II), and Formula (III) can be its derivatives, analogs, stereoisomer's, diastereomers, geometrical isomers, polymorphs, solvates, co-crystals, intermediates, metabolites, prodrugs or pharmaceutically acceptable salts and compositions.

The compounds according to Formula (I), Formula (II), and Formula (III) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in Formula (I), Formula (II), and Formula (III), or in any chemical structure illustrated herein, is not specified, the structure is intended to encompass any, stereoisomer and all mixtures thereof. Thus, compounds according to Formula (I), Formula (II), and Formula (III) containing one or more chiral centres may be used as racemic modifications including racemic mixtures and racemates, enantiomerically-enriched mixtures, or as enantiomerically-pure individual stereoisomers.

Individual stereoisomers of a compound according to Formula (I), Formula (II), and Formula (III) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form.

Alternatively, specific stereoisomers may be synthesised by asymmetric synthesis using optically active reagents, substrates, catalysts or solvents, or by converting one enantiomer to the other by asymmetric transformation.

It is to be understood that the references herein to compounds of Formula (I), Formula (II), and Formula (III) and salts thereof covers the compounds of Formula (I), Formula (II), and Formula (III) as free bases, or as salts thereof, for example as pharmaceutically acceptable salts thereof. Thus, in one embodiment, the disclosure is directed to compounds of Formula (I), Formula (II), and Formula (III) as the free base. In another embodiment, the disclosure is directed to compounds of Formula (I), Formula (II), and Formula (III) and salts thereof. In a further embodiment, the disclosure is directed to compounds of Formula (I), Formula (II), and Formula (III) and pharmaceutically acceptable salts thereof.

It will be appreciated that pharmaceutically acceptable salts of the compounds according to Formula (I, II and III) may be prepared. Indeed, in certain embodiments of the disclosure, pharmaceutically acceptable salts of the compounds according to Formula (I), Formula (II), and Formula (III) may be preferred over the respective free base because such salts impart greater stability or solubility to the molecule thereby facilitating formulation into a dosage form. Accordingly, the disclosure is further directed to compounds of Formula (I), Formula (II), and Formula (III) and pharmaceutically acceptable salts thereof.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, 'enantiomerically enriched' refers to products whose enantiomeric excess is greater than 50% ee, greater than 75% ee, and greater than 90% ee. 'Enantiomerically pure' refers to products whose enantiomeric excess is 99% or greater.

Included within the scope of the 'compounds of the disclosure' are all solvates (including hydrates), complexes, polymorphs, prodrugs, radiolabelled derivatives, and stereoisomers of the compounds of Formula (I), Formula (II), and Formula (III) and salts thereof.

The compounds of the disclosure may exist in solid or liquid form. In the solid state, the compounds of the disclosure may exist in crystalline or non-crystalline form, or as a mixture thereof. For compounds of the disclosure that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as 'hydrates'. Hydrates include stoichiometric hydrates as well as compositions containing variable amounts of water. The disclosure includes all such solvates.

It will be further appreciated that certain compounds of the disclosure that exist in crystalline form, including the various solvates thereof, may exhibit polymorphism (i.e. the capacity to occur in different crystalline structures). These different crystalline forms are typically known as 'polymorphs'. The disclosure includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The disclosure also includes isotopically-labelled compounds, which are identical to the compounds of Formula (I, II and III) and salts thereof, but for the fact that one or more atoms are replaced by an atom having an atomic mass or mass number different from the atomic mass or mass number most commonly found in nature. Examples of isotopes that can be incorporated into the compounds of the disclosure include isotopes of hydrogen, carbon, nitrogen, oxygen and fluorine, such as $^{3}H$, $^{11}C$, $^{14}C$ and $^{18}F$.

The term "co-crystals" refers to solids that are crystalline single-phase materials composed of two or more different molecular and/or ionic compounds generally in a stoichiometric ratio which are neither solvates nor simple salts.

The term "substituted" in reference to a group indicates that a hydrogen atom attached to a member atom within a group is replaced. It should be understood that the term 'substituted' includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as tong as such substitution is in accordance with the permitted valence of the atom. Suitable substituents are defined herein for each substituted or optionally substituted group.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "prodrugs" refers to the precursor of the compound of Formula (I, II, and III) which on administration undergoes chemical conversion by metabolic processes before becoming active pharmacological substances. In general, such prodrugs will be functional derivatives of a compound of the disclosure, which are readily convertible in vivo into a compound of the disclosure.

The term "alkyl" refers to a saturated hydrocarbon chain having the specified number of carbon atoms. For example, which are not limited, $C_{1-6}$ alkyl refers to an alkyl group having from 1-6 carbon atoms, or 1-3 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, and isobutyl.

The term "C(O) alkyl" refers to an alkyl group as defined above attached via carbonyl linkage to the rest of the molecule. For example, $C(O)C_{1-6}$ alkyl refers to an alkyl group having from 1-6 carbon atoms, or 1-3 carbon atoms attached via carbonyl linkage to the rest of the molecule. Preferred C(O) alkyl groups include, without limitation, —C(O)CH$_3$, —C(O)CH$_2$CH$_3$, and the like.

The term "SO$_2$ alkyl" refers to an alkyl group as defined above attached via sulfonyl linkage to the rest of the molecule. For example, $SO_2C_{1-6}$ alkyl refers to an alkyl group having from 1-6 carbon atoms, or 1-3 carbon atoms attached via sulfonyl linkage to the rest of the molecule. Preferred SO$_2$ alkyl groups include, without limitation, —SO$_2$CH$_3$, —SO$_2$CH$_2$CH$_3$, and the like.

The term "alkoxy" refers to an alkyl group attached via an oxygen linkage to the rest of the molecule. For example, $C_{1-6}$ alkoxy refers to an alkyl group having from 1-6 carbon atoms, or 1-3 carbon atoms attached via an oxygen linkage to the rest of the molecule. Preferred alkoxy groups include, without limitation, —OCH$_3$ (methoxy), —OC$_2$H$_5$(ethoxy) and the like.

The term "alkylamino" refers to an alkyl group as defined above attached via amino linkage to the rest of the molecule. For example, $C_{1-6}$ alkylamino refers to an alkyl group having from 1-6 carbon atoms, or 1-3 carbon atoms attached via amino linkage to the rest of the molecule. Preferred alkylamino groups include, without limitation, —NHCH$_3$, —N(CH$_3$)$_2$, and the like.

The term "C(O)NR" refers to an alkylamino group as defined above attached via a carbonyl linkage to the rest of the molecule. Preferred C(O)NR groups include, C(O)NCH$_3$, C(O)NCH$_2$CH$_3$, and the like.

The term "SO$_2$NR" refers to an alkylamino group as defined above attached via a sulfonyl linkage to the rest of the molecule. Preferred SO$_2$NR groups include, SO$_2$NCH$_3$, SO$_2$NCH$_2$CH$_3$, and the like.

The term "C(O) alkylamino" refers to an alkylamino group as defined above attached via carbonyl linkage to the rest of the molecule. For example, $C(O)C_{1-6}$ alkylamino refers to an alkylamino group having from 1-6 carbon atoms, or 1-3 carbon atoms attached via carbonyl linkage to the rest of the molecule. Preferred C(O) alkylamino groups include, without limitation, —C(O)NHCH$_3$, —C(O)N(CH$_3$)$_2$, and the like.

The term "SO$_2$ alkylamino" refers to an alkylamino group as defined above attached via sulfonyl linkage to the rest of the molecule. For example, $SO_2C_{1-6}$ alkylamino refers to an alkylamino group having from 1-6 carbon atoms, or 1-3 carbon atoms attached via sulfonyl linkage to the rest of the molecule. Preferred SO$_2$ alkylamino groups include, without limitation, —SO$_2$NHCH$_3$, —SO$_2$N(CH$_3$)$_2$, and the like.

The term "acylamino" refers to an acyl group attached via amino linkage to the rest of the molecule. For example, $C_{1-6}$ acylamino refers to an acyl group having from 1-6 carbon atoms, or 1-3 carbon atoms attached via amino linkage to the rest of the molecule. Preferred acylamino groups include, without limitation, —(CO)NHCH$_3$, —(CO)N(CH$_3$)$_2$, and the like.

The term "haloalkyl" refers to an alkyl group as defined above attached via halo linkage to the rest of the molecule. For example, $C_{1-6}$ haloalkyl refers to an alkyl group having from 1-6 carbon atoms, or 1-3 carbon atoms attached via halo linkage to the rest of the molecule. Preferred haloalkyl groups include, without limitation, —CH$_2$Cl, —CHCl$_2$, and the like.

The term "C(O) haloalkyl" refers to an haloalkyl group as defined above attached via carbonyl linkage to the rest of the molecule. For example, $C(O)C_{1-6}$ haloalkyl refers to an haloalkyl group having from 1-6 carbon atoms, or 1-3 carbon atoms attached via carbonyl linkage to the rest of the molecule. Preferred C(O) haloalkyl groups include, without limitation, —(CO)CH$_2$Cl, —C(O)CHCl$_2$, and the like.

The term "SO$_2$ haloalkyl" refers to an haloalkyl group as defined above attached via sulfonyl linkage to the rest of the molecule. For example, $SO_2C_{1-6}$ haloalkyl refers to an haloalkyl group having from 1-6 carbon atoms, or 1-3 carbon atoms attached via sulfonyl linkage to the rest of the molecule. Preferred SO$_2$ haloalkyl groups include, without limitation, —SO$_2$CH$_2$Cl, —SO$_2$CHCl$_2$, and the like.

The term "haloalkoxy" refers to an alkoxy group as defined above attached via oxygen linkage of the haloalkoxy group to the rest of the molecule. For example, $C_{1-6}$ haloalkoxy refers to an alkoxy group having from 1-6 carbon atoms, or 1-3 carbon atoms attached via oxygen linkage to the rest of the molecule. Preferred haloalkoxy groups include, without limitation, —OCH$_2$Cl, —OCHCl$_2$, and the like.

The term "halogen" refers to a halogen radical, for example, fluoro, chloro, bromo, or iodo. "Haloalkyl" refers to an alkyl group, as herein before defined, in which at least one of the hydrogen atoms has been replaced with a halogen radical. "$C_{1-6}$ haloalkyl" refers to a $C_{1-6}$ alkyl group in which at least one of the hydrogen atoms has been replaced with a halogen radical. An example of 'haloalkyl' is trifluoromethyl or 2,2,2-trifluoroethyl.

The term "cycloalkyl" refers to a saturated hydrocarbon ring having a specified number of carbon atoms. For example, which are not limited, $C_{3-6}$ cycloalkyl refers to a cycloalkyl group having from 3 to 6 member atoms, or 3 member atoms. Preferred cycloalkyl groups include, without limitation, cyclopropyl, cyclobutyl, cyclopentyl, cyclohexyl, groups and the like.

The term "SO$_2$C$_{3-6}$ cycloalkyl" refers to a cycloalkyl group as defined above attached via sulfonyl linkage to the rest of the molecule. For example, SO$_2$C$_{3-6}$ cycloalkyl refers to a cycloalkyl group having from 3-6 carbon atoms attached via sulfonyl linkage to the rest of the molecule. Preferred SO$_2$ cycloalkyl groups include, without limitation, —SO$_2$C$_3$ cycloalkyl, and the like.

The term "aryl" refers to aromatic ring having a specified number of carbon atoms. For example, $C_{5-6}$ aryl refers to a aryl group having 5 or 6 member atoms, or 6 member atoms. Preferred aryl groups include, without limitation, phenyl, and the like.

The term "C(O) aryl" refers to an aryl group as defined above attached via carbonyl linkage to the rest of the molecule. For example, C(O)C$_{5-6}$ aryl refers to an aryl group having from 5-6 carbon atoms attached via carbonyl linkage to the rest of the molecule. Preferred C(O) aryl groups include, without limitation, —C(O) C$_6$H$_5$, —C(O) C$_5$H$_5$, and the like.

The term "SO$_2$ aryl" refers to an aryl group as defined above attached via sulfonyl linkage to the rest of the molecule. For example, SO$_2$C$_{5-6}$ aryl refers to an aryl group having from 5-6 carbon atoms attached via sulfonyl linkage to the rest of the molecule. Preferred SO$_2$ aryl groups include, without limitation, —SO$_2$C$_6$H$_5$, —SO$_2$C$_5$H$_5$, and the like.

The term "heteroaryl" refers to aromatic rings containing from 1 to 5 heteroatoms in the ring. "Heteroaryl" groups may be substituted with one or one or more substituents if so defined herein. The "C$_{1-6}$ heteroaryl" rings having 1 or 6 carbon as member atoms. The "heteroaryl" includes pyridinyl, tetrazolyl and pyrazolyl. "Heteroatom" refers to a nitrogen, sulfur, or oxygen atom, for example a nitrogen atom or an oxygen atom.

The term "C(O) heteroaryl" refers to an heteroaryl group as defined above attached via carbonyl linkage to the rest of the molecule. For example, C(O)C$_{1-6}$ heteroaryl refers to an alkyl group having from 1-6 carbon atoms attached via carbonyl linkage to the rest of the molecule. Preferred C(O) heteroaryl groups include, without limitation, —C(O) pyridinyl, —C(O) pyrazolyl, and the like.

The term "SO$_2$ heteroaryl" refers to an aryl group as defined above attached via sulfonyl linkage to the rest of the molecule. For example, SO$_2$C$_{1-6}$ heteroaryl refers to an aryl group having from 1-6 carbon atoms attached via sulfonyl linkage to the rest of the molecule. Preferred SO$_2$ heteroaryl groups include, without limitation, —SO$_2$ pyridinyl, —SO$_2$ pyrazolyl, and the like.

The term "heterocyclic" and "heterocyclyl" refer to saturated or unsaturated monocyclic aliphatic rings containing 5, 6, or 7 ring members including 1-5 heteroatoms or to saturated or unsaturated bicyclic aliphatic rings containing 5, 6 or 7 ring members each including 1-5 heteroatoms. In certain embodiments, 'heterocyclyl' groups are saturated. In other embodiments, 'heterocyclyl' groups are unsaturated. 'Heterocyclyl' groups containing more than one heteroatom may contain different heteroatoms. 'Heterocyclyl' groups may be substituted with one or more substituents as defined herein. 'Heterocyclyl' includes piperidinyl, tetrahydropyranyl, azepinyl, oxazepinyl, azabicyclo[3.1.0]hexanyl.

The phrase "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid. The pharmaceutically acceptable salt selected derived from inorganic bases such as like Li, Na, K, Ca, Mg, Fe, Cu, Zn and Mn; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, ammonium, substituted ammonium salts, aluminum salts and the like. Salts also include amino acid salts such as glycine, alanine, cystine, cysteine, lysine, arginine, phenylalanine, and guanidine. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates.

Salts and solvates having non-pharmaceutically acceptable counter-ions or associated solvents are within the scope of the present disclosure, for example, for use as intermediates in the preparation of other compounds of Formula (I), Formula (II), and Formula (III) and their pharmaceutically acceptable salts. Thus, one embodiment of the disclosure embraces compounds of Formula (I), Formula (II), and Formula (III) and salts thereof. Compounds according to Formula (I), Formula (II), and Formula (III) contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

The term "PAD inhibitor" or "inhibitor of PAD" is used to identify a compound, which is capable of interacting with neutrophil extracellular traps (NETs) and more specifically in the histone citrullination that occurs during NETosis. Inhibiting PAD4 enzymatic activity means reducing the ability of PAD4 enzyme so as to inhibit the formation of citrulline through citrullination process. Preferably, such inhibition is specific to PAD4 enzyme.

A term once described, the same meaning applies for it, throughout the patent.

The utility of PAD4 inhibitors is vast as described in the background section. However, the identification and development of PAD4 inhibitor compounds still remains a problem, despite of their vast utility. Therefore, new PAD4 inhibitor compounds treating PAD4 mediated disorders are required.

In an embodiment of the present disclosure, there is provided a compound of Formula (I) their polymorphs, stereoisomers, prodrugs, solvates, co-crystals, intermediates, pharmaceutically acceptable salts, and metabolites thereof, wherein

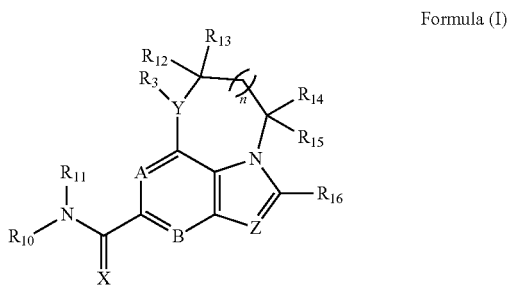

Formula (I)

X is selected from O or S; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; R$_{10}$ is hydrogen; R$_{11}$ is selected from the group consisting of hydrogen, C$_{1-6}$ alkyl, C$_{3-6}$ cycloalkyl, C$_{1-6}$ alkylamino C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; and 5-10 membered monocyclic or bicyclic saturated heterocyclic ring with 1-3 heteroatoms selected from N, S or O, or R$_{10}$ and R$_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, C$_{1-6}$ alkylamino, C$_{1-6}$ acylamino, —NHC(NH)CH$_2$Cl, NHC(O)CH=CHCH$_2$N(CH$_3$)$_2$, C$_{1-6}$ alkyl, halogen, C$_{1-6}$ alkoxy, and hydroxyl; R$_{12}$, R$_{13}$, R$_{14}$, and R$_{15}$ are independently selected from the group consisting of hydrogen, C$_{1-6}$ alkyl, C$_{1-6}$ haloalkyl, C$_{1-6}$ alkylamino, C$_{5-6}$ aryl, and C$_{1-6}$ heteroaryl; or R$_{12}$ and R$_{13}$ can be taken together to form =O or =O; or R$_{14}$ and R$_{15}$ can be taken together to form =O or =O; R$_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, C$_{1-6}$ alkyl, C$_{1-6}$ alkoxy, C$_{3-6}$ cycloalkyl, C$_{1-6}$ haloalkyl, C$_{1-6}$ haloalkoxy, C$_{1-6}$ acylamino, C$_{1-6}$ alkylamino, C$_{5-6}$ aryl, C$_{1-6}$ alkyl-C$_{5-6}$ aryl, C$_{2-6}$ alkenyl-C$_{5-6}$ aryl, C$_{1-6}$ heterocyclyl, C$_{1-6}$ alkyl-C$_{1-6}$ heterocyclyl, C$_{1-6}$ heteroaryl, and C$_{1-6}$ alkyl-C$_{1-6}$ heteroaryl, wherein C$_{1-6}$ alkyl, C$_{1-6}$ alkoxy, C$_{3-6}$ cycloalkyl, C$_{5-6}$ aryl, C$_{1-6}$ alkyl-C$_{5-6}$ aryl, C$_{1-6}$ heteroaryl, C$_{1-6}$ alkyl-C$_{1-6}$ heteroaryl, and C$_{1-6}$ alkyl-C$_{1-6}$ heterocyclyl is optionally substituted with one or more of the groups selected from hydrogen, C$_{1-6}$ alkyl, C$_{1-6}$ alkoxy, C$_{3-8}$ cycloalkyl, C$_{1-6}$ heteroaryl, halogen, hydroxyl, —CH$_2$OH, —COOH, and cyano; R$_{17}$ is selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; and R$_{18}$ is independently selected from the group consisting of hydrogen, C$_{1-6}$ alkyl, and combinations thereof.

In an embodiment of the present disclosure, there is provided a compound of Formula (I) as described herein, wherein X is S; Y is selected from O, N, S, S(O), SO$_2$ or C; Z is selected from N or CR$_{17}$; A is selected from N or CR$_1$; B is selected from N or CR$_2$; n is 0-2; R$_1$, and R$_2$ are independently selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; R$_3$ is absent or is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; R$_{10}$ is hydrogen; R$_{11}$ is selected from the group consisting of hydrogen, C$_{1-6}$ alkyl, C$_{3-6}$ cycloalkyl, C$_{1-6}$ alkylamino C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; and 5-10 membered monocyclic or bicyclic saturated heterocyclic ring with 1-3 heteroatoms selected from N, S or O, or R$_{10}$ and R$_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, C$_{1-6}$ alkylamino, C$_{1-6}$ acylamino, —NHC(NH)CH$_2$Cl, NHC(O)CH=CHCH$_2$N(CH$_3$)$_2$, C$_{1-6}$ alkyl, halogen, C$_{1-6}$ alkoxy, and hydroxyl; R$_{12}$, R$_{13}$, R$_{14}$, and R$_{15}$ are independently selected from the group consisting of hydrogen, C$_{1-6}$ alkyl, C$_{1-6}$ haloalkyl, C$_{1-6}$ alkylamino, C$_{5-6}$ aryl, and C$_{1-6}$ heteroaryl; or R$_{12}$ and R$_{13}$ can be taken together to form =O or =O; or R$_{14}$ and R$_{15}$ can be taken together to form =O or =O; R$_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, C$_{1-6}$ alkyl, C$_{1-6}$ alkoxy, C$_{3-6}$ cycloalkyl, C$_{1-6}$ haloalkyl, C$_{1-6}$ haloalkoxy, C$_{1-6}$ acylamino, C$_{1-6}$ alkylamino, C$_{5-6}$ aryl, C$_{1-6}$ alkyl-C$_{5-6}$ aryl, C$_{2-6}$ alkenyl-C$_{5-6}$ aryl, C$_{1-6}$ heterocyclyl, C$_{1-6}$ alkyl-C$_{1-6}$ heterocyclyl, C$_{1-6}$ heteroaryl, and C$_{1-6}$ alkyl-C$_{1-6}$ heteroaryl, wherein C$_{1-6}$ alkyl, C$_{1-6}$ alkoxy, C$_{3-6}$ cycloalkyl, C$_{5-6}$ aryl, C$_{1-6}$ alkyl-C$_{5-6}$ aryl, C$_{1-6}$ heteroaryl, C$_{1-6}$ alkyl-C$_{1-6}$ heteroaryl, and C$_{1-6}$ alkyl-C$_{1-6}$ heterocyclyl is optionally substituted with one or more of the groups selected from hydrogen, C$_{1-6}$ alkyl, C$_{1-6}$ alkoxy, C$_{3-8}$ cycloalkyl, C$_{1-6}$ heteroaryl, halogen, hydroxyl, —CH$_2$OH, —COOH, and cyano; R$_{17}$ is selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; and R$_{18}$ is independently selected from the group consisting of hydrogen, C$_{1-6}$ alkyl, and combinations thereof.

In an embodiment of the present disclosure, there is provided a compound of Formula (I) as described herein, wherein X is O or S; Y is selected from O or N; Z is selected from N or CR$_{17}$; A is selected from N or CR$_1$; B is selected from N or CR$_2$; n is 0-2; R$_1$, and R$_2$ are independently selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is O; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is N; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is N; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O) $C_{1-6}$ alkyl, C(O)$C_{1-6}$ haloalkyl, C(O)$NR_{18}$, C(O)$C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, C(O)$C_{5-6}$ aryl, C(O)$C_{1-6}$ heteroaryl, $SO_2C_{5-6}$ aryl, and $SO_2C_{1-6}$ heteroaryl, wherein $C_{1-6}$ alkyl, (CO)$C_{1-6}$ alkyl, C(O)$C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)$NR_{18}$, C(O)$C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, C(O)$C_{5-6}$ aryl, C(O)$C_{1-6}$ heteroaryl, $SO_2C_{5-6}$ aryl, and $SO_2C_{1-6}$ heteroaryl, wherein $C_{1-6}$ alkyl, (CO)$C_{1-6}$ alkyl, C(O)$C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)$CH_2Cl$, NHC(O)CH=$CHCH_2N$ $(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is selected from N or $CR_1$; B is $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O) $C_{1-6}$ alkyl, C(O)$C_{1-6}$ haloalkyl, C(O)$NR_{18}$, C(O)$C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, C(O)$C_{5-6}$ aryl, C(O)$C_{1-6}$ heteroaryl, $SO_2C_{5-6}$ aryl, and $SO_2C_{1-6}$ heteroaryl, wherein $C_{1-6}$ alkyl, (CO)$C_{1-6}$ alkyl, C(O)$C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)$NR_{18}$, C(O)$C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, C(O)$C_{5-6}$ aryl, C(O)$C_{1-6}$ heteroaryl, $SO_2C_{5-6}$ aryl, and $SO_2C_{1-6}$ heteroaryl, wherein $C_{1-6}$ alkyl, (CO)$C_{1-6}$ alkyl, C(O)$C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)$CH_2Cl$, NHC(O)CH=$CHCH_2N$ $(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is selected from N or $CR_1$; B is selected from N or $CR_2$; n is 0; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is selected from N or $CR_1$; B is selected from N or $CR_2$; n is 1; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, and $C_{1-4}$ alkyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-6}$ alkyl, (CO)$C_{1-6}$ alkyl, C(O)$C_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-6}$ alkyl, (CO)$C_{1-6}$ alkyl, C(O)$C_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from hydrogen; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-6}$ alkyl, (CO)$C_{1-6}$ alkyl, C(O)$C_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-6}$ alkyl, (CO)$C_{1-6}$ alkyl, C(O)$C_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-4}$ alkyl, $C_{3-5}$ cycloalkyl, $C_{1-4}$ alkylamino, $C_{1-4}$ haloalkyl, C(O)$C_{1-4}$ alkyl, C(O)$C_{1-4}$ haloalkyl, C(O)NR$_{18}$, C(O)$C_{1-4}$ alkylamino, SO$_2$C$_{1-4}$ alkyl, SO$_2$C$_{1-4}$ haloalkyl, SO$_2$C$_{3-6}$ cycloalkyl, SO$_2$NR$_{18}$, SO$_2$NC$_{1-4}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-4}$ alkyl, (CO)$C_{1-4}$ alkyl, C(O)$C_{1-4}$ haloalkyl, SO$_2$C$_{5-6}$ aryl, and SO$_2$C$_{1-6}$ alkyl, is optionally substituted with $C_{1-4}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-6}$ alkyl, (CO)$C_{1-6}$ alkyl, C(O)$C_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O or S; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$C$_{5-6}$ aryl, and SO$_2$C$_{1-6}$ heteroaryl, wherein $C_{1-6}$ alkyl, (CO)$C_{1-6}$ alkyl, C(O)$C_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH═CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form ═O or ═O; or $R_{14}$ and $R_{15}$ can be taken together to form ═O or ═O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is selected from the group consisting of hydrogen, $C_{1-4}$ alkyl, $C_{3-5}$ cycloalkyl, $C_{1-4}$ alkylamino, $C_{1-4}$ haloalkyl, C(O)$C_{1-4}$ alkyl, C(O)$C_{1-4}$ haloalkyl, C(O)NR$_{18}$, C(O)$C_{1-4}$ alkylamino, SO$_2$$C_{1-4}$ alkyl, SO$_2$$C_{1-4}$ haloalkyl, SO$_2$$C_{3-6}$ cycloalkyl, SO$_2$NR$_{18}$, SO$_2$NC$_{1-4}$ alkylamino, $C_{5-6}$ aryl, $C_{1-6}$ heteroaryl, C(O)$C_{5-6}$ aryl, C(O)$C_{1-6}$ heteroaryl, SO$_2$$C_{5-6}$ aryl, and SO$_2$$C_{1-6}$ heteroaryl, wherein $C_{1-4}$ alkyl, (CO)$C_{1-4}$ alkyl, C(O)$C_{1-4}$ haloalkyl, SO$_2$$C_{5-6}$ aryl, and SO$_2$$C_{1-6}$ alkyl, is optionally substituted with $C_{1-4}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$$C_{1-6}$ alkyl, SO$_2$$C_{1-6}$ haloalkyl, SO$_2$$C_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$$C_{5-6}$ aryl, and SO$_2$$C_{1-6}$ heteroaryl, wherein $C_{1-6}$ alkyl, (CO)$C_{1-6}$ alkyl, C(O)$C_{1-6}$ haloalkyl, SO$_2$$C_{5-6}$ aryl, and SO$_2$$C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH═CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form ═O or ═O; or $R_{14}$ and $R_{15}$ can be taken together to form ═O or ═O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2$$C_{1-6}$ alkyl, SO$_2$$C_{1-6}$ haloalkyl, SO$_2$$C_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2$$C_{5-6}$ aryl, and SO$_2$$C_{1-6}$ heteroaryl, wherein $C_{1-6}$ alkyl, (CO)$C_{1-6}$ alkyl, C(O)$C_{1-6}$ haloalkyl, SO$_2$$C_{5-6}$ aryl, and SO$_2$$C_{1-6}$ alkyl, is optionally substituted with $C_{1-6}$ alkoxy, $C_{5-6}$ aryl, and $C_{1-6}$ heteroaryl; $R_{10}$ and $R_{11}$ are taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, —NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2C_{1-6}$ alkyl, SO$_2C_{1-6}$ haloalkyl, SO$_2C_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2C_{5-6}$ aryl, and SO$_2C_{1-6}$ heteroaryl, wherein $C_{1-6}$ alkyl, (CO)$C_{1-6}$ alkyl, C(O)$C_{1-6}$ haloalkyl, SO$_2C_{5-6}$ aryl, and SO$_2C_{1-6}$ alkyl, and SO$_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2C_{1-6}$ alkyl, SO$_2C_{1-6}$ haloalkyl, SO$_2C_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2C_{5-6}$ aryl, and SO$_2C_{1-6}$ heteroaryl, wherein $C_{1-6}$ alkyl, (CO)$C_{1-6}$ alkyl, C(O)$C_{1-6}$ haloalkyl, SO$_2C_{5-6}$ aryl, and SO$_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-4}$ alkyl, $C_{1-4}$ haloalkyl, $C_{1-4}$ alkylamino, $C_{5-6}$ aryl, and $C_{1-6}$ heteroaryl; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), SO$_2$ or C; Z is selected from N or CR$_{17}$; A is selected from N or CR$_1$; B is selected from N or CR$_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2C_{1-6}$ alkyl, SO$_2C_{1-6}$ haloalkyl, SO$_2C_{3-6}$ cycloalkyl, SO$_2$NR$_{18}$, SO$_2$NC$_{1-6}$ alkylamino, $C_{5-6}$ aryl, $C_{1-6}$ heteroaryl, C(O)$C_{5-6}$ aryl, C(O)$C_{1-6}$ heteroaryl, SO$_2C_{5-6}$ aryl, and SO$_2C_{1-6}$ heteroaryl, wherein $C_{1-6}$ alkyl, (CO)$C_{1-6}$ alkyl, C(O)$C_{1-6}$ haloalkyl, SO$_2C_{5-6}$ aryl, and SO$_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, C(O)$C_{1-6}$ alkyl, C(O)$C_{1-6}$ haloalkyl, C(O)NR$_{18}$, C(O)$C_{1-6}$ alkylamino, SO$_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from hydrogen, and $C_{1-4}$ alkyl; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —$COOH$, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from hydrogen; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —$COOH$, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered bicyclic aryl, and 5-10 membered bicyclic heteroaryl with 1-2 heteroatoms selected from N or S, wherein 5-10 membered bicyclic aryl, and 5-10 membered bicyclic heteroaryl are optionally substituted with 1-3 substituents selected from the group consisting of halogen, $C_{1-6}$ alkyl, $C_{1-6}$ alkoxy, $C_{1-6}$ haloalkyl, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O; Y is O or N; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is S; Y is O or N; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkyl-hydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O or N; Z is N; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O; Y is selected from O or N; Z is N; A is $CR_1$; B is $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O or N; Z is N; A is $CR_1$; B is $CR_2$; n is 0-1; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O; Y is selected from O or N; Z is N; A is $CR_1$; B is $CR_2$; n is 0; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, $NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O; Y is O or N; Z is N; A is $CR_1$; B is $CR_2$; n is 1; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkyl-hydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ In an embodiment of the present disclosure, there is provided a compound of Formula (I) as described herein, wherein X is O or S; Y is O or N; Z is N; A is $CR_1$; B is $CR_2$; n is 0-1; $R_1$, and $R_2$ are independently selected from hydrogen; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)$ $C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O) CH=CHCH$_2$N(CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is O or N; Z is N; A is $CR_1$; B is $CR_2$; n is 0-1; $R_1$, and $R_2$ are independently selected from hydrogen; $R_3$ is absent or is selected from the group consisting of hydrogen, $C_{1-4}$ alkyl, $C(O)C_{1-4}$ alkyl, $C_{3-6}$ cycloalkyl, $SO_2C_{3-6}$ cycloalkyl, $SO_2C_{5-6}$ aryl, and $SO_2C_{1-6}$ alkyl, wherein $C_{1-4}$ alkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)CH$_2$Cl, NHC(O)CH=CHCH$_2$N (CH$_3$)$_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; and $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano.

In an embodiment of the present disclosure, there is provided a compound of Formula (I) as described herein, wherein X is O or S; Y is O or N; Z is N; A is $CR_1$; B is $CR_2$; n is 0-1; $R_1$, and $R_2$ are independently selected from hydrogen; $R_3$ is absent or is selected from the group consisting of hydrogen, $C_{1-4}$ alkyl, $C_{3-6}$ cycloalkyl, $C(O)C_{1-4}$ alkyl, $SO_2C_{3-6}$ cycloalkyl, $SO_2C_{5-6}$ aryl, and $SO_2C_{1-6}$ alkyl, wherein $C_{1-4}$ alkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ and $R_{11}$ are taken together to form a 5-6 membered monocyclic saturated heterocyclic ring, wherein the 5-6 membered monocyclic saturated heterocyclic ring is optionally substituted with the substituents selected from the group consisting of amino, $C_{1-6}$ alkylamino, and NHC(O)CH=CHCH$_2$N(CH$_3$)$_2$; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; and $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, Cu-6 alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, —COOH, and cyano.

In an embodiment of the present disclosure, there is provided a compound of Formula (I) as described herein, wherein X is O or S; Y is O or N; Z is N; A is $CR_1$; B is $CR_2$; n is 0-1; $R_1$, and $R_2$ are independently selected from hydrogen; $R_3$ is absent or is selected from the group consisting of hydrogen, $C_{1-4}$ alkyl, $C_{3-6}$ cycloalkyl, $C(O)C_{1-4}$ alkyl, $SO_2C_{3-6}$ cycloalkyl, $SO_2C_{5-6}$ aryl, and $SO_2C_{1-6}$ alkyl, wherein $C_{1-4}$ alkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ and $R_{11}$ is taken together to form a 5-6 membered monocyclic saturated heterocyclic ring, wherein the 5-6 membered monocyclic saturated heterocyclic ring is optionally substituted with the substituents selected from the group consisting of amino, $C_{1-6}$ alkylamino, and $NHC(O)CH=CHCH_2N(CH_3)_2$; $R_{12}$, $R_{13}$, $R_{14}$, and $R_{15}$ are independently selected from hydrogen, and $C_{1-6}$ alkyl; and $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano.

In an embodiment of the present disclosure, there is provided a compound of Formula (I) as described herein, wherein X is O; Y is O or N; Z is N; A is $CR_1$; B is $CR_2$; n is 0-1; $R_1$, and $R_2$ are independently selected from hydrogen; $R_3$ is absent or is selected from the group consisting of hydrogen, $C_{1-4}$ alkyl, $C_{3-6}$ cycloalkyl, $C(O)C_{1-6}$ alkyl, $SO_2C_3$-6 cycloalkyl, $SO_2C_{5-6}$ aryl, and $SO_2C_{1-6}$ alkyl, wherein $C_{1-4}$ alkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ and $R_{11}$ is taken together to form a 5-6 membered monocyclic saturated heterocyclic ring, wherein the 5-6 membered monocyclic saturated heterocyclic ring is optionally substituted with the substituents selected from the group consisting of amino, $C_{1-6}$ alkylamino, and $NHC(O)CH=CHCH_2N(CH_3)_2$; $R_{12}$, $R_{13}$, $R_{14}$, and $R_{15}$ are independently selected from hydrogen, and $C_{1-6}$ alkyl; $R_{16}$ is selected from the group consisting of hydrogen, 5-10 membered bicyclic aryl, and 5-10 membered bicyclic heteroaryl with 1-2 heteroatoms selected from N or S, wherein 5-10 membered bicyclic aryl, and 5-10 membered bicyclic heteroaryl are optionally substituted with 1-3 substituents selected from the group consisting of halogen, $C_{1-6}$ alkyl, $C_{1-6}$ alkoxy, $C_{1-6}$ haloalkyl, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —COOH, and cyano.

In an embodiment of the present disclosure, there is provided a compound of Formula (I) as described herein, wherein X is selected from O or S; Y is selected from O, N, S, S(O), $SO_2$ or C; Z is selected from N or $CR_{17}$; A is selected from N or $CR_1$; B is selected from N or $CR_2$; n is 0-1; $R_1$, and $R_2$ are independently selected from the group consisting of hydrogen, hydroxyl, $C_{1-6}$ alkyl, $C_{1-6}$ alkoxy, $C_{1-6}$ haloalkyl, and $C_{1-6}$ haloalkoxy, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{12}$ is selected from the group consisting of hydrogen, $C_{1-6}$ alkyl, $C_{3-6}$ cycloalkyl, $C_{1-6}$ alkylamino $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, —$NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is selected from O or S; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C(O)C_{1-6}$ alkyl, $C(O)NR_{18}$, $C(O)C_{1-6}$ alkylamino, $SO_2C_{1-6}$ alkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ and $R_{11}$ are taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{2-4}$ alkylamino, $C_{2-4}$ acylamino, —NHC(NH)$CH_2Cl$, —NHC(O)CH=CHCH$_2$N(CH$_3$)$_2$, $C_{2-4}$ alkyl, halogen, $C_{2-4}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, and $C_{1-6}$ haloalkoxy, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is selected from O or S; Y is selected from O, N, S, S(O), $SO_2$ or C; Z is selected from N or $CR_{17}$; A is selected from N or $CR_1$; B is selected from N or $CR_2$; n is 0-1; $R_1$, and $R_2$ are independently selected from the group consisting of hydrogen, hydroxyl, $C_{1-6}$ alkyl, $C_{1-6}$ alkoxy, $C_{1-6}$ haloalkyl, and $C_{1-6}$ haloalkoxy, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ and $R_{11}$ are taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{2-4}$ alkylamino, $C_{2-4}$ acylamino, —NHC(NH)$CH_2Cl$, —NHC(O)CH=CHCH$_2$N(CH$_3$)$_2$, $C_{2-4}$ alkyl, halogen, $C_{2-4}$ alkoxy, and hydroxyl; $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, and $C_{1-6}$ haloalkoxy, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (I) as described herein, wherein X is O or S; Y is selected from O, N, S, S(O), $SO_2$ or C; Z is selected from N or $CR_{17}$; A is $CR_1$; B is $CR_2$; n is 0-1; $R_1$, and $R_2$ are independently selected from hydrogen; $R_3$ is absent or is selected from hydrogen, $C_{1-6}$ alkyl, $C_{3-6}$ cycloalkyl, $C(O)C_{1-6}$ alkyl, $SO_2C_{3-6}$ cycloalkyl, $SO_2C_{5-6}$ aryl, and $SO_2C_{1-6}$ alkyl, wherein $SO_2C_{1-6}$ alkyl is optionally substituted with $C_{1-6}$ alkoxy, halogen, $C_{5-6}$ aryl, and $C_{1-6}$ heteroaryl; $R_{10}$ and $R_{11}$ is taken together to form a 5-6 membered monocyclic saturated heterocyclic ring, wherein the 5-6 membered monocyclic saturated heterocyclic ring is optionally substituted with the substituents selected from amino, NHC(O)CH=CHCH$_2$N(CH$_3$)$_2$, or $C_{1-6}$ alkylamino; $R_{12}$, $R_{13}$, $R_{14}$, and $R_{15}$ are independently selected from hydrogen or $C_{1-6}$ alkyl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered bicyclic aryl, and 5-10 membered bicyclic heteroaryl with 1-2 heteroatoms selected from N or S, wherein 5-10 membered bicyclic aryl, and 5-10 membered bicyclic heteroaryl are optionally substituted with 1-3 substituents selected from the group consisting of halogen, $C_{1-6}$ alkyl, $C_{1-6}$ alkoxy, $C_{1-6}$ haloalkyl, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —COOH, and cyano; $R_{17}$ is selected from hydrogen, or $C_{1-6}$ alkyl; and $R_{18}$ is independently selected from the group consisting of hydrogen, $C_{1-6}$ alkyl, and combinations thereof.

In an embodiment of the present disclosure, there is provided a compound of Formula (II) their polymorphs, stereoisomers, prodrugs, solvates, co-crystals, intermediates, pharmaceutically acceptable salts, and metabolites thereof, wherein Formula (II)

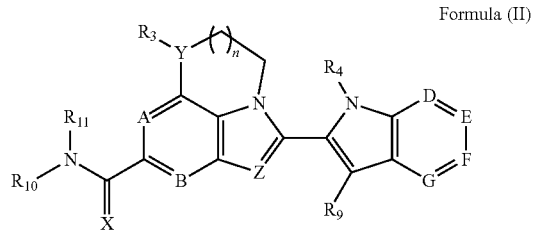

X is selected from O or S; Y is selected from O, N, S, S(O), $SO_2$ or C; Z is selected from N or $CR_{17}$; A is selected from N or $CR_1$; B is selected from N or $CR_2$; D is selected from N or $CR_5$; E is selected from N or $CR_6$; F is selected from N or $CR_7$; G is selected from N or $CR_8$; n is 0-2; $R_1$, $R_2$, $R_5$, $R_6$, $R_7$, $R_8$, and $R_9$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)$ $C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, (CO) $C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, —$CH_2OH$, —COOH, and cyano; $R_{10}$ is hydrogen; $R_{11}$ is selected from the group consisting of $C_{1-6}$ alkylamino, and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, NHC $(O)CH=CHCH_2N(CH_3)_2$, $C_{1-6}$ alkyl, halogen, $C_{1-6}$ alkoxy, and hydroxyl; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (II) as described herein, wherein X is selected from O or S; Y is selected from O, N, S, S(O), $SO_2$ or C; Z is selected from N or $CR_{17}$; A is selected from N or $CR_1$; B is selected from N or $CR_2$; D is selected from N or $CR_5$; E is selected from N or $CR_6$; F is selected from N or $CR_7$; G is selected from N or $CR_8$; n is 1-2; $R_1$, $R_2$, $R_8$, and $R_9$ are independently selected from the group consisting of hydrogen, halogen, hydroxyl, $C_{1-6}$ alkyl, $C_{1-6}$ alkoxy, $C_{1-6}$ haloalkyl, and $C_{1-6}$ haloalkoxy, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_5$, $R_6$, and $R_7$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, $C_{2-6}$ alkenyl-$C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and SO$_2$C$_{1-6}$ heteroaryl, wherein C$_{1-6}$ alkyl, C$_{1-6}$ alkoxy, C$_{3-6}$ cycloalkyl, C$_{5-6}$ aryl, C$_{1-6}$ heteroaryl, C$_{1-6}$ alkyl-C$_{5-6}$ aryl, C$_{1-6}$ heterocyclyl, C$_{1-6}$ alkyl-C$_{1-6}$ heterocyclyl, C$_{1-6}$ alkyl-C$_{1-6}$ heteroaryl, (CO)C$_{1-6}$ alkyl, C(O)C$_{1-6}$ haloalkyl, and SO$_2$C$_{1-6}$ alkyl, is optionally substituted with one or more groups selected from hydrogen, C$_{1-6}$ alkyl, C$_{1-6}$ alkoxy, C$_{3-8}$ cycloalkyl, C$_{5-6}$ aryl, C$_{1-6}$ heteroaryl, halogen, hydroxyl, —CH$_2$OH, COOH, and cyano; R$_{10}$ is hydrogen; R$_{11}$ is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; and 5-10 membered monocyclic or bicyclic saturated heterocyclic ring with 1-3 heteroatoms selected from N, S or O, or R$_{10}$ and R$_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, C$_{1-6}$ alkylamino, C$_{1-6}$ acylamino, —NHC(NH)CH$_2$Cl, NHC(O)CH=CHCH$_2$N(CH$_3$)$_2$, C$_{1-6}$ alkyl, halogen, C$_{1-6}$ alkoxy, and hydroxyl; R$_{17}$ is selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; and R$_{18}$ is independently selected from the group consisting of hydrogen, C$_{1-6}$ alkyl, and combinations thereof.

In an embodiment of the present disclosure, there is provided a compound of Formula (II) as described herein, wherein X is selected from O or S; Y is selected from O, N, S, S(O), SO$_2$ or C; Z is selected from N or CR$_{17}$; A is selected from N or CR$_1$; B is selected from N or CR$_2$; D is selected from N or CR$_5$; E is selected from N or CR$_6$; F is selected from N or CR$_7$; G is selected from N or CR$_8$; n is 0-2; R$_1$, R$_2$, R$_8$, and R$_9$ are independently selected from the group consisting of hydrogen, halogen, hydroxyl, C$_{1-6}$ alkyl, C$_{1-6}$ alkoxy, C$_{1-6}$ haloalkyl, and C$_{1-6}$ haloalkoxy, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; R$_5$, R$_6$, and R$_7$ are independently selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, C$_{2-6}$ alkenyl-C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; R$_3$ is absent or is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; R$_4$ is selected from the group consisting of hydrogen, C$_{1-6}$ alkyl, C$_{1-6}$ haloalkyl, C$_{1-6}$ alkoxy, C$_{3-6}$ cycloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$NR$_{18}$, SO$_2$NC$_{1-6}$ alkylamino, C$_{5-6}$ aryl, C$_{1-6}$ alkyl-C$_{5-6}$ aryl, C$_{1-6}$ heterocyclyl, C$_{1-6}$ alkyl-C$_{1-6}$ heterocyclyl, C$_{1-6}$ heteroaryl, C$_{1-6}$ alkyl-C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, C$_{1-6}$ alkoxy, C$_{3-6}$ cycloalkyl, C$_{5-6}$ aryl, C$_{1-6}$ heteroaryl, C$_{1-6}$ alkyl-C$_{5-6}$ aryl, C$_{1-6}$ heterocyclyl, C$_{1-6}$ alkyl-C$_{1-6}$ heterocyclyl, C$_{1-6}$ alkyl-C$_{1-6}$ heteroaryl, (CO)C$_{1-6}$ alkyl, C(O)C$_{1-6}$ haloalkyl, and SO$_2$C$_{1-6}$ alkyl, is optionally substituted with one or more groups selected from hydrogen, C$_{1-6}$ alkyl, C$_{1-6}$ alkoxy, C$_{3-8}$ cycloalkyl, C$_{5-6}$ aryl, C$_{1-6}$ heteroaryl, halogen, hydroxyl, —CH$_2$OH, COOH, and cyano; R$_{10}$ is hydrogen; R$_{11}$ is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with C$_{1-6}$ alkoxy, halogen, C$_{5-6}$ aryl, and C$_{1-6}$ heteroaryl; and 5-10 membered monocyclic or bicyclic saturated heterocyclic ring with 1-3 heteroatoms selected from N, S or O, or R$_{10}$ and R$_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, C$_{1-6}$ alkylamino, C$_{1-6}$ acylamino, —NHC(NH)CH$_2$Cl, NHC(O)CH=CHCH$_2$N(CH$_3$)$_2$, C$_{1-6}$ alkyl, halogen, C$_{1-6}$ alkoxy, and hydroxyl; R$_{17}$ is selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; and R$_{18}$ is independently selected from the group consisting of hydrogen, C$_{1-6}$ alkyl, and combinations thereof.

In an embodiment of the present disclosure, there is provided a compound of Formula (II) as described herein, wherein X is selected from O or S; Y is selected from O, N, S, S(O), SO$_2$ or C; Z is selected from N or CR$_{17}$; A is CR$_1$; B is CR$_2$; D is selected from N or CR$_5$; E is CR$_6$; F is CR$_7$; G is CR$_8$; n is 0-2; R$_1$, R$_2$, R$_5$, R$_6$, R$_7$, R$_8$, and R$_9$ are independently selected from the group consisting of hydrogen, hydroxyl, cyano, halogen, C$_{1-6}$ alkyl, C$_{1-6}$ alkoxy, C$_{1-6}$ haloalkyl, C$_{1-6}$ haloalkoxy, C$_{1-6}$ acylamino, C$_{1-6}$ alkylamino, C$_{5-6}$ aryl, C$_{2-6}$ alkenyl-C$_{5-6}$ aryl, and C$_{1-6}$ heteroaryl, wherein C$_{1-6}$ alkoxy, and C$_{1-6}$ haloalkoxy, is optionally substituted with one or more of the groups selected from hydrogen, C$_{1-6}$ alkyl, C$_{1-6}$ alkoxy, C$_{1-6}$ haloalkyl, C$_{1-6}$ alkylhydroxy, cyano, and hydroxyl; R$_3$ is absent or is selected from the group consisting of hydrogen, C$_{1-6}$ alkyl, C$_{3-6}$ cycloalkyl, C$_{1-6}$ alkylamino, C$_{1-6}$ haloalkyl, C(O)C$_{1-6}$ alkyl, C(O)C$_{1-6}$ haloalkyl, C(O)NR$_{18}$, C(O)C$_{1-6}$ alkylamino, SO$_2$C$_{1-6}$ alkyl, SO$_2$C$_{1-6}$ haloalkyl, SO$_2$C$_{3-6}$ cycloalkyl, SO$_2$NR$_{18}$, SO$_2$NC$_{1-6}$ alkylamino, C$_{5-6}$ aryl, C$_{1-6}$ heteroaryl, C(O)C$_{5-6}$ aryl, C(O)C$_{1-6}$ heteroaryl, SO$_2$C$_{5-6}$ aryl, and SO$_2$C$_{1-6}$ heteroaryl, wherein C$_{1-6}$ alkyl, (CO)C$_{1-6}$ alkyl, C(O)C$_{1-6}$ haloalkyl, SO$_2$C$_{5-6}$ aryl, and SO$_2$C$_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ heteroaryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ alkyl-$C_{1-6}$ heteroaryl, $(CO)C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, —$CH_2OH$, COOH, and cyano; $R_{10}$ and $R_{11}$ are taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{2-4}$ alkylamino, $C_{2-4}$ acylamino, —NHC(NH)$CH_2$Cl, NHC(O)CH=CH$CH_2$N($CH_3$)$_2$, $C_{2-4}$ alkyl, halogen, $C_{2-4}$ alkoxy, and hydroxyl; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure, there is provided a compound of Formula (II) as described herein, wherein X is O; Y is selected from O, or N; Z is N; A is $CR_1$; B is $CR_2$; D is selected from N or $CR_5$; E is $CR_6$; F is $CR_7$; G is $CR_8$; n is 1-2; $R_1$, $R_2$, $R_8$, and $R_9$ are independently selected from hydrogen or halogen; $R_5$, $R_6$, and $R_7$ are independently selected from the group consisting of hydrogen, halogen, $C_1$ alkyl, $C_1$ alkoxy, $C_{2-6}$ alkenyl-$C_{5-6}$ aryl, and $C_{1-6}$ heteroaryl; $R_3$ is absent or is selected from hydrogen, $C_{1-6}$ alkyl, $C(O)C_{1-6}$ alkyl, $SO_2C_{3-6}$ cycloalkyl, $C_{3-6}$ cycloalkyl, and $SO_2C_{1-6}$ alkyl, $SO_2C_{5-6}$ aryl, and $SO_2C_{1-6}$ alkyl, wherein $SO_2C_{1-6}$ alkyl, and $SO_2C_{5-6}$ aryl is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ alkyl-$C_{5-6}$ aryl, $C_{1-6}$ alkyl-$C_{1-6}$ heterocyclyl, and $C_{1-6}$ alkyl-$C_{1-6}$ heteroaryl, wherein $C_{1-6}$ alkyl, $C_{1-6}$ alkyl-$C_{5-6}$ aryl, $C_{1-6}$ alkyl-$C_{1-6}$ heterocyclyl, and $C_{1-6}$ alkyl-$C_{1-6}$ heteroaryl, is optionally substituted with one or more groups selected from hydrogen, halogen, $C_{1-6}$ alkyl, $C_{1-6}$ alkoxy, $C_{3-8}$ cycloalkyl, $C_{5-6}$ aryl, $C_{1-6}$ heteroaryl, hydroxyl, —$CH_2OH$, COOH, and halogen; $R_{10}$ and $R_{11}$ are taken together to form a 5-6 membered monocyclic saturated heterocyclic ring, wherein the 5-6 membered monocyclic saturated heterocyclic ring is optionally substituted with the substituents selected from amino, $C_{1-6}$ alkylamino or NHC(O)CH=CH$CH_2$N($CH_3$)$_2$; and $R_{18}$ is independently selected from the group consisting of hydrogen, $C_{1-6}$ alkyl, and combinations thereof.

In an embodiment of the present disclosure, there is provided a compound of Formula (III) their polymorphs, stereoisomers, prodrugs, solvates, co-crystals, intermediates, pharmaceutically acceptable salts, and metabolites thereof, wherein Formula (III)

X is selected from O or S; Y is selected from O, N, S, S(O), $SO_2$ or C; Z is selected from N or $CR_{17}$; n is 0-2; $R_1$, $R_2$, $R_5$, $R_6$, $R_7$, $R_8$, and $R_9$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, $C_{2-6}$ alkenyl-$C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, (CO)$C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, $CH_2OH$, COOH, and cyano; $R_{10}$ is hydrogen; $R_{11}$ is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cyclo alkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)$CH_2$Cl, —NHC(O)CH=CH$CH_2$N($CH_3$)$_2$, $C_{1-6}$ alkyl, halogen, $C_{1-6}$ alkoxy, and hydroxyl; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkyl, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment of the present disclosure there is provided compound of Formula (I) or its polymorphs, stereoisomers, prodrugs, solvates, co-crystals, intermediates, pharmaceutically acceptable salts, and metabolites thereof, which is selected from a group consisting of:

1) (R)-(3-aminopiperidin-1-yl)(2-(1-(cyclopropylmethyl)-1H-indol-2-yl)-3,4-dihydro-5-oxa-1,2a-diazaacenaphthylen-7-yl)methanone,
2) (R)-(3-aminopyrrolidin-1-yl)(2-)1-(cyclopropylmethyl)-1H-indol-2-yl)-3,4-dihydro-5-oxa-1,2a-diazaacenaphthylen-7-yl)methanone,
3) (R)-(3-aminopiperidin-1-yl)(2-(1-ethyl-1H-indol-2-yl)-3,4-dihydro-5-oxa-1,2a-diazaacenaphthylen-7-yl)methanone,
4) (2-(aminomethyl)piperidin-1-yl)(2-(1-(cyclopropylmethyl)-1H-indol-2-yl)-3,4-dihydro-5-oxa-1,2a-diazaacenaphthylen-7-yl)methanone,
5) (R)-(3-aminopiperidin-1-yl)(2-(1-ethyl-1H-pyrrolo [2,3-b]pyridin-2-yl)-3,4-dihydro-5-oxa-1,2a-diazaacenaphthylen-7-yl)methanone,
6) (R)-(3-aminopiperidin-1-yl)(1-(1-(cyclopropylmethyl)-1H-indol-2-yl)-8,9-dihydro-7H-6-oxa-2,9a-diazabenzo[cd]azulen-4-yl)methanone,
7) (R)-(3-aminopyrrolidin-1-yl)(1-(1-(cyclopropylmethyl)-1H-indol-2-yl)-8,9-dihydro-7H-6-oxa-2,9a-diazabenzo[cd]azulen-4-yl)methanone,
8) (R)-(3-aminopiperidin-1-yl)(2-(1-(cyclopropylmethyl)-7-methyl-1H-indol-2-yl)-3,4-dihydro-5-oxa-1,2a-diazaacenaphthylen-7-yl)methanone,
9) (R)-(3-aminopiperidin-1-yl)(2-(1-(cyclopropylmethyl)-5-fluoro-1H-indol-2-yl)-3,4-dihydro-5-oxa-1,2a-diazaacenaphthylen-7-yl)methanone,
10) (R)-(3-aminopiperidin-1-yl)(2-(1-(pyridin-4-ylmethyl)-1H-indol-2-yl)-3,4-dihydro-5-oxa-1,2a-diazaacenaphthylen-7-yl)methanone,
11) (R)-(3-aminopiperidin-1-yl)(2-(1-(pyridin-2-ylmethyl)-1H-indol-2-yl)-3,4-dihydro-5-oxa-1,2a-diazaacenaphthylen-7-yl)methanone,
12) (R)-(3-aminopiperidin-1-yl)(2-(3-ethylbenzo[b]thiophen-2-yl)-3,4-dihydro-5-oxa-1,2a-diazaacenaphthylen-7-yl)methanone,
13) (R)-(3-aminopiperidin-1-yl)(2-(1-(4-chlorobenzyl)-1H-indol-2-yl)-3,4-dihydro-5-oxa-1,2a-diazaacenaphthylen-7-yl)methanone,
14) (R)-(3-aminopiperidin-1-yl)(2-(1-(2-fluorobenzyl)-1H-indol-2-yl)-3,4-dihydro-5-oxa-1,2a-diazaacenaphthylen-7-yl)methanone,
15) (R)-(3-aminopiperidin-1-yl)(2-(1-(4-fluorobenzyl)-1H-indol-2-yl)-3,4-dihydro-5-oxa-1,2a-diazaacenaphthylen-7-yl)methanone,
16) (R)-(3-aminopiperidin-1-yl)(2-(1-(pyridin-3-ylmethyl)-1H-indol-2-yl)-3,4-dihydro-5-oxa-1,2a-diazaacenaphthylen-7-yl)methanone,
17) (R)-(3-aminopiperidin-1-yl)(2-(1-(cyclopropylmethyl)-5,6-dimethoxy-1H-indol-2-yl)-3,4-dihydro-5-oxa-1,2a-diazaacenaphthylen-7-yl)methanone,
18) (R)-(3-aminopiperidin-1-yl)(2-(1-benzyl-1H-indol-2-yl)-3,4-dihydro-5-oxa-1,2a-diazaacenaphthylen-7-yl)methanone,
19) (R)-(3-aminopiperidin-1-yl)(2-(1-(4-methoxybenzyl)-1H-indol-2-yl)-3,4-dihydro-5-oxa-1,2a-diazaacenaphthylen-7-yl)methanone,
20) (R)-(3-aminopiperidin-1-yl)(2-(1-(2-methoxyethyl)-1H-indol-2-yl)-3,4-dihydro-5-oxa-1,2a-diazaacenaphthylen-7-yl)methanone,
21) (R)-(3-aminopiperidin-1-yl)(2-(6-methoxy-1-(2-methoxyethyl)-1H-indol-2-yl)-3,4-dihydro-5-oxa-1,2a-diazaacenaphthylen-7-yl)methanone,
22) (R)-(3-aminopiperidin-1-yl)(2-(1-(2-hydroxyethyl)-1H-indol-2-yl)-3,4-dihydro-5-oxa-1,2a-diazaacenaphthylen-7-yl)methanone,
23) (R)-(3-aminopiperidin-1-yl)(2-(1-(cyclopropylmethyl)-6-methoxy-1H-indol-2-yl)-3,4-dihydro-5-oxa-1,2a-diazaacenaphthylen-7-yl)methanone,
24) (R)-(3-aminopiperidin-1-yl)(2-(1-((3-fluoropyridin-4-yl)methyl)-1H-indol-2-yl)-3,4-dihydro-5-oxa-1,2a-diazaacenaphthylen-7-yl)methanone,
25) (R)-(3-aminopiperidin-1-yl)(2-(1-(pyrazin-2-ylmethyl)-1H-indol-2-yl)-3,4-dihydro-5-oxa-1,2a-diazaacenaphthylen-7-yl)methanone,
26) (R)-(3-aminopiperidin-1-yl)(2-(1-((3-fluoropyridin-2-yl)methyl)-1H-indol-2-yl)-3,4-dihydro-5-oxa-1,2a-diazaacenaphthylen-7-yl)methanone,
27) (R)-(3-aminopiperidin-1-yl)(2-(1-(pyrimidin-2-ylmethyl)-1H-indol-2-yl)-3,4-dihydro-5-oxa-1,2a-diazaacenaphthylen-7-yl)methanone,
28) (R)-(3-aminopiperidin-1-yl)(2-(1-(cyclopropylmethyl)-6-fluoro-1H-indol-2-yl)-3,4-dihydro-5-oxa-1,2a-diazaacenaphthylen-7-yl)methanone,
29) (R)-(3-aminopiperidin-1-yl)(2-(1-(pyrimidin-5-ylmethyl)-1H-indol-2-yl)-3,4-dihydro-5-oxa-1,2a-diazaacenaphthylen-7-yl)methanone,
30) (R)-(3-aminopiperidin-1-yl)(2-(1-(pyridazin-3-ylmethyl)-1H-indol-2-yl)-3,4-dihydro-5-oxa-1,2a-diazaacenaphthylen-7-yl)methanone,
31) (R)-(3-aminopiperidin-1-yl)(2-(1-isobutyl-1H-indol-2-yl)-3,4-dihydro-5-oxa-1,2a-diazaacenaphthylen-7-yl)methanone,
32) (R)-(3-aminopiperidin-1-yl)(2-(1-(cyclopropylmethyl)-5,6-difluoro-1H-indol-2-yl)-3,4-dihydro-5-oxa-1,2a-diazaacenaphthylen-7-yl)methanone,
33) (R)-(3-aminopiperidin-1-yl)(2-(1-((3-fluoropyridin-2-yl)methyl)-6-methoxy-1H-indol-2-yl)-3,4-dihydro-5-oxa-1,2a-diazaacenaphthylen-7-yl)methanone,
34) (R)-(3-aminopiperidin-1-yl)(2-(7-chloro-1-((3-fluoropyridin-2-yl)methyl)-1H-indol-2-yl)-3,4-dihydro-5-oxa-1,2a-diazaacenaphthylen-7-yl)methanone,
35) (R)-(3-aminopiperidin-1-yl)(2-(6-fluoro-1-((3-fluoropyridin-2-yl)methyl)-1H-indol-2-yl)-3,4-dihydro-5-oxa-1,2a-diazaacenaphthylen-7-yl)methanone,
36) (R)-(3-aminopiperidin-1-yl)(2-(7-chloro-1-(2-methoxyethyl)-1H-indol-2-yl)-3,4-dihydro-5-oxa-1,2a-diazaacenaphthylen-7-yl)methanone,
37) (R)-(3-aminopiperidin-1-yl)(2-(1-(4-(hydroxymethyl)benzyl)-1H-indol-2-yl)-3,4-dihydro-5-oxa-1,2a-diazaacenaphthylen-7-yl)methanone trifluoroacetic acid salt,
38) (R,E)-N-(1-(2-(1-(cyclopropylmethyl)-1H-indol-2-yl)-3,4-dihydro-5-oxa-1,2a-diazaacenaphthylene-7-carbonyl)piperidin-3-yl)-4-(dimethylamino)but-2-enamide trifluoroacetic acid salt,
39) (R)-(3-aminopiperidin-1-yl)(2-(7-chloro-1-(4-methoxybenzyl)-1H-indol-2-yl)-3,4-dihydro-5-oxa-1,2a-diazaacenaphthylen-7-yl)methanone, 40) (R)-(3-aminopiperidin-1-yl)(2-(1-((tetrahydro-2H-pyran-4-yl)methyl)-1H-indol-2-yl)-3,4-dihydro-5-oxa-1,2a-diazaacenaphthylen-7-yl)methanone,
41) (R)-(3-aminopiperidin-1-yl)(2-(1-(cyclobutylmethyl)-1H-indol-2-yl)-3,4-dihydro-5-oxa-1,2a-diazaacenaphthylen-7-yl)methanone,
42) (R)-2-(2-(7-(3-aminopiperidine-1-carbonyl)-3,4-dihydro-5-ox 1,2a-diazaacenaphthylen-2-yl)-1H-indol-1-yl)acetic acid,
43) (R)-(3-aminopiperidin-1-yl)(2-(1-(piperidin-4-ylmethyl)-1H-indol-2-yl)-3,4-dihydro-5-oxa-1,2a-diazaacenaphthylen-7-yl)methanone,
44) (R)-(3-aminopiperidin-1-yl)(2-(1-(oxetan-3-ylmethyl)-1H-indol-2-yl)-3,4-dihydro-5-oxa-1,2a-diazaacenaphthylen-7-yl)methanone,
45) (R)-(3-aminopiperidin-1-yl)(2-(1-((l-methylpiperidin-4-yl)methyl)-1H-indol-2-yl)-3,4-dihydro-5-oxa-1,2a-diazaacenaphthylen-7-yl)methanone,
46) (R)-(3-aminopiperidin-1-yl)(2-(5-fluoro-1-(4-methoxybenzyl)-1H-indol-2-yl)-3,4-dihydro-5-oxa-1,2a-diazaacenaphthylen-7-yl)methanone,
47) (R)-(3-aminopiperidin-1-yl)(2-(1-(2,2-difluoroethyl)-1H-indol-2-yl)-3,4-dihydro-5-oxa-1,2a-diazaacenaphthylen-7-yl)methanone,
48) (R)-(3-aminopiperidin-1-yl)(2-(5-fluoro-1-(2-methoxyethyl)-1H-indol-2-yl)-3,4-dihydro-5-oxa-1,2a-diazaacenaphthylen-7-yl)methanone,
49) (R)-(3-aminopiperidin-1-yl)(2-(6-fluoro-1-(4-fluorobenzyl)-1H-indol-2-yl)-3,4-dihydro-5-oxa-1,2a-diazaacenaphthylen-7-yl)methanone,
50) (R)-(3-aminopiperidin-1-yl)(2-(6-fluoro-1-(4-methoxybenzyl)-1H-indol-2-yl)-3,4-dihydro-5-oxa-1,2a-diazaacenaphthylen-7-yl)methanone,
51) (R)-(3-aminopiperidin-1-yl)(2-(1-(4-fluorobenzyl)-6-methoxy-1H-indol-2-yl)-3,4-dihydro-5-oxa-1,2a-diazaacenaphthylen-7-yl)methanone,
52) 3-aminopiperidin-1-yl)(2-(6-fluoro-1-(2-methoxyethyl)-1H-indol-2-yl)-3,4-dihydro-5-oxa-1,2a-diazaacenaphthylen-7-yl)methanone,
53) (R)-(3-aminopiperidin-1-yl)(2-(7-chloro-1-(cyclobutylmethyl)-1H-indol-2-yl)-3,4-dihydro-5-oxa-1,2a-diazaacenaphthylen-7-yl)methanone,
54) (R)-(3-aminopiperidin-1-yl)(2-(5,6-difluoro-1-(2-methoxyethyl)-1H-indol-2-yl)-3,4-dihydro-5-oxa-1,2a-diazaacenaphthylen-7-yl)methanone,
55) (R)-(3-aminopiperidin-1-yl)(2-(7-chloro-1-isobutyl-1H-indol-2-yl)-3,4-dihydro-5-oxa-1,2a-diazaacenaphthylen-7-yl)methanone,
56) (R)-(3-aminopiperidin-1-yl)(2-(7-chloro-1-(2,2-difluoroethyl)-1H-indol-2-yl)-3,4-dihydro-5-oxa-1,2a-diazaacenaphthylen-7-yl)methanone,
57) (R)-(3-aminopiperidin-1-yl)(2-(7-chloro-1-(cyclopropylmethyl)-1H-indol-2-yl)-3,4-dihydro-5-oxa-1,2a-diazaacenaphthylen-7-yl)methanone,
58) (R,E)-(3-aminopiperidin-1-yl)(2-(1-(cyclopropylmethyl)-5-styryl-1H-indol-2-yl)-3,4-dihydro-5-oxa-1,2a-diazaacenaphthylen-7-yl)methanone,
59) (R)-(3-aminopiperidin-1-yl)(2-(1-((4-methylthiazol-2-yl)methyl)-1H-indol-2-yl)-3,4-dihydro-5-oxa-1,2a-diazaacenaphthylen-7-yl)methanone,
60) (R)-(3-aminopiperidin-1-yl)(2-(1-(cyclopropylmethyl)-5-methoxy-1H-indol-2-yl)-3,4-dihydro-5-oxa-1,2a-diazaacenaphthylen-7-yl)methanone,
61) (R)-(3-aminopiperidin-1-yl)(2-(1-(cyclopropylmethyl)-6-(hydroxymethyl)-1H-indol-2-yl)-3,4-dihydro-5-oxa-1,2a-diazaacenaphthylen-7-yl)methanone,
62) (R)-(3-aminopiperidin-1-yl)(2-(1-(cyclopropylmethyl)-1H-indol-2-yl)-3,3-dimethyl-3,4-dihydro-5-oxa-1,2a-diazaacenaphthylen-7-yl)methanone,
63) (R)-(3-aminopiperidin-1-yl)(2-(1-(cyclopropylmethyl)-1H-indol-2-yl)-5,6-dihydro-4H-imidazo [1,5,4-de]quinoxalin-8-yl)methanone,
64) (R)-(3-aminopiperidin-1-yl)(2-(1-(cyclopropylmethyl)-5-fluoro-1H-indol-2-yl)-5,6-dihydro-4H-imidazo [1,5,4-de]quinoxalin-8-yl)methanone,
65) (R)-(3-aminopiperidin-1-yl)(2-(1-(cyclopropylmethyl)-6-fluoro-1H-indol-2-yl)-5,6-dihydro-4H-imidazo [1,5,4-de]quinoxalin-8-yl)methanone,
66) (R)-(3-aminopiperidin-1-yl)(2-(1-(pyridin-3-ylmethyl)-1H-indol-2-yl)-5,6-dihydro-4H-imidazo [1,5,4-de]quinoxalin-8-yl)methanone,
67) (R)-(3-aminopiperidin-1-yl)(2-(5-bromo-1-(cyclopropylmethyl)-1H-indol-2-yl)-5,6-dihydro-4H-imidazo [1,5,4-de]quinoxalin-8-yl)methanone,
68) (R)-(3-aminopiperidin-1-yl)(2-(1-(cyclopropylmethyl)-5-(pyridin-3-yl)-1H-indol-2-yl)-5,6-dihydro-4H-imidazo [1,5,4-de]quinoxalin-8-yl)methanone,
69) (R)-(3-aminopiperidin-1-yl)(2-(1-(pyridin-2-ylmethyl)-1H-indol-2-yl)-5,6-dihydro-4H-imidazo[1,5,4-de]quinoxalin-8-yl)methanone,
70) (R)-(3-aminopiperidin-1-yl)(2-(1-(2-fluorobenzyl)-1H-indol-2-yl)-5,6-dihydro-4H-imidazo[1,5,4-de]quinoxalin-8-yl)methanone,
71) (R)-(3-aminopiperidin-1-yl)(2-(1-(pyridin-4-ylmethyl)-1H-indol-2-yl)-5,6-dihydro-4H-imidazo[1,5,4-de]quinoxalin-8-yl)methanone,
72) (R)-(3-aminopiperidin-1-yl)(2-(1-(cyclopropylmethyl)-1H-indol-2-yl)-6-methyl-5,6-dihydro-4H-imidazo[1,5,4-de]quinoxalin-8-yl)methanone,
73) (R)-(3-aminopiperidin-1-yl)(2-(1-(cyclopropylmethyl)-6-methoxy-1H-indol-2-yl)-5,6-dihydro-4H-imidazo[1,5,4-de]quinoxalin-8-yl)methanone,
74) (R)-(3-aminopiperidin-1-yl)(2-(1-(cyclopropylmethyl)-6-methoxy-1H-indol-2-yl)-6-methyl-5,6-dihydro-4H-imidazo[1,5,4-de]quinoxalin-8-yl)methanone,
75) (R)-(3-aminopiperidin-1-yl)(2-(1-(cyclopropylmethyl)-5-fluoro-1H-indol-2-yl)-6-methyl-5,6-dihydro-4H-imidazo[1,5,4-de]quinoxalin-8-yl)methanone,
76) (R)-(3-aminopiperidin-1-yl)(2-(1-(cyclopropylmethyl)-1H-indol-2-yl)-6-(methylsulfonyl)-5,6-dihydro-4H-imidazo[1,5,4-de]quinoxalin-8-yl)methanone,
77) (R)-(3-aminopiperidin-1-yl)(2-(1-(cyclopropylmethyl)-5,6-difluoro-1H-indol-2-yl)-5,6-dihydro-4H-imidazo[1,5,4-de]quinoxalin-8-yl)methanone,
78) (R)-(3-aminopiperidin-1-yl)(6-cyclopropyl-2-(1-(cyclopropylmethyl)-1H-indol-2-yl)-5,6-dihydro-4H-imidazo[1,5,4-de]quinoxalin-8-yl)methanone,
79) (R)-(3-aminopiperidin-1-yl)(2-(1-(cyclopropylmethyl)-1H-indol-2-yl)-6-(phenethylsulfonyl)-5,6-dihydro-4H-imidazo[1,5,4-de]quinoxalin-8-yl)methanone,
80) (R)-(3-aminopiperidin-1-yl)(2-(1-(cyclopropylmethyl)-4-fluoro-1H-indol-2-yl)-5,6-dihydro-4H-imidazo[1,5,4-de]quinoxalin-8-yl)methanone,
81) (R)-(3-aminopiperidin-1-yl)(6-((4-chlorophenyl)sulfonyl)-2-(1-(cyclopropylmethyl)-1H-indol-2-yl)-5,6-dihydro-4H-imidazo[1,5,4-de]quinoxalin-8-yl)methanone,
82) (R)-(3-aminopiperidin-1-yl)(2-(1-(cyclopropylmethyl)-1H-indol-2-yl)-6-(cyclopropylsulfonyl)-5,6-dihydro-4H-imidazo[1,5,4-de]quinoxalin-8-yl)methanone,
83) (R)-(3-aminopiperidin-1-yl)(2-(1-(cyclopropylmethyl)-1H-indol-2-yl)-6-((2-ethoxyethyl)sulfonyl)-5,6-dihydro-4H-imidazo[1,5,4-de]quinoxalin-8-yl)methanone, 84) (R)-(3-aminopiperidin-1-yl)(2-(1-(cyclopropylmethyl)-7-methyl-1H-indol-2-yl)-5,6-dihydro-4H-imidazo [1,5,4-de]quinoxalin-8-yl)methanone, 85) (R)-(1-(8-(3-aminopiperidine-1-carbonyl)-2-(1-(cyclopropylmethyl)-1H-indol-2-yl)-4,5-dihydro-6H-imidazo [1,5,4-de]quinoxalin-6-yl)ethan-1-one, 86) (R)-(3-aminopiperidin-1-yl)(2-(1-(cyclopropylmethyl)-1H-indol-2-yl)-5,6-dihydro-4H-imidazo [1,5,4-de]quinoxalin-8-yl)methanethione.

87) (R)-(3-aminopiperidin-1-yl)(2-(7-chloro-1-(cyclopropylmethyl)-6-fluoro-1H-indol-2-yl)-3,4-dihydro-5-oxa-1,2a-diazaacenaphthylen-7-yl)methanone, and (R)-(3-aminopiperidin-1-yl)(2-(7-chloro-1-(pyrimidin-5-ylmethyl)-1H-indol-2-yl)-3,4-dihydro-5-oxa-1,2a-diazaacenaphthylen-7-yl)methanone In an embodiment, the present disclosure relates to a process of preparation of compounds of Formula (I), Formula (II), and Formula (III) or its polymorphs, stereoisomers, prodrugs, solvates, co-crystals, intermediates, pharmaceutically acceptable salts, and metabolites thereof.

In an embodiment, the disclosure relates to a process of preparation of compounds of Formula (I), or its polymorphs, stereoisomers, prodrugs, solvates, co-crystals, intermediates, pharmaceutically acceptable salts, and metabolites thereof, the process comprising reacting Formula (IV) and $R_{16}C(O)H$

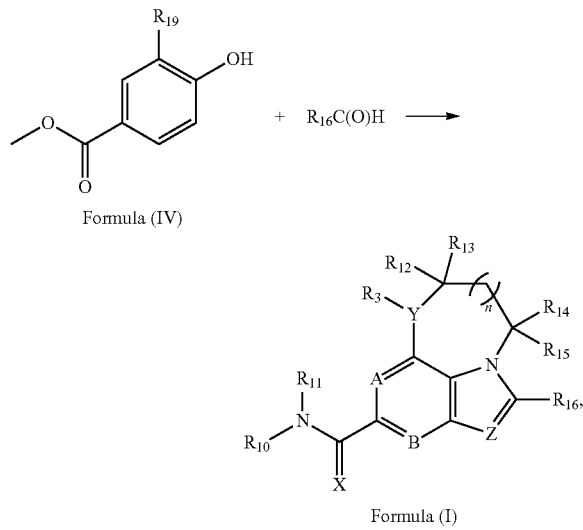

wherein $R_{19}$ of Formula (IV) is selected from nitro, and $C_{1-6}$ alkoxy; $R_{16}$ of $R_{16}C(O)H$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, $C_{1-6}$ alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; X of Formula (I) is selected from O or S; Y is selected from O, N, S, S(O), $SO_2$ or C; Z is selected from N or $CR_{17}$; A is selected from N or $CR_1$; B is selected from N or $CR_2$; n is 0-2; $R_1$, and $R_2$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{3-6}$ cycloalkyl, $SO_2C_{1-6}$ haloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_{10}$ is hydrogen; $R_{11}$ is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —$NHC(NH)CH_2Cl$, —$NHC(O)CH=CHCH_2N(CH_3)_2$, $C_{1-6}$ alkyl, halogen, $C_{1-6}$ alkoxy, and hydroxyl; $R_{12}$, $R_{13}$, $R_{14}$, and $R_{15}$ are independently selected from the group consisting of hydrogen, $C_{1-6}$ alkyl, $C_{1-6}$ haloalkyl, $C_{1-6}$ alkylamino, $C_{5-6}$ aryl, and $C_{1-6}$ heteroaryl; or $R_{12}$ and $R_{13}$ can be taken together to form =O or =O; or $R_{14}$ and $R_{15}$ can be taken together to form =O or =O; $R_{16}$ is selected from the group consisting of hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-6}$ aryl, Cu-6 alkyl-$C_{5-6}$ aryl, $C_{2-6}$ alkenyl-$C_{5-6}$ aryl, $C_{1-6}$ heterocyclyl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, —COOH, and cyano; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof.

In an embodiment, the present disclosure relates to a process of preparation of compounds of Formula (II), or its polymorphs, stereoisomers, prodrugs, solvates, co-crystals, intermediates, pharmaceutically acceptable salts, and metabolites thereof, the process comprising reacting Formula (IV) and Formula (V)

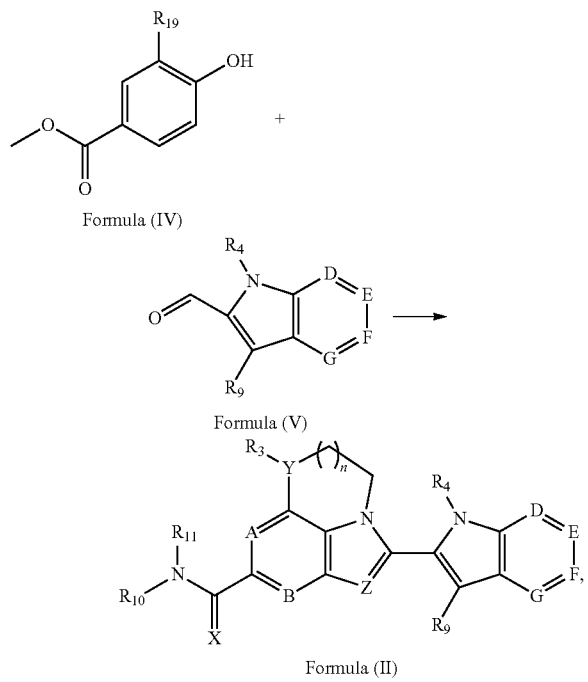

Formula (IV)

Formula (V)

Formula (II)

wherein $R_{19}$ of Formula (IV) is selected from nitro, and $C_{1-6}$ alkoxy; X of Formula (II) is selected from O or S; Y is selected from O, N, S, S(O), $SO_2$ or C; Z is selected from N or $CR_{17}$; A is selected from N or $CR_1$; B is selected from N or $CR_2$; D is selected from N or $CR_5$; E is selected from N or $CR_6$; F is selected from N or $CR_7$; G is selected from N or $CR_8$; n is 0-2; $R_1$, $R_2$, $R_5$, $R_6$, $R_7$, $R_8$, and $R_9$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, $C_{2-6}$ alkenyl-$C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, (CO)$C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, $-CH_2OH$, $-COOH$, and cyano; $R_{10}$ is hydrogen; $R_{11}$ is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, $-NHC(NH)CH_2Cl$, $-NHC(O)CH=CHCH_2N(CH_3)_2$, $C_{1-6}$ alkyl, halogen, $C_{1-6}$ alkoxy, and hydroxyl; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof; D of Formula (V) is selected from N or $CR_5$; E is selected from N or $CR_6$; F is selected from N or $CR_7$; G is selected from N or $CR_8$, $R_9$ is H; and $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, (CO) $C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, $-CH_2OH$, $-COOH$, and cyano.

In an embodiment, the present disclosure relates to a process of preparation of compounds of Formula (III), or its polymorphs, stereoisomers, prodrugs, solvates, co-crystals, intermediates, pharmaceutically acceptable salts, and metabolites thereof, the process comprising reacting Formula (IV) and Formula (VI)

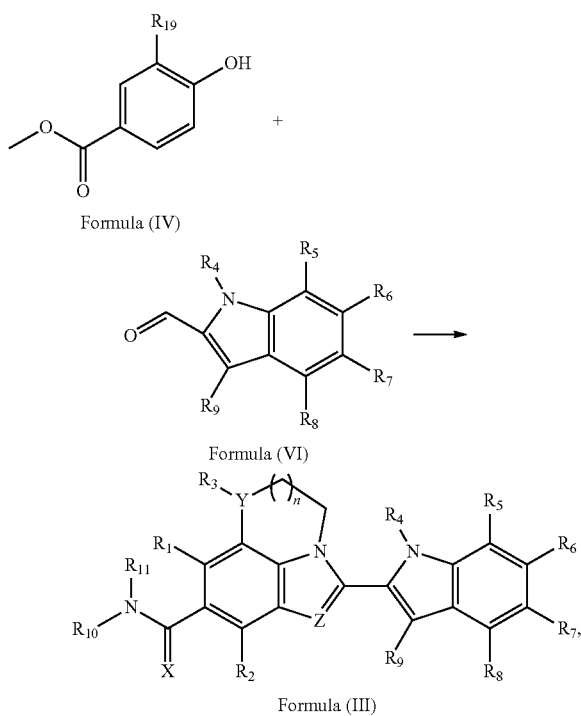

Formula (IV)

Formula (VI)

Formula (III)

wherein $R_{19}$ of Formula (IV) is selected from nitro, and $C_{1-6}$ alkoxy; X of Formula (III) is selected from O or S; Y is selected from O, N, S, S(O), $SO_2$ or C; Z is selected from N or $CR_{17}$; n is 0-2; $R_1$, $R_2$, $R_5$, $R_6$, $R_7$, $R_8$, and $R_9$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, $C_{2-6}$ alkenyl-$C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_3$ is absent or is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$ haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, (CO) $C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, —$CH_2OH$, COOH, and cyano; $R_{10}$ is hydrogen; $R_{11}$ is selected from the group consisting of hydrogen, $C_{1-6}$ alkyl, $C_{3-6}$ cycloalkyl, $C_{1-6}$ alkylamino, $C_{1-6}$ haloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{3-6}$ cycloalkyl, $SO_2NR_{18}$, $SO_2NC_{1-6}$ alkylamino, $C_{5-6}$ aryl, $C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $(CO)C_{1-6}$ alkyl, $C(O)C_{1-6}$ haloalkyl, $SO_2C_{5-6}$ aryl, and $SO_2C_{1-6}$ alkyl, is optionally substituted with $C_{1-6}$ alkoxy, halogen, $C_{5-6}$ aryl, and $C_{1-6}$ heteroaryl; and 5-10 membered monocyclic or bicyclic saturated heterocyclic ring with 1-3 heteroatoms selected from N, S or O, or $R_{10}$ and $R_{11}$ can be taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, $C_{1-6}$ acylamino, —NHC(NH)$CH_2Cl$, —NHC(O)CH=$CHCH_2N(CH_3)_2$, $C_{1-6}$ alkyl, halogen, $C_{1-6}$ alkoxy, and hydroxyl; $R_{17}$ is selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; and $R_{18}$ is independently selected from the group consisting of hydrogen, $C_{1-6}$ alkyl, and combinations thereof; and $R_5$, $R_6$, $R_7$, $R_8$, and $R_9$ are independently selected from the group consisting of hydrogen, hydroxyl, cyano, halogen, $C_{1-6}$ alkyl, $C_{1-6}$ alkoxy, $C_{1-6}$ haloalkyl, $C_{1-6}$ haloalkoxy, $C_{1-6}$ acylamino, $C_{1-6}$ alkylamino, $C_{5-6}$ aryl, $C_{2-6}$ alkenyl-$C_{5-6}$ aryl, and $C_{1-6}$ heteroaryl, wherein $C_{1-6}$ alkoxy, and $C_{1-6}$ haloalkoxy, is optionally substituted with one or more of the groups selected from hydrogen, $C_{1-6}$ alkyl, $C_{1-6}$ alkoxy, $C_{1-6}$ haloalkyl, $C_{1-6}$ alkylhydroxy, cyano, and hydroxyl; $R_4$ is selected from the group consisting of hydrogen, $C_{1-6}$ alkyl, $C_{1-6}$ haloalkyl, $C_{1-6}$ alkoxy, $C_{3-6}$ cycloalkyl, $C(O)C_{1-6}$ alkyl, $C(O)C_{1-6}$ haloalkyl, $C(O)NR_{18}$, $C(O)C_{1-6}$ alkylamino, $SO_2C_{1-6}$ alkyl, $SO_2C_{1-6}$haloalkyl, $SO_2NR_{18}$, $SO_2NC_{1-6}$ alkylamino, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $C(O)C_{5-6}$ aryl, $C(O)C_{1-6}$ heteroaryl, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-6}$ aryl, $C_{1-6}$ alkyl-$C_{5-6}$ aryl, $C_{1-6}$ heterocyclyl, $C_{1-6}$ alkyl-$C_{1-6}$ heterocyclyl, $C_{1-6}$ heteroaryl, $C_{1-6}$ alkyl-$C_{1-6}$ heteroaryl, $(CO)C_{1-6}$ alkyl, $C(O)C_{1-6}$ haloalkyl, and $SO_2C_{1-6}$ alkyl, is optionally substituted with one or more groups selected from hydrogen, $C_{1-6}$ alkyl, $C_{1-6}$ alkoxy, $C_{3-8}$ cycloalkyl, $C_{5-6}$ aryl, $C_{1-6}$ heteroaryl, halogen, hydroxyl, —$CH_2OH$, COOH, and cyano; and $R_{18}$ is independently selected from the group consisting of hydrogen, $C_{1-6}$ alkyl, and combinations thereof.

In another embodiment, the present disclosure relates to a pharmaceutical composition comprising a compound of Formula (I), Formula (II), and Formula (III) or a pharmaceutically acceptable salt thereof together with a pharmaceutically acceptable carrier, optionally in combination with one or more other pharmaceutical compositions.

In yet another embodiment, the present disclosure relates to the pharmaceutical composition as described herein, wherein the composition is in the form selected from the group consisting of a tablet, capsule, powder, syrup, solution, aerosol, and suspension.

In an embodiment of the present disclosure, there is provided compounds of Formula (I), Formula (II), and Formula (III) or a pharmaceutically acceptable salt thereof as described herein, wherein the pharmaceutically acceptable salt selected derived from inorganic bases such as like Li, Na, K, Ca, Mg, Fe, Cu, Zn and Mn; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, ammonium, substituted ammonium salts, aluminum salts and the like. Salts also include amino acid salts such as glycine, alanine, cystine, cysteine, lysine, arginine, phenylalanine, and guanidine. Salts may include acid addition salts where appropriate which are sulphates, nitrates, phosphates, perchlorates, borates, hydrohalides, acetates, tartrates, maleates, citrates, succinates, palmoates, methane sulphonates, tosylates, benzoates, salicylates, hydroxynaphthoates, benzene sulfonates, ascorbates, glycerophosphates, ketoglutarates.

In an embodiment of the present disclosure, there is provided compounds of Formula (I), Formula (II), and Formula (III) or a pharmaceutically acceptable salt thereof as described herein, wherein the pharmaceutically acceptable salt thereof for use in the manufacture of a medicament for inhibiting one or more PADs in a cell.

In an embodiment, the present disclosure relates to a method for inhibiting one or more PAD family in a cell with an effective amount of the compounds of Formula (I), Formula (II), and Formula (III) or a pharmaceutically acceptable salt thereof together with a pharmaceutically acceptable carrier, optionally in combination with one or more other pharmaceutical compositions.

In an embodiment, the present disclosure relates to a method of treating a condition mediated by one or more PADs, comprising administering to a subject suffering from a condition mediated by one or more PAD family, a therapeutically effective amount of the compounds of Formula (I), Formula (II), and Formula (III) or a pharmaceutically acceptable salt thereof together with a pharmaceutically acceptable carrier, optionally in combination with one or more other pharmaceutical compositions.

In an embodiment, the present disclosure relates to a method for the treatment and/or prevention of PAD mediated disorder or disorders associated with PAD activity, comprising administering to a subject suffering from PAD mediated disorder or disorders associated with PAD activity a therapeutically effective amount of the compounds of Formula (I), Formula (II), and Formula (III) or a pharmaceutically acceptable salt thereof together with a pharmaceutically acceptable carrier, optionally in combination with one or more other pharmaceutical compositions.

In an embodiment, the present disclosure relates to a method for the treatment and/or prevention of PAD mediated disorder or disorders associated with PAD, is selected from the group consisting of rheumatoid arthritis, vasculitis, systemic lupus erythematosus, ulcerative colitis, cancer, cystic fibrosis, asthma, cutaneous lupus erythematosis, and psoriasis.

In an embodiment, the present disclosure relates to a method for the treatment of PAD mediated disorder, said method comprising administering a combination of compounds of Formula (I), Formula (II), and Formula (III) or a pharmaceutically acceptable salts thereof together with a pharmaceutically acceptable carrier, optionally in combination with one or more other pharmaceutical compositions, and/or with other clinically relevant agents or biological agents to a subject in need thereof.

In an embodiment, the present disclosure relates to a method for the treatment and/or prevention of PAD mediated disorder or disorders associated with PAD, is selected from the group consisting of acid-induced lung injury, respiratory distress syndrome, allergen induced asthma, allergic bronchopulmonary, aspergillosis, allergic conjunctivitis, alopecia, amyotropic lateral sclerosis, inflammation, arthritis, asthma, atherosclerosis, atopic dermatitis, autoimmune diseases, bone pain, bronchiolitis, chronic lung disease of prematurity, chronic obstructive pulmonary disease, colitis, complex regional pain syndrome, crohn's disease, cystic fibrosis, familial cold urticarial, gout, gouty arthritis, graft versus-host disease, gut diseases, inflammatory bowel disease, inflammatory lung disease, inflammatory neuropathy, inflammatory pain, insect bite-induced inflammation, irritant-induced inflammation, juvenile rheumatoid arthritis, kidney disease, kidney injury caused by parasitic infections, kidney transplant rejection prophylaxis, lung injury, lupus, lupus nephritis, multiple sclerosis, muscle wasting, muscular dystrophy, non-allergen induced asthma, osterarthritis, periodontitis, peritoneal endometriosis, plant irritant-induced inflammation, psoriasis, pulmonary disease, pulmonary fibrosis, pyogenic sterile arthritis, renal disease, rheumatic carditis, rheumatic disease, rheumatoid arthritis, sepsis, severe pain and ulcerative colitis.

In an embodiment, the present disclosure relates to the use of compounds of Formula (I), Formula (II), and Formula (III) or a pharmaceutically acceptable salts thereof together with a pharmaceutically acceptable carrier, optionally in combination with one or more other pharmaceutical compositions for treatment of a condition mediated by one or more PAD family; or treatment and/or prevention of PAD mediated disorder; or treatment of PAD mediated disorder together with other clinically relevant agents or biological agents.

In an embodiment, the present disclosure relates to a method for the treatment and/or prevention of a condition mediated by one or more PAD family or a proliferative disorder or cancer, comprising administering to a subject suffering from the condition mediated by one or more PAD family or PAD mediated disorder, a therapeutically effective amount of the compound of the present disclosure or the pharmaceutical composition of the present disclosure.

In an embodiment, the present disclosure relates to a method comprising administering a combination of the compounds of Formula (I), Formula (II), and Formula (III) or the pharmaceutical composition with other clinically relevant agents or biologicalagents to a subject in need thereof.

In an embodiment, the present disclosure relates to a method for the treatment of cancer, said method comprising administering a combination of compounds of Formula (I), Formula (II), and Formula (III) or a pharmaceutically acceptable salt thereof together with a pharmaceutically acceptable carrier, optionally in combination with one or more other pharmaceutical compositions, with other clinically relevant immune modulators agents to a subject in need of thereof.

EXAMPLES

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further punt Specifically, the following abbreviations may be used in the examples and throughout the specification:

Abbreviations:
AcOH Acetic acid
BOC$_2$O Di-tert-butyl dicarbonate
nBuLi n-Butyllithium
BuOH Butanol
Bz Benzyl
Cbz Carboxybenzyl
cHex Cyclohexane
Cs$_2$CO$_3$ Caesium carbonate
DCM/CH$_2$Cl$_2$ Dichloromethane
DIAD Diisopropyl azodicarboxylate
Dioxane 1,4-dioxane
DIPEA N, N-diisopropylethylamine
DMSO Dimethylsulfoxide
DMF N,N-dimethylformamide
Et$_3$N Tri ethyl amine
Ether Diethyl ether
EtOAc Ethyl acetate
HATU o-(7-Azabenzotriazol-1-yl)-N,N,N',N'-tetramethyluronium hexafluorophosphate
HPLC High performance liquid chromatography
IPA Isopropyl alcohol
K$_2$CO$_3$ Potassium carbonate
KOH Potassium hydroxide
LiOH Lithium hydroxide
LCMS or LC/MS Liquid chromatography-mass spectroscopy
MeOH Methanol
min Minutes
Na$_2$SO$_4$ Sodium sulfate
NaHCO$_3$ Sodium bicarbonate
NH$_4$Cl Ammonium chloride
Palladium tetrakis palladium tetrakistriphenylphosphine
Pd/C Palladium on carbon
PTSA p-Toluenesulfonic acid
rb round-bottomed (flask)
r.t/rt. Room temperature
Rt Retention time
TFA Trifluoroacetic acid
TFAA Trifluoroacetic anhydride
thf Tetrahydrofuran
TLC/tlc Thin layer chromatography
TMEDA Tetramethyl ethyl enediamine The following examples provide the details about the synthesis, activities, and applications of the compounds of the present disclosure. It should be understood the following is representative only, and that the present disclosure is not limited by the details set forth in these examples.

The compounds of the present disclosure may be made by a variety of methods, including standard chemistry. Any previously defined variable will continue to have the previously defined meaning unless otherwise indicated. Illustrative general synthetic methods are set out in the following schemes and can be readily adapted to prepare other compounds of the disclosure.

There is also provided a general process as shown in the following Scheme-1, for the preparation of compounds of the Formula (I, II, and III), wherein all the groups are as defined earlier.

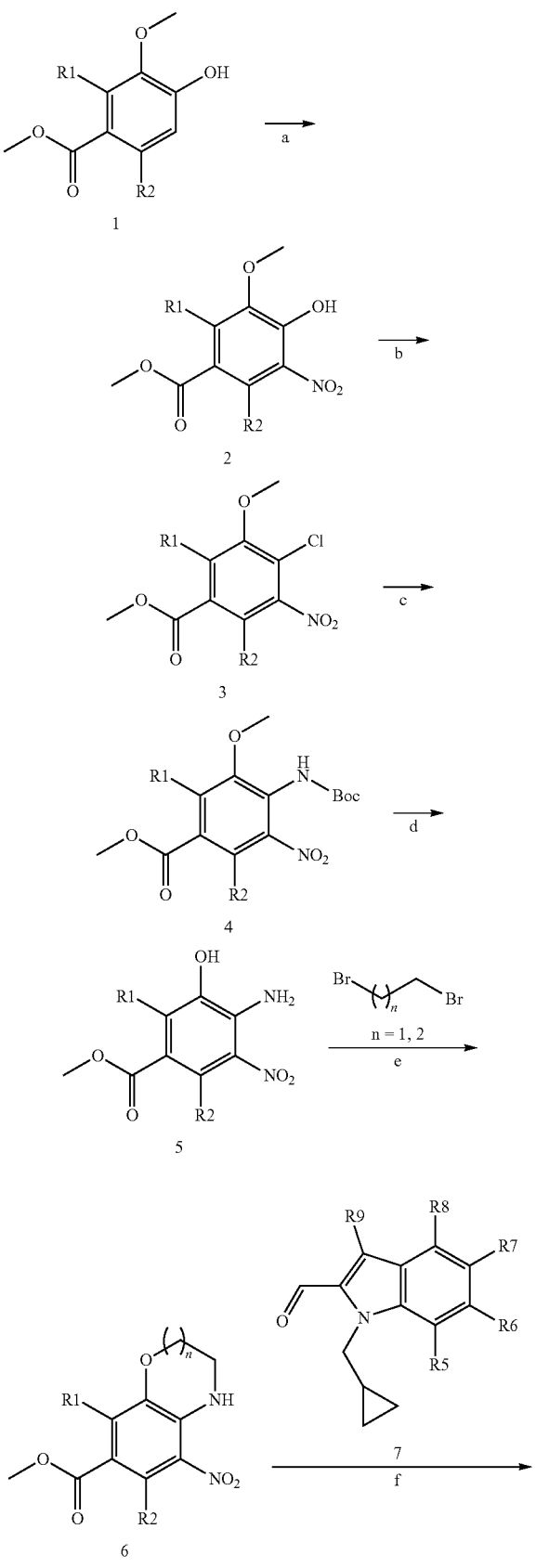

Scheme 1

-continued

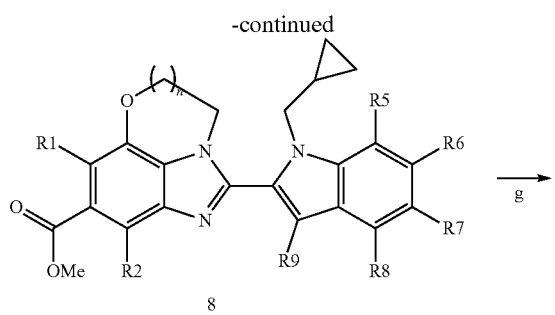
8

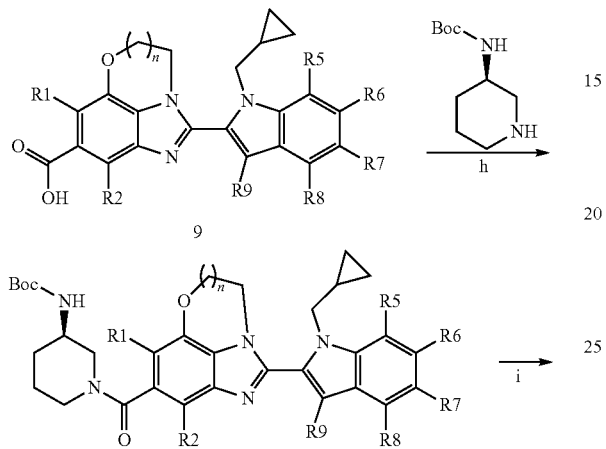
9

10

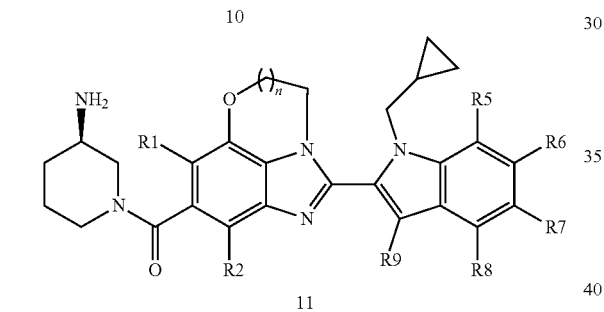
11

The said process for the preparation of the compounds of Formula (I, II, and III) comprises of the following steps:

Step 1: Compound 1 was converted to compound 2 under standard conditions using $CH_3COOH$ and $HNO_3$ (reaction condition a).

Step 2: Treatment of compound 2 with oxalyl chloride (reaction condition b) gave intermediate 3.

Step 3: Intermediate 3 was converted to compound 4 using tert-butyl carbamate, $Cs_2CO_3$ and X-Phos (reaction condition c).

Step 4: Treatment of compound 4 with $BBr_3$ (reaction condition d) gave intermediate 5.

Step 5: Intermediate 5 was converted to compound 6 by reacting with 1, ω-dibromoalkane and $K_2CO_3$ (reaction condition e).

Step 6: Compound 6 was coupled with substituted indole-2-carbaldehyde 7 (reaction condition f) to give compound 8.

Step 7: Compound 8 was hydrolysed (Reaction condition g) to give compound 9.

Step 8: Coupling of compound 9 with tert-butyl (R)-piperidin-3-ylcarbamate (reaction condition h) gave intermediate 10.

Step 9: Compound 10 was converted to final compound 11 by Boc deprotection (reaction condition i).

The examples given below are provided by the way of illustration only and therefore should not be construed to limit the scope of the disclosure.

Example-1

Synthesis of ((R)-(3-aminopiperidin-1-yl)(2-(1-(cyclopropylmethyl)-1H-indol-2-yl)-3,4-dihydro-5-oxa-1,2a-diazaacenaphthylen-7-yl)methanone (Example-1)

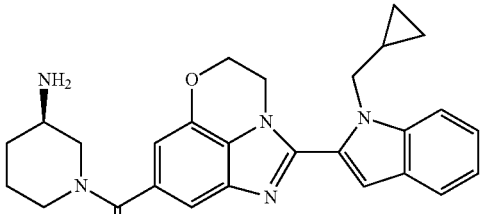
Example 1

Scheme 2

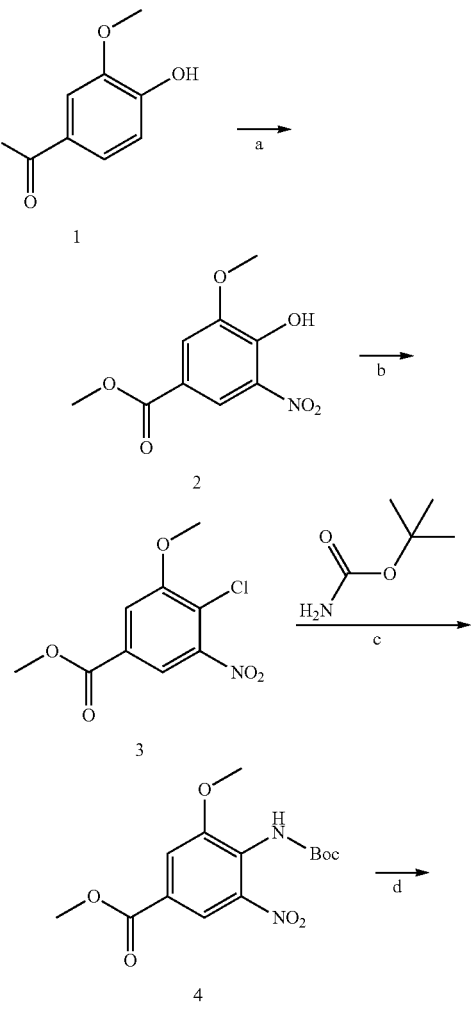

-continued

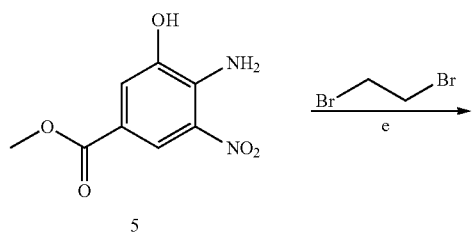

5

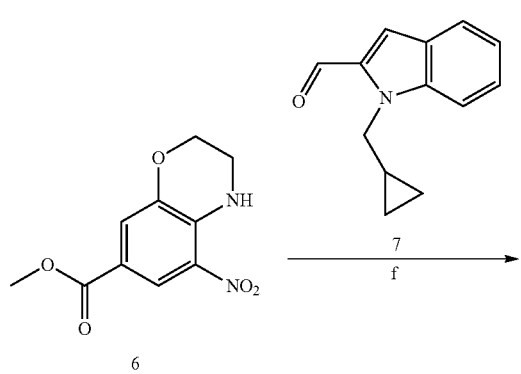

6

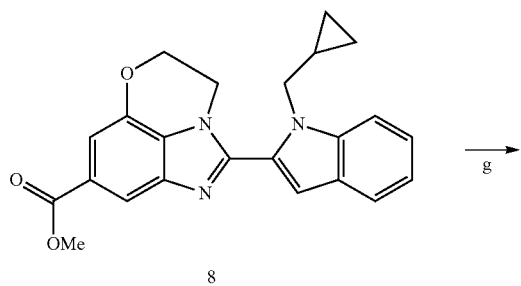

8

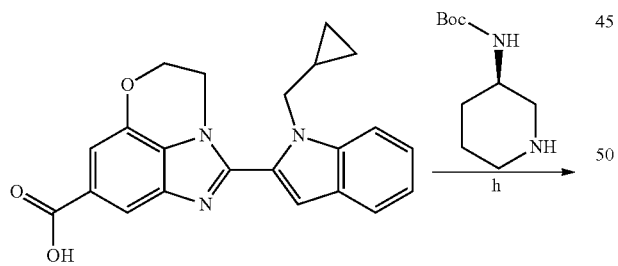

9

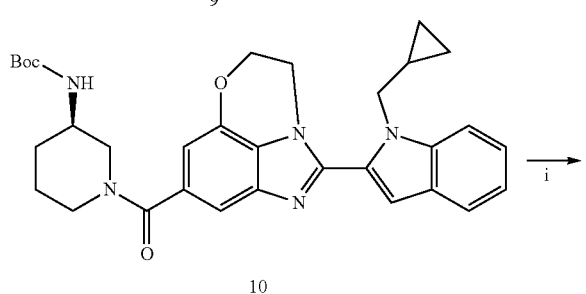

10

-continued

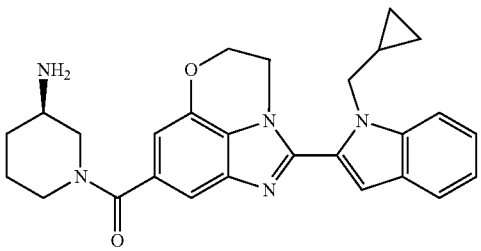

Example 1

Step 1: Preparation of Methyl 4-hydroxy-3-methoxy-5-nitrobenzoate (2)

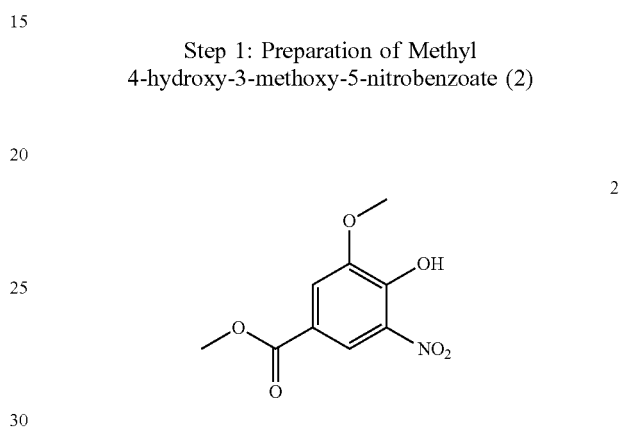

2

To a stirred solution of methyl-4-hydroxy-3-methoxybenzoate (1, 20 g, 109.7 mmol) in $CH_3COOH$ (100 mL) was added $HNO_3$ (5.9 mL, 94.4 mmol) under 0° C. drop wise and then reaction mixture was stirred at room temperature for 4-5 h (reaction condition a). To the reaction mixture ice cold water was added and the reaction mixture was filtered to obtain the precipitate which was dried using high vacuum to get the product as yellow solid (18 g, 75% yield). MS (ESI): mass calcd. for $C_9H_9NO_6$, 227.04; m/z found, 228 $[M+H]^+$.

Step 2: Preparation of Methyl 4-chloro-3-methoxy-5-nitrobenzoate (3)

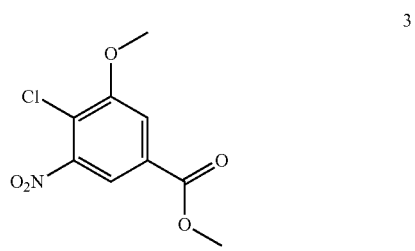 [SMILES: COC(=O)c1cc(OC)c(Cl)c([N+](=O)[O-])c1]

3

To a stirred solution of methyl 4-hydroxy-3-methoxy-5-nitrobenzoate (2, 18 g, 79.29 mmol) in DMF (100 mL) was added oxalyl chloride (14.27 mL, 113.28 mmol) under 0° C. slowly, then the reaction mixture was refluxed under 80° C. for about 12 h (reaction condition b). To the reaction mixture ice cold water was added and the resulting solid was filtered. The solid was dried under high vacuum to obtain the product as brown solid (17.5 g, 90% yield). MS (ESI): mass calcd. for $C_9H_8ClNO_5$, 245.01; m/z found, 246 $[M+H]^+$.

Step 3: Preparation of Methyl 4-((tert-butoxycarbonyl) amino)-3-methoxy-5-nitrobenzoate (4)

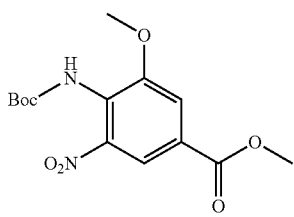

4

To a stirred solution of methyl 4-chloro-3-methoxy-5-nitrobenzoate (3, 6 g, 24.42 mmol) in t-butanol (50 mL) was added tert-butyl carbamate (2.86 g, 24.42 mmol), Cs$_2$CO$_3$ (9.5 g, 29.31 mmol) and X-Phos (1.16 g, 2.44 mmol) under N$_2$. Pd$_2$(dba)$_3$, (0.44 g, 0.48 mmol) was added and stirred for about 10 min at room temperature and then resulting mixture was heated to 100° C. for 12 h (reaction condition c). The reaction mixture was cooled to room temperature and diluted with ethyl acetate (100 mL×3) and the organic phase was washed with water and brine, dried over sodium sulphate and concentrated under reduced pressure to afford the crude compound which was purified by column chromatography (silica gel, 0-20% EtOAc in hexane) to afford methyl 4-((tert-butoxycarbonyl) amino)-3-methoxy-5-nitrobenzoate (2.5 g, 75% yield) as colourless liquid. MS (ESI): Mass calcd. for C$_{14}$H$_{18}$NO$_2$O$_7$, 325.0; m/z found, 326.3 [M+H]$^+$.

Step 4: Preparation of Methyl 4-amino-3-hydroxy-5-nitrobenzoate (5)

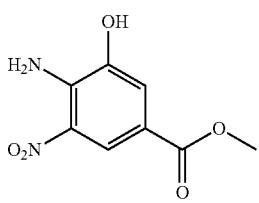

5

To a stirred solution of methyl 4-((tert-butoxycarbonyl) amino)-3-methoxy-5-nitrobenzoate (4, 3.5 g, 10.74 mmol) in DCM (30 mL) was added BBr$_3$ (3.5 mL) at −78° C. and the resulting mixture was allowed to stir under room temperature for 3 h (reaction condition d). The progress of the reaction was monitored by TLC. The reaction mixture was quenched with ice and sodium bicarbonate solution (30 mL) and extracted with DCM (50 mL×3). The combined organic extract was washed with brine, dried over sodium sulphate and concentrated under reduced pressure to afford methyl 4-amino-3-hydroxy-5-nitrobenzoate (0.7 g, 35% yield) as brown solid. MS (ESI): Mass calcd. for C$_8$H$_8$N$_2$O$_5$, 212.1; m/z found, 213 [M+H]$^+$.

Step 5: Preparation of Methyl 5-nitro-3,4-dihydro-2H-benzo[b][1,4]oxazine-7-carboxylate (6)

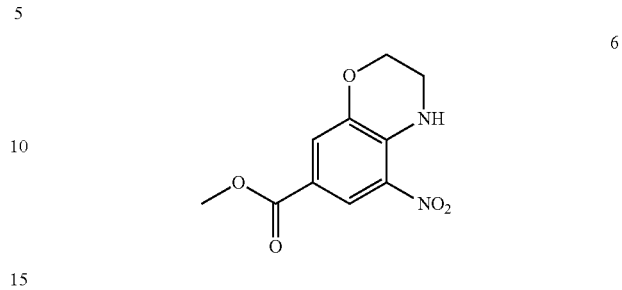

6

To a stirred solution of methyl 4-amino-3-hydroxy-5-nitrobenzoate (5, 1.1 g, 5.12 mmol) in DMF (10 mL) was added 1,2-dibromo ethane (0.44 mL) and K$_2$CO$_3$ (0.86 g, 2.38 mmol) the resulting mixture was heated to 80° C. for 12 h (reaction condition e). The progress of the reaction was monitored by TLC. The reaction mixture was quenched with water and extracted with ethyl acetate (20 mL×2). The combined organic extract was washed with brine, dried over sodium sulphate and concentrated under reduced pressure to afford the crude compound which was purified by column chromatography (SiO$_2$, 0-20% EtOAc in hexane) to afford methyl 5-nitro-3,4-dihydro-2H-benzo[b][1,4]oxazine-7-carboxylate (0.45 g, 89% yield) as brown solid. MS (ESI): Mass calcd. for C$_{10}$H$_{10}$N$_2$O$_5$, 238.2; m/z found, 239.1 [M+H]$^+$.

Step 6: Preparation of Methyl 2-(1-(cyclopropylmethyl)-1H-indol-2-yl)-3,4-dihydro-5-oxa-1,2diazaacenaphthylene-7-carboxylate (8)

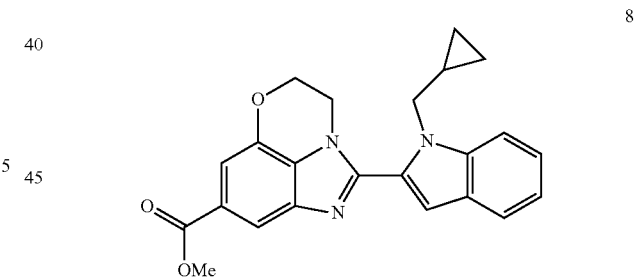

8

To the stirred solution of mixture of methyl 5-nitro-3,4-dihydro-2H-benzo[b][1,4]oxazine-7-carboxylate (6, 0.2 g, 0.84 mmol) and 1-(cyclopropylmethyl)-1H-indole-2-carbaldehyde (7, 0.18 g, 0.92 mmol) in EtOH (10 mL), was added Na$_2$S$_2$O$_4$ (0.73 g, 4.20 mmol) in water (5 mL) and stirred at 95° C. for 16 h (Reaction condition f). The reaction mixture was cooled to room temperature, water was added and compound was extracted with ethyl acetate (20 mL×2). Combined organic extracts were washed with brine, dried over sodium sulfate and evaporated to get crude product. The crude residue was purified by gradient column chromatography using silica gel with eluent 15-20% ethyl acetate in hexane to afford methyl 2-(1-(cyclopropylmethyl)-1H-indol-2-yl)-3,4-dihydro-5-oxa-1,2diazaacenaphthylene-7-carboxylate as yellow solid (0.18 g. 12% yield). MS (ESI): Mass calcd. for C$_{23}$H$_{21}$N$_3$O$_3$, 387.4; m/z found, 388.1 [M+H]$^+$.

Step 7: Preparation of 2-(1-(cyclopropylmethyl)-1H-indol-2-yl)-3,4-dihydro-5-oxa-1,2a-diazaacenaphthylene-7-carboxylic acid (9)

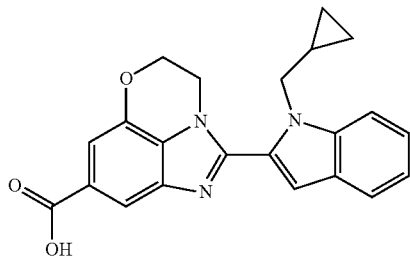

9

To the stirred solution of methyl 2-(1-(cyclopropylmethyl)-1H-indol-2-yl)-3,4-dihydro-5-oxa-1,2diazaacenaphthylene-7-carboxylate (8, 0.18 g, 0.46 mmol) in MeOH (2 mL), was added 5N NaOH solution (0.4 mL) and stirred at 75° C. for 1 h (reaction condition g). The reaction mixture was evaporated completely. The resulting crude was dissolved in water and acidified using citric acid (pH ~4-6), extracted with DCM (20 mL×2). Combined organic extracts were washed with brine, dried over sodium sulfate, filtered and evaporated to get crude product as a yellow solid to afford the 2-(1-(cyclopropylmethyl)-1H-indol-2-yl)-3,4-dihydro-5-oxa-1,2a-diazaacenaphthylene-7-carboxylic acid as brown solid (0.07 g, 41% yield). MS (ESI): Mass calcd. for $C_{22}H_{19}N_3O_3$, 373.4; m/z found, 374.1 $[M+H]^+$.

Step 8: Preparation of tert-butyl (R)-(1-(2-(1-(cyclopropylmethyl)-1H-indol-2-yl)-3,4-dihydrooxa-1,2a-diazaacenaphthylene-7-carbonyl)piperidin-3-yl)carbamate

10

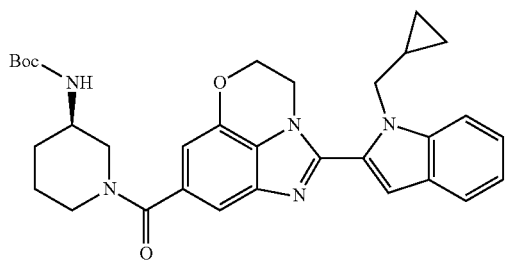

To the stirred solution of 2-(1-(cyclopropylmethyl)-1H-indol-2-yl)-3-methyl-3H-imidazo[4,5-b]pyridine-6-carboxylic acid (9, 0.089 g, 0.24 mmol) in DCM (2 mL), were added tert-butyl (R)-piperidin-3-ylcarbamate (0.05 g, 0.26 mmol), triethylamine (0.1 g, 0.72 mmol) followed by 50% solution of T3P in ethyl acetate (0.2 g, 0.72 mmol) and stirred at room temperature for 12 h (reaction condition h). To the reaction mixture was added water and compound was extracted with DCM (20 mL×2). Combined organic extracts were washed with brine, dried over sodium sulfate and evaporated to get crude product. The crude residue was purified by gradient column chromatography using 5% MeOH in DCM to afford the product as yellow solid (0.07 g, 53.8% yield). MS (ESI): Mass calcd. for $C_{32}H_{37}N_5O$, 555.6; m/z found, 556.3 $[M+H]^+$.

Step 9: Preparation of (R)-(3-aminopiperidin-1-yl)(2-(1-(cyclopropylmethyl)-1H-indol-2-yl)-3,4-dihydro-5-oxa-1,2a-diazaacenaphthylen-7-yl)methanone (Example-1)

Example-1

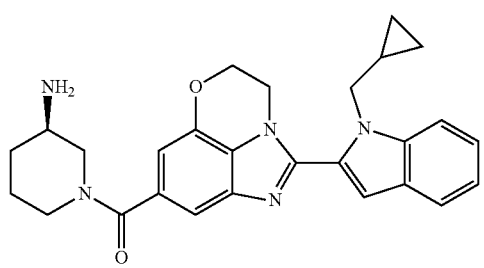

To the stirred solution of tert-butyl (R)-(1-(2-(1-(cyclopropylmethyl)-1H-indol-2-yl)-3,4-dihydro-5-oxa-1,2a-diazaacenaphthylene-7-carbonyl)piperidin-3-yl)carbamate (10, 0.08 g, 0.14 mol) in dichloromethane (10 mL), was added trifluroacetic acid (0.5 mL) and stirred at room temperature for 2 h (reaction condition i). The reaction mixture was evaporated completely, dissolved in minimum volume of water (30 mL) and basified by saturated $NaHCO_3$ (20 mL) solution. The compound was extracted with ethyl acetate (50 mL×2)). Combined organic extracts were washed with brine, dried over sodium sulfate and evaporated to get the product as pale yellow solid (0.044 g, 67.5% yield). $^1$HNMR (400 MHz, DMSO-d6): δ (ppm): 7.68 (t, J=4.4 Hz, 2H), 7.29 (t, J=5.2 Hz, 2H), 7.15-7.10 (m, 2H), 6.74 (s, 1H), 4.69-4.68 (m, 4H), 4.55 (s, 2H), 3.56 (m, 2H), 2.92 (s, 1H), 4.13 (s, 2H), 2.69-2.65 (m, 1H), 1.88-1844 (m, 2H), 1.64 (m, 1H), 1.43-1.41 (m, 1H), 1.23-1.22 (m, 2H), 0.32 (d, J=8 Hz, 2H), 0.28-0.27 (m, 2H). MS (ESI): mass calcd. for $C_{32}H_{37}N_5O_4$, 455.0; m/z found, 456.4 $[M+H]^+$.

Following compounds (Examples 2-8) were synthesized using the above procedure as exemplified for Example-1 above with corresponding reactants.

Example-2

(R)-(3-aminopyrrolidin-1-yl)(2-(1-(cyclopropylmethyl)-1H-indol-2-yl)-3,4-dihydro-5-oxa-1,2a-diazaacenaphthylen-7-yl)methanone

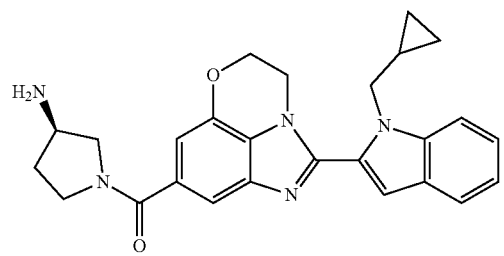 [SMILES: N[C@@H]1CCN(C(=O)c2cc3c4c(c2)nc(-c2cc5ccccc5n2CC2CC2)n4CCO3)C1]

$^1$HNMR (400 MHz, DMSO-d6): δ (ppm): 7.69 (t, J=12 Hz, 2H), 7.43 (s, 1H), 7.29-7.26 (m, 1H), 7.18-7.10 (m, 2H), 6.87 (s, 1H), 4.69 (d, J=8 Hz, 2H), 4.64 (d, J=4 Hz, 2H), 4.56-4.55 (m, 2H), 3.65-3.59 (m, 2H), 3.56-3.45 (m, 2H), 1.97 (m, 2H), 1.64 (m, 2H), 1.31-1.22 (m, 2H), 0.32 (d, J=8 Hz, 2H), 0.27-0.26 (m, 2H). MS (ESI): mass calcd. for $C_{26}H_{27}N_5O_2$, 441.22; m/z found, 442.0 [M+H]+.

Example-3

(R)-(3-aminopiperidin-1-yl)(2-(1-ethyl-1H-indol-2-yl)-3,4-dihydro-5-oxa-1,2a-diazaacenaphthylen-7-yl)methanone

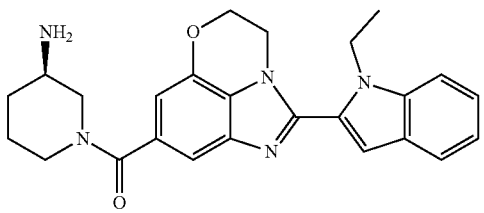 [SMILES: CCn1c(-c2nc3cc(C(=O)N4CCC[C@@H](N)C4)cc4c3n2CCO4)cc2ccccc21]

$^1$HNMR (400 MHz, DMSO-d6): δ (ppm): 7.67 (d, J=8 Hz, 1H), 7.62 (d, J=8 Hz, 1H), 7.31-7.27 (m, 2H), 7.14-7.11 (m, 2H), 6.70 (s, 1H), 4.80 (m, 2H), 4.77 (m, 2H), 4.75 (m, 2H) 4.00 (m, 2H), 3.60 (m, 2H), 2.94 (bs, 1H), 2.78 (bs, 2H), 1.89 (m, 1H), 1.73 (m, 1H), 1.42 (m, 1H), 1.35 (m, 3H), 1.31 (m, 1H). MS (ESI): Mass calcd. for $C_{25}H_{27}N_5O_2$, 429.52; m/z found, 430.2 [M+H]+.

Example-4

(2-(aminomethyl)piperidin-1-yl)(2-(1-(cyclopropylmethyl)-1H-indol-2-yl)-3,4-dihydro-5-oxa-1,2a-diazaacenaphthylen-7-yl)methanone

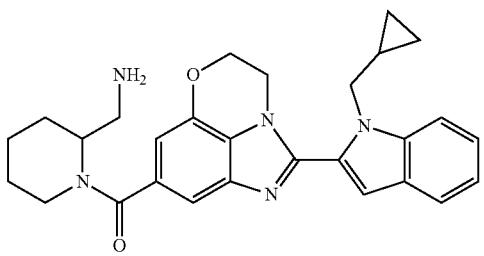 [SMILES: NCC1CCCCN1C(=O)c1cc2c3c(c1)nc(-c1cc4ccccc4n1CC1CC1)n3CCO2]

$^1$HNMR (400 MHz, DMSO-d6): δ (ppm): 7.68 (t, J=8 Hz, 2H), 7.50 (m, 1H), 7.29-7.26 (m, 2H), 7.14-7.05 (m, 3H), 6.74 (d, J=8 Hz, 1H), 4.68 (d, J=8 Hz, 2H), 4.64 (m, 2H), 4.54 (m, 2H), 3.97-3.96 (m, 2H), 2.87-2.81 (m, 1H), 1.54-1.49 (m, 2H), 1.28 (m, 1H), 1.13 (m, 6H), 0.37-0.27 (m, 4H). MS (ESI): Mass calcd. for $C_{28}H_{31}N_5O_2$, 469.59; m/z found, 470.3 [M+H]+.

Example-5

(R)-(3-aminopiperidin-1-yl)(2-(1-ethyl-1H-pyrrolo[2,3-b]pyridin-2-yl)-3,4-dihydro-5-oxa-1,2a-diazaacenaphthylen-7-yl)methanone

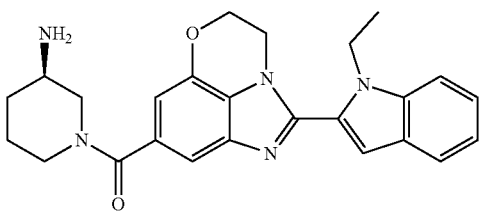 [SMILES: CCn1c(-c2nc3cc(C(=O)N4CCC[C@@H](N)C4)cc4c3n2CCO4)cc2ccccc21]

$^1$HNMR (400 MHz, DMSO-d6): δ (ppm): 8.42 (d, J=4 Hz, 1H), 8.11 (d, J=4 Hz, 1H), 7.31 (s, 1H), 7.22-7.19 (m, 2H), 6.75 (s, 1H), 4.89-4.86 (m, 2H), 4.68 (m, 2H), 4.56 (m, 2H), 3.51 (m, 2H), 2.91-2.87 (m, 1H), 1.97 (m, 1H), 1.86-1.83 (m, 2H), 1.65 (m, 3H), 1.43-1.33 (m, 5H). MS (ESI): Mass calcd. for $C_{24}H_{26}N_6O_2$, 430.51; m/z found, 431.4 [M+H]+.

Example-6

(R)-(3-aminopiperidin-1-yl)(1-(1-(cyclopropylmethyl)-1H-indol-2-yl)-8,9-dihydro-7H-6-oxa-2,9a-diazabenzo[cd]azulen-4-yl)methanone

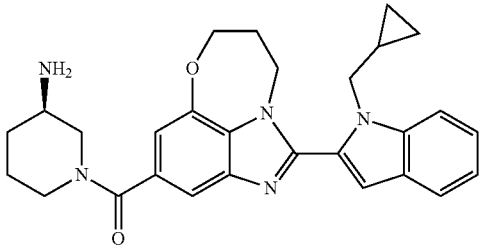 [SMILES: N[C@@H]1CCCN(C(=O)c2cc3c4c(c2)nc(-c2cc5ccccc5n2CC2CC2)n4CCCO3)C1]

$^1$HNMR (400 MHz, DMSO-d6): δ (ppm): 7.65 (m, 2H), 7.35 (s, 1H), 7.27 (m, 1H), 7.12 (m, 1H), 7.04 (m, 1H), 6.82 (s, 1H), 4.45-4.38 (m, 6H), 2.65 (m, 2H), 1.89 (m, 2H), 1.67 (m, 3H), 1.45-1.31 (m, 2H), 1.22 (m, 4H), 0.83 (s, 1H), 0.30 (m, 2H), 0.06 (m, 2H). MS (ESI): Mass calcd. for $C_{28}H_{31}N_5O_2$, 469.59; m/z found, 470.2 [M+H]+.

Example-7

(R)-(3-aminopyrrolidin-1-yl)(1-(1-(cyclopropylmethyl)-1H-indol-2-yl)-8,9-dihydro-7H-6-oxa-2,9a-diazabenzo[cd]azulen-4-yl)methanone

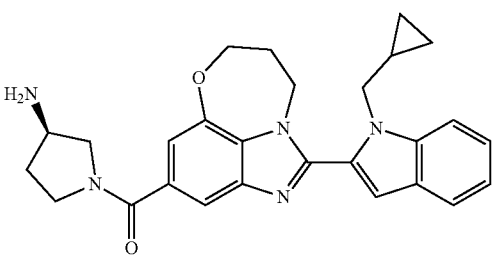 [SMILES: N[C@@H]1CCN(C(=O)c2cc3c4c(c2)nc(-c2cc5ccccc5n2CC2CC2)n4CCCO3)C1]

¹HNMR (400 MHz, DMSO-d6): δ (ppm): 7.68-7.64 (m, 2H), 7.46-7.44 (m, 1H), 7.29 (t, J=16 Hz, 1H), 7.14-7.10 (m, 1H) 7.04 (bs, 1H), 6.92 (s, 1H), 4.44-4.36 (m, 6H), 3.64 (m, 2H), 3.55-3.48 (m, 2H), 2.43 (m, 2H), 1.97 (m, 1H), 1.86 (m, 1H), 1.60 (m, 1H), 1.31 (m, 1H), 1.06 (m, 1H), 0.83 (m, 1H), 0.31 (m, 2H), 0.05 (m, 2H). MS (ESI): Mass calcd. for $C_{27}H_{29}N_5O_2$, 455.56; m/z found, 456.3 $[M+H]^+$.

Example-8

(R)-(3-aminopiperidin-1-yl)(2-(1-(cyclopropylmethyl)-7-methyl-1H-indol-2-yl)-3,4-dihydro-5-oxa-1,2a-diazaacenaphthylen-7-yl)methanone

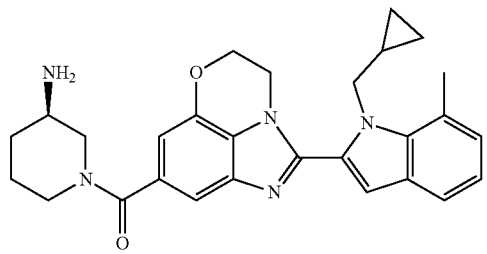 [SMILES: Cc1cccc2cc(-c3nc4cc(C(=O)N5CCC[C@@H](N)C5)cc5c4n3CCO5)n(CC3CC3)c12]

¹HNMR (400 MHz, DMSO-d6): δ (ppm): 7.51 (d, J=6.0 Hz, 1H), 7.27 (s, 1H), 7.12 (s, 1H), 7.03-7.00 (m, 2H), 6.75 (s, 1H), 4.89 (d, J=6.0 Hz, 2H), 4.57 (d, J=7.2 Hz, 4H), 4.30 (s, 1H), 3.65 (s, 1H), 2.90 (s, 1H), 2.78 (s, 3H), 2.65 (s, 1H), 1.84-1.65 (m, 4H), 1.41 (d, J=10.8 Hz, 1H), 1.22 (m, 2H), 0.94 (bs, 1H), 0.21 (d, J=7.6 Hz, 2H), 0.15 (d, J=4.4 Hz, 2H). MS (ESI): mass calcd. for $C_{28}H_{31}N_5O_2$, 469.5; m/z found, 470 (M+H)⁺.

Example-9

Synthesis of (R)-(3-aminopiperidin-1-yl)(2-(1-(cyclopropylmethyl)-5-fluoro-1H-indol-2-yl)-3,4-dihydro-5-oxa-1,2a-diazaacenaphthylen-7-yl)methanone (Example-9)

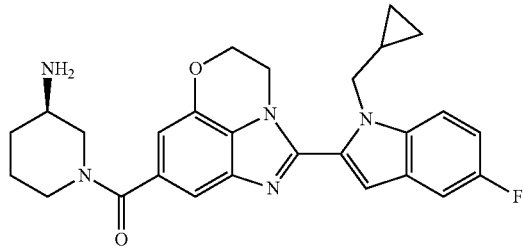 [SMILES: N[C@@H]1CCCN(C(=O)c2cc3c4c(c2)nc(-c2cc5cc(F)ccc5n2CC2CC2)n4CCO3)C1]

Scheme 3

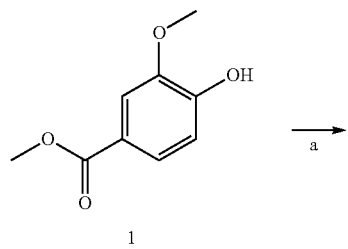

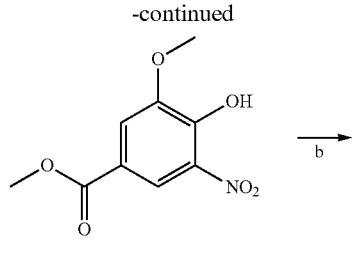

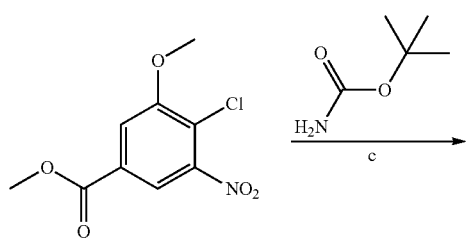

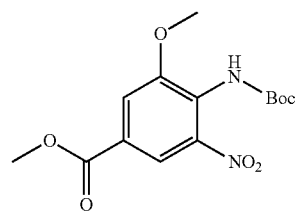

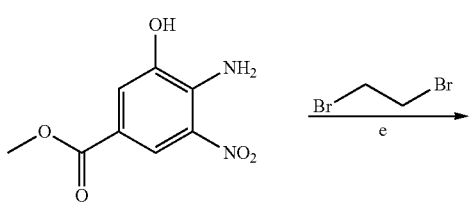

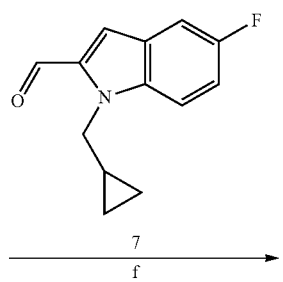

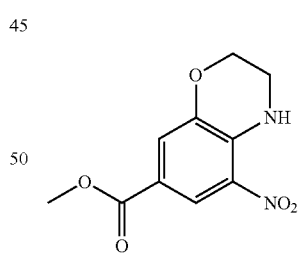

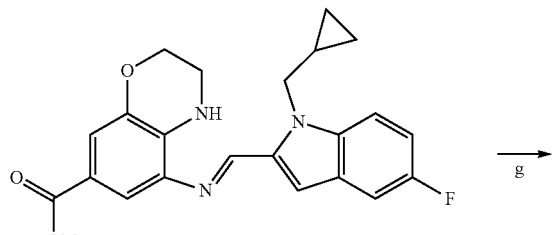

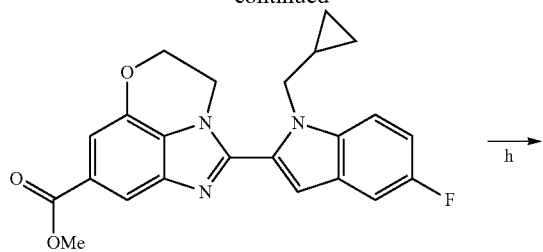

9

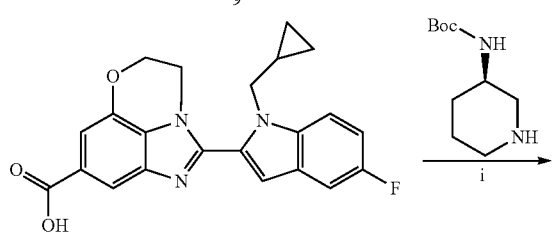

10

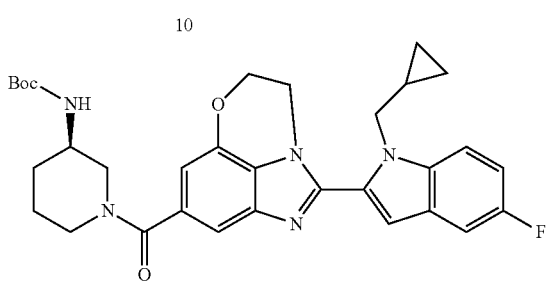

11

↓ j

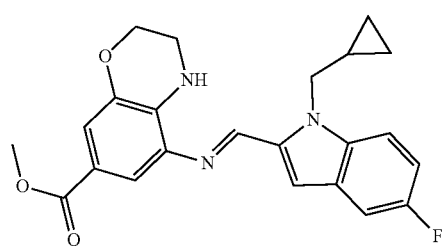

Example 9

The reaction procedure followed to obtain intermediate (6) was similar to the procedure outlined for the preparation of Example-1 in Scheme-2 above.

Step 6: Preparation of methyl (E)-5-(((1-(cyclopropylmethyl)-5-fluoro-1H-indol-2-yl)methylene)amino)-3,4-dihydro-2H-benzo[b][1,4]oxazine-7-carboxylate (8)

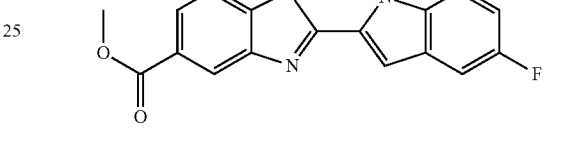

8

To a stirred solution methyl 5-nitro-3,4-dihydro-2H-benzo[b][1,4]oxazine-7-carboxylate (6, 0.25 g, 1.05 mmol) in ethanol (6 mL), were added 1-(cyclopropylmethyl)-5-fluoro-1H-indole-2-carbaldehyde (7, 0.27 g, 1.26 mmol), sodium dithionite (0.91 g, 5.25 mmol) and water (3 mL). Then the reaction mixture was heated to 90° C. for 12 h in a sealed tube (reaction condition f). The reaction mixture was evaporated, diluted with water and extracted with ethyl acetate (20 mL×2). Combined organic extracts were washed with water, brine, dried over sodium sulfate, filtered and evaporated to get crude product as a yellow solid (0.25 g, crude). MS (ESI): mass calcd. for $C_{23}H_{22}FN_3O_3$, 407.45; m/z found, 408.1 $[M+H]^+$.

Step 7: Preparation of Methyl 2-(1-(cyclopropylmethyl)-5-fluoro-1H-indol-2-yl)-3,4-dihydro-5-oxa-1,2a-diazaacenaphthylene-7-carboxylate (9)

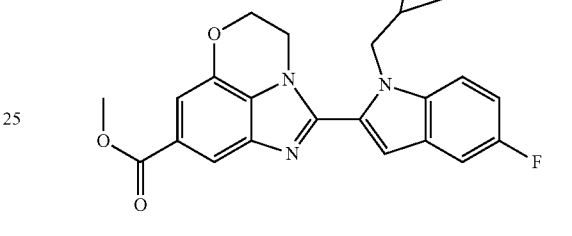

9

To a stirred solution methyl (E)-5-(((1-(cyclopropylmethyl)-5-fluoro-1H-indol-2-yl)methylene)amino)-3,4-dihydro-2H-benzo[b][1,4]oxazine-7-carboxylate (8, 0.25 g, 0.61 mmol) in toluene (3 mL), was added p-toluene sulfonic acid (0.012 g, 0.0614 mmol) at room temperature. Then the reaction mixture was heated to 90° C. for 12 h (reaction condition g). The reaction mixture was quenched with sodium bicarbonate, extracted with ethyl acetate (20 mL×2). Combined organic extracts were washed with brine, dried over sodium sulfate, filtered and evaporated to get crude product. Crude residue was purified by gradient column chromatography using silica gel and eluent 15-20% ethyl acetate in hexane to get the product as a yellow solid (0.15 g, 35% yield). MS (ESI): mass calcd. for $C_{23}H_{20}FN_3O_3$, 405.43; m/z found, 406.1 $[M+H]^+$.

Step 8: Preparation of 2-(1-(cyclopropylmethyl)-5-fluoro-1H-indol-2-yl)-3,4-dihydro-5-oxa-1,2a-diazaacenaphthylene-7-carboxylic Acid (10)

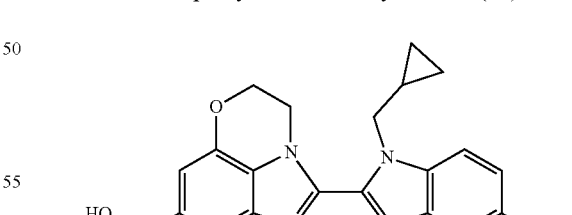

10

To a stirred solution of methyl 2-(1-(cyclopropylmethyl)-5-fluoro-1H-indol-2-yl)-3,4-dihydro-5-oxa-1,2a-diazaacenaphthylene-7-carboxylate (9, 0.15 g, 0.37 mmol) in methanol (5 mL) was added 5N NaOH (0.37 mL, 1.85 mmol) solution and heated to 80° C. for 1 h (reaction condition h). The solvent was evaporated completely and dissolved in water (10 mL) and acidified using citric acid, extracted with DCM (20 mL×2). Combined organic extracts were washed with brine, dried over sodium sulfate, filtered and evaporated to get crude product as a yellow solid (0.13 g, 90% yield). MS (ESI): mass calcd. for $C_{22}H_{18}FN_3O_3$, 391.40; m/z found, 392.1 [M+H]$^+$.

Step 9: Preparation of Tert-butyl (R)-(1-(2-(1-(cyclopropylmethyl)-5-fluoro-1H-indol-2-yl)-3,4-dihydro-5-oxa-1,2a-diazaacenaphthylene-7-carbonyl)piperidin-3-yl)carbamate (11)

11

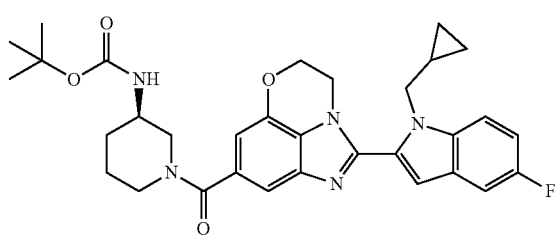

To a stirred solution of 2-(1-(cyclopropylmethyl)-5-fluoro-1H-indol-2-yl)-3,4-dihydro-5-oxa-1,2a-diazaacenaphthylene-7-carboxylic acid (10, 0.13 g, 0.33 mmol) in DCM (4 mL), were added tert-butyl (R)-piperidin-3-ylcarbamate (0.079 g, 0.398 mmol), triethylamine (0.09 mL, 0.66 mmol), propyl phosphonic anhydride in 50% ethyl acetate (0.316 mL, 0.498 mmol). The reaction mixture was allowed to stir at room temperature for 1 h (reaction condition i). The reaction mixture was quenched with sodium bicarbonate solution (20 mL), extracted with ethyl acetate (20 mL×2). Combined organic extracts were washed with brine, dried over sodium sulfate, filtered and evaporated to get crude product. Crude residue was purified by gradient column chromatography using silica gel and eluent 5-10% methanol in DCM to get the product as a yellow solid (0.13 g, 68% Yield). MS (ESI): mass calcd. for $C_{32}H_{36}FN_5O_4$, 573.67; m/z found, 574.3 [M+H]$^+$.

Step 10: Preparation of (R)-(3-aminopiperidin-1-yl)(2-(1-(cyclopropylmethyl)-5-fluoro-1H-indol-2-yl)-3,4-dihydro-5-oxa-1,2a-diazaacenaphthylen-7-yl)methanone (Example-9)

Example 9

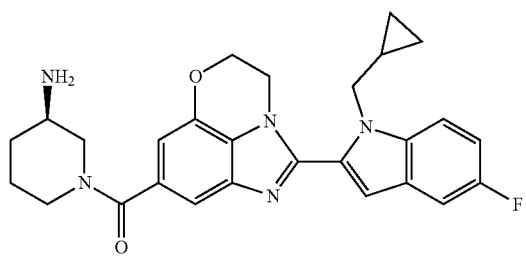

To a stirred solution of Tert-butyl (R)-(1-(2-(1-(cyclopropylmethyl)-5-fluoro-1H-indol-2-yl)-3,4-dihydro-5-oxa-1,2a-diazaacenaphthylene-7-carbonyl)piperidin-3-yl)carbamate (11, 0.13 g, 0.226 mmol) in DCM (4 mL) was added trifluoro acetic acid (0.5 mL) at 0° C. Then the reaction mixture was allowed to stir at room temperature for 1 h (reaction condition j). Reaction mixture was evaporated under reduced pressure, washed with ether and the reaction mixture was basified using saturated sodium bicarbonate solution (20 mL) and extracted with ethyl acetate (20 mL×2). Combined organic extracts were washed with brine, dried over sodium sulfate, filtered and evaporated to get crude product. Crude residue was purified by gradient column chromatography using silica gel and eluent 5-10% methanol in DCM to get the product as off white solid (0.06 g, 57% Yield). $^1$HNMR (400 MHz, DMSO-d$_6$) δ (ppm): δ 7.72-7.68 (m, 1H), 7.44 (d, J=7.2 Hz, 1H), 7.29 (s, 1H), 7.13 (t, J=7.2 Hz, 2H), 6.75 (s, 1H), 4.69-4.64 (m, 4H), 4.55 (s, 2H), 4.15 (bs, 1H), 3.77 (bs, 1H), 2.91 (bs, 1H), 2.65 (bs, 2H), 1.84 (d, J=11.6 Hz, 2H), 1.64 (bs, 1H), 1.42 (d, J=10.8 Hz, 1H), 1.22 (bs, 3H), 0.34-0.27 (m, 4H). MS (ESI): mass calcd. for $C_{27}H_{28}FN_5O_2$, 473.55; m/z found, 474.2 [M+H]$^+$.

Following compounds (Examples 10-60) were synthesized using the above procedure as exemplified for Example-9.

Example-10

(R)-(3-aminopiperidin-1-yl)(2-(1-(pyridin-4-ylmethyl)-1H-indol-2-yl)-3,4-dihydro-5-oxa-1,2a-diazaacenaphthylene-7-yl)methanone

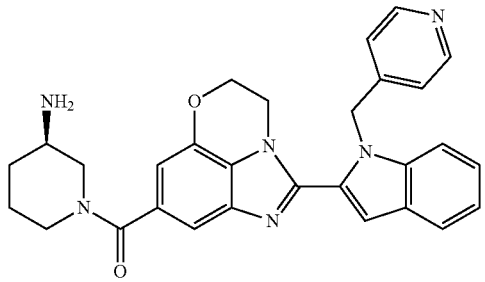 [SMILES: N[C@@H]1CCCN(C(=O)c2cc3c4c(c2)nc(-c2cc5ccccc5n2Cc2ccncc2)n4CCO3)C1]

$^1$HNMR (400 MHz, DMSO-d$_6$) δ (ppm): 8.40-8.38 (m, 2H), 7.74-7.72 (m, 1H), 7.44-7.42 (m, 1H), 7.33 (s, 1H), 7.28 (s, 1H), 7.26-7.22 (m, 1H), 7.17-7.13 (m, 1H), 7.01-6.99 (m, 2H), 6.77 (s, 1H), 6.16 (s, 2H), 4.71 (m, 2H), 4.56-4.55 (m, 2H), 4.11 (m, 2H), 3.0 (m, 2H), 2.01-1.8 (m, 3H), 1.67 (m, 1H), 1.44 (bs, 3H). MS (ESI): mass calcd. for $C_{29}H_{28}N_6O_2$, 492.23; m/z found, 493 [M+H]$^+$.

Example-11

(R)-(3-aminopiperidin-1-yl)(2-(1-(pyridine-2-ylmethyl)-1H-indol-2-yl)-3,4-dihydro-5-oxa-1,2a-diazaacenaphthylen-7-yl)methanone

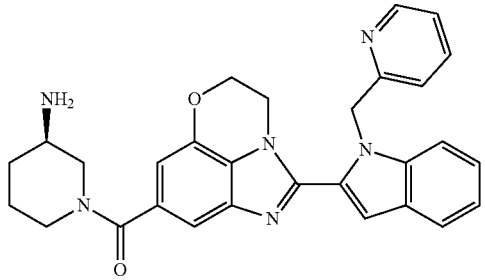 [SMILES: N[C@@H]1CCCN(C(=O)c2cc3c4c(c2)nc(-c2cc5ccccc5n2Cc2ccccn2)n4CCO3)C1]

¹HNMR (400 MHz, DMSO-d$_6$) δ (ppm): 8.43 (d, J=4 Hz, 1H), 7.72-7.70 (m, 1H), 7.61-7.57 (m, 1H), 7.46-7.44 (m, 1H), 7.22 (s, 2H), 7.27 (s, 1H), 7.19-7.09 (m, 3H), 6.72 (s, 1H), 6.17 (s, 2H), 4.68 (m, 2H), 4.55 (m, 2H), 3.94 (m, 2H), 2.87 (m, 2H), 1.84-1.81 (m, 2H), 1.62 (m, 3H), 1.40 (bs, 2H). MS (ESI): mass calcd. for C$_{29}$H$_{28}$N$_6$O$_2$, 492.23; m/z found, 493.2 [M+H]$^+$.

Example-12

(R)-(3-aminopiperidin-1-yl)(2-(3-ethylbenzo[b]thiophen-2-yl)-3,4-dihydro-5-oxa-1,2a-diazaacenaphthylen-7-yl)methanone

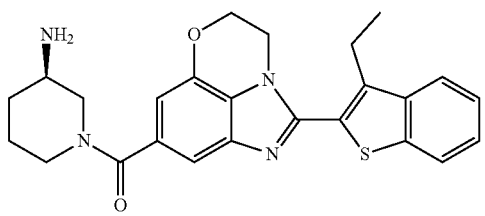 [SMILES: CCc1c(-c2nc3cc(C(=O)N4CCC[C@@H](N)C4)cc4c3n2CCO4)sc2ccccc12]

¹HNMR (400 MHz, DMSO-d$_6$) δ (ppm): 8.08 (m, 1H), 8.06-7.98 (m, 1H), 7.53-7.49 (m, 2H), 7.36 (s, 1H), 6.79 (s, 1H), 4.48 (d, J=8 Hz, 4H), 4.00 (bs, 2H), 3.28 (m, 2H), 3.22 (m, 3H), 1.95 (m, 1H), 1.70 (m, 1H), 1.48 (m, 2H), 1.31-1.21 (m, 5H). MS (ESI): mass calcd. for C$_{25}$H$_{26}$N$_4$O$_2$S, 446.57; m/z found, 447.2 [M+H]$^+$.

Example-13

(R)-(3-aminopiperidin-1-yl)(2-(1-(4-chlorobenzyl)-1H-indol-2-yl)-3,4-dihydro-5-oxa-1,2a-diazaacenaphthylene-7-yl)methanone

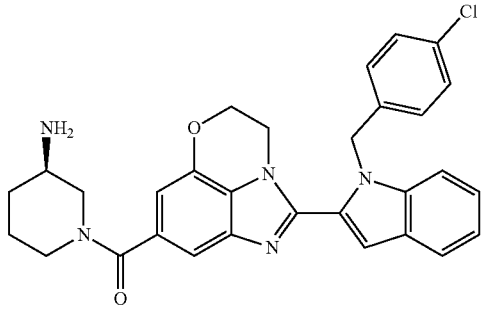

¹HNMR (400 MHz, DMSO-d$_6$) δ (ppm): 7.71 (d, J=8 Hz, 1H), 7.47-7.45 (m, 1H), 7.28-7.21 (m, 4H), 7.15-7.09 (m, 4H), 6.74 (s, 1H), 6.09 (s, 2H), 4.68 (m, 2H), 4.55 (m, 2H), 2.92 (m, 2H), 2.73 (m, 2H), 1.97 (m, 2H), 1.88 (m, 2H), 1.62 (m, 3H). MS (ESI): mass calcd. for C$_{30}$H$_{28}$ClN$_5$O$_2$, 525.19; m/z found, 526.2 [M+H]$^+$.

Example-14

(R)-(3-aminopiperidin-1-yl)(2-(1-(2-fluorobenzyl)-1H-indol-2-yl)-3,4-dihydro-5-oxa-1,2a-diazaacenaphthylene-7-yl)methanone

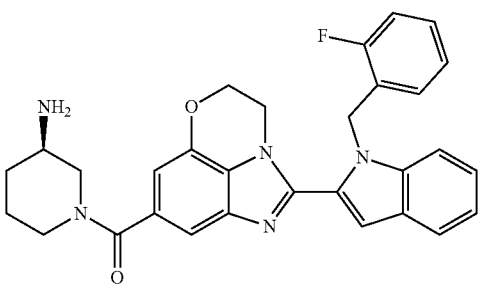 [SMILES: N[C@@H]1CCCN(C(=O)c2cc3c4c(c2)nc(-c2cc5ccccc5n2Cc2ccccc2F)n4CCO3)C1]

¹HNMR (400 MHz, DMSO-d$_6$) δ (ppm): 7.72 (d, J=8 Hz, 1H), 7.46 (d, J=8 Hz, 1H), 7.29-7.26 (m, 1H), 7.24-7.18 (m, 3H), 7.16-7.12 (m, 2H), 6.96-6.93 (m, 1H), 6.73 (s, 1H), 6.67-6.63 (bs, 1H), 6.17 (s, 2H), 4.66 (m, 2H), 4.55 (m, 2H), 4.00 (m, 2H), 2.48 (m, 1H), 2.89 (s, 1H), 2.00 (m, 2H), 1.85 (m, 1H), 1.62 (m, 1H), 1.41-1.39 (m, 1H), 1.22 (m, 2H). MS (ESI): mass calcd. for C$_{30}$H$_{28}$FN$_5$O$_2$, 509.22; m/z found, 510.2[M+H]$^+$.

Example-15

(R)-(3-aminopiperidin-1-yl)(2-(1-(4-fluorobenzyl)-1H-indol-2-yl)-3,4-dihydro-5-oxa-1,2a-diazaacenaphthylen-7-yl)methanone

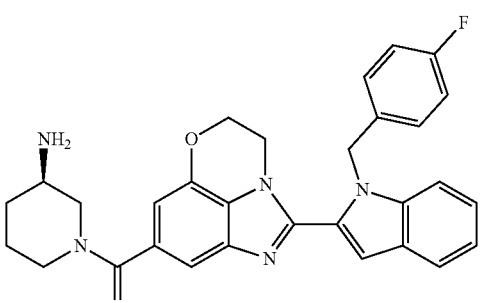

¹HNMR (400 MHz, DMSO-d$_6$) δ (ppm): 7.71 (d, J=8 Hz, 1H), 7.50-7.48 (d, J=8 Hz, 1H), 7.25 (s, 2H), 7.22 (m, 1H), 7.16-7.10 (m, 3H), 7.05 (t, J=8.8 Hz, 2H), 6.73 (s, 1H), 6.08 (s, 2H), 4.67 (m, 2H), 4.56 (m, 2H), 4.01 (m, 2H), 2.88 (m, 2H), 1.98-1.97 (m, 2H), 1.82 (m, 1H), 1.70 (m, 2H), 1.41-1.31 (m, 2H). MS (ESI): mass calcd. for C$_{30}$H$_{28}$FN$_5$O$_2$, 509.59; m/z found, 510.2 [M+H]$^+$.

Example-16

(R)-(3-aminopiperidin-1-yl)(2-(1-(pyridin-3-ylmethyl)-1H-indol-2-yl)-3,4-dihydro-5-oxa-1,2a-diazaacenaphthylen-7-yl)methanone

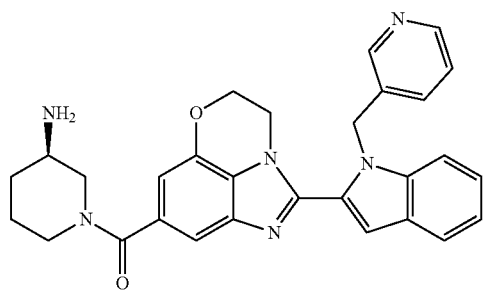 [SMILES: N[C@@H]1CCCN(C(=O)c2cc3c4c(c2)nc(-c2cc5ccccc5n2Cc2cccnc2)n4CCO3)C1]

$^1$HNMR (400 MHz, DMSO-d$_6$) δ (ppm): 8.40 (s, 1H), 8.36 (d, J=3.6 Hz, 1H), 7.70 (d, J=8 Hz, 1H), 7.54 (d, J=8 Hz, 1H), 7.46 (d, J=8 Hz, 1H), 7.29-7.12 (m, 4H), 7.16-7.12 (m, 1H), 6.74 (s, 1H), 6.14 (s, 2H), 4.68-4.55 (m, 4H), 4.12 (m, 2H), 2.90 (m, 1H), 2.71-2.65 (m, 2H), 1.88-1.83 (m, 2H), 1.63 (m, 1H), 1.42-1.12 (m, 3H). MS (ESI): mass calcd. for C$_{29}$H$_{28}$N$_6$O$_2$, 492.58; m/z found, 493.4 [M+H]$^+$.

Example-17

(R)-(3-aminopiperidin-1-yl)(2-(1-(cyclopropylmethyl)-5,6-dimethoxy-1H-indol-2-yl)-3,4-dihydro-5-oxa-1,2a-diazaacenaphthylen-7-yl)methanone

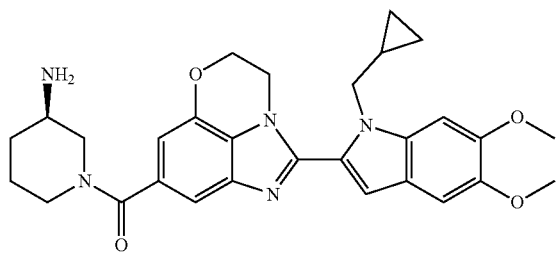 [SMILES: COc1cc2cc(-c3nc4cc(C(=O)N5CCC[C@@H](N)C5)cc5c4n3CCO5)n(CC3CC3)c2cc1OC]

$^1$HNMR (400 MHz, DMSO-d$_6$) δ (ppm): 7.25 (s, 1H), 7.18 (s, 1H), 7.13 (s, 1H), 6.99 (s, 1H), 6.72 (s, 1H), 4.68 (d, J=6.4 Hz, 2H), 4.61 (s, 2H), 4.54 (s, 2H), 3.85 (s, 3H), 3.78 (s, 3H), 4.30-4.00 (s, 1H), 3.15 (d, J=4.0 Hz, 1H), 2.92 (bs, 2H), 2.70 (bs, 2H), 1.91 (bs, 1H), 1.81 (bs, 1H), 1.65 (bs, 1H), 1.44 (bs, 2H), 0.84 (s, 1H), 0.33-0.28 (m, 4H). MS (ESI): mass calcd. for C$_{29}$H$_{33}$FN$_5$O$_4$, 515.61; m/z found, 516.3[M+H]$^+$.

Example-18

(R)-(3-aminopiperidin-1-yl)(2-(1-benzyl-1H-indol-2-yl)-3,4-dihydro-5-oxa-1,2a-diazaacenaphthylen-7-yl)methanone

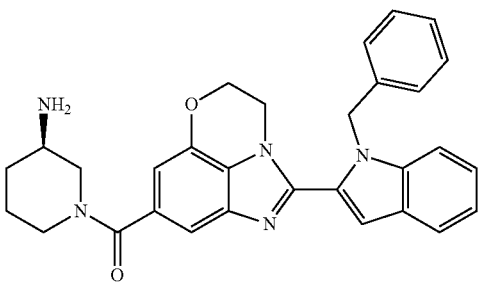 [SMILES: N[C@@H]1CCCN(C(=O)c2cc3c4c(c2)nc(-c2cc5ccccc5n2Cc2ccccc2)n4CCO3)C1]

$^1$HNMR (400 MHz, DMSO-d$_6$) δ (ppm): 7.70 (d, J=8.0 Hz, 1H), 7.47 (d, J=8.0 Hz, 1H), 7.26-7.10 (m, 7H), 7.06 (d, J=7.2 Hz, 2H), 6.73 (s, 1H), 6.11 (s, 2H), 4.66 (d, J=5.0 Hz, 2H), 4.55 (d, J=5.0 Hz, 2H), 3.65 (bs, 1H), 2.88 (bs, 1H), 2.65 (bs, 1H), 1.98 (d, J=7.6 Hz, 1H), 1.83 (d, J=11.6 Hz, 1H), 1.63 (bs, 1H), 1.41-1.22 (m, 4H), 0.84 (s, 1H). MS (ESI): mass calcd. for C$_{30}$H$_{29}$N$_5$O$_2$, 491.6; m/z found, 492.2 (M+H)$^+$.

Example-19

(R)-(3-aminopiperidin-1-yl)(2-(1-(4-methoxybenzyl)-1H-indol-2-yl)-3,4-dihydro-5-oxa-1,2a-diazaacenaphthylen-7-yl)methanone

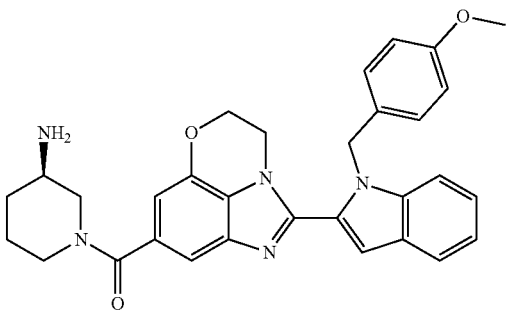 [SMILES: COc1ccc(Cn2c(-c3nc4cc(C(=O)N5CCC[C@@H](N)C5)cc5c4n3CCO5)cc3ccccc32)cc1]

$^1$HNMR (400 MHz, DMSO-d$_6$) δ (ppm): 7.68 (d, J=8 Hz, 1H), 7.45 (d, J=8 Hz, 1H), 7.25 (s, 1H), 7.23-7.22 (m, 2H), 7.12 (t, J=7.2 Hz, 1H), 7.03 (d, J=8.4 Hz, 2H), 6.76 (s, 1H), 6.74 (s, 2H), 6.01 (bs, 2H), 4.65-4.55 (m, 2H), 4.55-4.54 (m, 2H), 4.12 (bs, 2H), 3.80 (s, 3H) 2.89 (m, 1H), 2.65 (m, 1H), 1.87 (m, 1H), 1.82 (m, 1H), 1.63 (m, 1H), 1.41 (m, 1H), 1.21-1.20 (m, 3H). MS (ESI): mass calcd. for C$_{31}$H$_{31}$N$_5$O$_3$, 521.62; m/z found, 522.2 [M+H]$^+$.

Example-20

Synthesis of (R)-(3-aminopiperidin-1-yl)(2-(1-(2-methoxyethyl)-1H-indol-2-yl)-3,4-dihydro-5-oxa-1,2a-diazaacenaphthylen-7-yl)methanone

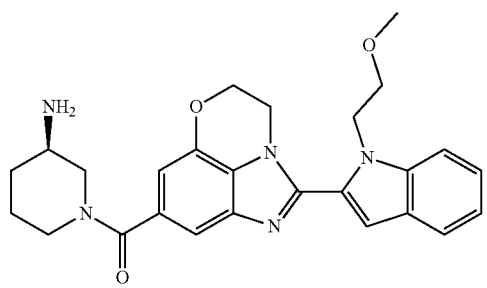 [SMILES: COCCn1c(-c2nc3cc(C(=O)N4CCC[C@@H](N)C4)cc4c3n2CCO4)cc2ccccc21]

$^1$HNMR (400 MHz, DMSO-d$_6$) δ (ppm): 7.69-7.63 (m, 2H), 7.31-7.27 (m, 2H), 7.16-7.12 (m, 2H), 6.76 (s, 1H), 4.91 (t, J=5.7 Hz, 2H), 4.64 (t, J=3.44 Hz, 2H), 4.56 (t, J=4.24 Hz, 2H), 4.16 (bs, 2H), 3.66 (t, J=5.28 Hz, 2H), 3.41 (bs, 1H), 3.09 (s, 3H), 2.91 (bs, 1H), 2.70 (m, 1H), 2.08 (s, 1H), 1.87 (d, J=12.04 Hz, 2H), 1.76-1.68 (m, 1H), 1.50-1.45 (m, 1H), 1.26-1.23 (m, 1H). MS (ESI): mass calcd for. C$_{26}$H$_{29}$N$_5$O$_3$ for 459.23; found m/z 460.10 [M+H]$^+$.

Example-21

(R)-(3-aminopiperidin-1-yl)(2-(6-methoxy-1-(2-methoxyethyl)-1H-indol-2-yl)-3,4-dihydro-5-oxa-1,2a-diazaacenaphthylen-7-yl)methanone

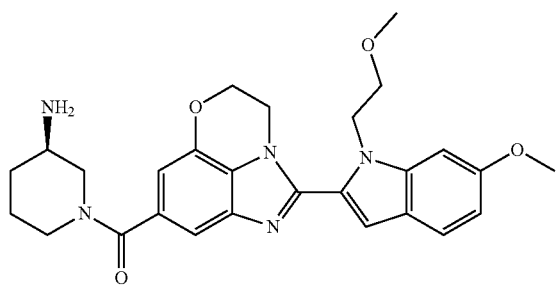 [SMILES: COCCn1c(-c2nc3cc(C(=O)N4CCC[C@@H](N)C4)cc4c3n2CCO4)cc2ccc(OC)cc21]

$^1$HNMR (400 MHz, DMSO-d$_6$) δ (ppm): 7.54 (d, J=8.64 Hz, 1H), 7.34 (s, 1H), 7.07 (s, 1H), 6.98 (s, 1H), 6.82-6.81 (m, 2H), 4.83 (d, J=11.12 Hz, 2H), 4.57 (s, 4H), 3.89 (s, 3H), 3.61 (t, J=5.04 Hz, 2H), 3.06 (s, 3H), 2.87 (d, J=10.28 Hz, 2H), 2.04 (d, J=11.80 Hz, 1H), 1.89-1.59 (m, 4H), 1.43-1.37 (m, 2H), 1.33-1.29 (m, 2H). MS (ESI): mass calcd for C$_{27}$H$_{31}$N$_5$O$_4$ 489.19; found m/z 490.27 [M+1]$^+$.

Example-22

(R)-(3-aminopiperidin-1-yl)(2-(1-(2-hydroxyethyl)-1H-indol-2-yl)-3,4-dihydro-5-oxa-1,2a-diazaacenaphthylen-7-yl)methanone

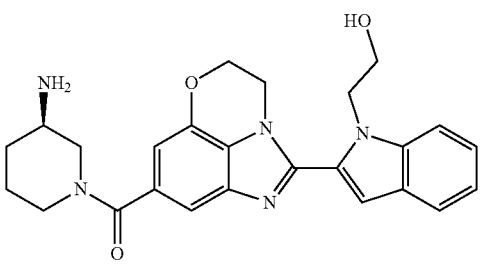 [SMILES: N[C@@H]1CCCN(C(=O)c2cc3c4c(c2)nc(-c2cc5ccccc5n2CCO)n4CCO3)C1]

$^1$HNMR (400 MHz, DMSO-d$_6$) δ (ppm): 7.69 (d, J=7.88 Hz, 1H), 7.65 (d, J=7.91 Hz, 1H), 7.31-7.27 (m, 2H), 7.16-7.12 (m, 2H), 6.76 (s, 1H), 4.99 (bs, 2H), 4.77 (t, J=5.36 Hz, 2H), 4.63 (d, J=3.84 Hz, 2H), 4.56 (s, 2H), 3.74 (t, J=5.52 Hz, 2H), 2.91 (s, 1H), 2.71-2.65 (m, 1H), 1.87 (s, 4H), 1.84 (s, 1H), 1.71-1.65 (m, 1H), 1.44-1.41 (m 1H), 1.24-1.22 (m, 1H). MS (ESI): mass calcd for C$_{25}$H$_{27}$N$_5$O$_3$ 445.21; found m/z 446.24 [M+H]$^+$.

Example-23

(R)-(3-aminopiperidin-1-yl)(2-(1-(cyclopropylmethyl)-6-methoxy-1H-indol-2-yl)-3,4-dihydro-5-oxa-1,2a-diazaacenaphthylen-7-yl)methanone

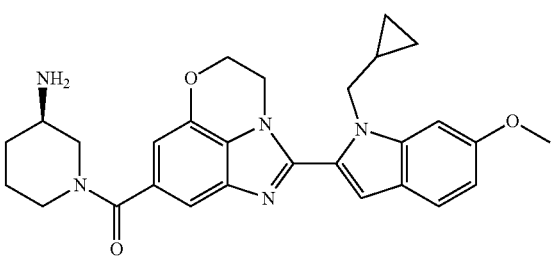 [SMILES: COc1ccc2cc(-c3nc4cc(C(=O)N5CCC[C@@H](N)C5)cc5c4n3CCO5)n(CC3CC3)c2c1]

$^1$HNMR (400 MHz, DMSO-d$_6$) δ (ppm): 7.56 (d, J=8.64 Hz, 1H), 7.28 (s, 1H), 7.17 (s, 1H), 7.09 (s, 1H), 6.79 (d, J=7.4 Hz, 1H), 6.74 (s, 1H), 4.70 (d, J=6.68 Hz, 2H), 4.64 (s, 2H), 4.55 (s, 2H), 4.15 (bs, 1H), 3.85 (s, 3H), 3.38 (d, J=6.92 Hz, 1H), 2.92 (bs, 2H), 2.07 (m, 2H), 1.86 (d, J=9.28 Hz, 1H), 1.67 (bs, 1H), 1.45 (m, 1H), 1.23 (m, 2H), 1.09 (t, J=7.00 Hz, 1H), 0.35-0.30 (m, 4H). MS (ESI): mass calcd. for C$_{28}$H$_{31}$N$_5$O$_3$ 485.24; found m/z 486.20 [M+H]$^{+1}$.

Example-24

(R)-(3-aminopiperidin-1-yl)(2-(1-((3-fluoropyridin-4-yl)methyl)-1H-indol-2-yl)-3,4-dihydro-5-oxa-1,2a-diazaacenaphthylen-7-yl)methanone

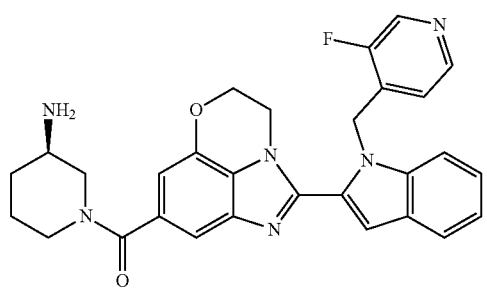 [SMILES: N[C@@H]1CCCN(C(=O)c2cc3c4c(c2)nc(-c2cc5ccccc5n2Cc2ccncc2F)n4CCO3)C1]

$^1$HNMR (400 MHz, DMSO-d$_6$) δ (ppm): 8.53 (s, 1H), 8.18 (d, J=4.72 Hz, 1H), 7.77 (d, J=7.84 Hz, 1H), 7.52 (d, J=8.28 Hz, 1H), 7.36 (s, 1H), 7.31 (t, J=7.32 Hz, 1H), 7.21-7.18 (m, 2H), 6.73 (s, 1H), 6.55 (t, J=5.64 Hz, 1H), 6.25 (s, 2H), 4.71 (t, J=4.16 Hz, 2H), 4.56 (t, J=3.08 Hz, 2H), 2.88 (bs, 1H), 2.63-2.57 (m, 2H), 1.84 (d, J=11.8 Hz, 2H), 1.64 (bs, 2H), 1.41 (m, 2H), 1.23-1.19 (m, 2H). MS (ESI): mass calcd. for C$_{29}$H$_{27}$FN$_6$O$_2$ 511.23; found m/z 511.14 [M+H]$^+$.

Example-25

(R)-(3-aminopiperidin-1-yl)(2-(1-(pyrazin-2-ylmethyl)-1H-indol-2-yl)-3,4-dihydro-5-oxa-1,2a-diazaacenaphthylen-7-yl)methanone

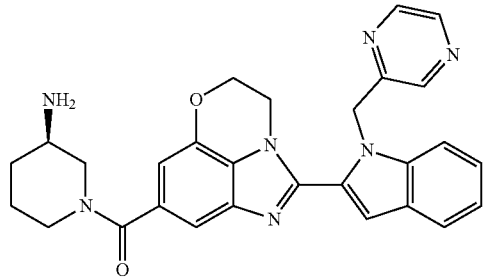 [SMILES: N[C@@H]1CCCN(C(=O)c2cc3c4c(c2)nc(-c2cc5ccccc5n2Cc2cnccn2)n4CCO3)C1]

$^1$HNMR (400 MHz, DMSO-d$_6$): δ (ppm): 8.49 (d, J=13.1 Hz, 1H), 8.41 (s, 1H), 7.73 (d, J=7.4 Hz, 1H), 7.57 (d, J=7.1 Hz, 1H), 7.30-7.24 (m, 3H), 7.18-7.16 (m, 2H), 6.75 (s, 1H), 6.25 (s, 2H), 4.72 (s, 2H), 4.56 (t, 2H), 4.15 (bs, 2H), 2.90 (bs, 2H), 2.69-2.63 (m, 1H), 1.84 (bs, 2H), 1.64 (bs, 2H), 1.42 (bs, 1H), 1.23-1.22 (m, 1H). MS (ESI): mass calcd. for C$_{28}$H$_{27}$N$_7$O$_2$ 493.12; found m/z 494.10 [M+H]$^+$.

Example-26

(R)-(3-aminopiperidin-1-yl)(2-(1-((3-fluoropyridin-2-yl)methyl)-1H-indol-2-yl)-3,4-dihydro-5-oxa-1,2a-diazaacenaphthylen-7-yl)methanone

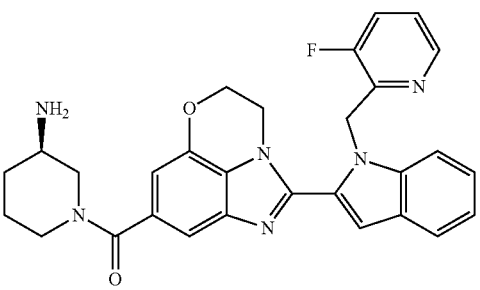 [SMILES: N[C@@H]1CCCN(C(=O)c2cc3c4c(c2)nc(-c2cc5ccccc5n2Cc2ncccc2F)n4CCO3)C1]

$^1$HNMR (400 MHz, DMSO-d6): δ (ppm): 8.12 (d, J=4.16 Hz, 1H), 7.70 (d, J=7.92 Hz, 1H), 7.62 (t, J=9.2 Hz, 1H), 7.53 (d, J=8.12 Hz, 1H), 7.28-7.20 (m, 4H), 7.13 (t, J=7.16 Hz, 1H), 6.72 (s, 1H), 6.28 (s, 2H), 4.65 (t, J=4.20 Hz, 2H), 4.55 (t, J=5.52 Hz, 2H), 4.18 (bs, 2H), 2.87 (bs, 1H), 2.61 (m, 2H), 1.84 (d, J=10.1 Hz, 2H), 1.75-1.66 (m, 1H), 1.45-1.41 (m, 1H), 1.23-1.19 (m, 2H). MS (ESI): mass calcd. for C$_{29}$H$_{27}$FN$_6$O$_2$ 510.22; found m/z 511.18 [M+H]$^+$.

Example-27

(R)-(3-aminopiperidin-1-yl)(2-(1-(pyrimidin-2-ylmethyl)-1H-indol-2-yl)-3,4-dihydro-5-oxa-1,2a-diazaacenaphthylen-7-yl)methanone

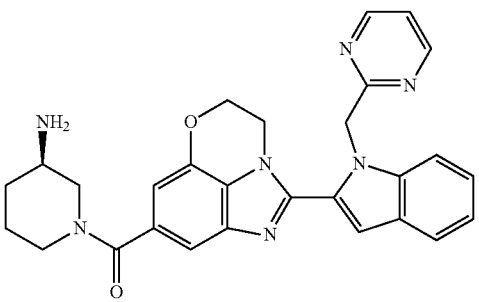 [SMILES: N[C@@H]1CCCN(C(=O)c2cc3c4c(c2)nc(-c2cc5ccccc5n2Cc2ncccn2)n4CCO3)C1]

$^1$HNMR (400 MHz, DMSO-d6): δ (ppm): 8.62 (d, J=4.84 Hz, 2H), 7.20 (d, J=7.7 Hz, 1H), 7.43 (d, J=8.2 Hz, 1H), 7.29-7.26 (m, 2H), 7.23-7.20 (t, J=7.28 Hz, 1H), 7.16-7.12 (m, 2H), 6.71 (s, 1H), 6.33 (s, 2H), 4.69 (t, J=6.24 Hz, 2H), 4.55 (t, J=4.88 Hz, 2H), 4.17 (bs, 1H), 3.54 (bs, 1H), 2.87 (bs, 1H), 2.61 (m, 1H), 1.83 (d, J=10.96 Hz, 3H), 1.63 (s, 1H), 1.41-1.38 (m, 1H), 1.23-1.19 (m, 2H). MS (ESI):): mass calcd. for C$_{28}$H$_{27}$N$_7$O$_2$ 493.22; found m/z 494.23 [M+H]$^+$.

Example-28

(R)-(3-aminopiperidin-1-yl)(2-(1-(cyclopropylmethyl)-6-fluoro-1H-indol-2-yl)-3,4-dihydro-5-oxa-1,2a-diazaacenaphthylen-7-yl)methanone

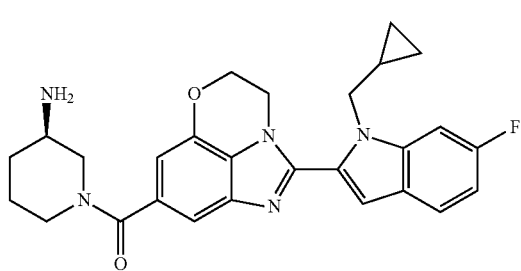 [SMILES: N[C@@H]1CCCN(C(=O)c2cc3c4c(c2)nc(-c2cc5ccc(F)cc5n2CC2CC2)n4CCO3)C1]

$^1$HNMR (400 MHz, DMSO-d$_6$) δ (ppm): 7.71-7.68 (m, 1H), 7.58 (d, J=7.9 Hz, 1H), 7.29 (s, 1H), 7.19 (s, 1H), 7.01 (t, J=9.2 Hz, 1H), 6.75 (s, 1H), 4.68-4.65 (m, 4H), 4.51 (s, 2H), 4.21 (bs, 1H), 3.61 (bs, 1H), 2.91 (bs, 1H), 2.63-2.61 (m, 1H), 1.86-1.84 (m, 2H), 1.66 (bs, 1H), 1.64-1.42 (m, 3H), 1.25-1.23 (m, 2H), 0.34-0.28 (m, 4H). MS (ESI): C$_{27}$H$_{28}$FN$_5$O$_2$ 473.12; found m/z 474.20 [M+H]$^+$.

Example-29

(R)-(3-aminopiperidin-1-yl)(2-(1-(pyrimidin-5-ylmethyl)-1H-indol-2-yl)-3,4-dihydro-5-oxa-1,2a-diazaacenaphthylen-7-yl)methanone

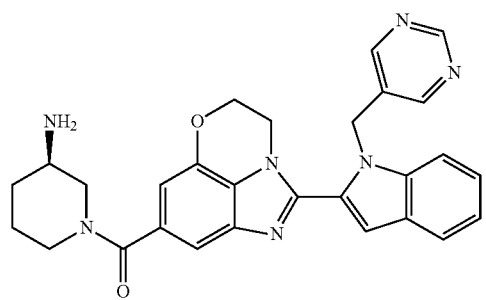 [SMILES: N[C@@H]1CCCN(C(=O)c2cc3c4c(c2)nc(-c2cc5ccccc5n2Cc2cncnc2)n4CCO3)C1]

$^1$HNMR (400 MHz, DMSO-d$_6$) δ (ppm): 9.03 (s, 1H), 8.65 (s, 2H), 7.75 (d, J=7.8 Hz, 1H), 7.63 (d, J=7.6 Hz, 1H), 7.33-7.26 (m, 3H), 7.18 (t, J=7.7 Hz, 1H), 6.76 (s, 1H), 6.17 (s, 2H), 4.72 (bs, 2H), 4.57 (bs, 2H), 4.18 (bs, 2H), 3.60 (bs, 2H), 3.17 (d, J=4.8 Hz, 1H), 2.88 (bs, 1H), 2.66-2.62 (m, 1H), 1.83 (bs, 1H), 1.65 (bs, 1H), 1.39-1.33 (bs, 1H), 1.23-1.22 (m, 1H). MS (ESI): mass calcd. for C$_{28}$H$_{27}$N$_7$O$_2$ 493.12; found m/z 494.27 [M+H]$^+$.

Example-30

(R)-(3-aminopiperidin-1-yl)(2-(1-(pyridazin-3-ylmethyl)-1H-indol-2-yl)-3,4-dihydro-5-oxa-1,2a-diazaacenaphthylen-7-yl)methanone

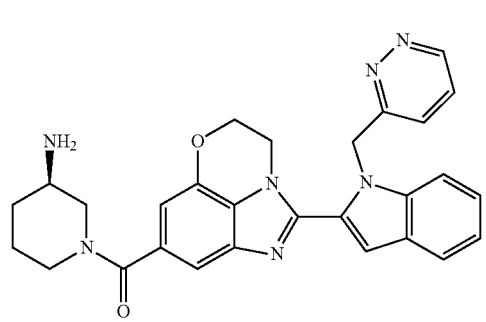 [SMILES: N[C@@H]1CCCN(C(=O)c2cc3c4c(c2)nc(-c2cc5ccccc5n2Cc2cccnn2)n4CCO3)C1]

$^1$HNMR (400 MHz, DMSO-d$_6$) δ (ppm): 9.07 (d, J=3.9 Hz, 1H), 7.74 (d, J=7.9 Hz, 1H), 7.58-7.52 (m, 2H), 7.36 (d, J=8.1 Hz, 1H), 7.32 (s, 1H), 7.27 (d, J=7.1 Hz, 1H), 7.23 (s, 1H), 7.16 (t, J=7.7 Hz, 1H), 6.77 (s, 1H), 6.37 (s, 2H), 4.71 (bs, 2H), 4.57 (bs, 2H), 4.15 (bs, 1H), 3.54 (bs, 1H), 2.88 (bs, 1H), 2.66-2.62 (m, 2H), 1.96 (bs, 2H), 1.85-1.82 (m, 1H), 1.64 (bs, 1H), 1.41-1.39 (m, 1H), 1.25-1.20 (m, 1H). MS (ESI): mass calcd. for C$_{28}$H$_{27}$N$_7$O$_2$ 493.12; found m/z 494.24 [M+H]$^+$.

Example-31

(R)-(3-aminopiperidin-1-yl)(2-(1-isobutyl-1H-indol-2-yl)-3,4-dihydro-5-oxa-1,2a-diazaacenaphthylen-7-yl)methanone

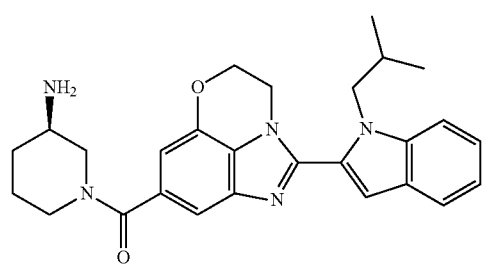 [SMILES: CC(C)Cn1c(-c2nc3cc(C(=O)N4CCC[C@@H](N)C4)cc4c3n2CCO4)cc2ccccc21]

$^1$HNMR (400 MHz, DMSO-d$_6$) δ (ppm): 7.68 (d, J=8.1 Hz, 1H), 7.64 (d, J=7.9 Hz, 1H), 7.30-7.26 (m, 2H), 7.16-7.11 (m, 2H), 6.75 (s, 1H), 4.64 (m, 4H), 4.56 (s, 2H), 4.17 (bs, 1H), 3.62 (bs, 1H), 2.90 (bs, 1H), 2.66 (m, 1H), 2.1-2.04 (m, 1H), 1.86 (d, J=9.84 Hz, 3H), 1.65 (bs, 1H), 1.43 (d, J=9.68 Hz, 1H), 1.23 (m, 2H), 0.73 (d, J=6.6 Hz, 6H). MS (ESI): mass calcd. for C$_{27}$H$_{31}$N$_5$O$_2$ 457.25; found m/z 458.28 [M+H]$^+$.

Example-32

(R)-(3-aminopiperidin-1-yl)(2-(1-(cyclopropylmethyl)-5,6-difluoro-1H-indol-2-yl)-3,4-dihydro-5-oxa-1,2a-diazaacenaphthylen-7-yl)methanone

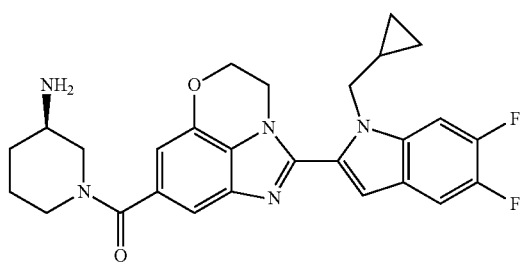 [SMILES: N[C@@H]1CCCN(C(=O)c2cc3c4c(c2)nc(-c2cc5cc(F)c(F)cc5n2CC2CC2)n4CCO3)C1]

¹HNMR (400 MHz, DMSO-d$_6$) δ (ppm): 7.90-7.86 (m, 1H), 7.70 (t, J=7.7 Hz, 1H), 7.30 (s, 1H), 7.17 (s, 1H), 6.76 (s, 1H), 4.68-4.62 (m, 4H), 4.56 (s, 2H), 4.24 (bs, 1H), 3.66 (bs, 1H), 2.98-2.89 (m, 2H), 2.67-2.63 (m, 1H), 1.86-1.84 (d, J=9.7 Hz, 1H), 1.67 (m, 2H), 1.23 (m, 3H), 1.44 (m, 1H), 0.34 (d, J=7.2 Hz, 2H), 0.29 (m, 2H). MS (ESI): mass calcd. for C$_{27}$H$_{27}$F$_2$N$_5$O$_2$ 491.12; found m/z 492.25 [M+H]$^+$.

Example-33

(R)-(3-aminopiperidin-1-yl)(2-(1-((3-fluoropyridin-2-yl)methyl)-6-methoxy-1H-indol-2-yl)-3,4-dihydro-5-oxa-1,2a-diazaacenaphthylen-7-yl)methanone

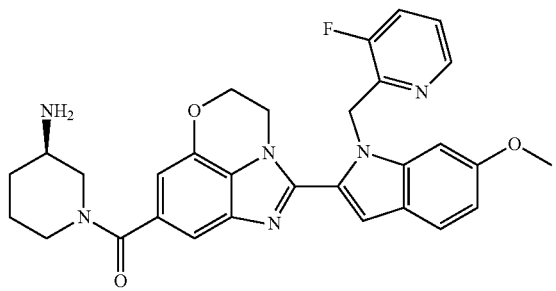 [SMILES: COc1ccc2cc(-c3nc4cc(C(=O)N5CCC[C@@H](N)C5)cc5c4n3CCO5)n(Cc3ncccc3F)c2c1]

¹HNMR (400 MHz, DMSO-d$_6$) δ (ppm): 8.14 (d, J=4.52 Hz, 1H), 7.62 (t, J=9.0 Hz, 1H), 7.57 (d, J=9.6 Hz, 1H), 7.30-7.28 (m, 1H), 7.17 (s, 1H), 7.08 (s, 1H), 6.81 (d, J=1.9 Hz, 2H), 6.78 (s, 1H), 6.27 (s, 2H), 4.64 (d, J=4.32 Hz, 2H), 4.54 (d, J=4.0 Hz, 2H), 4.08 (bs, 2H), 3.76 (s, 3H), 3.20-3.10 (m, 4H), 2.00-1.97 (m, 2H), 1.72-1.71 (m, 1H), 1.55-1.53 (m, 2H). MS (ESI): mass calcd. for C$_{30}$H$_{29}$FN$_6$O$_3$ 540.60; found m/z 541.29 [M+H]$^+$.

Example-34

(R)-(3-aminopiperidin-1-yl)(2-(7-chloro-1-((3-fluoropyridin-2-yl)methyl)-1H-indol-2-yl)-3,4-dihydro-5-oxa-1,2a-diazaacenaphthylen-7-yl)methanone

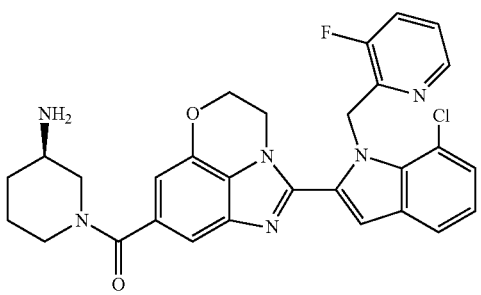 [SMILES: N[C@@H]1CCCN(C(=O)c2cc3c4c(c2)nc(-c2cc5cccc(Cl)c5n2Cc2ncccc2F)n4CCO3)C1]

¹HNMR (400 MHz, DMSO-d$_6$) δ (ppm): 8.06 (d, J=4.3 Hz, 1H), 7.22-7.63 (m, 2H), 7.34 (s, 1H), 7.28-7.22 (m, 3H), 7.12 (t, J=7.6 Hz, 1H), 6.74 (m, 1H), 6.62 (s, 2H), 4.63 (s, 2H), 4.53 (s, 2H), 4.01 (bs, 1H), 3.75 (bs, 1H), 2.88 (bs, 1H), 2.66 (bs, 1H), 1.83 (d, J=10.2 Hz, 2H), 1.68 (m, 2H), 1.42 (s, 1H), 1.26-1.23 (m, 2H). MS (ESI): mass calcd. for C$_{29}$H$_{26}$ClFN$_6$O$_2$ 544.18; found m/z 545.27 [M+H]$^+$.

Example-35

(R)-(3-aminopiperidin-1-yl)(2-(6-fluoro-1-((3-fluoropyridin-2-yl)methyl)-1H-indol-2-yl)-3,4-dihydro-5-oxa-1,2a-diazaacenaphthylen-7-yl)methanone

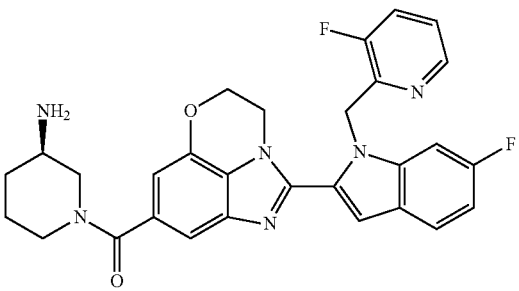 [SMILES: N[C@@H]1CCCN(C(=O)c2cc3c4c(c2)nc(-c2cc5ccc(F)cc5n2Cc2ncccc2F)n4CCO3)C1]

¹HNMR (400 MHz, DMSO-d$_6$) δ (ppm): 8.12 (d, J=7.7 Hz, 1H), 7.73-7.70 (m, 1H), 7.63 (t, J=8.1 Hz, 1H), 7.45 (d, J=9.7 Hz, 1H), 7.29-7.26 (m, 2H), 7.18 (s, 1H), 7.04 (t, J=9.6 Hz, 1H), 6.71 (s, 1H), 6.25 (s, 2H), 4.63 (s, 2H), 4.53 (s, 2H), 4.28 (bs, 1H), 2.88 (m, 1H), 2.72-2.62 (m, 2H), 1.85 (d, J=11.1 Hz, 2H), 1.65 (bs, 2H), 1.39 (m, 1H), 1.23-1.17 (m, 2H) MS (ESI): mass calcd. for C$_{29}$H$_{26}$F$_2$N$_6$O$_2$ 528.18; found m/z 529.26 [M+H]$^+$.

Example-36

(R)-(3-aminopiperidin-1-yl)(2-(7-chloro-1-(2-methoxyethyl)-1H-indol-2-yl)-3,4-dihydro-5-oxa-1,2a-diazaacenaphthylen-7-yl)methanone

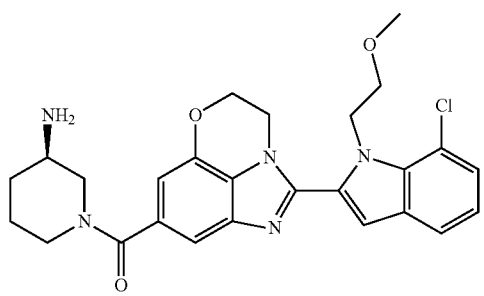 [SMILES: COCCn1c(-c2nc3cc(C(=O)N4CCC[C@@H](N)C4)cc4c3n2CCO4)cc2cccc(Cl)c21]

$^1$HNMR (400 MHz, DMSO-d$_6$) δ (ppm): 7.68 (d, J=7.8 Hz, 1H), 7.34 (d, J=7.9 Hz, 1H), 7.31 (s, 1H), 7.22 (s, 1H), 7.15 (t, J=7.7 Hz, 1H), 6.77 (s, 1H), 5.23 (t, J=5.4 Hz, 2H), 4.57 (s, 4H), 3.58 (t, J=5.48 Hz, 2H), 2.97 (s, 3H), 2.92 (bs, 2H), 2.66 (m, 2H), 1.85 (d, J=10.2 Hz, 2H), 1.66 (bs, 2H), 1.43 (m, 1H), 1.23-1.15 (m, 2H). MS (ESI): mass calcd. for C$_{26}$H$_{28}$ClN$_5$O$_3$ 493.1; found m/z 494.5 [M+H]$^+$.

Example-37

(R)-(3-aminopiperidin-1-yl)(2-(1-(4-(hydroxymethyl)benzyl)-1H-indol-2-yl)-3,4-dihydro-5-oxa-1,2a-diazaacenaphthylen-7-yl)methanone Trifluoroacetic Acid Salt

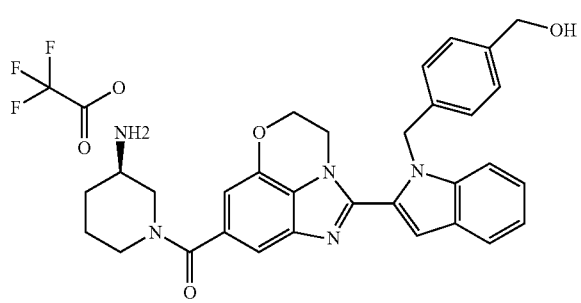

$^1$HNMR (400 MHz, DMSO-d$_6$) δ (ppm): 7.71 (d, J=7.7 Hz, 1H), 7.47 (d, J=8.3 Hz, 1H), 7.27 (s, 2H), 7.23 (t, J=7.5 Hz, 1H), 7.15-7.11 (m, 3H), 7.02 (d, J=8.0 Hz, 2H), 6.75 (s, 1H), 6.10 (s, 2H), 5.04 (bs, 1H), 4.69 (s, 2H), 4.56 (s, 2H), 4.36 (s, 2H), 2.91 (bs, 2H), 2.69 (m, 2H), 1.90-1.83 (m, 2H), 1.64 (m, 2H) 1.39 (m, 1H), 1.25-1.23 (m, 2H). MS (ESI): mass calcd. for C$_{31}$H$_{31}$N$_5$O$_3$ 521.2; found m/z 522.2 [M+H]$^+$.

Example-38

(R,E)-N-(1-(2-(1-(cyclopropylmethyl)-1H-indol-2-yl)-3,4-dihydro-5-oxa-1,2a-diazaacenaphthylene-7-carbonyl)piperidin-3-yl)-4-(dimethylamino)but-2-enamide trifluoroacetic acid salt

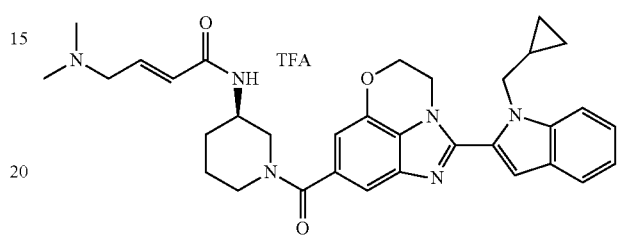

$^1$HNMR (400 MHz, DMSO-d6) δ (ppm): 9.62 (bs, 1H), 8.29 (bs, 1H), 7.68 (t, J=6.92 Hz, 2H), 7.33-7.28 (m, 2H), 7.17-7.12 (m, 2H), 6.77 (s, 1H), 6.28 (d, J=15.1 Hz, 1H), 4.71-4.66 (m, 4H), 4.56 (s, 2H), 3.86 (m, 4H), 3.24-3.06 (m, 2H), 2.76 (s, 6H), 1.90 (bs, 1H), 1.76 (m, 2H), 1.56-1.50 (m, 2H), 1.27-1.21 (m, 2H), 0.35-0.28 (m, 4H). MS (ESI)): mass calcd. for C$_{35}$H$_{39}$N$_6$F$_3$O$_4$ 566.30; m/z found 567.42.

Example-39

(R)-(3-aminopiperidin-1-yl)(2-(7-chloro-1-(4-methoxybenzyl)-1H-indol-2-yl)-3,4-dihydro-5-oxa-1,2a-diazaacenaphthylen-7-yl)methanone

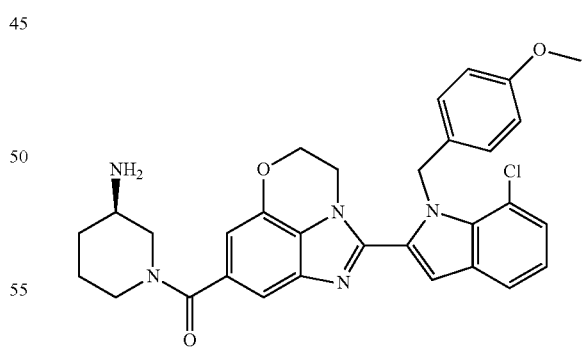

$^1$HNMR (400 MHz, DMSO-d$_6$) δ (ppm): 7.71 (d, J=7.7 Hz, 1H), 7.36 (s, 1H), 7.29 (d, J=5.4 Hz, 2H), 7.14 (t, J=7.7 Hz, 1H), 6.76 (s, 1H), 6.73-6.67 (m, 4H), 6.34 (s, 2H), 4.59 (t, J=3.9 Hz, 2H), 4.53 (t, J=3.3 Hz, 2H), 4.16 (bs, 2H), 3.61 (s, 3H), 2.89 (bs, 1H), 2.66 (bs, 2H), 1.88-1.82 (m, 2H), 1.64 (bs, 1H), 1.41-1.39 (m, 1H), 1.25-1.20 (m, 2H). MS (ESI): mass calcd. for C$_{31}$H$_{30}$ClN$_5$O$_3$ 555.18; found m/z 556.36 [M+H]$^+$.

Example-40

(R)-(3-aminopiperidin-1-yl)(2-(1-((tetrahydro-2H-pyran-4-yl)methyl)-1H-indol-2-yl)-3,4-dihydro-5-oxa-1,2a-diazaacenaphthylen-7-yl)methanone

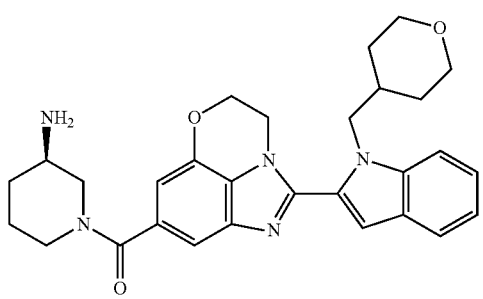 [SMILES: N[C@@H]1CCCN(C(=O)c2cc3c4c(c2)nc(-c2cc5ccccc5n2CC2CCOCC2)n4CCO3)C1]

$^1$HNMR (400 MHz, DMSO-d$_6$) δ (ppm): 7.69 (d, J=8.32 Hz, 2H), 7.33-7.28 (m, 2H), 7.17-7.12 (m, 2H), 6.76 (s, 1H), 4.74 (d, J=6.68 Hz, 2H), 4.65 (s, 2H), 4.56 (s, 2H), 4.18 (bs, 1H), 3.70 (d, J=9.4 Hz, 2H), 3.40-3.39 (m, 1H), 3.09 (t, J=10.88 Hz, 2H), 2.92 (bs, 1H), 2.66 (m, 1H), 2.08-2.05 (m, 1H), 1.85 (d, J=10.28 Hz, 2H), 1.69 (bs, 2H), 1.44-1.41 (m, 2H), 1.28-1.17 (m, 5H). MS (ESI): mass calcd. for C$_{29}$H$_{33}$N$_5$O$_3$ 499.26; found m/z 500.30 [M+H]$^+$.

Example-41

(R)-(3-aminopiperidin-1-yl)(2-(1-(cyclobutylmethyl)-1H-indol-2-yl)-3,4-dihydro-5-oxa-1,2a-diazaacenaphthylen-7-yl)methanone

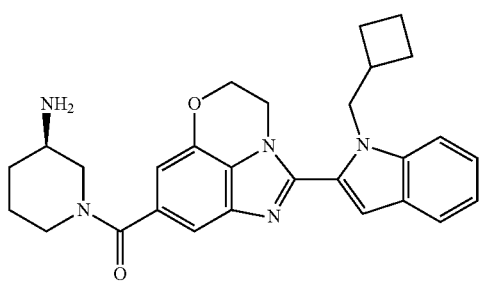 [SMILES: N[C@@H]1CCCN(C(=O)c2cc3c4c(c2)nc(-c2cc5ccccc5n2CC2CCC2)n4CCO3)C1]

$^1$HNMR (400 MHz, DMSO-d$_6$) δ (ppm): 7.67 (d, J=8.1 Hz, 2H), 7.34 (s, 1H), 7.29 (t, J=8.3 Hz, 1H), 7.14-7.11 (m, 2H), 6.78 (s, 1H), 4.87 (d, J=7.0 Hz, 2H), 4.65 (s, 2H), 4.56 (s, 2H), 4.14 (bs, 2H), 2.97 (bs, 1H), 2.81 (m, 2H), 2.72-2.65 (m, 1H), 1.88 (m, 1H), 1.77-1.66 (m, 6H), 1.63-1.57 (m, 3H), 1.51-1.45 (m, 1H), 1.23 (s, 1H). MS (ESI): mass calcd. for C$_{28}$H$_{31}$N$_5$O$_2$ 469.25; found m/z 470.31 [M+H]$^+$.

Example-42

(R)-2-(2-(7-(3-aminopiperidine-1-carbonyl)-3,4-dihydro-5-oxa 1,2adiazaacenaphthylen-2-yl)-1H-indol-1-yl)acetic Acid

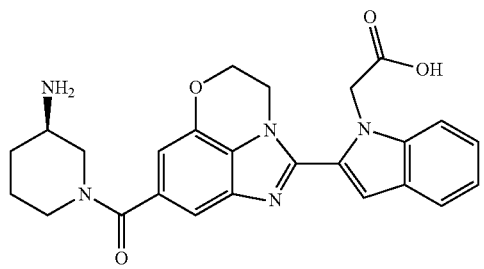 [SMILES: N[C@@H]1CCCN(C(=O)c2cc3c4c(c2)nc(-c2cc5ccccc5n2CC(=O)O)n4CCO3)C1]

$^1$HNMR (400 MHz, DMSO-d$_6$) δ (ppm): 7.67 (d, J=7.7 Hz, 1H), 7.48 (d, J=8.2 Hz, 1H), 7.31 (s, 1H), 7.24 (t, J=7.4 Hz, 1H), 7.13-7.10 (m, 2H), 6.74 (s, 1H), 5.32 (s, 2H), 4.64 (s, 2H), 4.55 (s, 2H), 4.17 (bs, 2H), 2.95-2.88 (m, 4H), 1.79 (bs, 3H), 1.25-1.08 (m, 3H). MS (ESI): mass calcd. for C$_{25}$H$_{25}$N$_5$O$_4$ 459.18; found m/z 460.21 [M+H]$^+$.

Example-43

(R)-(3-aminopiperidin-1-yl)(2-(1-(piperidin-4-ylmethyl)-1H-indol-2-yl)-3,4-dihydro-5-oxa-1,2a-diazaacenaphthylen-7-yl)methanone

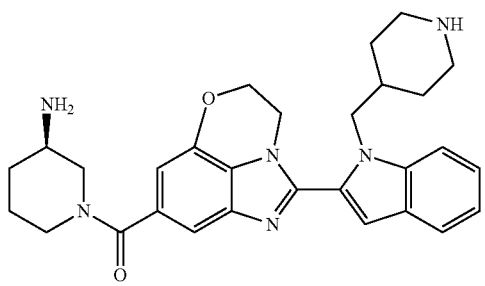 [SMILES: N[C@@H]1CCCN(C(=O)c2cc3c4c(c2)nc(-c2cc5ccccc5n2CC2CCNCC2)n4CCO3)C1]

$^1$HNMR (400 MHz, DMSO-d$_6$) δ (ppm): 7.69 (d, J=7.7 Hz, 1H), 7.64 (d, J=8.32 Hz, 1H), 7.30-7.27 (m, 2H), 7.14-7.11 (m, 2H) 6.75 (s, 1H), 4.71 (d, J=6.68 Hz, 2H), 4.64 (s, 2H), 4.56 (s, 2H), 4.10 (bs, 1H), 2.91 (bs, 1H), 2.73 (d, J=11.8 Hz, 2H), 2.66-2.64 (m, 3H), 2.19 (t, J=11.3 Hz, 2H), 1.83 (bs, 2H), 1.66 (bs, 2H), 1.44-1.41 (m, 2H), 1.25-1.23 (m, 3H), 0.97-0.89 (m, 3H). MS (ESI): mass calcd. for C$_{29}$H$_{34}$N$_6$O$_2$ 498.1; found m/z 499.29 [M+H]$^+$.

Example-44

(R)-(3-aminopiperidin-1-yl)(2-(1-(oxetan-3-ylmethyl)-1H-indol-2-yl)-3,4-dihydro-5-oxa-1,2a-diazaacenaphthylen-7-yl)methanone

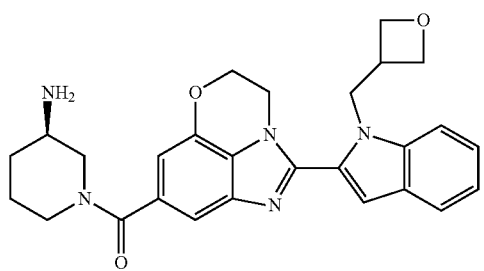 [SMILES: N[C@@H]1CCCN(C(=O)c2cc3c4c(c2)nc(-c2cc5ccccc5n2CC2COC2)n4CCO3)C1]

¹HNMR (400 MHz, DMSO-d$_6$) δ (ppm): 7.71 (d, J=7.9 Hz, 1H), 7.51 (d, J=8.4 Hz, 1H), 7.32 (s, 1H), 7.28 (t, J=7.7 Hz, 1H), 7.22 (s, 1H), 7.15 (t, J=7.9 Hz, 1H), 6.78 (s, 1H), 5.47 (s, 2H), 5.01-5.05 (m, 1H), 4.91 (s, 1H), 4.66 (s, 2H), 4.56 (s, 2H), 4.36 (s, 1H), 3.80 (s, 2H), 2.98-2.87 (m, 4H), 1.90 (m, 2H), 1.69 (m, 1H), 1.46-1.37 (m, 2H). MS (ESI): mass calcd. for $C_{27}H_{29}N_5O_3$ 471.23; found m/z 472.27 [M+H]⁺.

Example-45

(R)-(3-aminopiperidin-1-yl)(2-(1-((1-methylpiperidin-4-yl)methyl)-1H-indol-2-yl)-3,4-dihydro-5-oxa-1,2a-diazacenaphthylen-7-yl)methanone

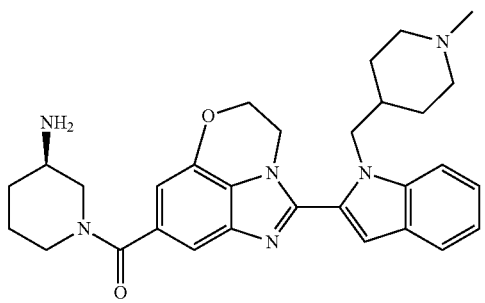 [SMILES: CN1CCC(Cn2c(-c3nc4cc(C(=O)N5CCC[C@@H](N)C5)cc5c4n3CCO5)cc3ccccc32)CC1]

¹HNMR (400 MHz, DMSO-d$_6$) δ (ppm): 7.69-7.64 (m, 2H), 7.30-7.27 (m, 2H), 7.15-7.12 (m, 2H), 6.70 (s, 1H), 4.73 (d, J=6.72 Hz, 2H), 4.65 (s, 2H), 4.56 (s, 2H), 4.15 (bs, 1H), 3.63 (bs, 1H), 2.90 (bs, 1H), 2.66-2.56 (m, 4H), 2.00 (s, 3H), 1.87-1.84 (m, 2H), 1.73-1.72 (m, 2H), 1.60 (t, J=11.3 Hz, 2H), 1.44-1.41 (m, 1H), 1.31-1.28 (m, 2H), 1.23-1.13 (m, 2H), 1.11-0.92 (m, 2H). MS (ESI): mass calcd. for $C_{30}H_{36}N_6O_2$ 512; found m/z 513.34 [M+H]⁺.

Example-46

(R)-(3-aminopiperidin-1-yl)(2-(5-fluoro-1-(4-methoxybenzyl)-1H-indol-2-yl)-3,4-dihydro-5-oxa-1,2a-diazaacenaphthylen-7-yl)methanone

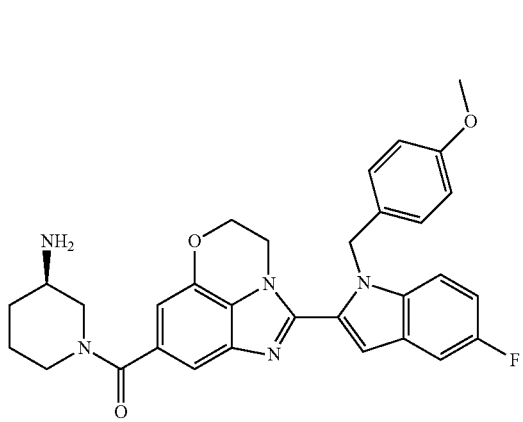 [SMILES: COc1ccc(Cn2c(-c3nc4cc(C(=O)N5CCC[C@@H](N)C5)cc5c4n3CCO5)cc3cc(F)ccc32)cc1]

¹HNMR (400 MHz, DMSO-d$_6$) δ (ppm): 7.56-7.53 (m, 1H), 7.47 (d, J=9.36 Hz, 1H), 7.28 (s, 1H), 7.22 (s, 1H), 7.10 (t, J=7.81 Hz, 1H), 7.05 (d, J=8.11 Hz, 2H), 6.77 (d, J=8.96 Hz, 3H), 6.02 (s, 2H), 4.66 (s, 2H), 4.56 (s, 2H), 4.18 (bs, 2H), 3.64 (s, 3H), 2.89 (bs, 1H), 2.62 (m, 1H), 1.83 (d, J=9.92 Hz, 2H), 1.63-1.42 (m, 3H), 1.21 (m, 2H). MS (ESI): mass calcd. for $C_{31}H_{30}FN_5O_3$ 539.23; found m/z 540.33 [M+H]⁺.

Example-47

(R)-(3-aminopiperidin-1-yl)(2-(1-(2,2-difluoroethyl)-1H-indol-2-yl)-3,4-dihydro-5-oxa-1,2a-diazaacenaphthylen-7-yl)methanone

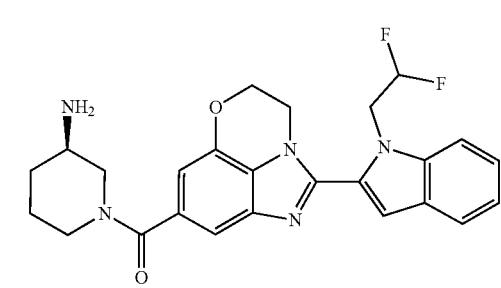 [SMILES: N[C@@H]1CCCN(C(=O)c2cc3c4c(c2)nc(-c2cc5ccccc5n2CC(F)F)n4CCO3)C1]

¹HNMR (400 MHz, DMSO-d$_6$) δ (ppm): 7.71 (t, J=7.2 Hz, 2H), 7.34 (t, J=7.1 Hz, 1H), 7.29-7.21 (m, 2H), 7.19 (t, J=7.1 Hz, 1H), 6.76 (s, 1H), 6.50 (t, J=55.4 Hz, 1H), 5.27 (t, J=13.1 Hz, 2H), 4.68 (s, 2H), 4.57 (s, 2H), 4.10 (bs, 1H), 3.70 (bs, 1H), 2.90 (m, 1H), 2.66 (m, 2H), 1.86 (t, J=10.5 Hz, 2H), 1.66 (bs, 2H), 1.44-1.41 (m, 1H), 1.24-1.21 (m, 1H). MS (ESI): mass calcd. for $C_{25}H_{25}F_2N_5O_2$ 465.12; found m/z 466.26 [M+H]⁺.

Example-48

(R)-(3-aminopiperidin-1-yl)(2-(5-fluoro-1-(2-methoxyethyl)-1H-indol-2-yl)-3,4-dihydro-5-oxa-1,2a-diazaacenaphthylen-7-yl)methanone

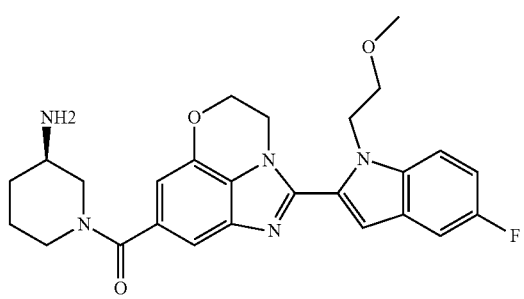 [SMILES: COCCn1c(-c2nc3cc(C(=O)N4CCC[C@@H](N)C4)cc4c3n2CCO4)cc2cc(F)ccc21]

$^1$HNMR (400 MHz, DMSO-d$_6$) δ (ppm): 7.69-7.66 (m, 1H), 7.45 (d, J=7.6 Hz, 1H), 7.29 (s, 1H), 7.17-7.14 (m, 2H), 6.76 (s, 1H), 4.90 (t, J=5.8 Hz, 2H), 4.63 (s, 2H), 4.56 (s, 2H), 4.20 (bs, 2H), 3.66 (t, J=5.1 Hz, 2H), 3.08 (s, 3H), 2.92 (bs, 1H), 2.65 (m, 2H), 1.85 (d, J=10.28 Hz, 1H), 1.69 (bs, 2H), 1.43 (m, 1H), 1.23 (m, 2H). MS (ESI): C$_{26}$H$_{28}$FN$_5$O$_3$ 477.23; found m/z 478.39 [M+H]$^+$.

Example-49

(R)-(3-aminopiperidin-1-yl)(2-(6-fluoro-1-(4-fluorobenzyl)-1H-indol-2-yl)-3,4-dihydro-5-oxa-1,2a-diazaacenaphthylen-7-yl)methanone

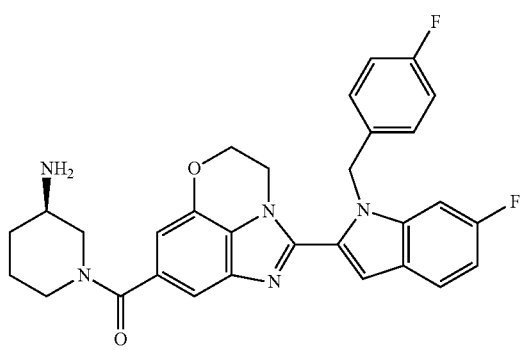 [SMILES: N[C@@H]1CCCN(C(=O)c2cc3c4c(c2)nc(-c2cc5ccc(F)cc5n2Cc2ccc(F)cc2)n4CCO3)C1]

$^1$HNMR (400 MHz, DMSO-d$_6$) δ (ppm): 7.75-7.71 (m, 1H), 7.41 (d, J=9.76 Hz, 1H), 7.28 (d, J=10.24 Hz, 2H), 7.18-7.14 (m, 2H), 7.08-7.00 (m, 3H), 6.75 (s, 1H), 6.07 (s, 2H), 4.66 (s, 2H), 4.56 (s, 2H), 4.18 (bs, 1H), 3.60 (bs, 1H), 2.90 (bs, 1H), 2.66 (bs, 2H), 1.96 (bs, 1H), 1.84 (d, J=9.68 Hz, 1H), 1.64 (bs, 1H), 1.42-1.39 (m, 1H), 1.23 (bs, 2H). MS (ESI): mass calcd. for C$_{30}$H$_{27}$F$_2$N$_5$O$_2$ 527.21; found m/z 528.36 [M+H]$^+$.

Example-50

(R)-(3-aminopiperidin-1-yl)(2-(6-fluoro-1-(4-methoxybenzyl)-1H-indol-2-yl)-3,4-dihydro-5-oxa-1,2a-diazaacenaphthylen-7-yl)methanone

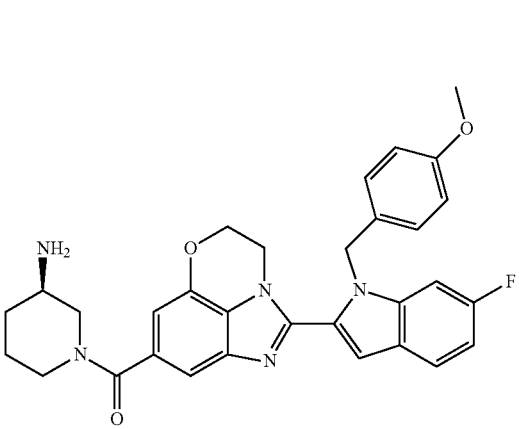 [SMILES: COc1ccc(Cn2c(-c3nc4cc(C(=O)N5CCC[C@@H](N)C5)cc5c4n3CCO5)cc3ccc(F)cc32)cc1]

$^1$HNMR (400 MHz, DMSO-d$_6$) δ (ppm): 7.73-7.70 (m, 1H), 7.41 (d, J=10.08 Hz, 1H), 7.27 (d, J=6.76 Hz, 2H), 7.02 (d, J=7.76 Hz, 2H), 6.99 (d, J=6.96 Hz, 1H), 6.78-6.72 (m, 3H), 6.01 (s, 2H), 4.65 (s, 2H), 4.56 (s, 2H), 4.11 (bs, 2H), 3.64 (s, 3H), 2.89 (bs, 1H), 2.66-2.62 (m, 1H), 1.84 (d, J=10.48 Hz, 1H), 1.64 (bs, 2H), 1.42 (m, 2H), 1.22-1.19 (m, 2H). MS (ESI): mass calcd. for C$_{31}$H$_{30}$FN$_5$O$_3$ 539.23; found m/z 540.27 [M+H]$^+$.

Example-51

(R)-(3-aminopiperidin-1-yl)(2-(1-(4-fluorobenzyl)-6-methoxy-1H-indol-2-yl)-3,4-dihydro-5-oxa-1,2a-diazaacenaphthylen-7-yl)methanone

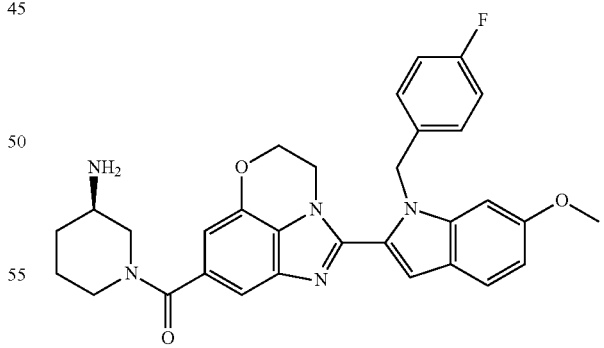

$^1$HNMR (400 MHz, DMSO-d$_6$) δ (ppm): 7.59 (d, J=8.64 Hz, 1H), 7.24 (s, 1H), 7.19 (s, 1H), 7.18-7.14 (m, 2H), 7.07-7.04 (m, 3H), 6.80 (d, J=8.52 Hz, 1H), 6.73 (s, 1H), 6.09 (s, 2H), 4.65 (s, 2H), 4.54 (s, 2H), 4.16 (bs, 1H), 3.76 (s, 3H), 3.60-3.45 (m, 1H), 2.88 (bs, 1H), 2.62 (bs, 2H), 1.83-1.65 (m, 3H), 1.39-1.33 (m, 1H), 1.23 (bs, 1H), 1.19-1.10 (m, 1H). MS (ESI): mass calcd. for C$_{31}$H$_{30}$FN$_5$O$_3$ 539.23; found m/z 540.42 [M+H]$^+$.

Example-52

3-aminopiperidin-1-yl)(2-(6-fluoro-1-(2-methoxy-ethyl)-1H-indol-2-yl)-3,4-dihydro-5-oxa-1,2a-diazaacenaphthylen-7-yl)methanone

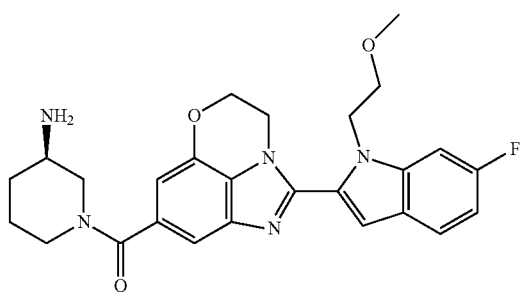 [SMILES: COCCn1c(-c2nc3cc(C(=O)N4CCC[C@@H](N)C4)cc4c3n2CCO4)cc2ccc(F)cc21]

¹HNMR (400 MHz, DMSO-d₆) δ (ppm): 7.71-7.67 (m, 1H), 7.51 (d, J=9.8 Hz, 1H), 7.28 (s, 1H), 7.18 (s, 1H), 7.01 (t, J=8.2 Hz, 1H), 6.75 (s, 1H), 4.88 (t, J=5.16 Hz, 2H), 4.63 (s, 2H), 4.56 (s, 2H), 4.13 (bs, 2H), 3.65 (t, J=4.9 Hz, 2H), 3.09 (s, 3H), 2.91-2.90 (m, 1H), 2.66 (m, 2H), 1.85 (d, J=11.2 Hz, 2H), 1.66 (bs, 2H), 1.42 (d, J=11.5 Hz, 1H), 1.27-1.17 (m, 1H). MS (ESI): mass calcd. for $C_{26}H_{28}FN_5O_3$ 477.12; found m/z 478.26 [M+H]⁺.

Example-53

(R)-(3-aminopiperidin-1-yl)(2-(7-chloro-1-(cyclobutylmethyl)-1H-indol-2-yl)-3,4-dihydro-5-oxa-1,2a-diazaacenaphthylen-7-yl)methanone

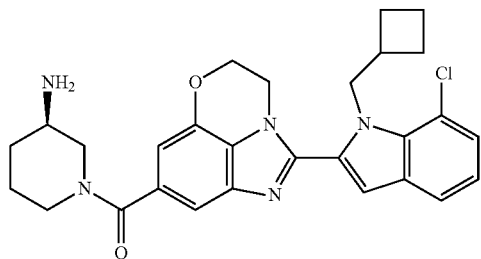 [SMILES: N[C@@H]1CCCN(C(=O)c2cc3c4c(c2)nc(-c2cc5cccc(Cl)c5n2CC2CCC2)n4CCO3)C1]

¹HNMR (400 MHz, DMSO-d₆) δ (ppm): 7.68 (d, J=7.8 Hz, 1H), 7.35-7.33 (m, 2H), 7.23 (s, 1H), 7.13 (t, J=7.7 Hz, 1H), 6.78 (s, 1H), 5.21 (d, J=6.9 Hz, 2H), 4.60-4.56 (m, 4H), 4.18 (bs, 1H), 3.64 (bs, 1H), 2.92 (bs, 1H), 2.68 (m, 1H), 2.62-2.55 (m, 1H), 1.86 (d, J=10.6 Hz, 2H), 1.69-1.52 (m, 6H), 1.42-1.38 (m, 4H), 1.23 (bs, 1H). MS (ESI): mass calcd. for $C_{28}H_{30}ClN_5O_2$ 503.26; found m/z 504.44 [M+H]⁺.

Example-54

(R)-(3-aminopiperidin-1-yl)(2-(5,6-difluoro-1-(2-methoxyethyl)-1H-indol-2-yl)-3,4-dihydro-5-oxa-1,2a-diazaacenaphthylen-7-yl)methanone

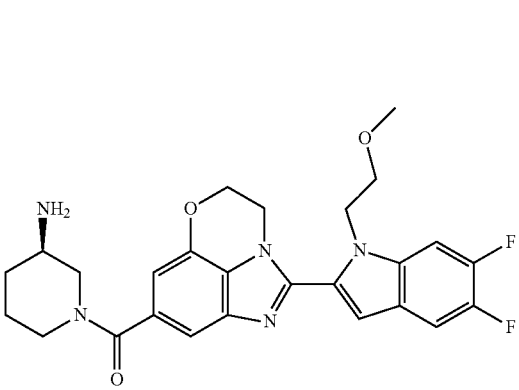 [SMILES: COCCn1c(-c2nc3cc(C(=O)N4CCC[C@@H](N)C4)cc4c3n2CCO4)cc2cc(F)c(F)cc21]

¹HNMR (400 MHz, DMSO-d₆) δ (ppm): 7.81-7.76 (m, 1H), 7.71-7.66 (m, 1H), 7.28 (s, 1H), 7.16 (s, 1H), 6.75 (s, 1H), 4.88 (t, J=5.08 Hz, 2H), 4.61 (d, J=4.44 Hz, 2H), 4.56 (d, J=4.16 Hz, 2H), 4.16 (bs, 1H), 3.65 (t, J=5.28 Hz, 2H), 3.07 (s, 3H), 2.90 (bs, 1H), 2.67-2.64 (m, 3H), 1.85 (d, J=11.04 Hz, 1H), 1.66 (bs, 2H), 1.42 (d, J=9.44 Hz, 1H), 1.26-1.20 (m, 2H). MS (ESI): $C_{26}H_{27}F_2N_5O_3$ 495.21; found m/z 496.15 [M+H]⁺.

Example-55

(R)-(3-aminopiperidin-1-yl)(2-(7-chloro-1-isobutyl-1H-indol-2-yl)-3,4-dihydro-5-oxa-1,2a-diazaacenaphthylen-7-yl)methanone

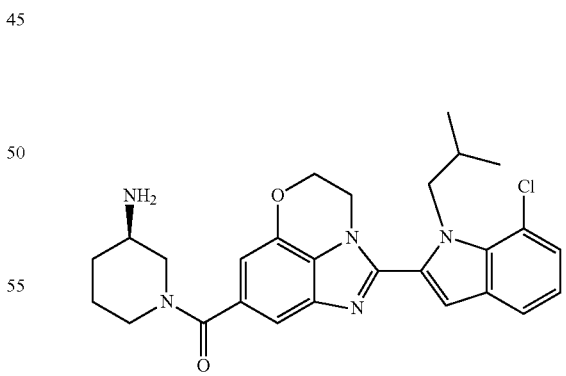

¹HNMR (400 MHz, DMSO-d₆) δ (ppm): 7.69 (d, J=8.9 Hz, 1H), 7.35-7.33 (m, 2H), 7.24 (s, 1H), 7.14 (t, J=7.8 Hz, 1H), 6.78 (s, 1H), 4.95 (d, J=7.24 Hz, 2H), 4.60 (s, 2H), 4.56 (s, 2H), 4.16 (bs, 1H), 3.68 (bs, 1H), 2.92 (bs, 1H), 2.67-2.62 (m, 1H), 2.08-1.91 (m, 1H), 1.87-1.71 (m, 4H), 1.44-1.41 (m, 1H), 1.23 (s, 2H), 0.60 (s, 6H) MS (ESI): mass calcd. for $C_{27}H_{30}ClN_5O_2$ 492.02; found m/z 492.41 [M+H]⁺.

Example-56

(R)-(3-aminopiperidin-1-yl)(2-(7-chloro-1-(2,2-difluoroethyl)-1H-indol-2-yl)-3,4-dihydro-5-oxa-1,2a-diazaacenaphthylen-7-yl)methanone

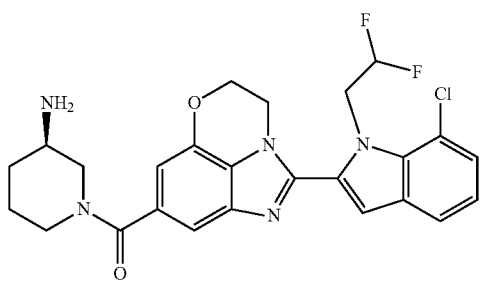 [SMILES: N[C@@H]1CCCN(C(=O)c2cc3c4c(c2)nc(-c2cc5cccc(Cl)c5n2CC(F)F)n4CCO3)C1]

¹HNMR (400 MHz, DMSO-d$_6$) δ (ppm): 7.70 (d, J=7.5 Hz, 1H), 7.39 (s, 2H), 7.32 (s, 1H), 7.21-7.19 (m, 1H), 6.78 (s, 1H), 6.39 (t, J=55.2 Hz, 1H), 5.71 (t, J=12.2 Hz, 2H), 4.64 (s, 2H), 4.57 (s, 2H), 4.13 (bs, 1H), 3.71 (bs, 1H), 2.92 (m, 1H), 2.66 (m, 1H), 1.84 (m, 1H), 1.65 (bs, 2H), 1.44 (m, 2H), 1.23 (m, 2H) MS (ESI): mass calcd. for $C_{25}H_{24}ClF_2N_5O_2$ 499.16; found m/z 500.35 [M+H]$^+$.

Example-57

(R)-(3-aminopiperidin-1-yl)(2-(7-chloro-1-(cyclopropylmethyl)-1H-indol-2-yl)-3,4-dihydro-5-oxa-1,2a-diazaacenaphthylen-7-yl)methanone

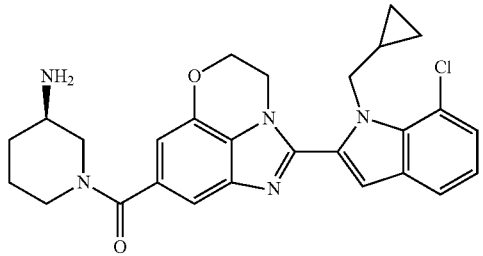 [SMILES: N[C@@H]1CCCN(C(=O)c2cc3c4c(c2)nc(-c2cc5cccc(Cl)c5n2CC2CC2)n4CCO3)C1]

¹HNMR (400 MHz, DMSO-d$_6$) δ (ppm): 7.69 (d, J=8.0 Hz, 1H), 7.36-7.33 (m, 2H), 7.26 (s, 1H), 7.16-7.12 (t, J=8.0 Hz, 1H), 6.81 (s, 1H), 6.0-5.9 (bs, 2H), 5.05 (d, J=7.2 Hz, 2H), 4.61-4.56 (m, 4H), 4.11 (d, J=4.0 Hz, 1H), 2.96-2.94 (m, 2H), 1.94-1.46 (m, 4H), 1.11 (s, 1H), 0.88-0.84 (m, 2H), 0.27-0.25 (m, 2H), 0.04-0.03 (m, 2H). MS (ESI): mass calcd. For $C_{27}H_{28}ClN_5O_2$, 490.0 m/z found, 490.2 (M+H).

Example-58

(R,E)-(3-aminopiperidin-1-yl)(2-(1-(cyclopropylmethyl)-5-styryl-1H-indol-2-yl)-3,4-dihydro-5-oxa-1,2a-diazaacenaphthylen-7-yl)methanone

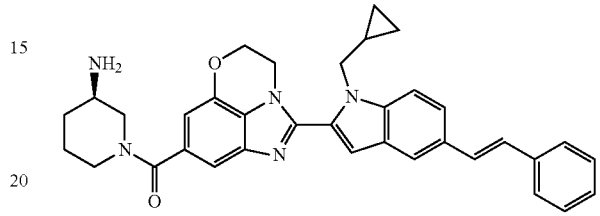

¹HNMR (400 MHz, DMSO-d$_6$) δ (ppm): 7.84 (s, 1H), 7.70-7.59 (m, 4H), 7.39-7.35 (m, 3H), 7.31 (s, 1H), 7.25-7.17 (m, 3H), 6.77 (s, 1H), 4.71-4.66 (m, 4H), 4.57 (s, 2H), 4.0-3.9 (bs, 2H), 2.95 (s, 2H), 2.77 (s, 2H), 1.89-1.22 (m, 5H), 0.88-0.84 (m, 1H). 0.33-0.26 (m, 4H). MS (ESI): mass calcd. For $C_{35}H_{35}N_5O_2$, 557.0 m/z found, 558.6 (M+H)$^+$.

Example-59

(R)-(3-aminopiperidin-1-yl)(2-(1-((4-methylthiazol-2-yl)methyl)-1H-indol-2-yl)-3,4-dihydro-5-oxa-1,2a-diazaacenaphthylen-7-yl)methanone

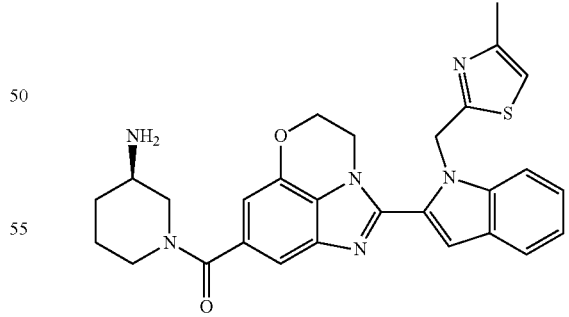

¹HNMR (400 MHz, DMSO-d$_6$) δ (ppm): 7.77-7.64 (m, 2H), 7.31-7.30 (m, 2H), 7.19 (s, 1H), 7.023 (s, 2H), 6.78 (s, 1H), 6.34 (s, 1H), 4.68 (m, 2H), 4.56 (m, 2H), 3.05-2.9 (m, 3H), 2.25 (s, 3H), 1.90-1.87 (m, 2H), 1.70-1.67 (m, 2H), 1.49-1.45 (m, 1H), 1.37-1.33 (m, 2H), 1.26-1.21 (m, 2H). MS (ESI): mass calcd. for $C_{27}H_{28}N_6OS$, 484.20; m/z found 485.1 (M+H)$^+$.

Example-60

(R)-(3-aminopiperidin-1-yl)(2-(1-(cyclopropylmethyl)-5-methoxy-1H-indol-2-yl)-3,4-dihydro-5-oxa-1,2a-diazaacenaphthylen-7-yl)methanone

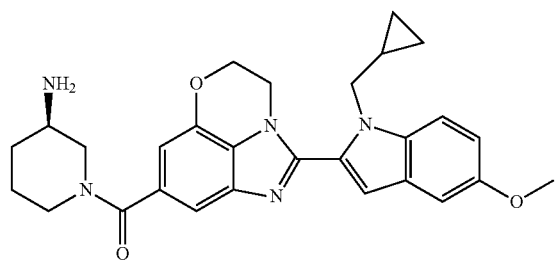 [SMILES: COc1ccc2c(c1)cc(-c1nc3cc(C(=O)N4CCC[C@@H](N)C4)cc4c3n1CCO4)n2CC1CC1]

$^1$HNMR (400 MHz, DMSO-d$_6$) δ (ppm): 7.56 (d, J=9.2 Hz, 1H), 7.30 (s, 1H), 7.14 (s, 1H), 7.04 (s, 1H), 6.94-6.91 (m, 1H), 6.75 (s, 1H), 4.65-4.63 (m, 4H), 4.55 (s, 2H), 3.96-3.9 (bs, 2H), 3.79 (s, 3H), 2.95 (s, 1H), 2.79 (d, J=7.2 Hz, 2H), 1.89-1.26 (m, 6H), 0.88-0.84 (m, 1H), 0.33-0.26 (m, 4H). MS (ESI): mass calcd. For C$_{28}$H$_{31}$N$_5$O$_3$, 485.5 m/z found, 486.5 (M+H)$^+$.

Example-61

(R)-(3-aminopiperidin-1-yl)(2-(1-(cyclopropylmethyl)-6-(hydroxymethyl)-1H-indol-2-yl)-3,4-dihydro-5-oxa-1,2a-diazaacenaphthylen-7-yl)methanone Scheme 4

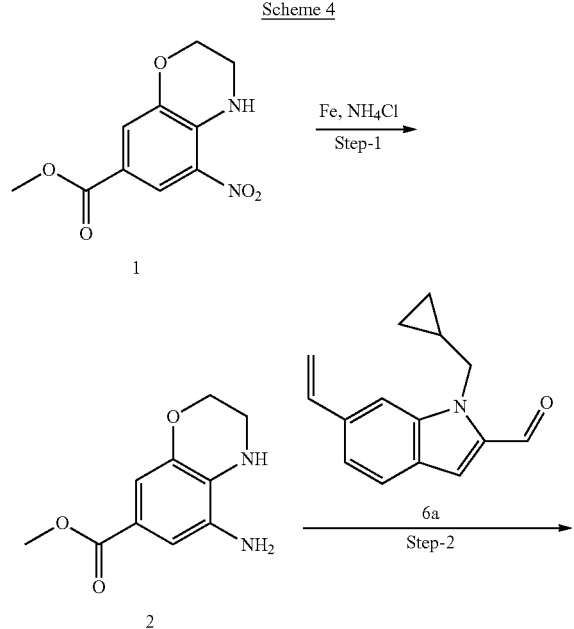

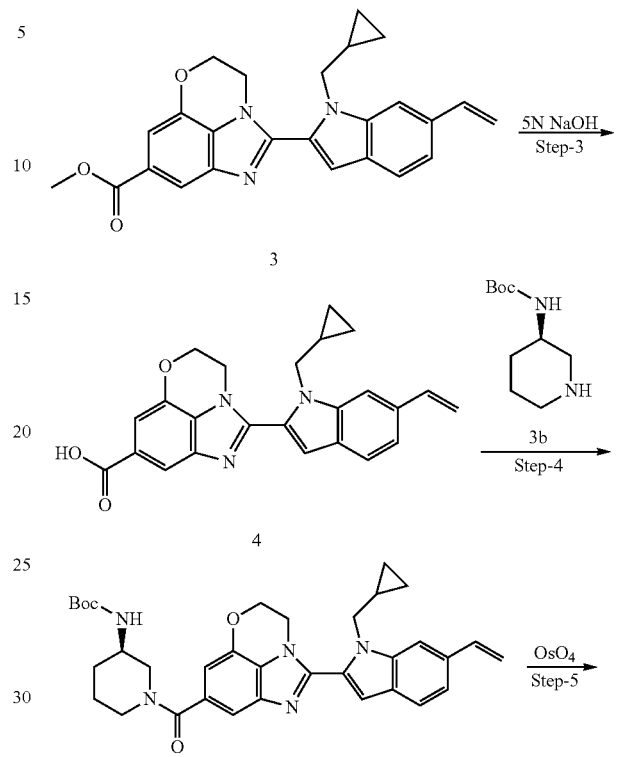

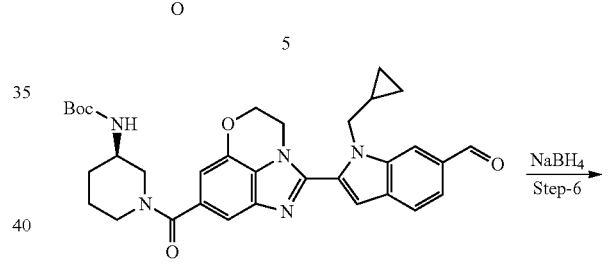

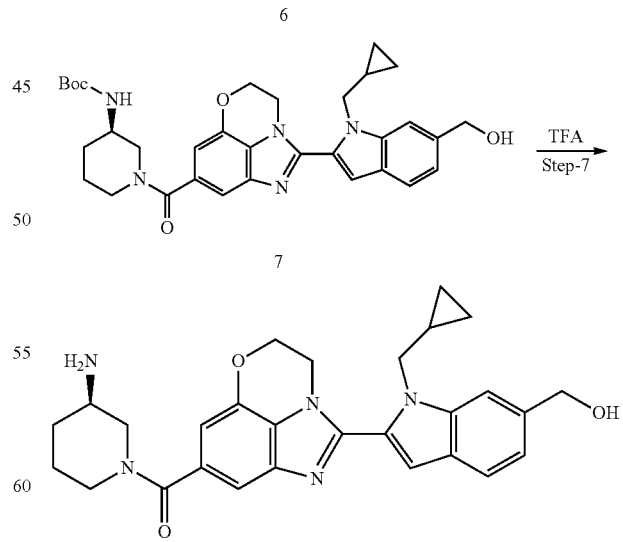

Example 61

Intermediate 1 was synthesized using the procedure described in Scheme-3.

Step 1: Synthesis of methyl 5-amino-3,4-dihydro-2H-benzo[b][1,4]oxazine-7-carboxylate (2)

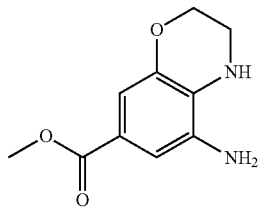

To a stirred solution of methyl 5-nitro-3,4-dihydro-2H-benzo[b][1,4]oxazine-7-carboxylate (1, 11.0 g, 46.18 mmol) in mixture of ethanol (110 mL, 10 vol) and water (33 mL, 3 vol) were added ammonium chloride (37.0 g, 692.0 mmol) and iron powder (38.6 g, 692.0 mmol) at room temperature and the resulting mixture was stirred at 80° C. for 3 h. The progress of the reaction was monitored by TLC. After completion of reaction, the reaction mixture was evaporated, filtered through celite and celite bed washed with ethyl acetate (200 mL×3). The combined ethyl acetate layer was washed with water and brine. Obtained organic layer was dried over anhydrous sodium sulphate and concentrated under reduced pressure to afford methyl 5-amino-3,4-dihydro-2H-benzo[b][1,4]oxazine-7-carboxylate (2) as brown solid. Yield: 9.0 g (93%).

$^1$HNMR (400 MHz, DMSO-$d_6$), δ (ppm): 6.86 (d, J=1.6 Hz, 1H), 6.67 (d, J=1.6 Hz, 1H), 5.39 (s, 2H), 4.73 (s, 1H), 4.06 (s, 2H), 3.70 (s, 3H), 3.35 (s, 2H). MS (ESI): 208.12, m/z found 209.20 [M+H]$^{+1}$.

Step-2: Synthesis of methyl-2-(1-(cyclopropylmethyl)-6-vinyl-1H-indol-2-yl)-3,4-dihydro-5-oxa-1,2a-diazaacenaphthylene-7-carboxylate (3)

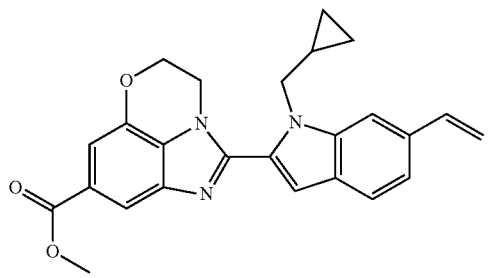 [SMILES: C=Cc1ccc2cc(-c3nc4cc(C(=O)OC)cc5c4n3CCO5)n(CC3CC3)c2c1]

To a stirred solution of methyl-5-amino-3,4-dihydro-2H-benzo[b][1,4]oxazine-7-carboxylate (2, 1.0 g, 4.80 mmol) and 1-(cyclopropylmethyl)-6-vinyl-1H-indole-2-carbaldehyde (6a, 1.2 g, 5.70 mmol) in N, N-dimethylformamide (10.0 mL) and water (3.0 mL), potassium peroxomonosulfate (0.88 g, 5.76 mmol) was added at room temperature. The reaction mixture was stirred at room temperature for 16 h. After completion of reaction, the reaction mixture was cooled to room temperature and water was added. Precipitated solid was filtered and washed with water (20 mL×2) and methanol (10 mL×2). The compound obtained was dried under vacuum to afford methyl 2-(1-(cyclopropylmethyl)-6-vinyl-1H-indol-2-yl)-3,4-dihydro-5-oxa-1,2a-diazaacenaphthylene-7-carboxylate (3) as yellow solid. Yield: 0.550 g (crude). MS (ESI) 413.17; m/z found 414.26 [M+H]$^{+1}$.

Step-3: Synthesis of 2-(1-(cyclopropylmethyl)-6-vinyl-1H-indol-2-yl)-3,4-dihydro-5-oxa-1,2a-diazaacenaphthylene-7-carboxylic Acid (4)

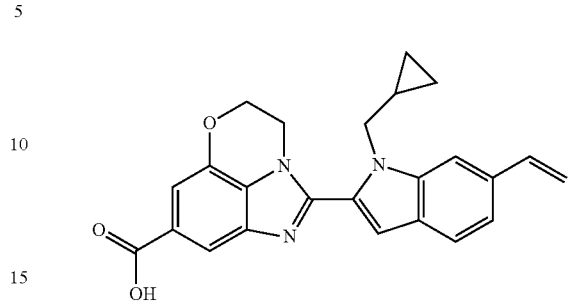

To a stirred solution of afford methyl 2-(1-(cyclopropylmethyl)-6-vinyl-1H-indol-2-yl)-3,4-dihydro-5-oxa-1,2a-diazaacenaphthylene-7-carboxylate (3, 0.55 g, 1.3 mmol) in tetrahydrofuran (5.0 mL) and methanol (3.0 mL) 5N sodium hydroxide solution (3.0 mL) was added and reaction mixture was stirred at 60° C. for 2 h. After completion of reaction, the reaction mixture was concentrated under reduced pressure. The resulting crude was dissolved in minimum volume of water and acidified with saturated citric acid solution at 0° C. up to pH 2-3. The precipitated solid was filtered, washed with water (10 mL×2). The compound obtained was dried under vacuum to afford 2-(1-(cyclopropylmethyl)-6-vinyl-1H-indol-2-yl)-3,4-dihydro-5-oxa-1,2a-diazaacenaphthylene-7-carboxylic acid (4) as white solid. Yield: 0.440 g (Crude). MS (ESI) 399.16; m/z found 400.16 [M+H]$^{+1}$.

Step-4: Synthesis of tert-butyl (R)-(1-(2-(1-(cyclopropylmethyl)-6-vinyl-1H-indol-2-yl)-3,4-dihydro-5-oxa-1,2a-diazaacenaphthylene-7-carbonyl)piperidin-3-yl)carbamate (5)

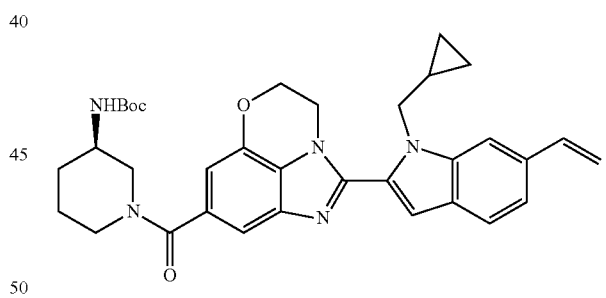

To a stirred solution of 2-(1-(cyclopropylmethyl)-6-vinyl-1H-indol-2-yl)-3,4-dihydro-5-oxa-1,2a-diazaacenaphthylene-7-carboxylic acid (4, 0.44 g, 1.10 mmol) in dichloromethane (10.0 mL), tert-butyl-(R)-piperidin-3-ylcarbamate (3b, 0.26 g, 1.29 mmol) and triethylamine (0.4 mL, 3.31 mmol) were added, followed by addition of propylphosphonic anhydride (50% solution in ethyl acetate, 0.8 mL, 3.37 mmol). The reaction mixture was stirred at room temperature for 2 h. After completion of reaction, the reaction mixture was diluted with water and extracted with dichloromethane (10 mL×2). The combined organic layers were washed with water and brine solution, further dried over anhydrous sodium sulfate, filtered and concentrated to get crude product. The crude was purified by CombiFlash using 12.0 g, RediSep and 70% ethyl acetate in hexane as eluent to afford tert-butyl (R)-(1-(2-(1-(cyclopropylmethyl)-

6-vinyl-1H-indol-2-yl)-3,4-dihydro-5-oxa-1,2a-diazaacenaphthylene-7-carbonyl)piperidin-3-yl)carbamate (5) as brown solid. Yield: 0.250 g (44%). MS (ESI) 581.30; m/z found 582.41 [M+1]$^+$.

Step-5: preparation of tert-butyl (R)-(1-(2-(1-(cyclopropylmethyl)-6-formyl-1H-indol-2-yl)-3,4-dihydro-5-oxa-1,2a-diazaacenaphthylene-7-carbonyl)piperidin-3-yl)carbamate (6)

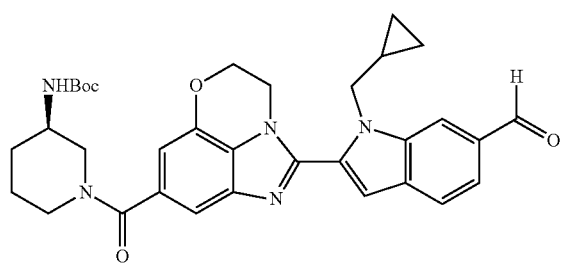 [SMILES: CC(C)(C)OC(=O)N[C@@H]1CCCN(C(=O)c2cc3c4c(c2)nc(-c2cc5ccc(C=O)cc5n2CC2CC2)n4CCO3)C1]

To a stirred solution of tert-butyl (R)-(1-(2-(1-(cyclopropylmethyl)-6-vinyl-1H-indol-2-yl)-3,4-dihydro-5-oxa-1,2a-diazaacenaphthylene-7-carbonyl) piperidin-3-yl)carbamate (5, 0.25 g, 0.43 mmol) in tetrahydrofuran (10.0 mL) and water (3.0 mL), osmium tetroxide (0.6 ml, 0.08 mmol) and sodium per iodate (0.29 g, 1.37 mmol) were added at 0° C. The reaction mixture was stirred at room temperature for 20 min. After completion of reaction, the reaction mixture was diluted with water and extracted with ethyl acetate (10 mL×2). The combined organic layers were washed with water and brine solution, further dried over anhydrous sodium sulfate, filtered and concentrated to get crude product. The crude was purified by CombiFlash using 12.0 g, RediSep and 70% ethyl acetate in hexane as eluent to afford tert-butyl (R)-(1-(2-(1-(cyclopropylmethyl)-6-formyl-1H-indol-2-yl)-3,4-dihydro-5-oxa-1,2a-diazaacenaphthylene-7-carbonyl)piperidin-3-yl)carbamate (6) as white solid. Yield: 0.200 g (80%). MS (ESI) 583.28; m/z found 584.30 [M+1]$^+$.

Step-6: preparation of tert-butyl (R)-(1-(2-(1-(cyclopropylmethyl)-6-(hydroxymethyl)-1H-indol-2-yl)-3,4-dihydro-5-oxa-1,2a-diazaacenaphthylene-7-carbonyl)piperidin-3-yl) Carbamate (7)

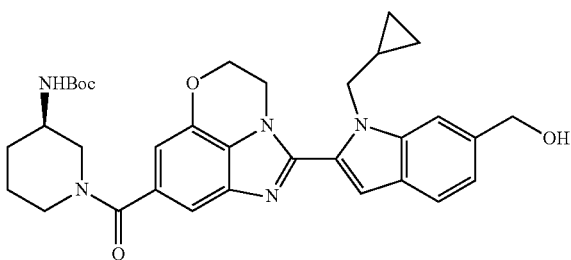 [SMILES: CC(C)(C)OC(=O)N[C@@H]1CCCN(C(=O)c2cc3c4c(c2)nc(-c2cc5ccc(CO)cc5n2CC2CC2)n4CCO3)C1]

To a stirred solution of tert-butyl (R)-(1-(2-(1-(cyclopropylmethyl)-6-formyl-1H-indol-2-yl)-3,4-dihydro-5-oxa-1,2a-diazaacenaphthylene-7-carbonyl) piperidin-3-yl)carbamate (6, 0.2 g, 0.34 mmol) in methanol (10.0 mL), sodium borohydride (0.014 g, 0.34 mmol) was added at 0° C. The reaction mixture was stirred at room temperature for 1 h. After completion of reaction, the reaction mixture was diluted with water and extracted with dichloromethane (10 mL×2). The combined organic layers were washed with water and brine solution, further dried over anhydrous sodium sulfate, filtered and concentrated to get crude product. The crude was purified by CombiFlash using 12.0 g, RediSep and 70% ethyl acetate in hexane as eluent to afford tert-butyl (R)-(1-(2-(1-(cyclopropylmethyl)-6-(hydroxymethyl)-1H-indol-2-yl)-3,4-dihydro-5-oxa-1,2a-diazaacenaphthylene-7-carbonyl)piperidin-3-yl)carbamate (7) as yellow solid. Yield: 0.100 g (51%). MS (ESI) 585.30; m/z found 586.30 [M+1]$^+$.

Step-7: Preparation of (R)-(3-aminopiperidin-1-yl) (2-(1-(cyclopropylmethyl)-6-(hydroxymethyl)-1H-indol-2-yl)-3,4-dihydro-5-oxa-1,2a-diazaacenaphthylen-7-yl) Methanone (Example-61)

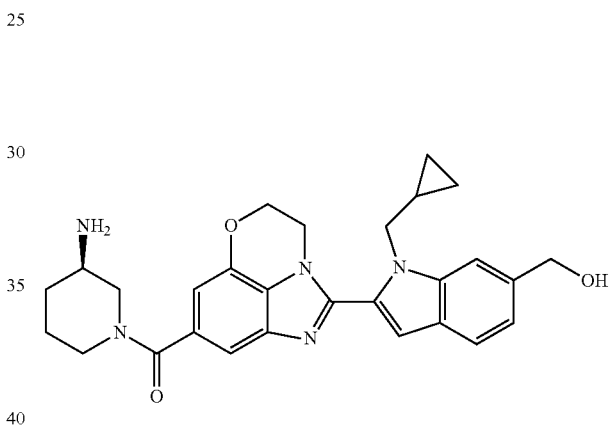

To a stirred solution tert-butyl (R)-(1-(2-(1-(cyclopropylmethyl)-6-(hydroxymethyl)-1H-indol-2-yl)-3,4-dihydro-5-oxa-1,2a-diazaacenaphthylene-7-carbonyl)piperidin-3-yl) carbamate (6, 0.1 g, 0.17 mmol) in dichloromethane (10.0 mL), trifluoroacetic acid (1.0 mL) was added at 0° C. and stirred at room temperature for 2 h. After completion of reaction, the reaction mixture was concentrated completely, basified by saturated sodium bicarbonate solution (10 mL). The compound was extracted with dichloromethane (10 mL×2). The combined organic extracts were washed with brine, dried over anhydrous sodium sulfate, filtered and concentrated to get crude product. The crude was purified by reverse prep HPLC to afford ((R)-(3-aminopiperidin-1-yl) (2-(1-(cyclopropylmethyl)-6-(hydroxymethyl)-1H-indol-2-yl)-3,4-dihydro-5-oxa-1,2a-diazaacenaphthylen-7-yl) methanone as off white solid. Yield: 0.0023 g (0.02%).

$^1$HNMR (400 MHz, DMSO-d$_6$) δ (ppm): 7.63 (d, J=8.1 Hz, 1H), 7.59 (s, 1H), 7.29 (s, 1H), 7.13 (s, 1H), 7.11 (d, J=8.2 Hz, 1H), 6.75 (s, 1H), 5.22 (s, 2H), 4.70-4.65 (m, 6H), 4.56 (s, 2H), 4.15 (s, 1H), 2.92 (s, 1H), 2.66 (m, 2H), 1.88-1.84 (m, 3H), 1.66 (s, 1H), 1.43 (m, 1H), 1.24 (m, 2H), 0.35-0.29-(m, 4H). MS (ESI): mass calcd. for $C_{28}H_{31}N_5O_3$ 485.24; found m/z 486.32 [M+H]$^+$.

Example-62

(R)-(3-aminopiperidin-1-yl)(2-(1-(cyclopropylmethyl)-1H-indol-2-yl)-3,3-dimethyl-3,4-dihydro-5-oxa-1,2a-diazaacenaphthylen-7-yl)methanone

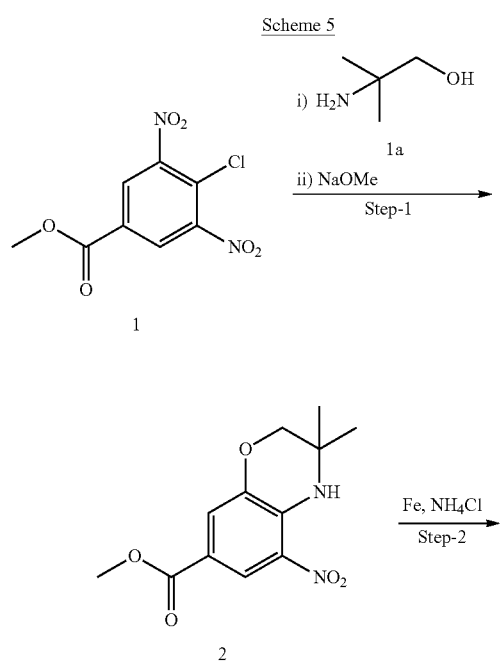

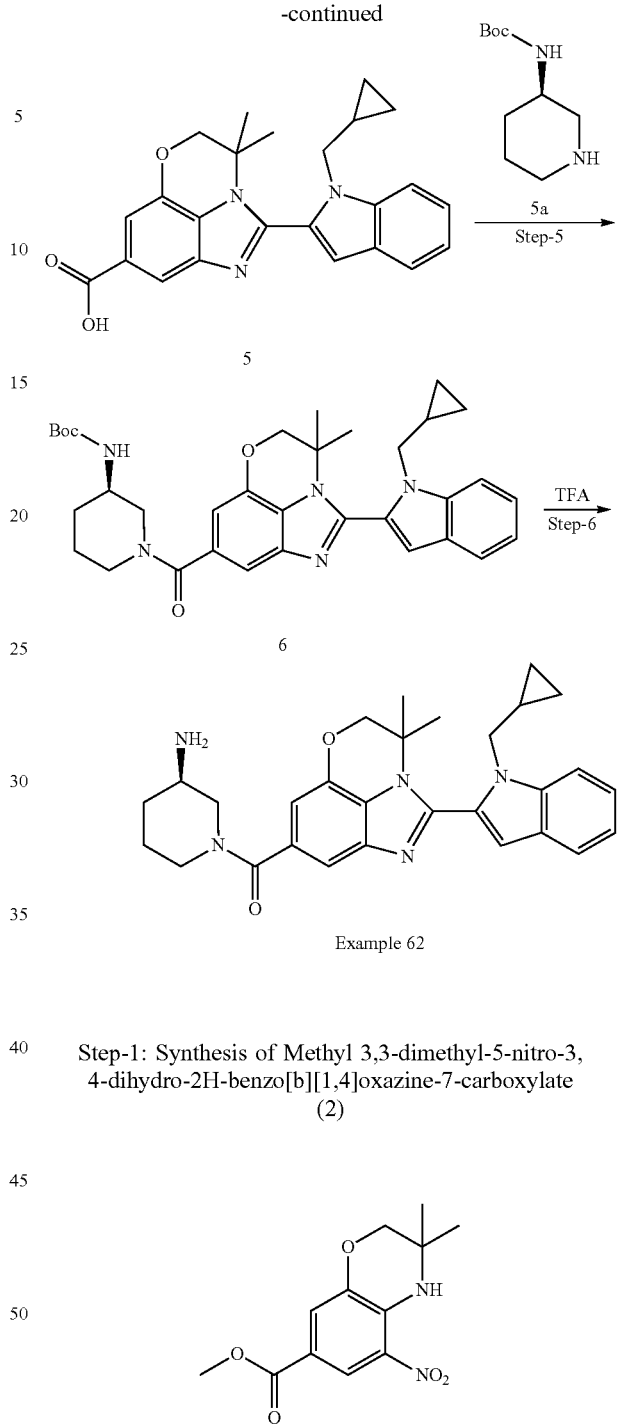

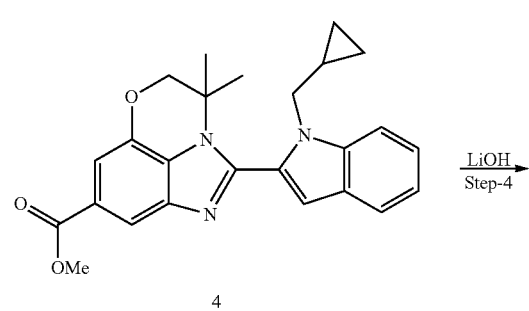

Step-1: Synthesis of Methyl 3,3-dimethyl-5-nitro-3,4-dihydro-2H-benzo[b][1,4]oxazine-7-carboxylate (2)

To the stirred solution of methyl-4-chloro-3,5-dinitrobenzoate (1, 5.0 g, 19.19 mmol) in methanol (30.0 mL), 2-amino-2-methylpropan-1-ol (1a, 2.6 g, 28.7 mmol) was added at room temperature. The reaction mixture was stirred at room temperature for 3 h. After 3 h, 25% sodium methoxide solution in methanol (12.5 mL, 57.6 mmol) was added in the reaction mixture at 0° C. The reaction mixture subjected to 80° C. for 3 h. After completion of reaction, the reaction mixture was diluted with water. Precipitated solid was filtered and washed with water. The crude was dried under reduced pressure to afford methyl 3,3-dimethyl-5- nitro-3,4-dihydro-2H-benzo[b][1,4]oxazine-7-carboxylate (2) as yellow solid. Yield: 1.8 g (35%). MS (ESI): 266.0, m/z found 267.1 [M+H]⁺¹.

Step-2: Synthesis of Methyl 5-amino-3,3-dimethyl-3,4-dihydro-2H-benzo[b][1,4]oxazine-7-carboxylate (3)

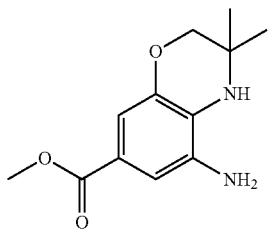

To a stirred solution of methyl 3,3-dimethyl-5-nitro-3,4-dihydro-2H-benzo[b][1,4]oxazine-7-carboxylate (2, 1.8 g, 6.76 mmol) in ethanol (20 mL)-water (10 mL) were added ammonium chloride (5.4 g, 101.4 mmol) and iron powder (5.6 g, 101.4 mmol) at room temperature and the resulting mixture was stirred at 60° C. for 3 h. The progress of the reaction was monitored by TLC. After completion of reaction, the reaction mixture was evaporated, filtered through celite and washed with ethyl acetate (50 mL×3). The combined ethyl acetate layer was washed with water and brine. The organic layer was dried over anhydrous sodium sulphate and concentrated under reduced pressure to afford methyl 5-amino-3,3-dimethyl-3,4-dihydro-2H-benzo[b][1,4]oxazine-7-carboxylate (3) as yellow solid.

Yield: 1.0 g (55%). MS (ESI): 236.11, m/z found 237.20 [M+H]⁺¹.

Step-3: Synthesis of Methyl 2-(1-(cyclopropylmethyl)-1H-indol-2-yl)-3,3-dimethyl-3,4-dihydro-5-oxa-1,2a-diazaacenaphthylene-7-carboxylate (4)

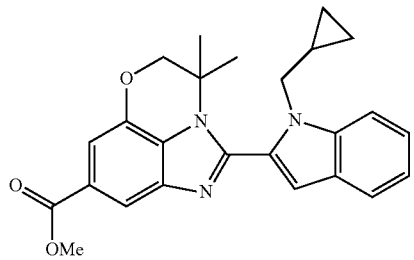 [SMILES: COC(=O)c1cc2c3c(c1)nc(-c1cc4ccccc4n1CC1CC1)n3C(C)(C)CO2]

To a stirred solution of methyl-5-amino-3,3-dimethyl-3,4-dihydro-2H-benzo[b][1,4]oxazine-7-carboxylate (3, 0.5 g, 2.12 mmol) and 1-(cyclopropylmethyl)-1H-indole-2-carbaldehyde (3a, 0.46 g, 2.33 mmol) in N, N-dimethylformamide (5.0 mL) and water (0.5 mL), potassium peroxomonosulfate (Oxone, 0.39 g, 2.54 mmol) was added at room temperature. The reaction mixture was stirred at room temperature for 16 h. After completion of reaction, the reaction mixture was cooled to room temperature and water was added. The precipitated solid was filtered and washed with water (10 mL×2) and methanol (5 mL×2). The compound obtained was dried under vacuum to afford methyl 2-(1-(cyclopropylmethyl)-1H-indol-2-yl)-3,3-dimethyl-3,4-dihydro-5-oxa-1,2a-diazaacenaphthylene-7-carboxylate (4) as yellow solid. Yield: 0.50 g, crude, MS (ESI) 415.19; m/z found 416.27 [M+H]⁺¹.

Step-4: Synthesis of 2-(1-(cyclopropylmethyl)-1H-indol-2-yl)-3,3-dimethyl-3,4-dihydro-5-oxa-1,2a-diazaacenaphthylene-7-carboxylic Acid (5)

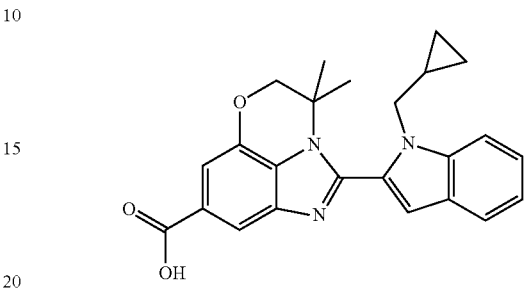

To a stirred solution of afford methyl 2-(1-(cyclopropylmethyl)-1H-indol-2-yl)-3,3-dimethyl-3,4-dihydro-5-oxa-1,2a-diazaacenaphthylene-7-carboxylate (4, 0.5 g, 1.2 mmol) in tetrahydrofuran (10.0 mL) and methanol (5.0 mL) 5N sodium hydroxide solution (5.0 mL) was added and reaction mixture was stirred at 60° C. for 3 h. After completion of reaction, the reaction mixture was concentrated under reduced pressure completely. The resulting crude was dissolved in minimum volume of water and acidified with saturated citric acid solution at 0° C. up to pH 2-3. The precipitated solid was filtered, washed with water (10 mL×2). The compound obtained was dried under vacuum to afford 2-(1-(cyclopropylmethyl)-1H-indol-2-yl)-3,3-dimethyl-3,4-dihydro-5-oxa-1,2a-diazaacenaphthylene-7-carboxylic acid (5) as orange solid. Yield: 0.50 g (Crude). MS (ESI) 401.17; m/z found 402.27 [M+H]⁺¹.

Step-5: Synthesis of tert-butyl (R)-(1-(2-(1-(cyclopropylmethyl)-1H-indol-2-yl)-3,3-dimethyl-3,4-dihydro-5-oxa-1,2a-diazaacenaphthylene-7-carbonyl)piperidin-3-yl)carbamate (6)

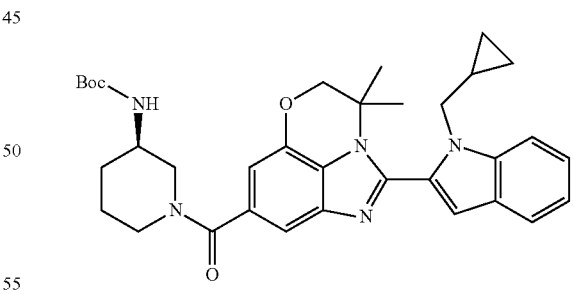

To a stirred solution of 2-(1-(cyclopropylmethyl)-1H-indol-2-yl)-3,3-dimethyl-3,4-dihydro-5-oxa-1,2a-diazaacenaphthylene-7-carboxylic acid (5, 0.5 g, 1.25 mmol) in dichloromethane (20.0 mL), tert-butyl-(R)-piperidin-3-ylcarbamate (5a, 0.3 g, 1.49 mmol) and triethylamine (0.6 mL, 3.99 mmol) were added, followed by addition of propylphosphonic anhydride (50% solution in ethyl acetate, 2.5 mL, 3.99 mmol). The reaction mixture was stirred at room temperature for 12 h. After completion of reaction, the reaction mixture was diluted with water and extracted with dichloromethane (40 mL×2). The combined organic layers were washed with water and brine solution, further dried over anhydrous sodium sulfate, filtered and concentrated to get crude product. The crude was purified by CombiFlash using 12.0 g, RediSep and 70% ethyl acetate in hexane as eluent to afford tert-butyl (R)-(1-(2-(1-(cyclopropylmethyl)-1H-indol-2-yl)-3,3-dimethyl-3,4-dihydro-5-oxa-1,2a-diazaacenaphthylene-7-carbonyl)piperidin-3-yl) carbamate (6) as yellow solid. Yield: 0.25 g (34%). MS (ESI) 583.32; m/z found 584.37 [M+1]$^+$.

Step-6: Preparation of (R)-(3-aminopiperidin-1-yl) (2-(1-(cyclopropylmethyl)-1H-indol-2-yl)-3,3-dimethyl-3,4-dihydro-5-oxa-1,2a-diazaacenaphthylen-7-yl)methanone (Example 62)

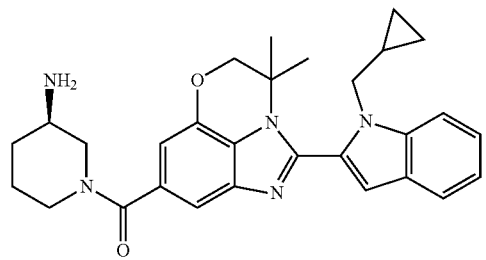

$^1$HNMR (400 MHz, DMSO-d$_6$) δ (ppm): 7.71-7.65 (m, 2H), 7.32 (s, 1H), 7.28 (t, J=7.7 Hz, 2H), 7.14 (t, J=7.8 Hz, 1H), 7.00 (s, 1H), 6.82 (s, 1H), 4.21 (s, 2H), 4.18 (d, J=6.8 Hz, 2H), 3.67 (bs, 2H), 2.92 (bs, 1H), 2.66-2.64 (m, 2H), 1.87-1.84 (m, 1H), 1.64-1.55 (m, 3H), 1.43 (s, 6H), 1.25-1.21 (m, 1H), 1.10-1.07 (m, 1H), 0.32 (d, J=5.0 Hz, 2H), 0.31 (d, J=4.3 Hz, 2H). MS (ESI): mass calcd. for C$_{29}$H$_{33}$N$_5$O$_2$ 483.2; found m/z 484.37 [M+H]$^+$.

Example-63

Synthesis of (R)-(3-aminopiperidin-1-yl) (2-(1-(cyclopropylmethyl)-1H-indol-2-yl)-5,6-dihydro-4H-imidazo[1,5,4-de]quinoxalin-8-yl) Methanone (Example-63)

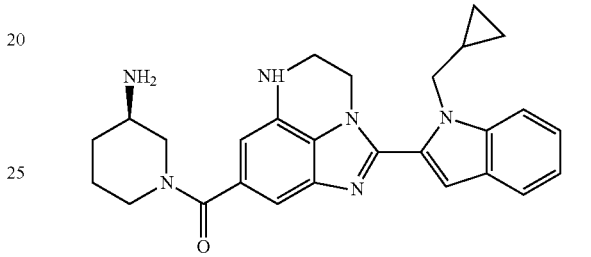

Example-63

Scheme 6

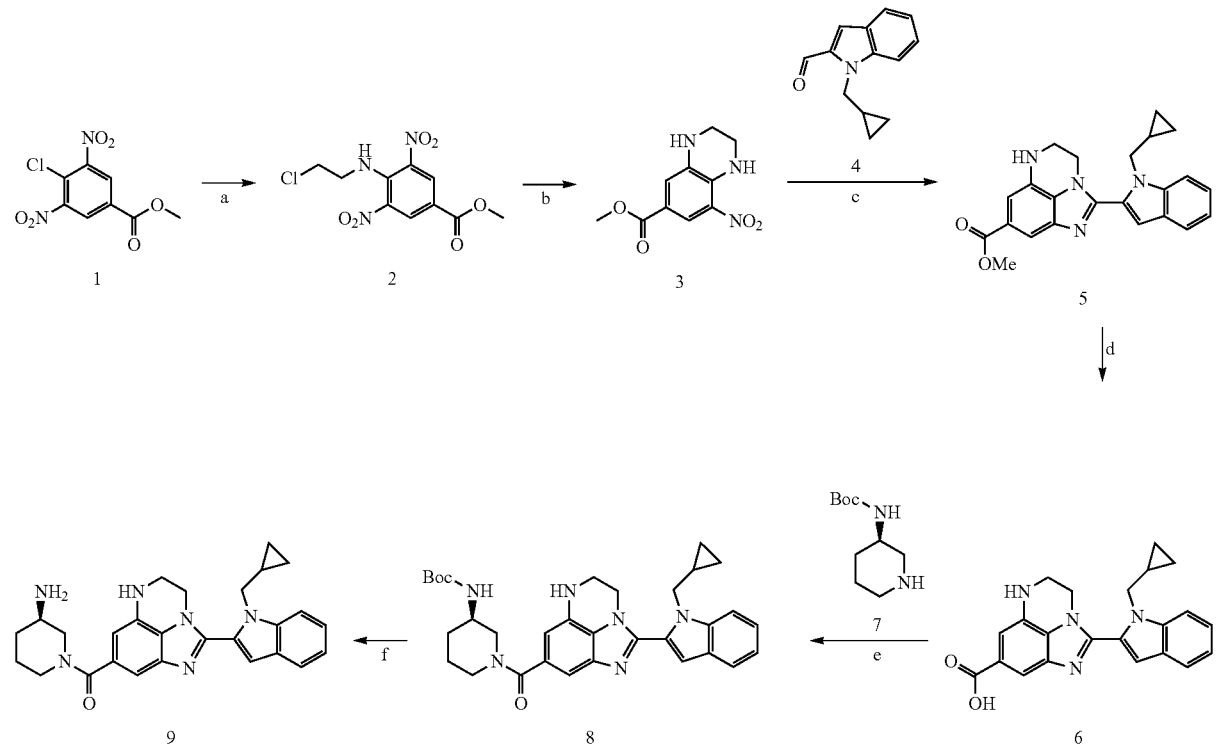

The intermediate (1) used for the preparation of Example-61 was purchased commercially (from Reddy N Reddy Pharmaceuticals). The intermediate (1) mentioned in Scheme-4 is equivalent to intermediate (3) of Scheme-2 above.

Step 3: Preparation of Methyl 4-((2-chloroethyl)amino)-3,5-dinitrobenzoate (2)

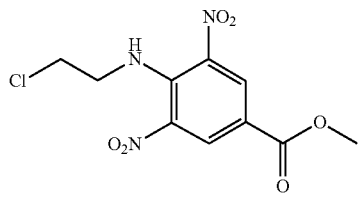

2

To a stirred solution of (1, 0.5 g 1.92 mmol) in MeOH (50 mL) was added 2-Chloro-ethylamine hydrochloride (0.46 g, 4.03 mmol), followed by triethylamine (0.7 ml, 4.031 mmol) then resulting mixture was heated to 80° C. for 1 h (Reaction condition a). The reaction mixture was cooled to room temperature and diluted with ethyl acetate (100 mL×2) and the organic phase was evaporated through vacuum and crude carried to next step without purification to give yellow color solid (0.9 g, 100% yield). MS (ESI): mass calcd. for $C_{10}H_{10}ClN_3O_6$, 303.66; m/z found, 304.0 [M+H]$^+$.

Step 4: Preparation of Methyl 8-nitro-1,2,3,4-tetrahydroquinoxaline-6-carboxylate (3)

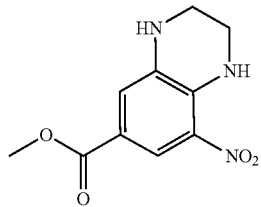

3

To a stirred solution of methyl 4-((2-chloroethyl)amino)-3,5-dinitrobenzoate (2, 0.3 g, 0.99 mmol) in AcOH (30 mL) was added iron powder (0.27 g, 4.95 mmol) at room temperature and the resulting mixture was allowed to stir under room temperature for 12 h (Reaction condition b). The progress of the reaction was monitored by TLC. Then reaction mixture was evaporated, filtered through celite and extracted with ethyl acetate (50 mL×3). The combined organic extract was washed NaHCO$_3$ solution with brine, dried over sodium sulphate and concentrated under reduced pressure to afford crude compound which was purified by column chromatography (silica gel, 0-20% EtOAc in hexane) to give dark brown solid (0.23 g, 99% yield). MS (ESI): mass calcd. for $C_{10}H_{11}N_3O_4$ 237.22; m/z found, 238.1 [M+H]$^+$.

Step 5: Preparation of Methyl 2-(1-(cyclopropylmethyl)-1H-indol-2-yl)-5,6-dihydro-4H-imidazo[1,5,4-de]quinoxaline-8-carboxylate (5)

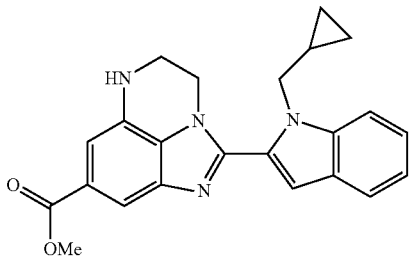

5

To the stirred solution of mixture of methyl 5-nitro-3,4-dihydro-2H-benzo[b][1,4]oxazine-7-carboxylate (3, 0.1 g, 0.42 mmol) and 1-(cyclopropylmethyl)-1H-indole-2-carbaldehyde (4, 0.09 g, 0.46 mmol) in EtOH (10 mL), was added Na$_2$S$_2$O$_4$ (0.4 g, 2.32 mmol) in water (5 mL) and the reaction mixture was stirred at 80° C. for 16 h (reaction condition c). The reaction mixture was cooled to room temperature, water was added and the compound was extracted with ethyl acetate (50 mL×2). Combined organic extracts were washed with brine, dried over sodium sulfate and evaporated to get crude product. The crude residue was purified by gradient column chromatography using silica gel and eluent 15-20% ethyl acetate in hexane to afford yellow solid (0.08 g, 62% Yield). MS (ESI): mass calcd. for, $C_{23}H_{22}N_4O_2$ 386.46; m/z found, 387.2 [M+H]$^+$.

Step 6: Preparation of 2-(1-(cyclopropylmethyl)-1H-indol-2-yl)-5,6-dihydro-4H-imidazo[1,5,4-de]quinoxaline-8-carboxylic Acid (6)

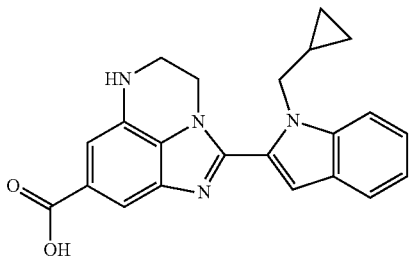 [SMILES: CC1(C)COc2cc(C(=O)O)cc3nc(-c4cc5ccccc5n4CC4CC4)n1c23]

6

To the stirred solution of methyl 2-(1-(cyclopropylmethyl)-1H-indol-2-yl)-5,6-dihydro-4H-imidazo[1,5,4-de]quinoxaline-8-carboxylate (5, 0.1 g, 0.25 mmol) in MeOH (2 mL), was added 5N NaOH solution (0.4 mL) and stirred at 75° C. for 1 h (reaction condition d). The reaction mixture was evaporated completely. The resulting crude was dissolved in minimum volume of water and acidified with saturated citric acid solution. Compound was extracted with DCM (50 mL×2), washed with brine, dried over sodium sulfate and evaporated to get crude product as pale yellow color solid (0.07 g, 72% Yield). MS (ESI): mass calcd. for, $C_{22}H_{20}N_4O_2$ 372.43; m/z found, 373 [M+H]$^+$.

Step 7: Preparation of tert-butyl (R)-(1-(2-(1-(cyclopropylmethyl)-1H-indol-2-yl)-5,6-dihydro-4H-imidazo[1,5,4-de]quinoxaline-8-carbonyl)piperidin-3-yl)carbamate (8)

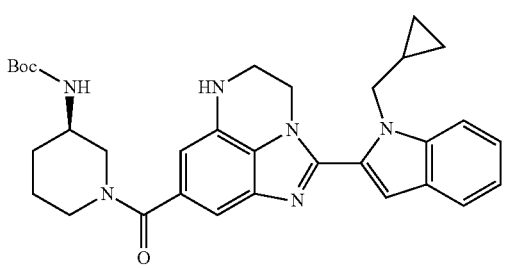 [SMILES: CC(C)(C)OC(=O)N[C@@H]1CCCN(C(=O)c2cc3c4c(c2)nc(-c2cc5ccccc5n2CC2CC2)n4C(C)(C)CO3)C1]

To the stirred solution of 2-(1-(cyclopropylmethyl)-1H-indol-2-yl)-5,6-dihydro-4H-imidazo[1,5,4-de]quinoxaline-8-carboxylic acid (6, 0.07 g, 0.18 mmol) in DCM (5 mL), were added tert-butyl-(R)-piperidin-3-ylcarbamate (7, 0.041 g, 0.206 mmol), triethylamine (0.07 mL, 0.56 mmol) followed by 50% solution of T3P in ethyl acetate (0.17 g, 0.565 mmol) and stirred at room temperature for 12 h (reaction condition e). To the reaction mixture was added water and compound was extracted with DCM (50 mL×2). Combined organic extracts were washed with brine, dried over sodium sulfate and evaporated to get crude product. The crude residue was purified by gradient column chromatography using silica gel and eluent 5% MeOH in DCM to afford the product as yellow solid (0.1 g, 71% Yield). MS (ESI): mass calcd. for $C_{32}H_{38}N_6O_3$, 554.7; m/z found, 555.3 [M+H]$^+$.

Step 8: Preparation of (R)-(3-aminopiperidin-1-yl)(2-(1-(cyclopropylmethyl)-1H-indol-2-yl)-5,6-dihydro-4H-imidazo[1,5,4-de]quinoxalin-8-yl)methanone (Example-63)

Example-63

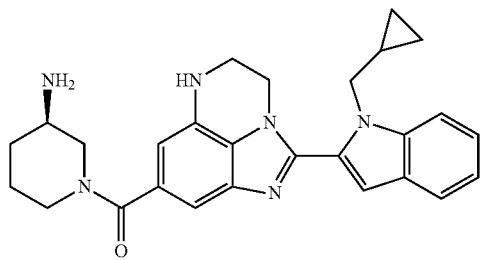

To the stirred solution Tert-butyl (R)-(1-(2-(1-(cyclopropylmethyl)-1H-indol-2-yl)-5,6-dihydro-4H-imidazo[1,5,4-de]quinoxaline-8-carbonyl)piperidin-3-yl)carbamate) (8, 0.05 g, 0.09 mmol) in dichloromethane (10 mL), was added trifluroacetic acid (0.5 mL) stirred at room temperature for 2 h (reaction condition f). The reaction mixture was evaporated completely, dissolved in minimum volume of water and basified by saturated NaHCO$_3$ solution (20 mL). The compound was extracted with DCM (20 mL×2). Combined organic extracts were washed with brine, dried over sodium sulfate and evaporated to get the product as pale yellow solid (0.025 g, 62.5% yield). $^1$HNMR (400 MHz, DMSO-d$_6$) δ (ppm): 7.67 (t, J=8 Hz, 2H), 7.28 (t, J=8 Hz, 1H), 7.13-7.07 (m, 2H), 6.94 (s, 1H), 6.40 (s, 1H) 6.37 (s, 1H), 4.65 (d, J=8 Hz, 2H), 4.48 (t, J=4 Hz, 2H), 3.93-3.88 (m, 2H), 3.53 (m, 2H), 2.87 (m, 1H), 2.66-2.65 (m, 2H), 1.88-1.85 (m, 2H), 1.64 (m, 1H), 1.42-1.17 (m, 4H), 0.33-0.199 (m, 4H). MS (ESI): mass calcd. for, $C_{27}H_{30}N_6O$ 455.58; m/z found, 456.2 [M+H]$^+$.

Following compounds (Examples 64-80) were synthesized using procedure as exemplified for Example-63.

Example-64

R-(3-aminopiperidin-1-yl)(2-(1-(cyclopropylmethyl)-5-fluoro-1H-indol-2-yl)-5,6-dihydro-4H-imidazo[1,5,4-de]quinoxalin-8-yl)methanone

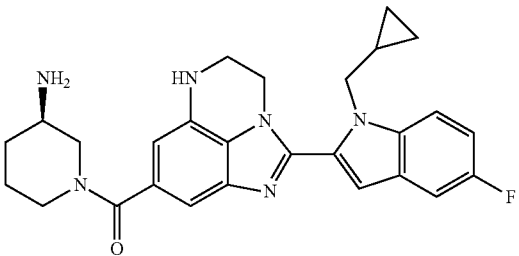 [SMILES: N[C@@H]1CCCN(C(=O)c2cc3c4c(c2)nc(-c2cc5cc(F)ccc5n2CC2CC2)n4CCN3)C1]

$^1$HNMR (400 MHz, DMSO-d$_6$) δ (ppm): 7.70-7.66 (m, 1H), 7.43-7.40 (m, 1H), 7.13-7.09 (m, 1H), 7.05 (s, 1H), 6.94 (s, 1H), 6.41 (s, 1H), 6.38 (s, 1H), 4.63 (d, J=6.8 Hz, 2H), 4.46 (m, 2H), 4.00 (s, 2H), 3.52 (m, 2H), 2.88 (m, 2H), 2.68 (m, 2H), 1.64 (m, 1H), 1.89-1.85 (m, 1H), 1.64 (m, 1H), 1.42-1.39 (m, 1H), 1.26-1.22 (m, 2H), 0.32 (d, J=7.6 Hz, 2H), 0.21 (m, 2H). MS (ESI): mass calcd. for $C_{27}H_{29}FN_6O$, 472.57; m/z found, 473.58 [M+H]$^+$.

Example-65

Synthesis of (R)-(3-aminopiperidin-1-yl)(2-(1-(cyclopropylmethyl)-6-fluoro-1H-indol-2-yl)-5,6-dihydro-4H-imidazo[1,5,4-de]quinoxalin-8-yl)methanone (Example-65)

Scheme-7

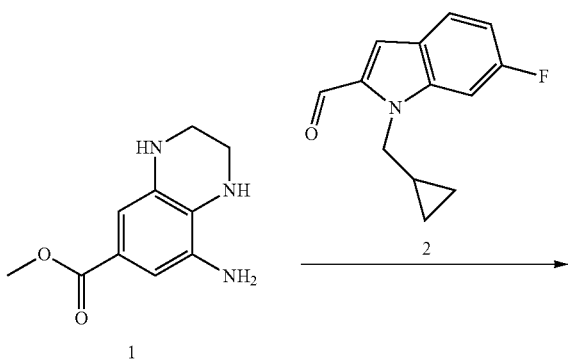

-continued

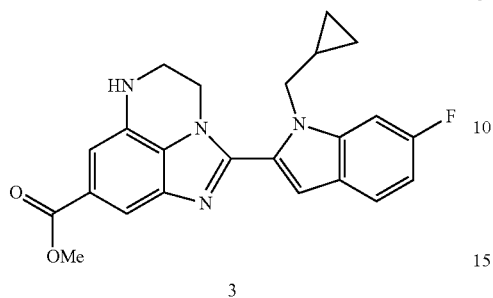

Intermediate (1) was synthesized from intermediate (3) of Scheme-6 under reduction conditions.

Step 5: Preparation of Methyl 2-(1-(cyclopropylmethyl)-6-fluoro-1H-indol-2-yl)-5,6-dihydro-4H-imidazo[1,5,4-de]quinoxaline-8-carboxylate (3)

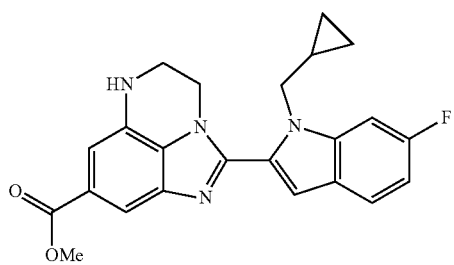

To the stirred solution of methyl 8-amino-1,2,3,4-tetrahydroquinoxaline-6-carboxylate (1, 0.1 g, 0.48 mmol) and 1-(cyclopropylmethyl)-6-fluoro-1H-indole-2-carbaldehyde (2, 0.11 g, 0.53 mmol) in DMF (3 mL), was added water (0.1 mL) and finally added oxone (0.09 g, 0.31 mmol). Then reaction mixture was allowed to stir under room temperature for about 1 h. The reaction mixture was quenched with potassium carbonate (0.005 g), extracted with ethyl acetate (20 mL×2). Combined organic extracts were washed with brine, dried over sodium sulfate, filtered and evaporated to get crude product. Crude residue was purified by gradient column chromatography using silica gel and eluent 20-30% ethyl acetate in hexane to get the product as a yellow solid (0.15 g, 65.2% yield). MS (ESI): mass calcd. for $C_{23}H_{21}FN_4O_2$, 404.16; m/z found, 405.2 [M+H]$^+$.

Following compounds (Examples 65-71) were synthesized using the above intermediate (3), and the procedure as exemplified for Example-63.

Example-65

(R)-(3-aminopiperidin-1-yl)(2-(1-(cyclopropylmethyl)-6-fluoro-1H-indol-2-yl)-5,6-dihydro-4H-imidazo[1,5,4-de]quinoxalin-8-yl)methanone

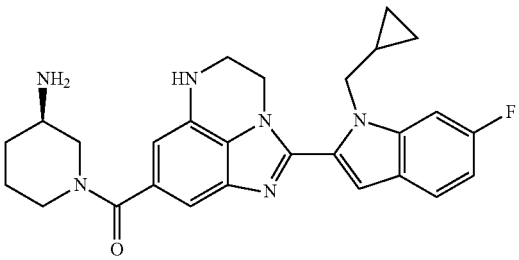 [SMILES: N[C@@H]1CCCN(C(=O)c2cc3c4c(c2)nc(-c2cc5ccc(F)cc5n2CC2CC2)n4CCN3)C1]

$^1$HNMR (400 MHz, DMSO-d$_6$) δ (ppm): 7.68-7.64 (m, 1H), 7.54 (d, J=8 Hz, 1H), 7.09 (s, 1H), 7.0 (s, 1H), 6.96 (d, J=12 Hz, 1H), 6.4-6.38 (m, 2H), 4.63-4.61 (m, 2H), 4.46 (m, 2H), 4.0 (m, 2H), 3.52 (m, 2H), 2.91 (m, 1H), 2.76 (m, 2H), 1.89 (m, 2H), 1.65 (m, 1H), 1.43 (m, 1H), 1.41 (m, 1H), 1.17 (m, 2H), 0.31-0.24 (m, 2H), 0.24-0.20 (m, 2H). MS (ESI): mass calcd. for $C_{27}H_{29}FN_6O$, 472.24; m/z found, 473.3 [M+H]$^+$.

Example-66

(R)-(3-aminopiperidin-1-yl)(2-(1-(pyridin-3-ylmethyl)-1H-indol-2-yl)-5,6-dihydro-4H-imidazo[1,5,4-de]quinoxalin-8-yl)methanone

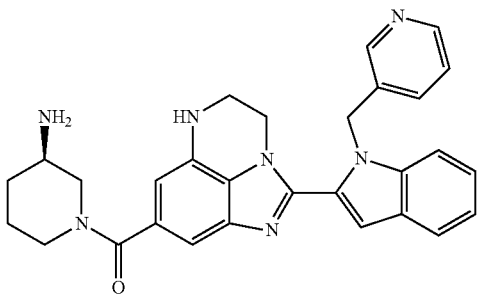 [SMILES: N[C@@H]1CCCN(C(=O)c2cc3c4c(c2)nc(-c2cc5ccccc5n2Cc2cccnc2)n4CCN3)C1]

$^1$HNMR (400 MHz, DMSO-d$_6$) δ (ppm): 8.36 (bs, 2H), 7.70-7.69 (m, 1H), 7.54-7.52 (m, 1H), 7.44-7.52 (m, 1H), 7.24-7.23 (m, 3H), 7.15-7.11 (m, 1H), 6.99 (bs, 1H), 6.77 (s, 1H), 6.39-6.37 (m, 1H), 6.10 (bs, 2H), 4.50 (m, 2H), 4.00 (m, 2H), 3.51 (m, 2H), 2.65-2.55 (m, 2H), 1.88-1.82 (m, 2H), 1.56 (m, 1H), 1.44 (m, 2H), 1.22 (m, 2H). MS (ESI): mass calcd. for $C_{29}H_{29}N_7O$, 491.60; m/z found, 492.4 [M+H]$^+$.

Example-67

(R)-(3-aminopiperidin-1-yl)(2-(5-bromo-1-(cyclopropylmethyl)-1H-indol-2-yl)-5,6-dihydro-4H-imidazo[1,5,4-de]quinoxalin-8-yl)methanone

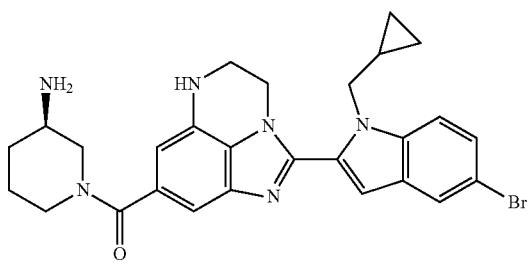 [SMILES: N[C@@H]1CCCN(C(=O)c2cc3c4c(c2)nc(-c2cc5cc(Br)ccc5n2CC2CC2)n4CCN3)C1]

$^1$HNMR (400 MHz, DMSO-d$_6$) δ (ppm): 7.85 (s, 1H), 7.65 (d, J=8.8 Hz, 1H), 7.36 (d, J=8.0 Hz, 1H), 7.06 (s, 1H), 6.98 (s, 1H), 6.42-6.40 (m, 2H), 5.40-5.30 (bs, 2H), 4.64 (d, J=7.2 Hz, 2H), 4.46 (s, 2H), 3.53 (s, 2H), 2.87-2.84 (m, 3H), 1.93-1.88 (m, 1H), 1.67 (s, 1H), 1.45-1.17 (m, 4H), 0.88-0.84 (m, 1H), 0.32-0.20 (m, 4H). MS (ESI): mass calcd. For, C$_{27}$H$_{29}$BrN$_6$O 533.47; m/z found, 497 [M+H]$^+$.

Example-69

(R)-(3-aminopiperidin-1-yl)(2-(1-(pyridin-2-ylmethyl)-1H-indol-2-yl)-5,6-dihydro-4H-imidazo[1,5,4-de]quinoxalin-8-yl)methanone

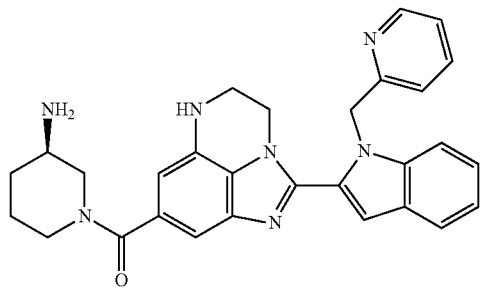

$^1$HNMR (400 MHz, DMSO-d$_6$) δ (ppm): 8.43 (d, J=4.6 Hz, 1H), 7.70 (d, J=7.7 Hz, 1H), 7.62-7.58 (m, 1H), 7.44 (d, J=7.7 Hz, 1H), 7.23-7.11 (m, 4H) 6.91 (s, 1H), 6.84 (d, J=7.68 Hz, 1H), 6.40 (s, 2H), 6.15 (s, 1H), 4.53 (bs, 2H), 3.53 (bs, 2H), 3.53 (m, 2H), 2.89 (m, 1H), 2.73-2.66 (m, 2H), 1.90-1.86 (m, 2H), 1.64 (bs, 1H), 1.44-1.08 (m, 4H). MS (ESI): mass calcd. For, C$_{29}$H$_{29}$N$_7$O 491.02; m/z found, 492.09 [M+H]$^+$.

Example-68

(R)-(3-aminopiperidin-1-yl)(2-(1-(cyclopropylmethyl)-5-(pyridin-3-yl)-1H-indol-2-yl)-5,6-dihydro-4H-imidazo[1,5,4-de]quinoxalin-8-yl)methanone

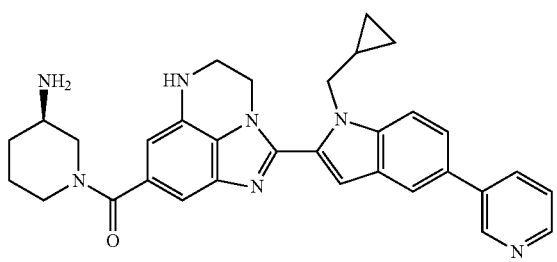 [SMILES: N[C@@H]1CCCN(C(=O)c2cc3c4c(c2)nc(-c2cc5cc(-c6cccnc6)ccc5n2CC2CC2)n4CCN3)C1]

$^1$HNMR (400 MHz, DMSO-d$_6$ δ (ppm): 8.93 (s, 1H), 8.52 (d, J=4.8 Hz, 1H), 8.09 (d, J=8.4 Hz, 1H), 7.99 (s, 1H), 7.78 (d, J=8.8 Hz, 1H), 7.61 (d, J=8.8 Hz, 1H), 7.48-7.45 (m, 1H), 7.14 (s, 1H), 6.96 (s, 1H), 6.41-6.39 (m, 2H), 4.68 (d, J=7.2 Hz, 2H), 4.49 (s, 2H), 4.12-3.80 (bs, 2H), 3.54 (s, 2H), 2.95 (s, 1H), 2.75 (s, 2H), 1.96-1.31 (m, 6H), 0.87-0.81 (m, 1H). 0.33-0.22 (m, 4H). MS (ESI): mass calcd. For, C$_{32}$H$_{33}$N$_7$O 531.6; m/z found, 533.2 [M+H]$^+$.

Example-70

(R)-(3-aminopiperidin-1-yl)(2-(1-(2-fluorobenzyl)-1H-indol-2-yl)-5,6-dihydro-4H-imidazo[1,5,4-de]quinoxalin-8-yl)methanone

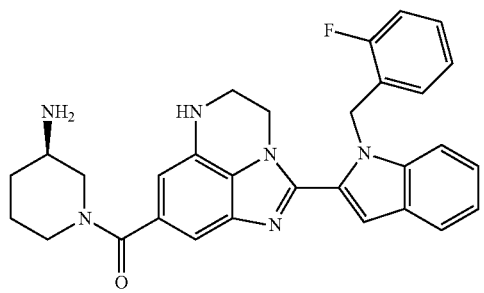 [SMILES: N[C@@H]1CCCN(C(=O)c2cc3c4c(c2)nc(-c2cc5ccccc5n2Cc2ccccc2F)n4CCN3)C1]

$^1$HNMR (400 MHz, DMSO-d$_6$) δ (ppm): 7.71 (d, J=7.3 Hz, 1H), 7.47 (t, J=7.8 Hz, 1H), 7.26-7.12 (m, 4H), 7.01-6.86 (m, 3H), 6.40 (s, 2H), 6.10 (s, 2H), 4.52 (d, J=3.36 Hz, 2H), 4.17 (bs, 2H), 3.53 (s, 2H), 2.83 (bs, 2H), 2.67 (bs, 2H), 1.84 (d, J=9.24 Hz, 2H), 1.64 (bs, 2H), 1.39 (bs, 2H). MS (ESI): mass calcd. for C$_{30}$H$_{29}$FN$_6$O 508.2; found m/z 509.16 [M+H]$^+$.

Example-71

(R)-(3-aminopiperidin-1-yl)(2-(1-(pyridin-4-ylmethyl)-1H-indol-2-yl)-5,6-dihydro-4H-imidazo[1,5,4-de]quinoxalin-8-yl)methanone

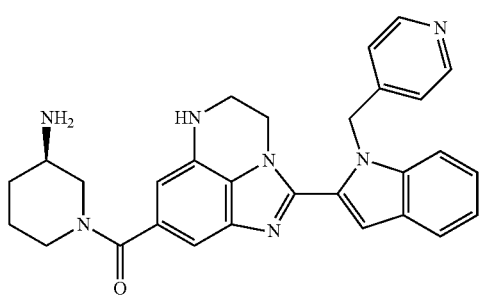 [SMILES: N[C@@H]1CCCN(C(=O)c2cc3c4c(c2)nc(-c2cc5ccccc5n2Cc2ccncc2)n4CCN3)C1]

$^1$HNMR (400 MHz, DMSO-d$_6$) δ (ppm): 8.39 (d, J=5.7 Hz, 1H), 7.73 (d, J=7.9 Hz, 1H), 7.43 (d, J=7.5 Hz, 1H), 7.25-7.21 (m, 2H), 7.15 (t, J=7.5 Hz, 1H), 6.98 (d, J=5.3 Hz, 2H), 6.87 (s, 2H), 6.39 (s, 2H), 6.15 (s, 2H), 4.54 (s, 2H), 4.34 (m, 2H), 3.53 (s, 2H), 2.89 (bs, 1H), 2.66 (m, 1H), 1.85 (d, J=12.8 Hz, 2H), 1.63-1.62 (m, 2H), 1.38-1.33 (m, 1H), 1.23-1.17 (m, 2H). MS (ESI): mass calcd. for C$_{29}$H$_{29}$N$_7$O 491.12; found m/z 492.22 [M+H]$^+$.

Following compound was synthesized using the above intermediate 3, and the procedure as exemplified for Example 63.

Example-72

R-(3-aminopiperidin-1-yl)(2-(1-(cyclopropylmethyl)-1H-indol-2-yl)-6-methyl-5,6-dihydro-4H-imidazo[1,5,4-de]quinoxalin-8-yl)methanone (Example-72)

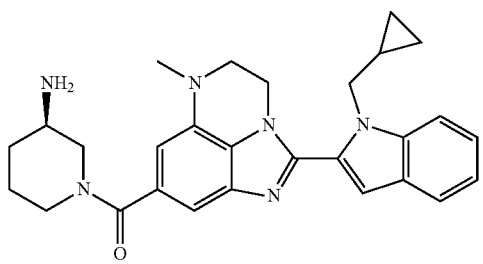 [SMILES: CN1CCn2c(-c3cc4ccccc4n3CC3CC3)nc3cc(C(=O)N4CCC[C@@H](N)C4)cc1c32]

Preparation of methyl 2-(1-(cyclopropylmethyl)-1H-indol-2-yl)-6-methyl-5,6-dihydro-4H-imidazo[1,5,4-de]quinoxaline-8-carboxylate (2)

The intermediate (3) obtained from the Scheme-6 above was methylated to obtain intermediate (2) as given below. Rest of the reaction steps were the same as exemplified for Example-63.

Scheme-8

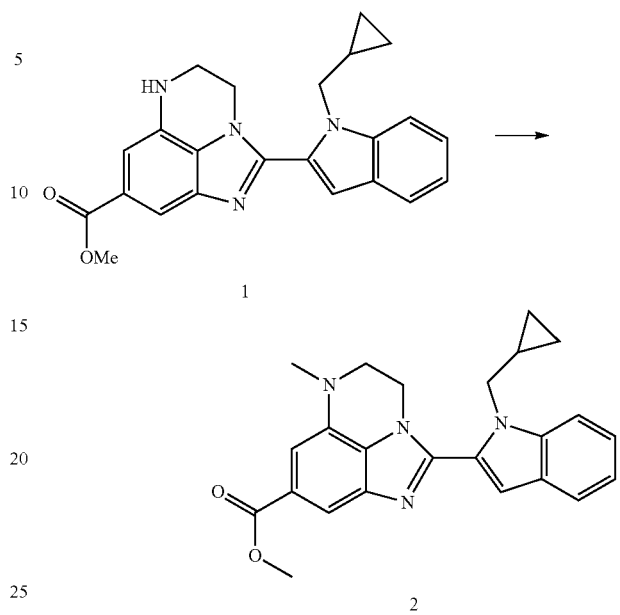

To a stirred solution of methyl 2-(1-(cyclopropylmethyl)-1H-indol-2-yl)-5,6-dihydro-4H-imidazo[1,5,4-de]quinoxaline-8-carboxylate (1 0.1 g, 0.25 mmol) in DMF (10 mL) was added potassium carbonate (0.07 g, 0.51 mmol) followed by methyl iodide (0.01 mL, 0.28 mmol) at room temperature and the resulting mixture was allowed to stir under room temperature for 12 h. The progress of the reaction was monitored by TLC. Then reaction mixture was evaporated, and extracted with ethyl acetate (50 mL×3), dried over sodium sulphate and concentrated under reduced pressure to afford crude compound which was purified by column chromatography (silica gel, 0-20% EtOAc in hexane) to give pale yellow solid (0.05 g, 50% yield). MS (ESI): mass calcd. for C$_{24}$H$_{24}$N$_4$O$_2$, 400.48; m/z found, 401.2 [M+H]$^+$.

R-(3-aminopiperidin-1-yl)(2-(1-(cyclopropylmethyl)-1H-indol-2-yl)-6-methyl-5,6-dihydro-4H-imidazo[1,5,4-de]quinoxalin-8-yl)methanone (Example-72)

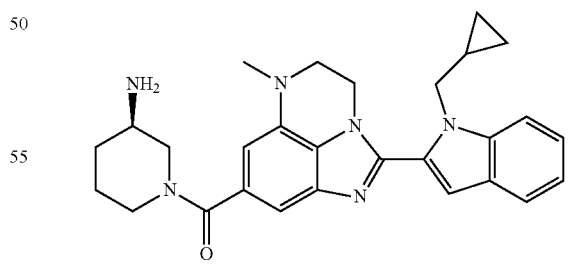

$^1$HNMR (400 MHz, DMSO-d$_6$) δ (ppm): 7.67 (t, J=8 Hz, 2H), 7.28 (t, J=8 Hz, 1H), 7.13-7.05 (m, 3H), 6.45 (s, 1H), 4.65 (d, J=8 Hz, 2H), 4.47 (m, 2H), 4.12 (m, 2H), 3.46 (m, 2H), 2.96 (s, 4H), 2.80 (m, 2H), 1.99 (m, 2H), 1.66 (m, 1H), 1.46-1.44 (m, 1H), 1.33-1.18 (m, 3H), 0.31-133 (m, 4H). MS (ESI): mass calcd. for C$_{28}$H$_{32}$N$_6$O, 468.61; m/z found, 469.3 [M+H]$^+$.

Following compounds (Examples 73, 77 and 80) were synthesized using the procedure as exemplified for Example-63.

Example-73

(R)-(3-aminopiperidin-1-yl)(2-(1-(cyclopropylmethyl)-6-methoxy-1H-indol-2-yl)-5,6-dihydro-4H-imidazo[1,5,4-de]quinoxalin-8-yl)methanone

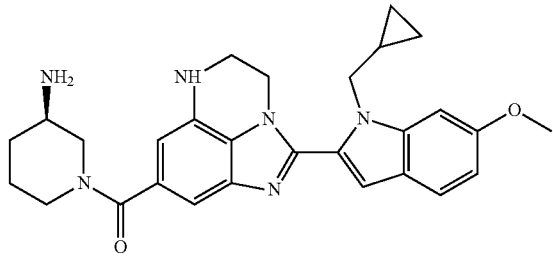 [SMILES: COc1ccc2cc(-c3nc4cc(C(=O)N5CCC[C@@H](N)C5)cc5c4n3CCN5)n(CC3CC3)c2c1]

$^1$HNMR (400 MHz, DMSO-d6) δ (ppm): 7.60 (m, 1H), 7.14 (bs, 1H), 6.98 (s, 1H), 6.91 (m, 1H), 6.74 (m, 1H), 6.38 (m, 2H), 4.65 (d, J=8 Hz, 2H), 4.45 (m, 2H), 3.83 (bs, 4H), 2.91 (bs, 1H), 2.53 (m, 3H), 1.88 (m, 2H), 1.64 (m, 2H), 1.41 (m, 2H), 1.22-1.17 (m, 3H), 0.21-0.20 (m, 2H), 0.01 (m, 2H). MS (ESI): mass calcd. for $C_{28}H_{32}N_6O_2$, 484.26; m/z found, 485.3 [M+H]$^x$.

Example-74

(R)-(3-aminopiperidin-1-yl)(2-(1-(cyclopropylmethyl)-6-methoxy-1H-indol-2-yl)-6-methyl-5,6-dihydro-4H-imidazo[1,5,4-de]quinoxalin-8-yl)methanone

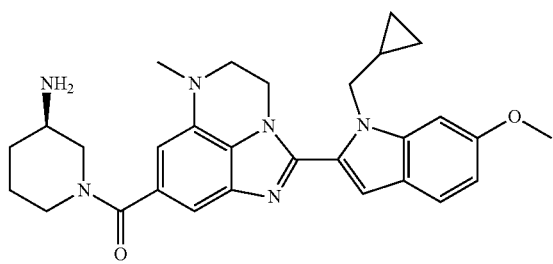 [SMILES: COc1ccc2cc(-c3nc4cc(C(=O)N5CCC[C@@H](N)C5)cc5c4n3CCN5C)n(CC3CC3)c2c1]

$^1$HNMR (400 MHz, DMSO-d$_6$) δ (ppm): 7.56 (d, J=9.2 Hz, 1H), 7.30 (s, 1H), 7.14 (s, 1H), 7.04 (s, 1H), 6.94-6.91 (m, 1H), 6.75 (s, 1H), 4.65-4.63 (m, 4H), 4.55 (s, 2H), 3.96-3.9 (bs, 2H), 3.79 (s, 3H), 2.95 (s, 3H), 2.79 (d, J=7.2 Hz, 2H), 1.89-1.26 (m, 4H), 0.88-0.84 (m, 1H). 0.33-0.26 (m, 4H). MS (ESI): mass calcd. For $C_{28}H_{31}N_5O_3$, 485.5 m/z found, 486.5 (M+H)$^+$.

Example-75

(R)-(3-aminopiperidin-1-yl)(2-(1-(cyclopropylmethyl)-5-fluoro-1H-indol-2-yl)-6-methyl-5,6-dihydro-4H-imidazo[1,5,4-de]quinoxalin-8-yl)methanone

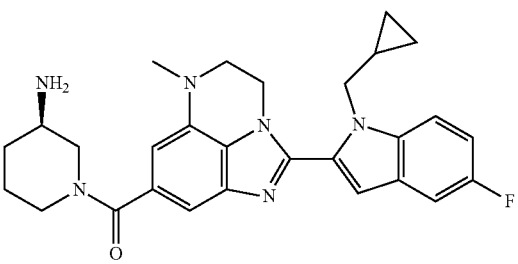 [SMILES: CN1CCn2c(-c3cc4cc(F)ccc4n3CC3CC3)nc3cc(C(=O)N4CCC[C@@H](N)C4)cc1c32]

$^1$HNMR (400 MHz, DMSO-d$_6$) δ (ppm): 7.70-7.63 (m, 1H), 7.43-7.40 (m, 1H), 7.14-7.02 (m, 3H), 6.44 (s, 1H), 4.64 (d, J=6.8 Hz, 2H), 4.58-4.56 (m, 2H), 3.45-3.44 (m, 2H), 2.96 (s, 3H), 2.89-2.79 (bs, 1H), 2.65 (bs, 2H), 2.01-1.97 (m, 2H), 1.88-1.84 (m, 2H), 1.43-1.37 (m, 2H), 1.35-1.26 (m, 2H), 0.87-0.84 (bs, 1H), 0.33-0.29 (m, 2H), 0.25-0.20 (m, 2H). MS (ESI) calculated for $C_{28}H_{31}FN_6O$ m/z 486.25 found (M+H)$^+$. 487.3.

Example-76

(R)-(3-aminopiperidin-1-yl)(2-(1-(cyclopropylmethyl)-1H-indol-2-yl)-6-(methylsulfonyl)-5,6-dihydro-4H-imidazo[1,5,4-de]quinoxalin-8-yl)methanone Scheme-9

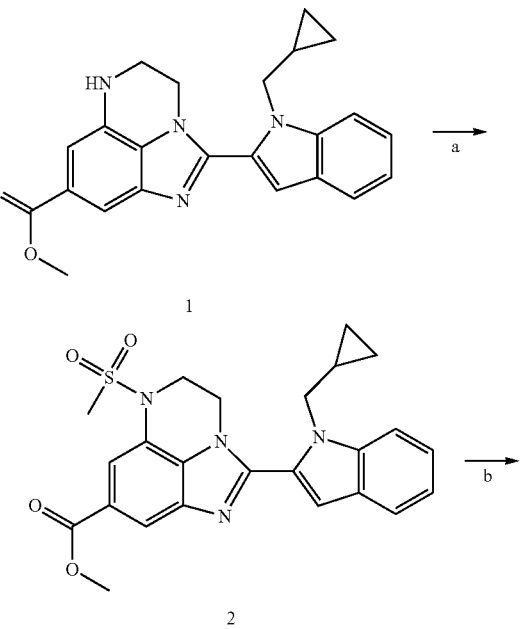

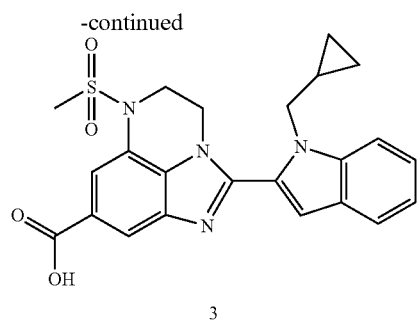

3

Intermediate (1) of the above Scheme-9 was obtained by a similar procedure as exemplified for Example-63 (Scheme 6).

Step 6: Preparation of Methyl 2-(1-(cyclopropylmethyl)-1H-indol-2-yl)-6-(methylsulfonyl)-5,6-dihydro-4H-imidazo[1,5,4-de]quinoxaline-8-carboxylate (2)

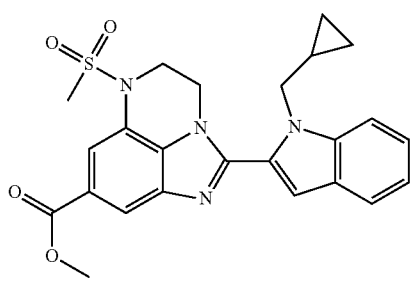

2

To a stirred solution of methyl 2-(1-(cyclopropylmethyl)-1H-indol-2-yl)-5,6-dihydro-4H-imidazo[1,5,4-de]quinoxaline-8-carboxylate (1, 0.15 g, 0.39 mmol) in DCM (10 mL) was added pyridine (0.061 g, 0.77 mmol) followed by methanesulfonyl chloride (0.03 ml, 0.39 mmol) at 0° C. and the resulting mixture was allowed to stir under room temperature for 1 h. The progress of the reaction was monitored by TLC. Then reaction mixture was evaporated, and extracted with DCM (50 mL×3), dried over sodium sulphate and concentrated under reduced pressure to give brown solid (0.18 g, crude). LC-MS m/z calcd for $C_{24}H_{24}N_4O_4S$, 464.5; m/z found, 465.1 [M+H]$^+$.

Step 7: Preparation of 2-(1-(cyclopropylmethyl)-1H-indol-2-yl)-6-(methylsulfonyl)-5,6-dihydro-4H-imidazo[1,5,4-de]quinoxaline-8-carboxylic Acid-(3)

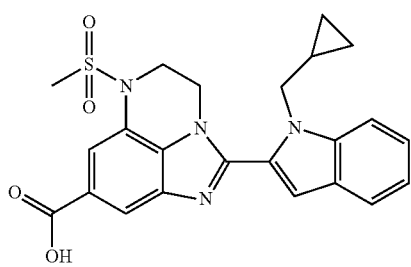

3

To the stirred solution of methyl 2-(1-(cyclopropylmethyl)-1H-indol-2-yl)-6-(methylsulfonyl)-5,6-dihydro-4H-imidazo[1,5,4-de]quinoxaline-8-carboxylate (2, 0.18 g, 0.39 mmol) in MeOH (5 mL) and Water (0.5 mL) was added LiOH·H$_2$O (0.027 g, 0.12 mmol) and stirred at 60° C. for 2 h. The reaction mixture was evaporated completely. The resulting crude was dissolved in minimum volume of water and acidified with saturated citric acid solution. Compound was extracted with DCM (30 mL×2), washed with brine, dried over sodium sulfate and evaporated to give crude product as a pale yellow solid (0.15 g, crude). MS (ESI): Mass calcd. for, $C_{23}H_{22}N_4O_4S$, 450.51; m/z found, 451.1 [M+H]$^+$. Further steps for Example-76 were carried using the similar procedure as exemplified for Example-63.

(R)-(3-aminopiperidin-1-yl)(2-(1-(cyclopropylmethyl)-1H-indol-2-yl)-6-(methylsulfonyl)-5,6-dihydro-4H-imidazo[1,5,4-de]quinoxalin-8-yl)methanone

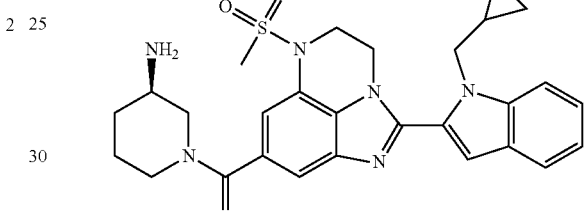

Example-76

$^1$HNMR (400 MHz, DMSO-d$_6$) δ (ppm): 7.68 (d, J=6.4 Hz, 2H), 7.52 (s, 1H), 7.31 (d, J=18 Hz, 2H), 7.15 (s, 2H), 4.66 (bs, 4H), 4.12 (s, 2H), 3.60 (bs, 1H), 3.21 (s, 3H), 2.95 (s, 1H), 2.68 (s, 2H), 1.86-1.68 (m, 4H), 1.44 (s, 1H), 1.23 (s, 3H), 0.33-0.27 (m, 4H). MS (ESI): mass calcd. For $C_{28}H_{32}N_6O_3S$ 532.6; m/z found 533 [M+H]$^+$.

Example-77

(R)-(3-aminopiperidin-1-yl)(2-(1-(cyclopropylmethyl)-5,6-difluoro-1H-indol-2-yl)-5,6-dihydro-4H-imidazo[1,5,4-de]quinoxalin-8-yl)methanone

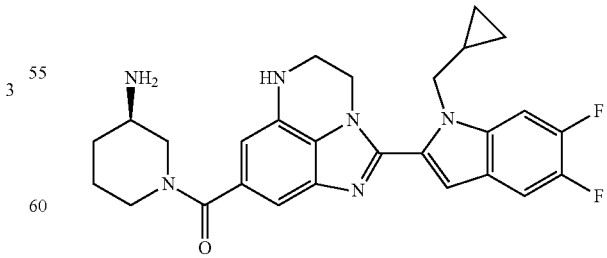

$^1$HNMR (400 MHz, DMSO-d$_6$) δ (ppm): 7.84 (m, 1H), 7.68-7.63 (m, 1H), 7.08 (s, 1H), 6.97 (s, 1H), 6.42-6.40 (m, 2H), 4.63-4.62 (m, 2H), 4.46 (m, 2H), 3.97 (m, 2H), 3.52 (m, 3H), 2.94 (m, 3H), 1.89 (m, 1H), 1.67 (m, 1H), 1.42-1.34 (m, 2H), 1.22-1.16 (m, 2H), 0.31 (m, 2H), 0.20 (m, 2H). MS (ESI): Mass calcd. for $C_{27}H_{28}F_2N_6O$, 490.23; m/z found, 491.2 $[M+H]^+$.

Example-78

(R)-(3-aminopiperidin-1-yl) (6-cyclopropyl-2-(1-(cyclopropylmethyl)-1H-indol-2-yl)-5,6-dihydro-4H-imidazo[1,5,4-de]quinoxalin-8-yl)methanone (Example-78)

Scheme-10

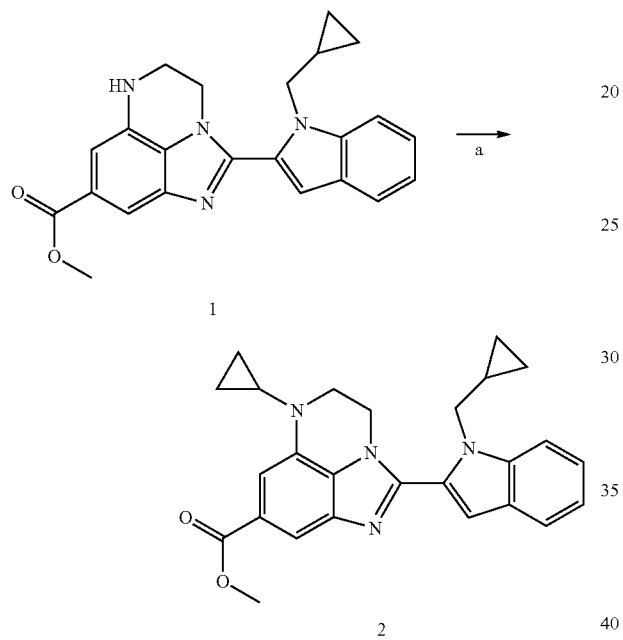

Step 6: Preparation of Methyl 6-cyclopropyl-2-(1-(cyclopropylmethyl)-1H-indol-2-yl)-5,6-dihydro-4H-imidazo[1,5,4-de]quinoxaline-8-carboxylate (2)

To a stirred solution of methyl 2-(1-(cyclopropylmethyl)-1H-indol-2-yl)-5,6-dihydro-4H-imidazo[1,5,4-de]quinoxaline-8-carboxylate (1, 0.2 g, 0.52 mmol) and cyclopropyl boronic acid (0.088 g, 1.04 mmol) in DCM (10 mL) was added copper (II) acetate (0.164 g, 1.036 mmol) followed by pyridine (0.1 mL, 1.04 mmol) at room temperature and the resulting mixture was allowed to stir under room temperature in the presence of air for 24 h. The progress of the reaction was monitored by TLC. Then reaction mixture was quenched with dilute HCl, extracted with DCM (50 mL×3), dried over sodium sulphate and concentrated under reduced pressure to afford crude compound. This was purified by column chromatography (silica gel, 0-20% EtOAc in hexane) to give pale yellow solid (0.11 g, 50% yield). MS (ESI): Mass calcd. for $C_{26}H_{26}N_4O_2$, 426.2; m/z found, 427 $[M+H]^+$.

Further steps for Example-78 were carried using the similar procedure as exemplified for Example-63.

(R)-(3-aminopiperidin-1-yl)(6-cyclopropyl-2-(1-(cyclopropylmethyl)-1H-indol-2-yl)-5,6-dihydro-4H-imidazo[1,5,4-de]quinoxalin-8-yl)methanone (Example-78)

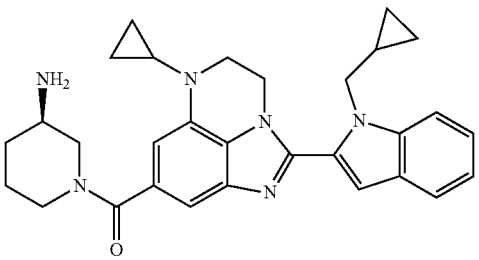 [SMILES: N[C@@H]1CCCN(C(=O)c2cc3c4c(c2)nc(-c2cc5ccccc5n2CC2CC2)n4CCN3C2CC2)C1]

$^1$HNMR (400 MHz, DMSO-$d_6$) δ (ppm): 7.65 (t, J=6.8 Hz, 2H), 7.26 (t, J=7.6 Hz, 1H), 7.13-7.09 (m, 2H), 7.054 (s, 1H), 6.74 (s, 1H), 4.65-4.64 (m, 2H), 4.52 (m, 2H), 4.00 (m, 2H), 3.54 (bs, 2H), 2.74 (m, 1H), 2.65 (bs, 2H), 1.88 (m, 2H), 1.69 (bs, 2H), 1.46-1.44 (m, 2H), 1.17 (m, 3H), 0.87-0.86 (m, 2H), 0.66 (s, 1H), 0.31-0.29 (m, 2H), 0.20-0.19 (m, 2H). MS (ESI): Mass calcd. for $C_{30}H_{34}N_6O$, 494.64; m/z found, 495.5 $[M+H]^+$.

Example 79 was synthesized using the above procedure as exemplified for Example-76.

Example 79

(R)-(3-aminopiperidin-1-yl)(2-(1-(cyclopropylmethyl)-1H-indol-2-yl)-6-(phenethylsulfonyl)-5,6-dihydro-4H-imidazo[1,5,4-de]quinoxalin-8-yl) methanone

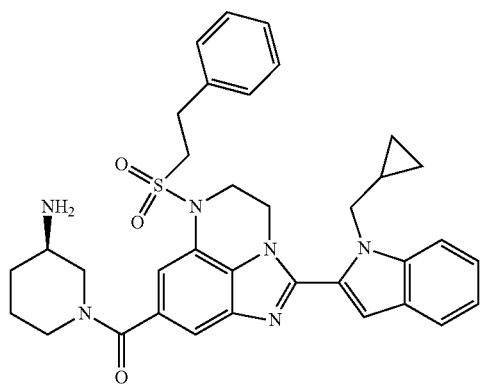 [SMILES: N[C@@H]1CCCN(C(=O)c2cc3c4c(c2)nc(-c2cc5ccccc5n2CC2CC2)n4CCN3S(=O)(=O)CCc2ccccc2)C1]

$^1$HNMR (400 MHz, DMSO-$d_6$) δ (ppm): 7.67 (d, J=7.2 Hz, 2H), 7.49 (s, 1H), 7.35 (s, 1H), 7.28 (d, J=7.6 Hz, 1H), 7.23-7.20 (m, 4H), 7.17-7.13 (m, 3H), 4.65-4.64 (m, 2H), 4.59-4.57 (m, 2H), 4.14-4.11 (m, 3H), 3.72-3.36 (m, 3H), 3.05 (t, J=8.0 Hz, 2H), 2.95-2.93 (m, 2H), 2.71-2.69 (m, 2H), 1.88-1.85 (m, 1H), 1.66-1.64 (m, 1H), 1.45-1.43 (m, 1H), 1.27-1.22 (m, 3H), 0.31 (d, J=8.0 Hz, 2H), 0.25 (d, J=3.6 Hz, 2H). MS (ESI): Mass calcd. for $C_{35}H_{38}N_6O_3S$, 622.27; m/z found 623.2 $(M+H)^+$.

Example-80

(R)-(3-aminopiperidin-1-yl)(2-(1-(cyclopropylmethyl)-4-fluoro-1H-indol-2-yl)-5,6-dihydro-4H-imidazo[1,5,4-de]quinoxalin-8-yl)methanone

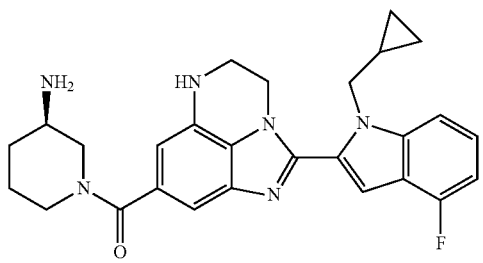 [SMILES: N[C@@H]1CCCN(C(=O)c2cc3c4c(c2)nc(-c2cc5c(F)cccc5n2CC2CC2)n4CCN3)C1]

¹HNMR (400 MHz, DMSO-d₆) δ (ppm): 7.52 (d, J=8.4 Hz, 1H), 7.27-7.21 (m, 1H), 7.13 (s, 1H), 6.95 (s, 1H), 6.92-6.88 (m, 1H), 6.41-6.38 (m, 2H), 4.66 (d, J=6.8 Hz, 2H), 4.49 (bs, 2H), 4.00 (m, 2H), 3.93 (m, 3H), 2.88 (m, 1H), 2.69 (m, 1H), 1.88 (m, 2H), 1.64 (m, 1H), 1.39 (m, 1H), 1.24-1.17 (m, 3H), 0.32 (d, J=7.6 Hz, 2H), 0.21 (m, 2H). MS (ESI): Mass calcd. for $C_{27}H_{29}FN_6O$, 472.57; m/z found, 473.2 [M+H]⁺.

Examples 81-83 were synthesized using the above procedure as exemplified for Example-76. Example 84 was synthesized using the above procedure as exemplified for Example-63.

Example-81

(R)-(3-aminopiperidin-1-yl)(6-((4-chlorophenyl)sulfonyl)-2-(1-(cyclopropylmethyl)-1H-indol-2-yl)-5,6-dihydro-4H-imidazo[1,5,4-de]quinoxalin-8-yl)methanone

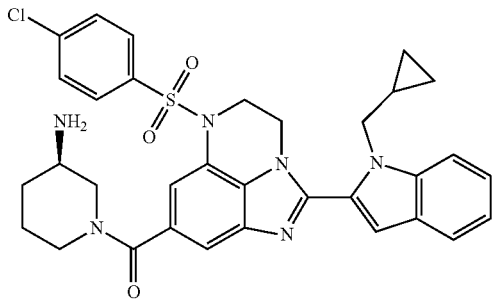 [SMILES: N[C@@H]1CCCN(C(=O)c2cc3c4c(c2)nc(-c2cc5ccccc5n2CC2CC2)n4CCN3S(=O)(=O)c2ccc(Cl)cc2)C1]

¹HNMR (400 MHz, DMSO-d₆) δ (ppm): 7.82 (d, J=8.4 Hz, 2H), 7.67-7.63 (m, 4H), 7.51 (s, 1H), 7.42 (s, 1H), 7.27 (t, J=7.2 Hz, 1H), 7.12 (t, J=7.6 Hz, 1H), 7.03 (s, 1H), 4.57 (d, J=6.4 Hz, 2H), 4.30-4.24 (m, 4H), 3.09-2.97 (bs, 2H), 2.74-2.65 (m, 1H), 1.88-1.86 (m, 2H), 1.70 (bs, 1H), 1.43-1.31 (m, 2H), 1.28-1.21 (m, 3H), 1.10 (bs, 2H), 0.25-0.23 (m, 2H), 0.13-0.12 (m, 2H). MS (ESI): mass calcd. for $C_{30}H_{34}N_6O_3S$, 629.18; m/z found, 629.2 [M+H]⁺.

Example-82

(R)-(3-aminopiperidin-1-yl)(2-(1-(cyclopropylmethyl)-1H-indol-2-yl)-6-(cyclopropylsulfonyl)-5,6-dihydro-4H-imidazo[1,5,4-de]quinoxalin-8-yl)methanone

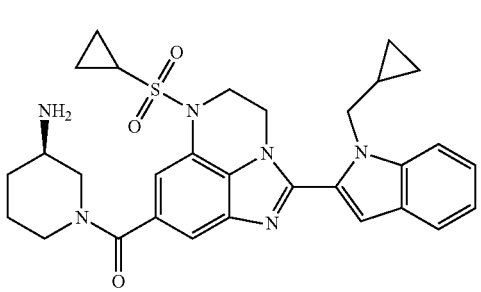 [SMILES: N[C@@H]1CCCN(C(=O)c2cc3c4c(c2)nc(-c2cc5ccccc5n2CC2CC2)n4CCN3S(=O)(=O)C2CC2)C1]

¹HNMR (400 MHz, DMSO-d₆) δ (ppm): 7.68 (t, J=7.2 Hz, 2H), 7.53 (s, 1H), 7.35 (s, 1H), 7.29 (t, J=7.2 Hz, 1H), 7.16-7.12 (m, 2H), 4.67-4.63 (m, 4H), 4.12 (bs, 2H), 2.96-2.87 (bs, 2H), 2.73-2.65 (m, 3H), 1.89 (m, 2H), 1.67 (bs, 1H), 1.43-1.31 (m, 1H), 1.28-1.22 (m, 4H), 1.03-1.01 (m, 4H), 0.33-0.31 (m, 2H), 0.26 (bs, 2H). MS (ESI): mass calcd. for $C_{30}H_{34}N_6O_3S$, 558.7; m/z found, 559.2 [M+H]⁺.

Example-83

(R)-(3-aminopiperidin-1-yl)(2-(1-(cyclopropylmethyl)-1H-indol-2-yl)-6-((2-ethoxyethyl)sulfonyl)-5,6-dihydro-4H-imidazo[1,5,4-de]quinoxalin-8-yl)methanone

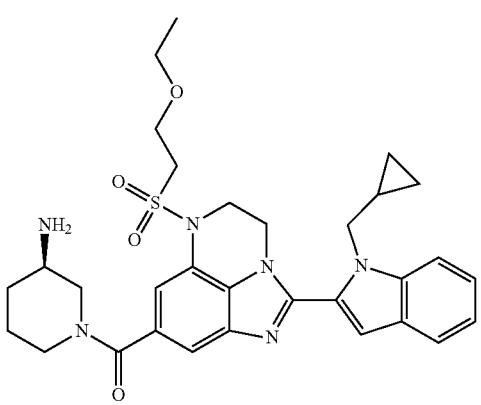 [SMILES: CCOCCS(=O)(=O)N1CCn2c(-c3cc4ccccc4n3CC3CC3)nc3cc(C(=O)N4CCC[C@@H](N)C4)cc1c32]

¹HNMR (400 MHz, DMSO-d₆) δ (ppm): 7.68 (d, J=7.2 Hz, 2H), 7.49 (s, 1H), 7.33-7.27 (m, 2H), 7.15-7.10 (m, 2H), 4.68-4.65 (m, 2H), 4.60-4.58 (m, 2H), 4.14-4.11 (m, 3H), 3.67-3.65 (m, 3H), 3.62-3.60 (m, 2H), 3.12-3.10 (m, 1H), 2.91-2.89 (m, 3H), 2.71-2.69 (m, 2H), 1.88-1.85 (m, 2H), 1.66-1.64 (m, 2H), 1.45-1.43 (m, 1H), 1.27-1.22 (m, 3H), 0.70-0.67 (m, 1H), 0.32 (d, J=6.8 Hz, 2H), 0.23 (d, J=3.6 Hz, 2H). MS (ESI): mass calcd. for $C_{31}H_{38}N_6O_4S$, 590.27; m/z found, 591.3 (M+H)⁺.

Example-84

(R)-(3-aminopiperidin-1-yl)(2-(1-(cyclopropylmethyl)-7-methyl-1H-indol-2-yl)-5,6-dihydro-4H-imidazo[1,5,4-de]quinoxalin-8-yl)methanone

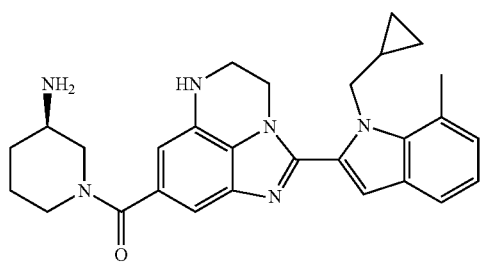 [SMILES: Cc1cccc2cc(-c3nc4cc(C(=O)N5CCC[C@@H](N)C5)cc5c4n3CCN5)n(CC3CC3)c12]

$^1$HNMR (400 MHz, DMSO-d$_6$) δ (ppm): 7.56 (m, 1H), 7.08 (m, 3H), 6.97 (s, 1H), 6.45 (m, 2H), 4.89 (d, J=8 Hz, 2H), 4.46 (m, 2H), 4.00 (m, 2H), 3.57 (bs, 2H), 2.83 (s, 3H), 2.70 (m, 2H), 1.93 (m, 2H), 1.80 (m, 2H), 1.30 (m, 1H), 1.26 (m, 1H), 0.98 (m, 2H), 0.24 (d, J=12 Hz, 2H), 0.19 (m, 2H). MS (ESI): mass calcd. for C$_{28}$H$_{32}$N$_6$O, 468.61; m/z found, 469.1 [M+H]$^+$.

Example-85

(R)-1-(8-(3-aminopiperidine-1-carbonyl)-2-(1-(cyclopropylmethyl)-1H-indol-2-yl)-4,5-dihydro-6H-imidazo[1,5,4-de]quinoxalin-6-yl)ethan-1-one Scheme-11

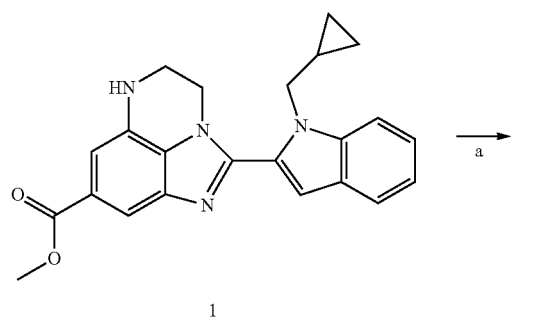

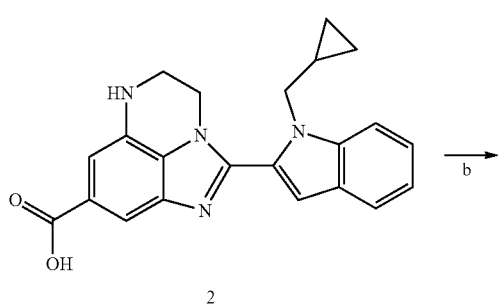

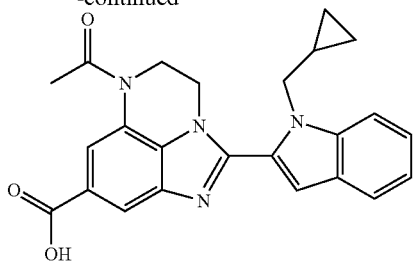

Intermediate (1) of the above Scheme-11 was obtained by a similar procedure as exemplified for Example-63 (Scheme 6).

Step 6: Preparation of 2-(1-(cyclopropylmethyl)-1H-indol-2-yl)-5,6-dihydro-4H-imidazo[1,5,4-de]quinoxaline-8-carboxylic Acid-(2)

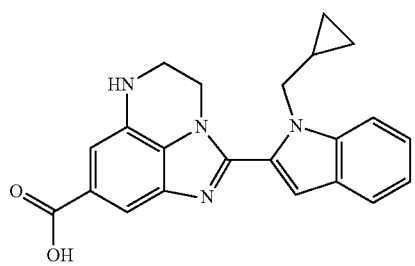

To the stirred solution of methyl methyl 2-(1-(cyclopropylmethyl)-1H-indol-2-yl)-5,6-dihydro-4H-imidazo[1,5,4-de]quinoxaline-8-carboxylate (1, 0.09 g, 0.21 mmol) in MeOH (5 mL) and water (0.5 mL) was added LiOH·H$_2$O (0.044 g, 1.05 mmol) and stirred at room temperature for 12 h. The reaction mixture was evaporated completely. The resulting crude was dissolved in minimum volume of water and acidified with saturated citric acid solution. Compound was extracted with DCM (30 mL×2), washed with brine, dried over sodium sulfate and evaporated to give the crude product as a pale yellow solid (0.07 g, crude). MS (ESI): Mass calcd. for C$_{22}$H$_{20}$N$_4$O$_2$, 372.43; m/z found, 373.0 [M+H]$^+$.

Step 7: Preparation of 6-acetyl-2-(1-(cyclopropylmethyl)-1H-indol-2-yl)-5,6-dihydro-4H-imidazo[1,5,4-de]quinoxaline-8-carboxylic Acid (3)

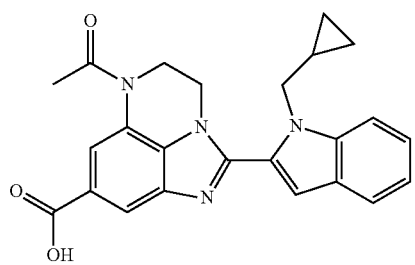

To a stirred solution of 2-(1-(cyclopropylmethyl)-1H-indol-2-yl)-5,6-dihydro-4H-imidazo[1,5,4-de]quinoxaline-8-carboxylic acid (0.07 g, 0.19 mmol) in DCM (10 mL) was added pyridine (0.03 mL, 0.37 mmol) followed by acetyl chloride (0.02 mL, 0.28 mmol) at 0° C. and the resulting mixture was stirred at room temperature for 1 h. The progress of the reaction was monitored by TLC. The reaction mixture was evaporated, extracted with DCM (50 mL×3), dried over sodium sulphate and concentrated under reduced pressure to give the brown solid (0.059 g, 76%). LC-MS m/z calcd for $C_{24}H_{22}N_4O_3$, 414.4, found 415.1 [M+H]$^+$.

The remaining steps for preparing Example-85 were carried using the similar procedure as exemplified for Example-63.

Example-85

(R)-1-(8-(3-aminopiperidine-1-carbonyl)-2-(1-(cyclopropylmethyl)-1H-indol-2-yl)-4,5-dihydro-6H-imidazo[1,5,4-de]quinoxalin-6-yl)ethan-1-one

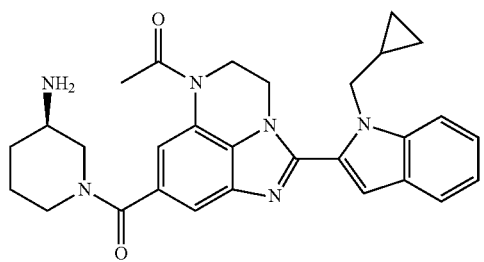 [SMILES: CC(=O)N1CCn2c(-c3cc4ccccc4n3CC3CC3)nc3cc(C(=O)N4CCC[C@@H](N)C4)cc1c32]

$^1$HNMR (400 MHz, DMSO-d$_6$) δ (ppm): 7.90 (s, 1H), 7.68 (t, J=7.6 Hz, 2H), 7.53 (s, 1H), 7.29 (t, J=7.6 Hz, 1H), 7.13 (t, J=6.8 Hz, 2H), 6.00 (bs, 2H), 4.67-4.58 (m, 4H), 4.17 (s, 3H), 3.00 (bs, 3H), 2.40 (s, 3H), 1.96 (s, 1H), 1.70 (s, 1H), 1.46 (s, 2H), 1.22 (s, 2H), 0.34-0.26 (m, 4H). MS (ESI): Mass calcd. for $C_{29}H_{32}N_6O_2$, 496.6; m/z found, 497.3 [M+H]$^+$.

Example-86

(R)-(3-aminopiperidin-1-yl)(2-(1-(cyclopropylmethyl)-1H-indol-2-yl)-5,6-dihydro-4H-imidazo[1,5,4-de]quinoxalin-8-yl)methanethione Scheme-12

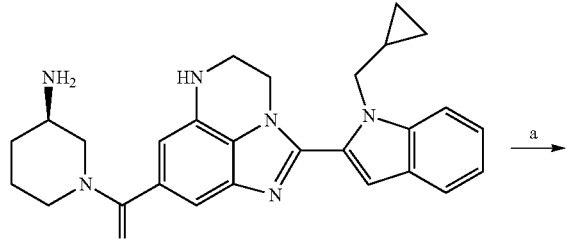

Ex-63

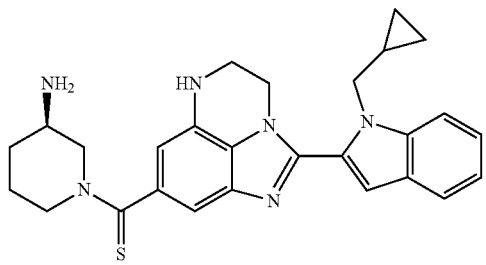

Ex-86

To the stirred solution (R)-(3-aminopiperidin-1-yl)(2-(1-(cyclopropylmethyl)-1H-indol-2-yl)-5,6-dihydro-4H-imidazo[1,5,4-de]quinoxalin-8-yl)methanone (Example-63, 0.07 g, 0.15 mmol) in Toluene (50 mL), was added Lawessons reagent (0.12 g, 0.39 mmol) at room temperature. The reaction mixture was reflux at bath temperature of 100° C. for 12 h. The reaction mixture was diluted with NaHCO$_3$ (50 mL×2) and extracted with ethyl acetate (50 mL×2). Combined organic extracts were washed with brine, dried over sodium sulfate and evaporated to get crude product. The crude residue was purified by gradient column chromatography using 15-100% ethyl acetate in hexane to afford (R)-(3-aminopiperidin-1-yl)(2-(1-(cyclopropylmethyl)-1H-indol-2-yl)-5,6-dihydro-4H-imidazo[1,5,4-de]quinoxalin-8-yl)methanethionen as yellow colour solid (0.007 g, 10% Yield). $^1$HNMR (400 MHz, DMSO-d$_6$) δ (ppm): 8.06 (m, 1H), 7.79 (m, 1H), 7.67 (t, J=8 Hz, 2H), 7.28 (t, J=12 Hz, 1H), 7.28-7.03 (m, 2H), 6.39 (m, 1H), 5.12 (m, 1H), 4.63 (m, 2H), 4.47 (bs, 2H), 3.79 (bs, 1H), 3.48 (bs, 2H), 2.04-1.97 (m, 3H), 1.72-1.61 (m, 4H), 1.44 (m, 2H), 0.83 (s, 1H), 0.32-0.31 (d. J=4 Hz, 2H), 0.21 (m, 2H). MS (ESI): Mass calcd. for $C_{27}H_{30}N_6S$, 470.64; m/z found 471.2[M+H]$^+$.

Example-87

Synthesis of (R)-(3-aminopiperidin-1-yl)(2-(7-chloro-1-(cyclopropylmethyl)-6-fluoro-1H-indol-2-yl)-3,4-dihydro-5-oxa-1,2a-diazaacenaphthylen-7-yl)methanone Scheme-13

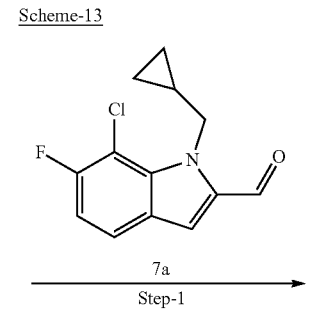

1

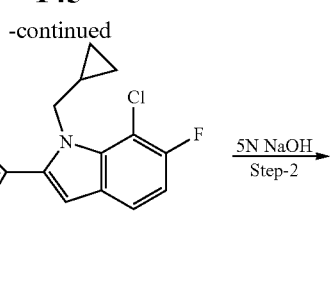

2

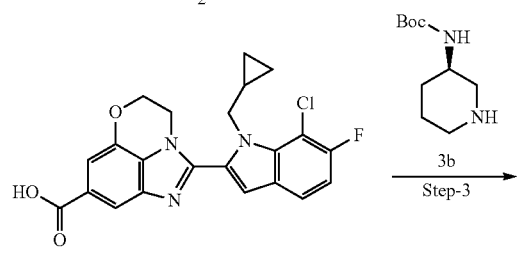

3

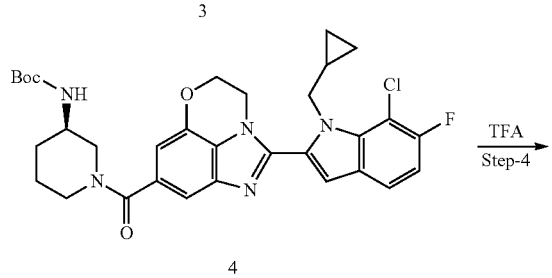

4

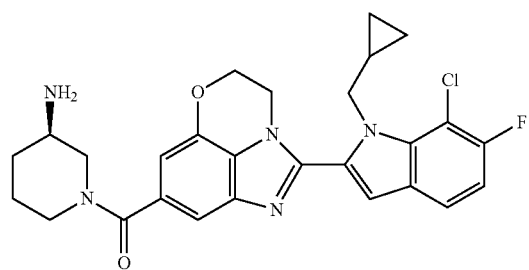

Example 87

Step-1: Synthesis of methyl-2-(7-chloro-1-(cyclopropylmethyl)-6-fluoro-1H-indol-2-yl)-3,4-dihydro-5-oxa-1,2a-diazaacenaphthylene-7-carboxylate (2)

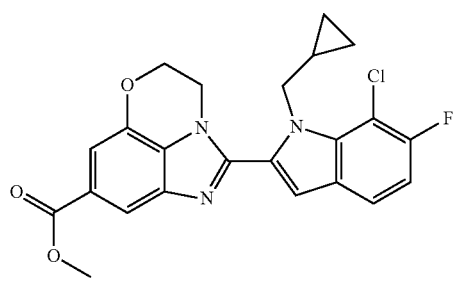 [SMILES: COC(=O)c1cc2c3c(c1)nc(-c1cc4ccc(F)c(Cl)c4n1CC1CC1)n3CCO2]

To a stirred solution of methyl-5-amino-3,4-dihydro-2H-benzo[b][1,4]oxazine-7-carboxylate (1, 0.33 g, 1.31 mmol) and 7-chloro-1-(cyclopropylmethyl)-6-fluoro-1H-indole-2-carbaldehyde (7a, 0.27 g, 1.31 mmol) in N, N-dimethylformamide (10.0 mL) and water (3.0 mL), potassium peroxomonosulfate (Oxone, 0.484 g, 1.57 mmol) was added at room temperature. The reaction mixture was stirred at room temperature for 16 h. After completion of reaction, the reaction mixture was cooled to room temperature, water was added. Precipitated solid was filtered and washed with water (20 mL×2) and methanol (10 mL×2). The compound obtained was dried under vacuum to afford methyl-2-(7-chloro-1-(cyclopropylmethyl)-6-fluoro-1H-indol-2-yl)-3,4-dihydro-5-oxa-1,2a-diazaacenaphthylene-7-carboxylate (2) as yellow solid. Yield: 0.12 g (22%). MS (ESI) 439.11; m/z found 440.28 $[M+H]^{+1}$.

Step-2: Synthesis of 2-(7-chloro-1-(cyclopropylmethyl)-6-fluoro-1H-indol-2-yl)-3,4-dihydro-5-oxa-1,2a-diazaacenaphthylene-7-carboxylic Acid (3)

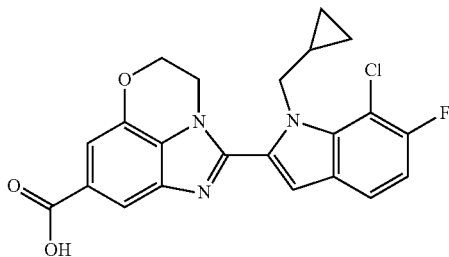 [SMILES: O=C(O)c1cc2c3c(c1)nc(-c1cc4ccc(F)c(Cl)c4n1CC1CC1)n3CCO2]

To a stirred solution of methyl-2-(7-chloro-1-(cyclopropylmethyl)-6-fluoro-1H-indol-2-yl)-3,4-dihydro-5-oxa-1,2a-diazaacenaphthylene-7-carboxylate (2, 0.12 g, 0.29 mmol) in tetrahydrofuran (5.0 mL) and methanol (3.0 mL), 5N sodium hydroxide solution (3.0 mL) was added and reaction mixture was stirred at 60° C. for 2 h. After completion of reaction, the reaction mixture was concentrated under reduced pressure. The resulting crude was dissolved in minimum volume of water and acidified with saturated citric acid solution at 0° C. up to pH 2-3. The precipitated solid was filtered, washed with water (10 mL×2). The compound obtained was dried under vacuum to afford 2-(7-chloro-1-(cyclopropylmethyl)-6-fluoro-1H-indol-2-yl)-3,4-dihydro-5-oxa-1,2a-diazaacenaphthylene-7-carboxylic acid (3) as white solid. Yield: 0.11 g (89%). MS (ESI) 425.09; m/z found 424.13 $[M-H]^{-1}$.

Step-3: Synthesis of tert-butyl (R)-(1-(2-(7-chloro-1-(cyclopropylmethyl)-6-fluoro-1H-indol-2-yl)-3,4-dihydro-5-oxa-1,2a-diazaacenaphthylene-7-carbonyl)piperidin-3-yl)carbamate (4)

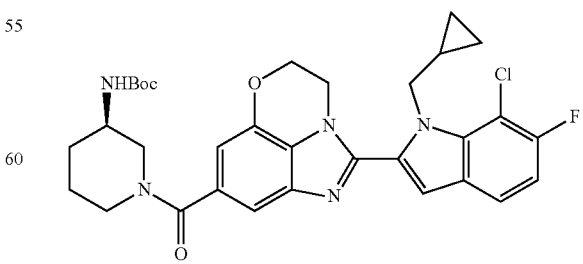

To a stirred solution of 2-(7-chloro-1-(cyclopropylmethyl)-6-fluoro-1H-indol-2-yl)-3,4-dihydro-5-oxa-1,2a-diazaacenaphthylene-7-carboxylic acid (3, 0.11 g, 0.25 mmol) in dichloromethane (10.0 mL), tert-butyl-(R)-piperidin-3-ylcarbamate (3b, 0.06 g, 0.31 mmol) and triethylamine (0.11 mL, 0.83 mmol) were added, followed by addition of propylphosphonic anhydride (50% solution in ethyl acetate, 0.25 mL, 0.86 mmol). The reaction mixture was stirred at room temperature for 2 h. After completion of reaction, the reaction mixture was diluted with water and extracted with dichloromethane (10 mL×2). The combined organic layers were washed with water and brine solution, further dried over anhydrous sodium sulfate, filtered and concentrated to get crude product. The crude was purified by CombiFlash using 4.0 g, RediSep column and 70% ethyl acetate in hexane as eluent to afford tert-butyl (R)-(1-(2-(7-chloro-1-(cyclopropylmethyl)-6-fluoro-1H-indol-2-yl)-3,4-dihydro-5-oxa-1,2a-diazaacenaphthylene-7-carbonyl)piperidin-3-yl)carbamate (4) as yellow solid. Yield: 0.07 g (45%). MS (ESI) 607.24; m/z found 608.32 [M+1]$^{+1}$.

Step-4: Synthesis of (R)-(3-aminopiperidin-1-yl)(2-(7-chloro-1-(cyclopropylmethyl)-6-fluoro-1H-indol-2-yl)-3,4-dihydro-5-oxa-1,2a-diazaacenaphthylen-7-yl)methanone (Example-87)

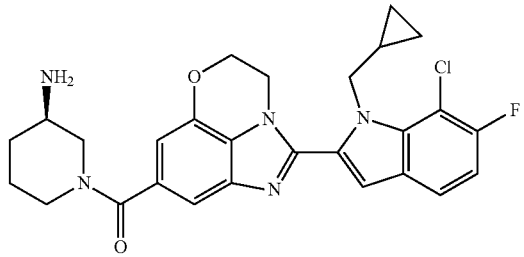 [SMILES: N[C@@H]1CCCN(C(=O)c2cc3c4c(c2)nc(-c2cc5ccc(F)c(Cl)c5n2CC2CC2)n4CCO3)C1]

To a stirred solution of tert-butyl (R)-(1-(2-(7-chloro-1-(cyclopropylmethyl)-6-fluoro-1H-indol-2-yl)-3,4-dihydro-5-oxa-1,2a-diazaacenaphthylene-7-carbonyl)piperidin-3-yl)carbamate (4, 0.07 g, 0.11 mmol) in dichloromethane (5.0 mL), trifluoroacetic acid (1.0 mL) was added at 0° C. and stirred at room temperature for 2 h. After completion of reaction, the reaction mixture was concentrated completely, basified by saturated sodium bicarbonate solution (10 mL). The compound was extracted with dichloromethane (10 mL×2). The combined organic extracts were washed with brine, dried over anhydrous sodium sulfate, filtered and concentrated to afford (R)-(3-aminopiperidin-1-yl)(2-(7-chloro-1-(cyclopropylmethyl)-6-fluoro-1H-indol-2-yl)-3,4-dihydro-5-oxa-1,2a-diazaacenaphthylen-7-yl)methanone, as white solid. Yield: 0.042 g (72%).

$^1$HNMR (400 MHz, DMSO-d$_6$) δ (ppm): 7.74-7.70 (m, 1H), 7.31 (s, 1H), 7.28 (s, 1H), 7.24 (t, J=9.16 Hz, 1H), 6.78 (s, 1H), 5.06 (d, J=6.8 Hz, 2H), 4.60-4.58 (m, 4H), 4.17 (bs, 1H), 3.60 (bs, 1H), 2.90 (bs, 2H), 2.64 (m, 1H), 1.86-1.83 (m, 1H), 1.64 (bs, 2H), 1.43 (m, 1H), 1.23-1.12 (m, 3H), 0.28 (d, J=7.68 Hz, 2H), 0.06 (d, J=4.36 Hz, 2H). MS (ESI): 507.18; found m/z 508.36 [M+H]$^+$.

Example-88

Synthesis of (R)-(3-aminopiperidin-1-yl)(2-(7-chloro-1-(pyrimidin-5-ylmethyl)-1H-indol-2-yl)-3,4-dihydro-5-oxa-1,2a-diazaacenaphthylen-7-yl)methanone Scheme-14

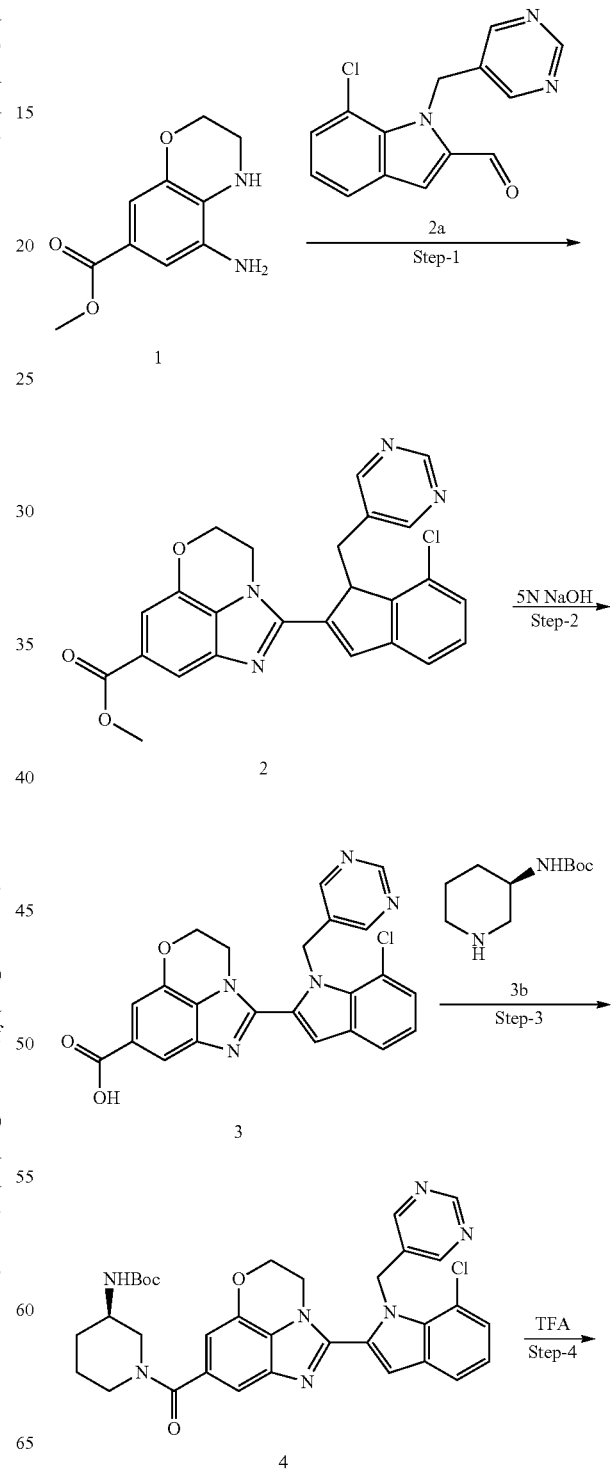

-continued

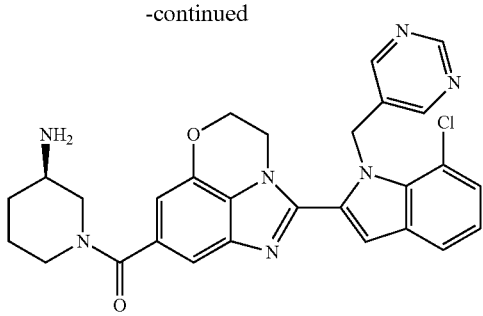

Example-88

Step-1: Synthesis of methyl-2-(7-chloro-1-(pyrimidin-5-ylmethyl)-1H-inden-2-yl)-3,4-dihydro-5-oxa-1,2a-diazaacenaphthylene-7-carboxylate (2)

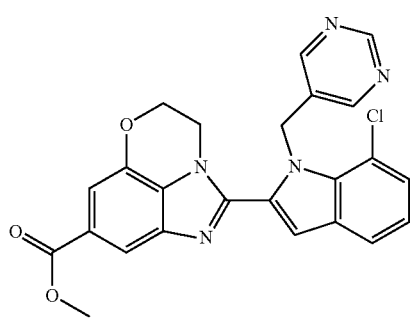 [SMILES: COC(=O)c1cc2c3c(c1)nc(-c1cc4cccc(Cl)c4n1Cc1cncnc1)n3CCO2]

To a stirred solution of methyl-5-amino-3,4-dihydro-2H-benzo[b][1,4]oxazine-7-carboxylate (1, 0.200 g, 0.96 mmol) and 7-chloro-1-(pyrimidin-5-ylmethyl)-1H-indole-2-carbaldehyde (2a, 0.260 g, 1.05 mmol) in N,N-dimethylformamide (5.0 mL) and water (1.5 mL), potassium peroxomonosulfate (Oxone, 0.175 g, 1.15 mmol) was added at room temperature. The reaction mixture was stirred at room temperature for 16 h. After completion of reaction, the reaction mixture was cooled to room temperature, water was added. Precipitated solid was filtered and washed with water (10 mL×2) and methanol (5 mL×2). The compound obtained was dried under vacuum to afford methyl 2-(7-chloro-1-(pyrimidin-5-ylmethyl)-1H-inden-2-yl)-3,4-dihydro-5-oxa-1,2a-diazaacenaphthylene-7-carboxylate (2) as yellow solid. Yield: 0.30 g (crude). MS (ESI) 458.90; m/z found 459.80 [M+H]$^{+1}$.

Step-2: Synthesis of 2-(7-chloro-1-(pyrimidin-5-ylmethyl)-1H-indol-2-yl)-3,4-dihydro-5-oxa-1,2a-diazaacenaphthylene-7-carboxylic Acid (3)

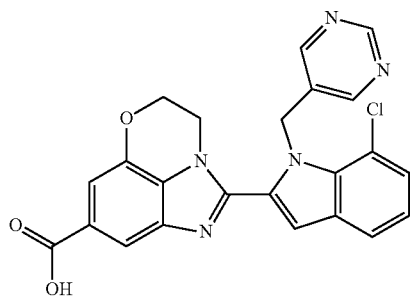 [SMILES: O=C(O)c1cc2c3c(c1)nc(-c1cc4cccc(Cl)c4n1Cc1cncnc1)n3CCO2]

To a stirred solution of methyl-2-(7-chloro-1-(pyrimidin-5-ylmethyl)-1H-inden-2-yl)-3,4-dihydro-5-oxa-1,2a-diazaacenaphthylene-7-carboxylate (2, 0.30 g, 0.65 mmol) in tetrahydrofuran (5.0 mL) and methanol (3.0 mL), 5N sodium hydroxide solution 3.0 mL) was added and reaction mixture was stirred at 60° C. for 2 h. After completion of reaction, the reaction mixture was concentrated under reduced pressure completely. The resulting crude was dissolved in minimum volume of water and acidified with saturated citric acid solution at 0° C. up to pH 2-3. The precipitated solid was filtered, washed with water (10 mL×2). The compound obtained was dried under vacuum to afford 2-(7-chloro-1-(pyrimidin-5-ylmethyl)-1H-indol-2-yl)-3,4-dihydro-5-oxa-1,2a-diazaacenaphthylene-7-carboxylic acid (3) as white solid. Yield: 0.250 g (Crude). MS (ESI) 445.86; m/z found 446.89 [M+H]$^{+1}$.

Step-3: Synthesis of tert-butyl (R)-(1-(2-(7-chloro-1-(pyrimidin-5-ylmethyl)-1H-indol-2-yl)-3,4-dihydro-5-oxa-1,2a-diazaacenaphthylene-7-carbonyl)piperidin-3-yl)carbamate (4)

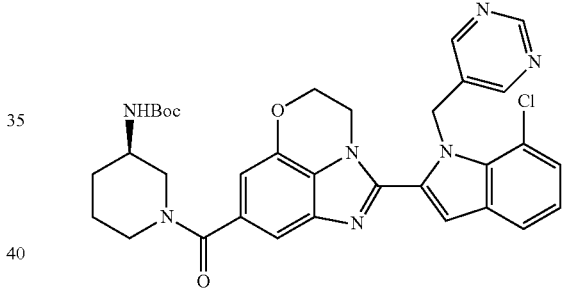

To a stirred solution of 2-(7-chloro-1-(pyrimidin-5-ylmethyl)-1H-indol-2-yl)-3,4-dihydro-5-oxa-1,2a-diazaacenaphthylene-7-carboxylic acid (3, 0.25 g, 0.56 mmol) in dichloromethane (10.0 mL), tert-butyl-(R)-piperidin-3-ylcarbamate (3b, 0.134 g, 0.67 mmol) and triethylamine (0.2 mL, 1.74 mmol) were added, followed by addition of propylphosphonic anhydride (50% solution in ethyl acetate, 0.5 mL, 1.96 mmol). The reaction mixture was stirred at room temperature for 2 h. After completion of reaction, the reaction mixture was diluted with water and extracted with dichloromethane (10 mL×2). The combined organic layers were washed with water, brine solution and dried over anhydrous sodium sulfate. The organic layer was filtered and concentrated to get crude product. The crude was purified by CombiFlash using 12.0 g, RediSep column and 70% ethyl acetate in hexane as eluent to afford tert-butyl (R)-(1-(2-(7-chloro-1-(pyrimidin-5-ylmethyl)-1H-indol-2-yl)-3,4-dihydro-5-oxa-1,2a-diazaacenaphthylene-7-carbonyl)piperidin-3-yl)carbamate (4) as white solid. Yield: 0.10 g (30%). MS (ESI) 628.13; m/z found 629.35 [M+1]$^{+}$.

Step-4: Synthesis of (R)-(3-aminopiperidin-1-yl)(2-(7-chloro-1-(pyrimidin-5-ylmethyl)-1H-indol-2-yl)-3,4-dihydro-5-oxa-1,2a-diazaacenaphthylen-7-yl)methanone (Example-88)

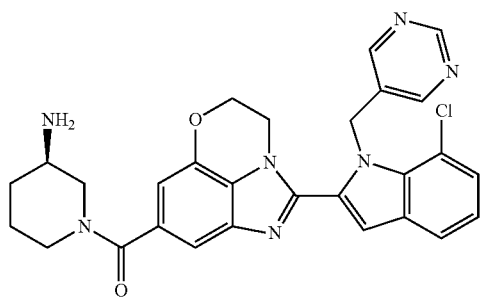 [SMILES: N[C@@H]1CCCN(C(=O)c2cc3c4c(c2)nc(-c2cc5cccc(Cl)c5n2Cc2cncnc2)n4CCO3)C1]

To a stirred solution tert-butyl (R)-(1-(2-(7-chloro-1-(pyrimidin-5-ylmethyl)-1H-indol-2-yl)-3,4-dihydro-5-oxa-1,2a-diazaacenaphthylene-7-carbonyl)piperidin-3-yl)carbamate (4, 0.1 g, 0.15 mmol) in dichloromethane (5.0 mL), trifluoroacetic acid (1.0 mL) was added at 0° C. and stirred at room temperature for 2 h. After completion of reaction, the reaction mixture was concentrated. The reaction mixture was basified by saturated sodium bicarbonate solution (5.0 mL). The compound was extracted with dichloromethane (10 mL×2). The combined organic extracts were washed with brine, dried over anhydrous sodium sulfate, filtered and concentrated under vacuum to afford (R)-(3-aminopiperidin-1-yl)(2-(7-chloro-1-(pyrimidin-5-ylmethyl)-1H-indol-2-yl)-3,4-dihydro-5-oxa-1,2a-diazaacenaphthylen-7-yl)methanone, as off white solid. Yield: 0.025 g (30%).

$^1$HNMR (400 MHz, DMSO-$d_6$) δ (ppm): 9.03 (s, 1H), 8.40 (s, 2H), 7.76 (d, J=7.84 Hz, 1H), 7.45 (s, 1H), 7.31 (d, J=7.52 Hz, 1H), 7.23 (s, 1H), 7.16 (t, J=7.76 Hz, 1H), 6.76 (s, 1H), 6.44 (s, 2H), 4.70 (d, J=4.28 Hz, 2H), 4.57 (d, J=4.24 Hz, 2H), 4.14 (s, 1H), 3.58 (s, 1H), 2.89 (bs, 1H), 2.69-2.66 (m, 1H), 2.17-1.89 (m, 2H), 1.84 (d, J=11.6 Hz, 1H), 1.63 (bs, 1H), 1.41 (m, 1H), 1.22 (m, 2H). MS (ESI): 528.01; found m/z 528.42 [M+H]$^+$.

Synthesis of Intermediates

Synthesis of 1-ethyl-1H-pyrrolo[2,3-b]pyridine-2-carbaldehyde (Intermediate for Example-5)

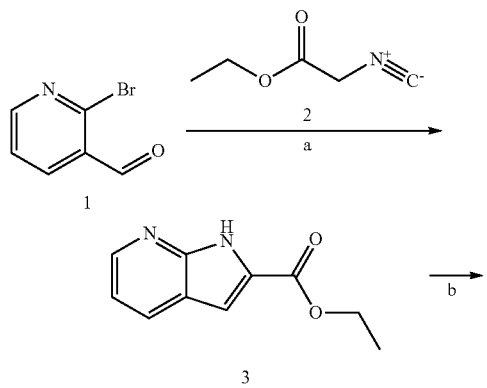

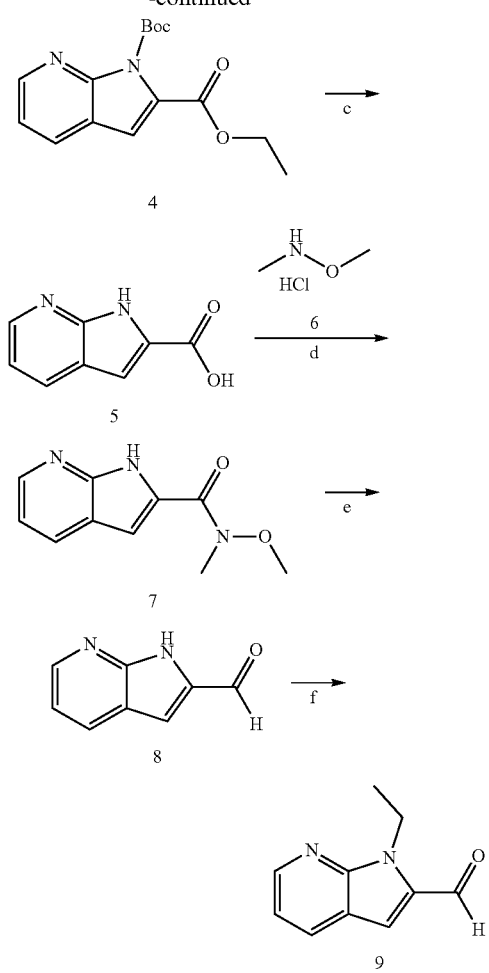

Step-1: Ethyl 1H-pyrrolo[2,3-b]pyridine-2-carboxylate (3)

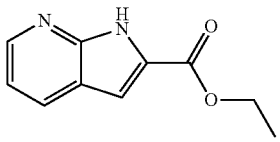

To the stirred solution of 2-bromonicotinaldehyde (1, 10.0 g, 53.7 mmol) in DMSO (100 mL), was added Cs$_2$CO$_3$ (35.0 g, 107 mmol), CuI (1.05 g, 5.37 mmol) followed by ethyl-2-isocyanoacetate (2, 7.9 mL, 69.8 mmol) and stirred at 80° C. for 16 h (reaction condition a). The reaction mixture was cooled to room temperature and filtered through celite. To this added water (100 mL) and compound was extracted with EtOAc (200 mL). Organic layer was dried over anhydrous Na$_2$SO$_4$ and evaporated under vacuum. Crude was purified by column chromatography using 30-50% EtOAc in Hexane to afford the product as brown gum. (Yield: 45%, 4.5 g). MS (ESI): mass calcd. for C$_{10}$H$_{10}$N$_2$O$_2$, 190.20; m/z found 191.0 (M+H)$^+$.

Step-2: 1-(Tert-butyl) 2-ethyl 1H-pyrrolo[2,3-b]pyridine-1,2-dicarboxylate (4)

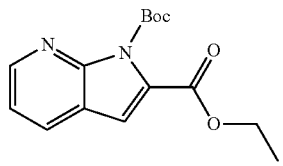

4

To the stirred solution of ethyl 1H-pyrrolo[2,3-b]pyridine-2-carboxylate (3, 34.5 g, 23.6 mmol) in THF (50 mL), was added triethylamine (6.5 mL, 47.3 mmol) followed by Boc anhydride (3.6 g, 35.5 mmol) and stirred at room temperature for 16 h (reaction condition b). To the reaction mixture was added water (100 mL) and extracted with EtOAc (200 mL). Organic layer was dried over anhydrous $Na_2SO_4$ and evaporated under vacuum. Crude was purified by column chromatography using silica gel and eluent 20-30% EtOAc in hexane to afford the product as brown gum. (Yield: 81%, 5.5 g). MS (ESI): mass calcd. for $C_{15}H_{18}N_2O_4$, 290.32; m/z found, 291.1 (M+H)$^+$.

Step-3: 1H-pyrrolo[2,3-b]pyridine-2-carboxylic Acid (5)

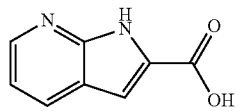

5

To a stirred solution 1-(tert-butyl) 2-ethyl 1H-pyrrolo[2,3-b]pyridine-1,2-dicarboxylate (4, 5.5 g, 18.9 mmol) in THF (40 mL), LiOH (3.9 g, 94.8 mmol) in water (10 mL) and stirred at room temperature for 4 h. The reaction mixture was evaporated and dissolved in minimum amount of water. To this, added saturated citric acid solution till acidic and precipitate formed was collected by filtration, dried to afford the product as white solid. (Yield: 81%, 2.5 g). MS (ESI): mass calcd. for $C_8H_6N_2O_2$, 162.04; m/z found, 163.1 (M+H)$^+$.

Step-4: N-methoxy-N-methyl-1H-pyrrolo[2,3-b]pyridine-2-carboxamide (7)

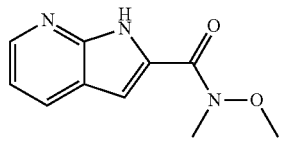

7

To the stirred solution of 1H-pyrrolo[2,3-b]pyridine-2-carboxylic acid (5, 2.5 g, 15.4 mmol) and N,O-dimethylhydroxylamine hydrochloride (6, 1.8 g, 18.5 mmol in DCM (50 mL), was added triethylamine (10.6 mL, 77.1 mmol), HOBt (3.54 g, 23.14 mmol) followed by EDC.HCl (4.42 g, 23.18 mmol) at 0° C. and the reaction mixture was stirred at room temperature for 16 h. The reaction mixture was cooled to room temperature, filtered through celite and evaporated the filtrate. To the crude, added water (10 mL) and compound was extracted with DCM (30 mL). Organic layer was dried over sodium sulfate and evaporated to get crude product. The crude residue was purified by gradient column chromatography using silica gel and eluent 2-4% MeOH in DCM to afford the product as off white solid. (Yield: 82%, 2.6 g). MS (ESI): mass calcd. for $C_{10}H_{11}N_3O_2$, 205.09; m/z found, 206.1 (M+H)$^+$.

Step-5: 1H-pyrrolo[2,3-b]pyridine-2-carbaldehyde (8)

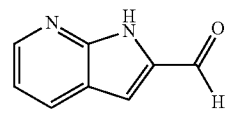

8

To a stirred solution N-methoxy-N-methyl-1H-pyrrolo[2,3-b]pyridine-2-carboxamide (7, 0.5 g, 2.43 mmol) in THF (10 mL), was added 1M LAH in THF (3.6 mL, 3.65 mmol) at −78° C. and the reaction mixture was stirred at same temperature for 3 h. The reaction mixture was basified using saturated $Na_2CO_3$ solution and extracted with DCM (2×25 mL). The reaction was quenched with saturated $NH_4Cl$ (10 mL) solution and compound was extracted with EtOAc (50 mL). The organic layer was dried over anhydrous $Na_2SO_4$. Crude was purified by flash column chromatography using 25-30% EtOAc in hexane to get the compound as white solid. (Yield: 85%, 0.3 g). MS (ESI): mass calcd. for $C_8H_6N_2O$, 146.15; m/z found, 147.1 (M+H)$^+$.

Step-6: 1-ethyl-1H-pyrrolo[2,3-b]pyridine-2-carbaldehyde (9)

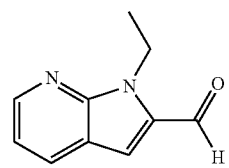

9

To a stirred solution 1H-pyrrolo[2,3-b]pyridine-2-carbaldehyde (8, 0.3 g, 2.19 mmol) in DMF (10 mL), was added $K_2CO_3$ (0.91 g, 6.57 mmol) followed by ethyl iodide (0.5 g, 3.28 mmol) and the reaction mixture was stirred at same temperature for 16 h. To the reaction mixture was added water (15 mL) and extracted with EtOAc (50 mL). The organic layer was dried over anhydrous $Na_2SO_4$. Crude was purified by flash column chromatography using 15-20% EtOAc in hexane to get the compound as colourless oil. (Yield: 95%, 0.34 g). $^1$HNMR (400 MHz, DMSO-$d_6$) δ, ppm: 9.94 (s, 1H), 8.52 (d, J=4.0 Hz, 1H), 8.23 (d, J=8.0 Hz, 1H), 7.49 (s, 1H), 7.23 (t, J=5.2 Hz, 1H), 4.65-4.60 (m, 2H), 1.27 (t, J=6.4 Hz, 3H). MS (ESI): mass calcd. for $C_{10}H_{10}N_2O$, 174.08; m/z found, 175.2 (M+H)$^+$.

Synthesis of 1-(cyclopropylmethyl)-6-methoxy-1H-indole-2-carbaldehyde (Intermediate for Example-74)

cheme:

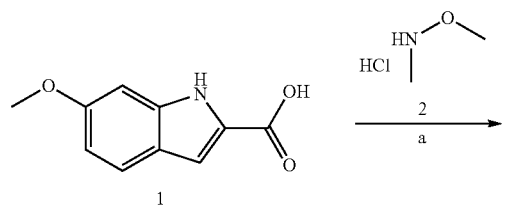

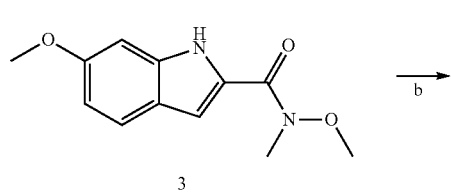

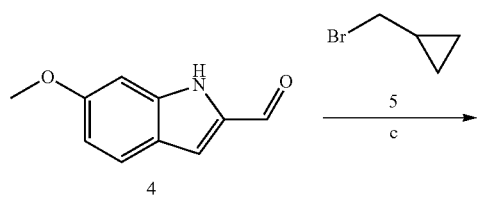

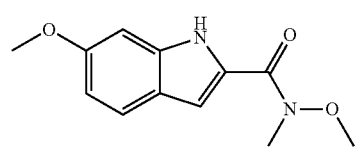

Step-1: Preparation of N,6-dimethoxy-N-methyl-1H-indole-2-carboxamide (3)

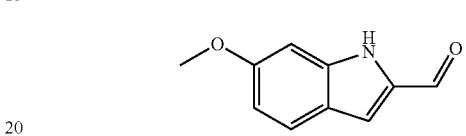

To a stirred solution 6-methoxy-1H-indole-2-carboxylic acid (1, 3 g, 15.69 mmol) in DCM (20 mL), was added N,O-dimethylhydroxylamine hydrochloride (2, 3 g, 31.38 mmol), followed by hydroxybenzotriazole (3.6 g, 23.5 mmol), N-(3-dimethylaminopropyl)-N'-ethylcarbodiimide hydrochloride (4.5 g, 23.5 mmol) and TEA (11.3 mL, 120.7 mmol), and the reaction mixture was stirred at same temperature for 5 h. The reaction mixture was quenched with water, extracted with ethyl acetate (50 mL×2). Combined organic extracts were washed with brine, dried over sodium sulfate, filtered and evaporated to get crude product. Crude residue was purified by gradient column chromatography using 25-30% ethyl acetate in hexane to get the product as beige colour solid. (Yield: 75%, 0.86 g). MS (ESI): mass calcd. for $C_{12}H_{14}N_2O_3$, 234.10; m/z found, 235 $(M+H)^+$.

Step-2: Preparation of 6-methoxy-1H-indole-2-carbaldehyde (4)

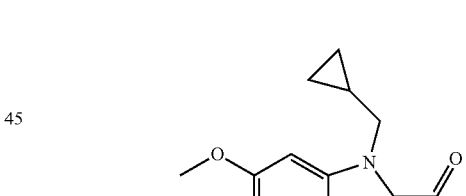

To a stirred solution of N,6-dimethoxy-N-methyl-1H-indole-2-carboxamide (3, 2 g, 8.54 mmol) in THF (20 mL), was added LAH 1M soln. in THF (12.8 mL, 12.75 mmol) slowly under cooling condition, and then the reaction mixture was allowed to stir at room temperature for 1 h. The reaction mixture was quenched with ammonium chloride, extracted with ethyl acetate (50 mL×2). Combined organic extracts were washed with brine, dried over sodium sulfate, filtered and evaporated to get crude product. Crude residue was purified by gradient column chromatography using 5-10% ethyl acetate in hexane to get the product as white solid. (Yield: 60%, 0.9 g). MS (ESI): mass calcd. for $C_{10}H_9NO_2$, 175.06; m/z found, 176.1 $(M+H)^+$.

Step-3: Preparation of 1-(cyclopropylmethyl)-6-methoxy-1H-indole-2-carbaldehyde

To a stirred solution of 6-methoxy-1H-indole-2-carbaldehyde (4, 0.28 g, 1.6 mmol) in DMF (5 mL), was added potassium carbonate (1.1 g, 8 mmol) followed by (bromomethyl)cyclopropane (5, 0.23 mL, 1.72 mmol) and the reaction mixture was stirred at same temperature for 4 h. The reaction mixture was quenched with water, extracted with ethyl acetate (20 mL×2). Combined organic extracts were washed with brine, dried over sodium sulfate, filtered and evaporated to get crude product. Crude residue was purified by gradient column chromatography using 5-10% ethyl acetate in hexane to get the product as brown liquid. (Yield: 63%, 0.23 g). $^1$HNMR (400 MHz, DMSO-$d_6$) δ (ppm): 9.72 (s, 1H), 7.62 (d, J=8 Hz, 1H), 7.3 (s, 1H), 7.07 (s, 1H), 6.78 (d, J=8 Hz, 1H), 4.43 (d, J=8 Hz, 2H), 3.84 (s, 3H), 1.26-1.21 (m, 1H), 0.40-0.38 (m, 4H). MS (ESI): mass calcd. for $C_{14}H_{15}NO_2$, 229.1; m/z found, 230.2 $(M+H)^+$.

Synthesis of 1-(4-chlorobenzyl)-1H-indole-2-carbaldehyde (Intermediate for Example-13)

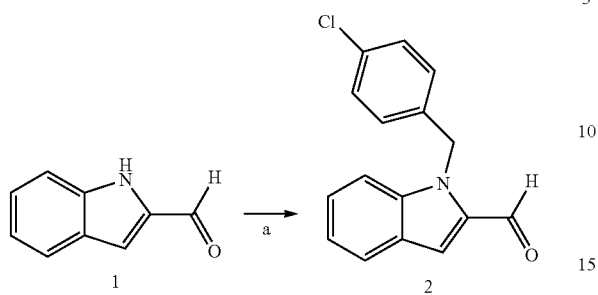

To a stirred solution 1H-indole-2-carbaldehyde (1, 0.5 g, 3.44 mmol) in DMF (10 mL), was added potassium carbonate (1.42 g, 10.3 mmol) followed by 1-(bromomethyl)-4-chlorobenzene (0.84 g, 4.13 mmol) and the reaction mixture was stirred at same temperature for 4 h. The reaction mixture was quenched with water, extracted with ethyl acetate (30 mL×2). Combined organic extracts were washed with brine, dried over sodium sulfate, filtered and evaporated to get crude product. Crude residue was purified by gradient column chromatography using 10-15% ethyl acetate in hexane to get the product as half white solid. (Yield: 93.4%, 0.86 g). $^1$HNMR (400 MHz, DMSO $d_6$) δ (ppm): 9.9 (s, 1H), 7.79 (d, J=8 Hz, 1H), 7.60-7.56 (m, 2H), 7.39-7.36 (m, 1H), 7.31 (d, J=8 Hz, 2H), 7.18-7.14 (m, 1H), 7.06 (d, J=8 Hz, 2H), 5.8 (s, 2H). MS (ESI): mass calcd. for $C_{16}H_{12}ClNO$, 269.73; m/z found, 270.1 (M+H)$^+$.

Synthesis of 1-(cyclopropylmethyl)-1H-indole-2-carbaldehyde (Intermediate for Examples-1, 2, 4, 6, 7, 38, 62, 72, 76, 78, 79, 85 and 86)

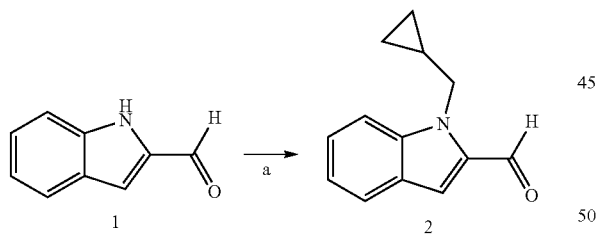

To the stirred solution of 1H-indole-2-carbaldehyde (1, 1 g, 6.89 mmol) in DMF (20 mL), were added potassium carbonate (2.8 g, 20.67 mmol) and (bromomethyl)cyclopropane (0.68 mL, 7.58 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(cyclopropylmethyl)-1H-indole-2-carbaldehyde as yellow solid (1 g, 76% Yield). $^1$HNMR (400 MHz, DMSO $d_6$) δ (ppm): 9.88 (s, 1H), 7.75 (d, J=8 Hz, 1H), 7.64 (d, J=8 Hz, 1H), 7.46 (s, 1H), 7.41-7.37 (m, 1H), 7.16-7.12 (m, 1H), 4.45 (d, J=8 Hz, 2H), 1.24-1.14 (m, 1H), 0.39-0.35 (m, 4H). MS (ESI): mass calcd. for $C_{13}H_{13}NO$, 199.1; m/z found, 200.1 (M+H)$^+$.

Synthesis of 1-(cyclopropylmethyl)-6-fluoro-1H-indole-2-carbaldehyde (Intermediate for Example-65)

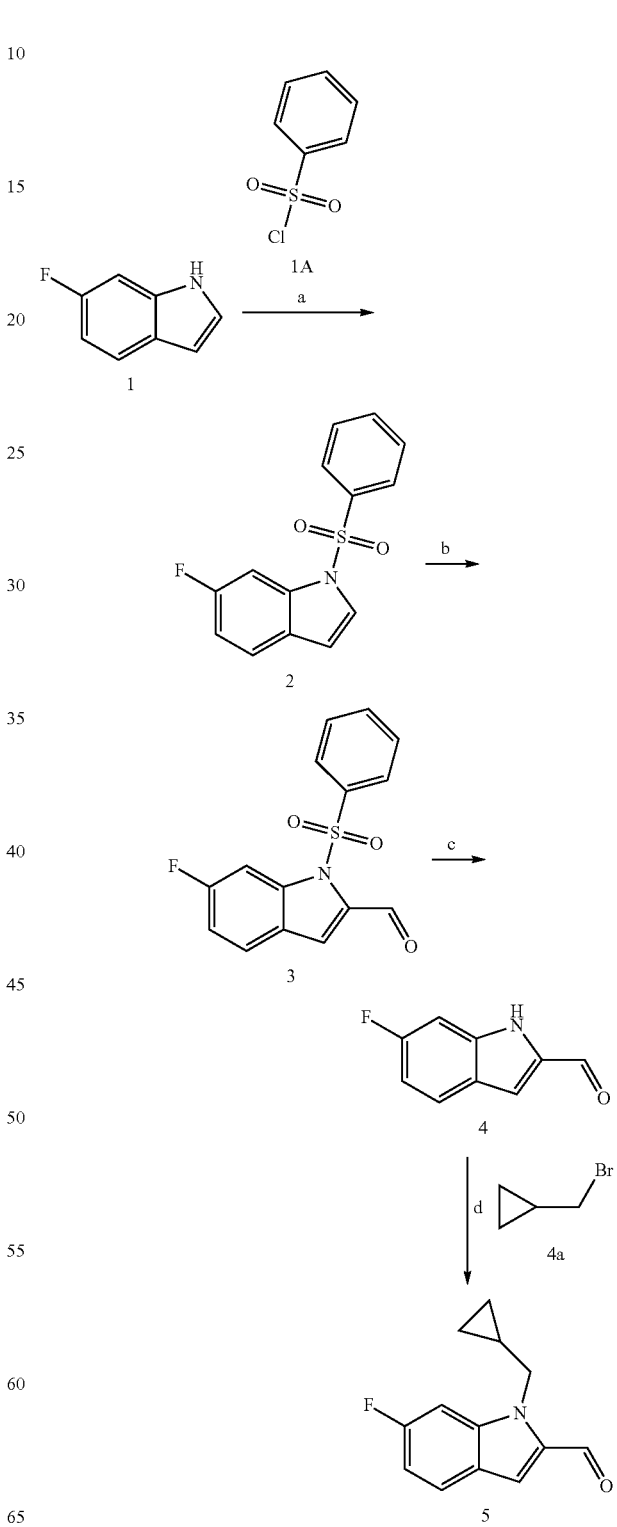

Step 1: Preparation of 6-fluoro-1-(phenylsulfonyl)-1H-indole (2)

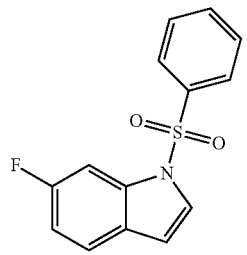

2

To a solution of sodium hydride (0.88 g, 22.2 mmol) in DMF (50 mL) was added solution of 6-fluoro-1H-indole (1, 3.0 g, 22.2 mmol) in DMF at 0° C., dropwise over 15 min. Benzenesulfonyl chloride in DMF (2.86 mL, 22.2 mmol) was added at 0° C. and stirred for 2 h at room temperature under $N_2$ atmosphere. To the reaction mixture was added ice cold water (50 mL), then filtered off the precipitate and washed with ice cold water to obtain white solid. (6.0 g, yield 98.19%).

Step 2: preparation 6-fluoro-1-(phenylsulfonyl)-1H-indole-2-carbaldehyde (3)

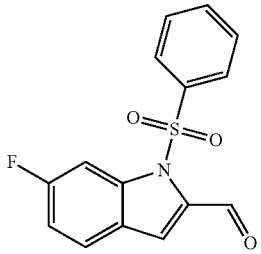

3

To a solution of 6-fluoro-1-(phenylsulfonyl)-1H-indole (2, 6.0 g, 22.0 mmol) in dry THF (60 mL) was added lithium diisopropylamide 2M in THF (10.9 mL g, 22.0 mmol) at −78° C. and stirred for 5-8 min, followed by addition of dry DMF (2.5 mL, 33.0 mmol) at −78° C. and stirred for 10 min at −78° C. under $N_2$ atmosphere. To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain yellow solid (6.0 g, yield 90.90%). MS (ESI): m/z 304.2 $(M+H)^+$.

Step 3: Preparation of 6-fluoro-1-(phenylsulfonyl)-1H-indole-2-carbaldehyde (4)

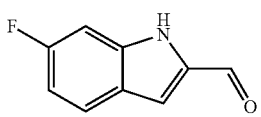

4

To the stirred solution of 6-Difluoro-1-(phenylsulfonyl)-1H-indole-2-carbaldehyde (3.1 g, 3.3 mmol) in THF (50 mL), was added TBAF (1M in THF) (9.15 mL, 16.5 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford 6-fluoro-1-(phenylsulfonyl)-1H-indole-2-carbaldehyde as sticky solid (0.45 g, 90% Yield) MS (ESI): Mass calcd. for $C_9H_6FNO$, 163 m/z; found, 164 $(M+H)^+$.

Step 4: Preparation of 1-(cyclopropylmethyl)-6-fluoro-1H-indole-2-carbaldehyde (5)

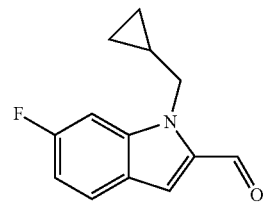

5

To a stirred solution 6-fluoro-1H-indole-2-carbaldehyde (4, 0.5 g, 3.44 mmol) in DMF (10 mL), was added potassium carbonate (1.42 g, 10.3 mmol) followed by (bromomethyl)cyclopropane (0.84 g, 4.13 mmol) and the reaction mixture was stirred at same temperature for 4 h. The reaction mixture was quenched with water, extracted with ethyl acetate (30 mL×2). Combined organic extracts were washed with brine, dried over sodium sulfate, filtered and evaporated to get crude product. Crude residue was purified by gradient column chromatography using 10-15% ethyl acetate in hexane to get the product as half white solid. (Yield: 93.4%, 0.86 g). $^1$HNMR (400 MHz, DMSO-$d_6$) δ (ppm): 9.81 (s, 1H), 7.69-7.66 (m, 1H), 7.25 (d, J=6.8 Hz, 1H), 7.07 (d, J=8 Hz, 1H), 6.97-6.91 (m, 1H), 4.43 (d, J=8 Hz, 2H), 1.32-1.25 (m, 1H), 0.5-0.45 (m, 2H), 0.42-0.38 (m, 2H). MS (ESI): mass calcd. for $C_{13}H_{12}FNO$, 217.09; m/z found, 218.0 $(M+H)^+$.

Synthesis of 1-(pyridin-4-ylmethyl)-1H-indole-2-carbaldehyde (Intermediate for Example-10)

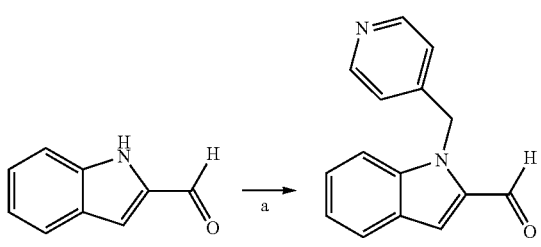

To the stirred solution of 1H-indole-2-carbaldehyde (1, 1 g, 6.89 mmol) in DMF (20 mL), were added cesium carbonate (6.7 g, 20.68 mmol) and (4-(bromomethyl)pyridine (1.1 g, 6.89 mmol) at room temperature. The reaction mixture was refluxed at 80° C. for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(pyridin-4-ylmethyl)-1H-indole-2-carbaldehyde as yellow solid (0.5 g, 31% Yield). $^1$HNMR (400 MHz, DMSO-$d_6$) δ (ppm): δ 9.92 (s, 1H), 8.54 (d, J=8 Hz, 2H), 7.79 (d, J=8 Hz, 1H), 7.67-7.64 (m, 1H), 7.56 (d, J=12 Hz, 2H), 7.37-7.33 (m, 1H), 7.22-7.19 (m, 1H), 6.88 (d, J=8 Hz, 1H), 5.89 (s, 2H). MS (ESI): mass calcd. for $C_{15}H_{12}N_2O$, 236.09; m/z found, 237.0 (M+H)$^+$.

Synthesis of 1-(pyridin-3-ylmethyl)-1H-indole-2-carbaldehyde (Intermediate for Examples-16, and 66)

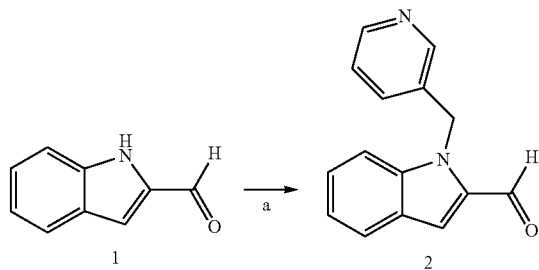 [SMILES: O=Cc1cc2ccccc2[nH]1 ; O=Cc1cc2ccccc2n1Cc1cccnc1]

To the stirred solution of 1H-indole-2-carbaldehyde (1, 1 g, 6.89 mmol) in DMF (20 mL), were added cesium carbonate (6.7 g, 20.68 mmol) and 3-(chloromethyl)pyridine hydrochloride (1.1 g, 6.89 mmol) at room temperature. The reaction mixture was refluxed at 80° C. for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(pyridin-3-ylmethyl)-1H-indole-2-carbaldehyde as yellow solid (0.4 g, 25% Yield). $^1$HNMR (400 MHz, DMSO-$d_6$) δ (ppm): 9.92 (s, 1H), 8.41-8.38 (m, 2H), 7.80 (d, J=8 Hz, 1H), 7.68 (d, J=8.4 Hz, 1H), 7.58 (bs, 1H)), 7.42-7.38 (m, 2H), 7.28-7.25 (m, 1H), 7.18 (t, J=16 Hz, 1H), 5.85 (s, 2H), MS (ESI): mass calcd. for $C_{15}H_{12}N_2O$, 236.27; m/z found, 237.1 (M+H)$^+$.

Synthesis of 1-(pyridin-2-ylmethyl)-1H-indole-2-carbaldehyde (Intermediate for Example-11 & 69)

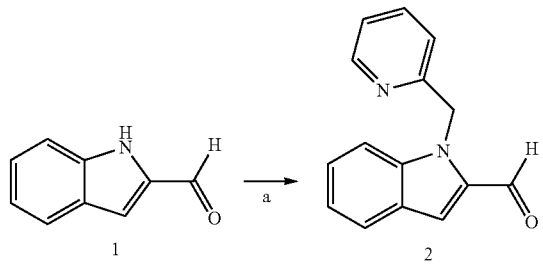 [SMILES: O=Cc1cc2ccccc2[nH]1 ; O=Cc1cc2ccccc2n1Cc1ccccn1]

To the stirred solution of 1H-indole-2-carbaldehyde (1, 1 g, 6.89 mmol) in DMF (20 mL), were added cesium carbonate (6.7 g, 20.68 mmol) and 2-(bromomethyl)pyridine (1.1 g, 6.89 mmol) at room temperature. The reaction mixture was refluxed at 80° C. for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(pyridin-2-ylmethyl)-1H-indole-2-carbaldehyde as yellow solid (0.8 g, 50% Yield). $^1$HNMR (400 MHz, DMSO-$d_6$) δ (ppm): 9.92 (s, 1H), 8.45 (d, J=4 Hz, 1H), 7.79 (d, J=8 Hz, 1H), 7.66 (m, 1H), 7.56 (d, J=12 Hz, 2H), 7.37-7.33 (m, 1H), 7.22-7.19 (m, 1H), 7.17-7.13 (m, 1H), 6.88 (d, J=8 Hz, 1H), 5.89 (s, 2H). MS (ESI): mass calcd. for $C_{16}H_{12}ClNO$, 269.73; m/z found, 270.1 (M+H)$^+$.

Synthesis of 1-ethyl-1H-indole-2-carbaldehyde (Intermediate for Example-3)

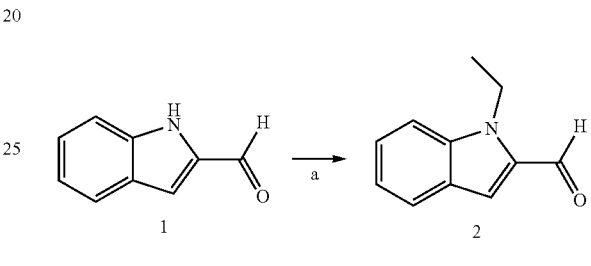

To a stirred solution 1H-indole-2-carbaldehyde (1, 1 g, 6.89 mmol) in DMF (15 mL), was added potassium carbonate (2.85 g, 20.6 mmol) followed by iodoethane (0.6 mL, 7.58 mmol) and the reaction mixture was stirred at same temperature for 4 h. Reaction mixture was poured into crushed ice, diluted with water and extracted with ethyl acetate. Organic layer was dried over anhydrous sodium sulfate evaporated under vacuum to give the crude. Crude was purified by flash column chromatography using ethyl acetate and hexane to obtain 1-ethyl-1H-indole-2-carbaldehyde as the viscous liquid. (Yield: 1 g, 90%). $^1$HNMR (400 MHz, DMSO-$d_6$) δ (ppm): 9.88 (s, 1H), 7.75 (d, J=8 Hz, 1H), 7.61 (d, 1H, J=8 Hz, 1H), 7.44 (s, 1H), 7.41-7.37 (m, 1H), 7.16-7.12 (m, 1H), 4.58-4.52 (m, 2H), 1.26-1.23 (m, 3H). MS (ESI): mass calcd. for $C_{11}H_{11}NO$, 173.08; m/z found, 174.0 (M+H)$^+$.

Synthesis of 1-benzyl-1H-indole-2-carbaldehyde (Intermediate for Example-18)

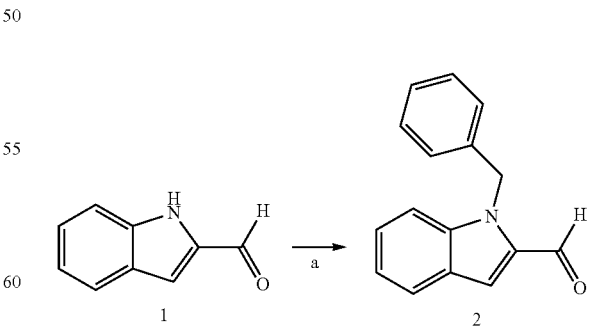

To the stirred solution of 1H-indole-2-carbaldehyde (1, 1 g, 6.89 mmol) in DMF (20 mL), were added potassium carbonate (2.8 g, 20.68 mmol) and (bromomethyl)benzene (1.2 g, 7.58 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to give the crude product. The crude residue was purified by gradient column chromatography using 3-7% ethyl acetate in hexane to afford the 1-benzyl-1H-indole-2-carbaldehyde as viscous liquid (0.5 g, 33% Yield). $^1$HNMR (400 MHz, DMSO-$d_6$) δ (ppm): 9.92 (s, 1H), 7.78 (d, J=8 Hz, 1H), 7.58 (d, J=8 Hz, 1H), 7.54 (s, 1H), 7.38-7.35 (m, 1H), 7.26-7.20 (m, 2H), 7.18-7.13 (m, 2H), 7.05 (d, J=4 Hz, 2H), 5.82 (s, 2H). MS (ESI): mass calcd. for $C_{16}H_{13}NO$, 235.10; m/z found, 236.1 (M+H)$^+$.

Synthesis of 1-(2-fluorobenzyl)-1H-indole-2-carbaldehyde (Intermediate for Example-14)

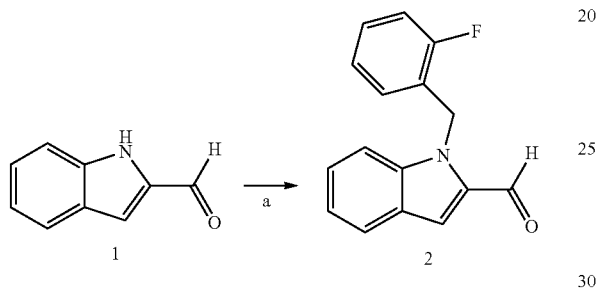

To a stirred solution 1H-indole-2-carbaldehyde (1, 1 g, 6.89 mmol) in DMF (15 mL), was added potassium carbonate (2.85 g, 20.6 mmol) followed by 1-(chloromethyl)-2-fluorobenzene (1.19 g, 8.26 mmol) and the reaction mixture was stirred at same temperature for 4 h. Reaction mixture was poured into crushed ice, diluted with water and extracted with ethyl acetate. Organic layer was dried over anhydrous sodium sulfate, evaporated under vacuum to give the crude. Crude was purified by flash column chromatography using ethyl acetate and hexane to afford the 1-(2-fluorobenzyl)-1H-indole-2-carbaldehyde as grey color solid (Yield: 1.8 g, 96.5%). $^1$HNMR (400 MHz, DMSO-$d_6$) δ (ppm): 9.90 (s, 1H), 7.81 (d, J=8 Hz, 1H), 7.58-7.54 (m, 2H), 7.40-7.36 (m, 1H), 7.28-7.15 (m, 3H), 7.01-6.97 (m, 1H), 6.55-6.51 (m, 1H), 5.88 (s, 2H). MS (ESI): mass calcd. for $C_{16}H_{12}FNO$, 253.09; m/z found, 254.0 (M+H)$^+$.

Synthesis of 1-(cyclopropylmethyl)-5-fluoro-1H-indole-2-carbaldehyde (Intermediate for Examples-9, 64 & 75)

Step 1: Preparation of 5-fluoro-1-(phenylsulfonyl)-1H-indole (3)

To a solution of sodium hydride (0.06 g, 15 mmol) in DMF (10 mL) was added a solution of 5-fluoro-1H-indole (1, 0.2 g, 15 mmol) in DMF at 0° C., drop wise over 15 min. followed by addition of a solution of benzenesulfonyl chloride (2, 0.26 g, 15 mmol) in DMF at 0° C. and the reaction mixture was stirred for 2 h at room temperature under $N_2$ atmosphere. To the reaction mixture was added ice cold water (50 mL), then the precipitate was filtered off and washed with ice cold water to obtain brown solid. (0.25 g, 62.50% Yield). MS (ESI) m/z 275.0 (M+H)⁺.

Step 2: Preparation of 5-fluoro-1-(phenylsulfonyl)-1H-indole-2-carbaldehyde (4)

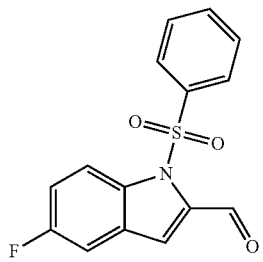

4

To a solution of 5-fluoro-1-(phenylsulfonyl)-1H-indole (3, 0.250 g, 1.0 mmol) in dry THF (50 mL) was added lithium diisopropylamide 1M in THF (0.5 mL g, 1.0 mmol) at −78° C., followed by addition of dry DMF (0.11 mL, 1.5 mmol) at −78° C. and stirred for 10 min at −78° C. under $N_2$ atmosphere. To the reaction mixture was added aqueous ammonium chloride (20 mL) and extracted with EtOAc. Organic layer was washed with saturated $NH_4Cl$ solution and brine, dried over sodium sulphate, filtered and concentrated under reduced pressure to obtain brown solid. (0.150 g, 54.54% Yield). MS (ESI) m/z 304.1 (M+H)⁺.

Step 3: Preparation of 5-fluoro-1H-indole-2-carbaldehyde (5)

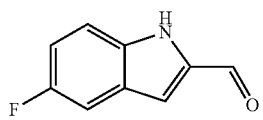

5

To the stirred solution of 5-fluoro-1-(phenylsulfonyl)-1H-indole-2-carbaldehyde (4, 1.85 g, 6.105 mmol) in THF (50 mL), was added TBAF (1M in THF) (9.15 mL, 9.158 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford the 5-fluoro-1H-indole-2-carbaldehyde as sticky solid (0.65 g, 65% Yield) MS (ESI): Mass calcd. for $C_9H_6FNO$, 163.15; m/z found, 162.0 [M−H]⁻.

Step 4: Preparation of 1-(cyclopropylmethyl)-5-fluoro-1H-indole-2-carbaldehyde (7)

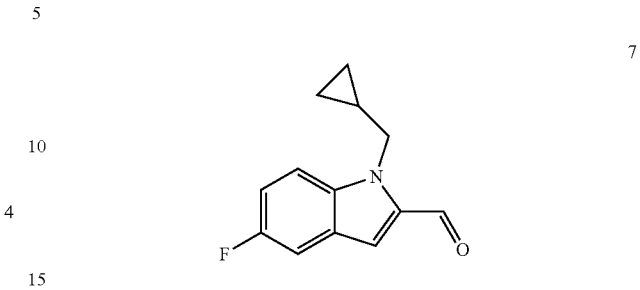

7

To the stirred solution of 5-fluoro-1H-indole-2-carbaldehyde (5, 0.65 g, 3.98 mmol) in DMF (50 mL), were added potassium carbonate (1.64 g, 11.94 mmol) and (bromomethyl)cyclopropane (6, 0.58 mL, 5.98 mmol) at room temperature. The reaction mixture was stirred at room temperature for 12 h. The reaction mixture was diluted with water and extracted with ethyl acetate (50 mL×2). Combined organic extracts were washed with brine, dried over sodium sulphate and evaporated to get crude product. The crude residue was purified by gradient column chromatography using 3-7% ethyl acetate in hexane to afford the 1-(cyclopropylmethyl)-5-fluoro-1H-indole-2-carbaldehyde as sticky solid (0.76 g, 88% Yield). ¹HNMR (400 MHz, DMSO-d6): δ 9.90 (s, 1H), 7.73-7.69 (m, 1H), 7.55-7.52 (m, 1H), 7.44 (s, 1H), 7.29-7.24 (m, 1H), 4.50 (d, J=7.2 Hz, 2H), 1.23-1.16 (m, 1H), 0.41-0.32 (m, 4H). MS (ESI): Mass calcd. for $C_{13}H_{12}FNO$, 217.24: m/z found, 218.1 [M+H]⁺.

Synthesis of 1-(cyclopropylmethyl)-7-methyl-1H-indole-2-carbaldehyde (Intermediate for Example-8 & 84)

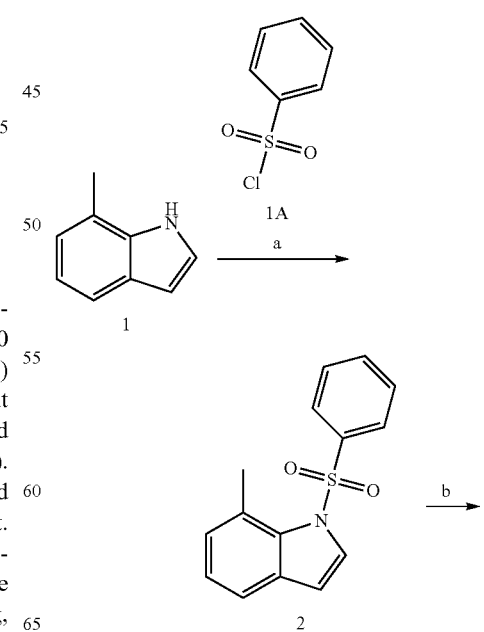

-continued

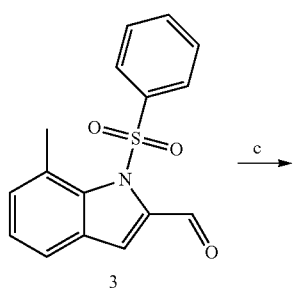

Step 2: preparation 7-methyl-1-(phenylsulfonyl)-1H-indole-2-carbaldehyde (3)

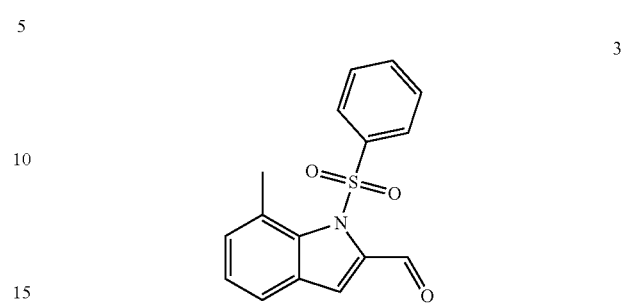

To a solution of 7-methyl-1-(phenylsulfonyl)-1H-indole (2, 5.3 g, 20.0 mmol) in dry THF (50 mL) was added lithium diisopropylamide 1.5M in THF (13.0 mL, 20.0 mmol) at −78° C. and stirred for 5-8 min, followed by addition of dry DMF (2.33 mL, 30.0 mmol) at −78° C. and stirred for 10 min at −78° C. under $N_2$ atmosphere. To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain red viscous liquid (5.0 g, 85.47%). MS (ESI) m/z 300.2 (M+H)$^+$.

Step 3: Preparation of 7-methyl-1H-indole-2-carbaldehyde (4)

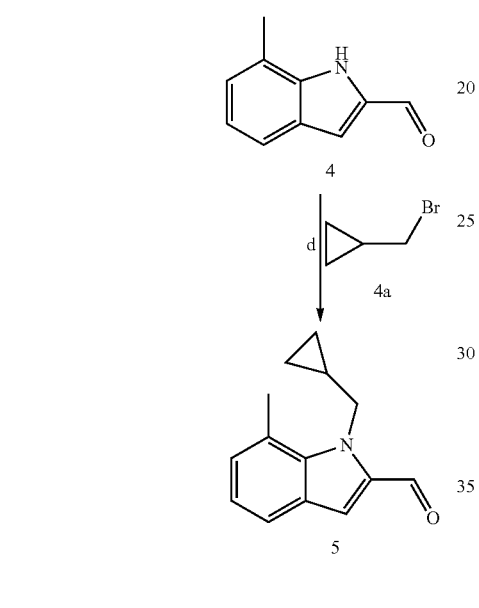

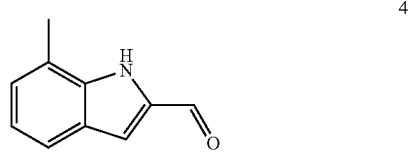

To the stirred solution of 7-methyl-1-(phenylsulfonyl)-1H-indole-2-carbaldehyde (3, 2 g, 6.68 mmol) in THF (20 mL), was added 1M solution of tetrabutyl ammonium fluoride in THF (10 mL, 10.2 mmol) and stirred at 80° C. for 1 h. Reaction mixture was cooled to room temperature, added water (20 mL) and extracted with EtOAc (100 mL). Organic layer was dried over anhydrous $Na_2SO_4$ and evaporated under vacuum. Crude was purified by column chromatography using 15-20% EtOAc in Hexane to afford the product as brown solid. (0.8 g, 58% Yield). MS (ESI): Mass calcd. for $C_{10}H_9NO$, 159.07; m/z found 160.1 (M+H)$^+$.

Step 4: 1-(cyclopropylmethyl)-7-methyl-1H-indole-2-carbaldehyde (5)

Step 1: preparation of 7-methyl-1-(phenylsulfonyl)-1H-indole (2)

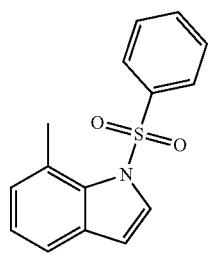

To a solution of sodium hydride (0.92 g, 23 mmol) in DMF (10 mL) was added solution of 7-methyl-1H-indole (1, 3.0 g, 23 mmol) in DMF at 0° C., dropwise over 15 min. Benzenesulfonyl chloride in DMF (2.96 mL, 23 mmol) was added at 0° C. and stirred for 2 h at room temperature under $N_2$ atmosphere. To the reaction mixture was added ice cold water (50 mL), then filtered off the precipitate and washed with ice cold water to obtain brown solid (5.30 g, 85.50%). MS (ESI) m/z 272.1 (M+H)$^+$.

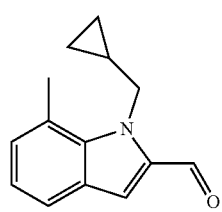

To the stirred solution of 7-methyl-1H-indole-2-carbaldehyde (4, 0.85 g, 5.345 mmol) in DMF (20 mL), were added potassium carbonate (2.21 g, 16.035 mmol) and (bromomethyl)cyclopropane (4a, 0.78 mL, 8.018 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(cyclopropylmethyl)-7-methyl-1H-indole-2-carbaldehyde as sticky solid (0.52 g, 45% Yield). $^1$HNMR (400 MHz, CDCl$_3$) δ (ppm): 9.82 (s, 1H), 7.58 (d, J=8.0 Hz, 1H), 7.26 (s, 1H), 7.13 (d, J=6.8 Hz, 1H), 6.26 (m, 1H), 4.83 (d, J=6.8 Hz, 2H), 2.77 (s, 3H), 1.15-1.10 (m, 1H), 0.41-0.33 (m, 4H). MS (ESI): Mass calcd. for C$_{14}$H$_{15}$NO, 213.28; m/z found, 214.1 [M+H]$^+$.

Synthesis of 1-(cyclopropylmethyl)-5,6-dimethoxy-1H-indole-2-carbaldehyde (Intermediate for Example-17)

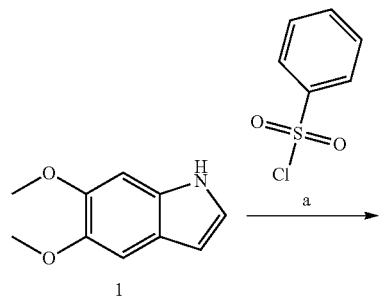

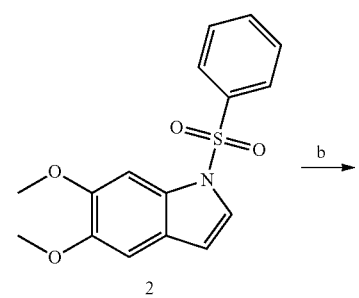

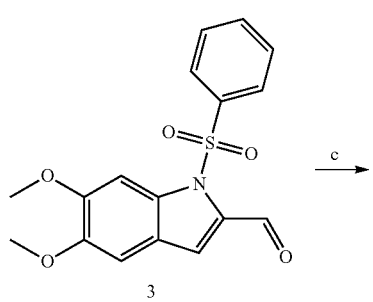

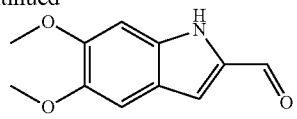

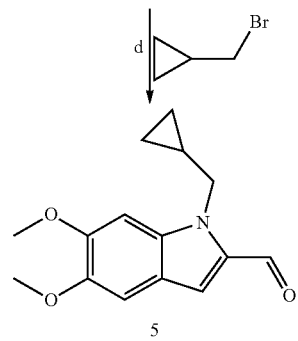

Step 1: Preparation of 5,6-dimethoxy-1-(phenylsulfonyl)-1H-indole (2)

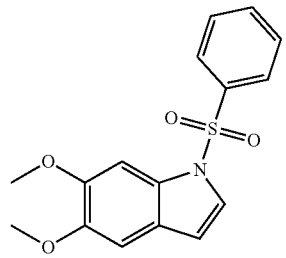

To a solution of sodium hydride (0.56 g, 14 mmol) in DMF (50 mL) was added solution of 5,6-dimethoxy-1H-indole (1, 2.5 g, 14 mmol) in DMF at 0° C., dropwise over 15 min. Benzenesulfonyl chloride (1.8 mL, 14 mmol) in DMF was added at 0° C. and stirred for 2 h at room temperature under N$_2$ atmosphere. To the reaction mixture was added ice cold water (50 mL), then filtered off the precipitate and washed with ice cold water to obtain white solid. (4.20 g, 93.95% Yield). MS (ESI): mass calcd. for C$_{16}$H$_{15}$NO$_4$S, 317.07; m/z found, 318.1 [M+H]$^+$.

Step 2: Preparation 5,6-dimethoxy-1-(phenylsulfonyl)-1H-indole-2-carbaldehyde (3)

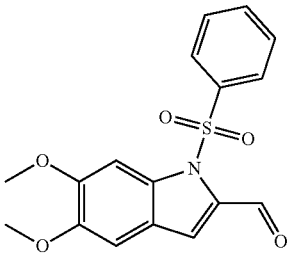

To a solution of 5,6-dimethoxy-1-(phenylsulfonyl)-1H-indole (2, 4.2 g, 13.2 mmol) in dry THF (60 mL) was added lithium diisopropylamide 2M in THF (8.8 mL g, 13.2 mmol) at −78° C. and stirred for 5-8 min, followed by addition of dry DMF (1.54 mL, 20.0 mmol) at −78° C. and stirred for 10 min at −78° C. under N₂ atmosphere. To the reaction mixture was added aqueous ammonium chloride (20 mL), then extracted in to EtOAc. Organic layer was washed with saturated NH₄Cl solution and brine, dried over sodium sulphate, filtered and concentrated under reduced pressure to obtain yellow solid (3.5 g, 78.26% Yield). MS (ESI): mass calcd. for $C_{17}H_{15}NO_5S$, 345.07; m/z found, 346.1 $[M+H]^+$.

Step 3: Preparation of 5,6-dimethoxy-1H-indole-2-carbaldehyde (4)

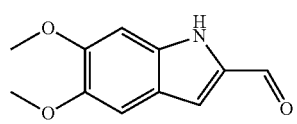

To the stirred solution of 5,6-dimethoxy-1-(phenylsulfonyl)-1H-indole-2-carbaldehyde (3, 2 g, 5.5 mmol) in THF (50 mL), was added TBAF (1M in THF) (8.8 mL, 8.2 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 5-10% ethyl acetate in hexane to afford desired compound as gummy solid (1 g, 88.6% Yield). MS (ESI): mass calcd. for $C_{11}H_{11}NO_3$, 205.07; m/z found, 206.1 $[M+H]^+$.

Step 4: Preparation of 1-(cyclopropylmethyl)-5,6-dimethoxy-1H-indole-2-carbaldehyde (5)

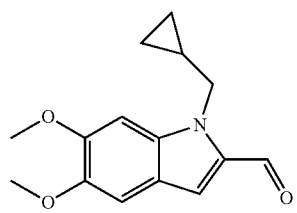

To the stirred solution of 5,6-dimethoxy-1H-indole-2-carbaldehyde (4, 1 g, 4.8 mmol) in DMF (20 mL), were added potassium carbonate (1.9 g, 14 mmol) and (bromomethyl)cyclopropane (0.7 g, 5.7 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 10% ethyl acetate in hexane to afford title compound as yellow solid (0.7 g, 56.3% Yield). ¹HNMR (400 MHz, CDCl₃) δ (ppm): 9.71 (s, 1H), 7.12 (s, 1H), 7.06 (s, 1H), 6.78 (s, 1H), 4.47 (d, J=6.4 Hz, 2H), 3.99 (s, 3H), 3.93 (s, 3H), 1.30-1.25 (m, 1H), 0.49-0.41 (m, 4H). MS (ESI): Mass calcd. for $C_{15}H_{17}NO_3$, 259.31; m/z found, 260.2 $[M+H]^+$.

Synthesis of Ethylbenzo[b]thiophene-2-carbaldehyde (Intermediate for Example-12)

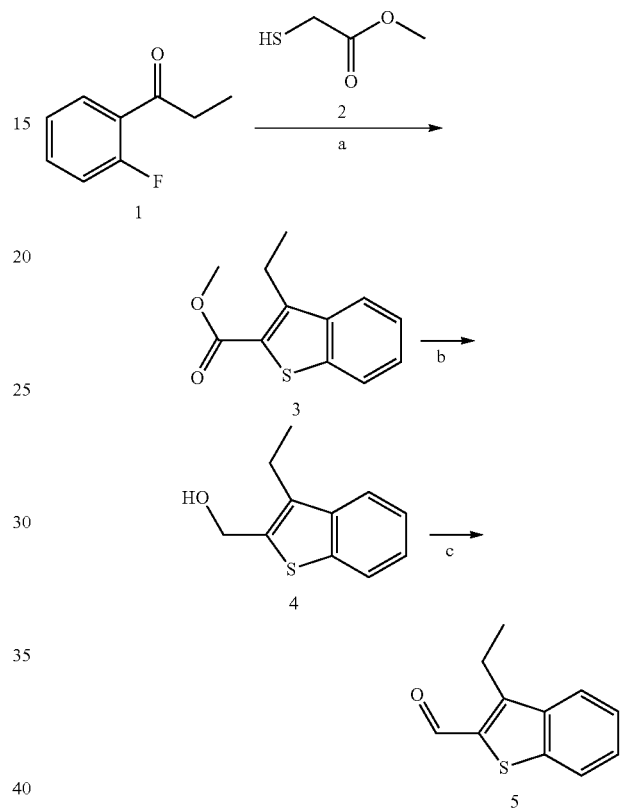

Step 1: Methyl 3-ethylbenzo[b]thiophene-2-carboxylate (3)

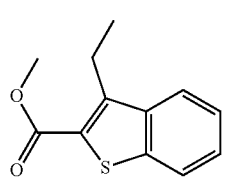

To a suspension of NaH (60% in oil, 0.17 g, 4.27 mmol) in THF (10 mL) was added methyl 2-mercaptoacetate (2, 0.41 g, 3.94 mmol) at room temperature and stirred at same temperature for 30 min. To the reaction was added solution of 1-(2-fluorophenyl)propan-1-one (1, 0.5 g, 3.28 mmol) in THF and allowed to reflux for 16 h (reaction condition a). Completion of the reaction was monitored by LCMS The reaction mixture was cooled to room temperature, diluted with EtOAc and washed with 1N NaOH and water. Organic layer was washed, dried over sodium sulphate, filtered and concentrated under reduced pressure. The crude mixture was purified by column chromatography to obtain the product as brown oil (Yield: 0.4 g, 57.14%). MS (ESI): mass calcd. for $C_{12}H_{12}O_2S$, 220.06; m/z found, 221.1 (M+H)$^+$.

Step 2: (3-Ethylbenzo[b]thiophen-2-yl) methanol (4)

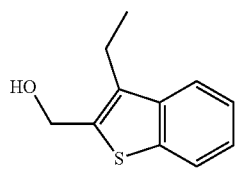

To a solution of methyl 3-ethylbenzo[b]thiophene-2-carboxylate (3, 0.5 g, 1.81 mmol) in THF (10 mL) was added 1M solution of LAH in THF (2.7 mL, 2.72 mmol) drop wise at 0° C. The reaction mixture was stirred for 2 h at 25° C. (Reaction condition b). The reaction was monitored by TLC (1:1, EtOAc: hexane). The reaction mixture was quenched with saturated NH$_4$Cl (10 mL), filtered through celite and extracted with EtOAc. Organic layer was washed with brine, dried over sodium sulphate, filtered and concentrated under reduced pressure. The crude mixture was purified by column chromatography to obtain the product as yellow oil (Yield: 0.24 g, 70.58%). MS (ESI): mass calcd. for $C_{11}H_{12}OS$, 192.06; m/z found, 192.9 (M+H)$^+$.

Step 3: Ethylbenzo[b]thiophene-2-carbaldehyde (5)

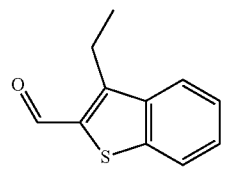

To a solution of (3-ethylbenzo[b]thiophen-2-yl) methanol (4, 0.24 g, 1.25 mmol) in DCM (10 mL) was added Dess martin periodinane (0.79 g, 1.87 mmol) at 0° C. (Reaction condition c). The reaction mixture was stirred for 2 h at 25° C. The reaction was monitored by TLC (1:1, EtOAc: hexane). The reaction mixture was quenched with saturated NaHCO$_3$ (10 mL), filtered through celite and extracted with DCM. Organic layer was washed with brine, dried over sodium sulphate, filtered and concentrated under reduced pressure. The crude mixture was purified by column chromatography to obtain the product as yellow solid. (Yield: 0.18 g, 81.8%). $^1$HNMR (400 MHz, DMSO-d$_6$) δ (ppm): 10.33 (s, 1H), 8.08-8.02 (m, 2H), 7.56 (t, J=6.8 Hz, 1H), 7.49 (t, J=7.6 Hz, 1H), 3.33-3.30 (m, 2H), 1.29 (t, J=7.2 Hz, 3H). MS (ESI): mass calcd. for $C_{11}H_{10}OS$, 190.05; m/z found, 191.0 (M+H)$^+$.

Synthesis of 1-(4-fluorobenzyl)-1H-indole-2-carbaldehyde (Intermediate for Example-15)

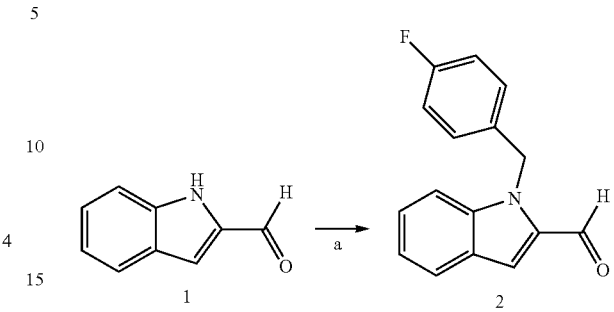

To the stirred solution of 1H-indole-2-carbaldehyde (1, 0.5 g, 3.44 mmol) in DMF (20 mL), were added potassium carbonate (1.42 g, 10.34 mmol) and 1-(bromomethyl)-4-fluorobenzene (0.716 g, 3.79 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to give the crude product. The crude residue was purified by gradient column chromatography using 3-7% ethyl acetate in hexane to afford the 1-(4-fluorobenzyl)-1H-indole-2-carbaldehyde as solid (0.8 g, 97% Yield). $^1$HNMR (400 MHz, CDCl$_3$) δ (ppm): 9.89 (s, 1H), 7.77 (d, J=8.4 Hz, 1H), 7.41 (m, 2H), 7.39 (s, 1H), 7.25-7.17 (m, 1H), 7.10-7.00 (m, 2H), 6.95 (t, J=8 Hz, 2H), 5.79 (s, 2H): MS (ESI): Mass calcd. for $C_{16}H_{12}FNO$, 253.28; m/z found, 254.0 [M+H]$^+$.

Synthesis of 1-(4-methoxybenzyl)-1H-indole-2-carbaldehyde (Intermediate for Example-19)

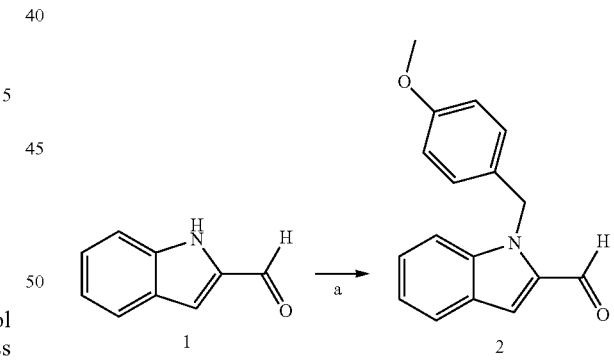

To the stirred solution of 1H-indole-2-carbaldehyde (1, 0.5 g, 3.44 mmol) in DMF (20 mL), were added potassium carbonate (1.42 g, 10.34 mmol) and 1-(bromomethyl)-4-methoxybenzene (0.76 g, 3.79 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(4-methoxybenzyl)-1H-indole-2-carbaldehyde as solid (0.4 g, 43% Yield). $^1$HNMR (400 MHz, DMSO-d$_6$) δ (ppm): 9.75 (s, 1H), 7.93

(d, J=8.4 Hz, 1H), 7.82 (m, 2H), 7.36 (s, 1H), 7.25-7.17 (m, 1H), 7.12 (m, 2H), 6.83 (t, J=8 Hz, 2H), 5.81 (s, 2H), 3.81 (s, 3H), MS (ESI): Mass calcd. for $C_{17}H_{15}NO_2$, 265.31; m/z found, 266.1 $[M+H]^+$.

Synthesis of 1-(2-methoxyethyl)-1H-indole-2-carbaldehyde (Intermediate for Example-20)

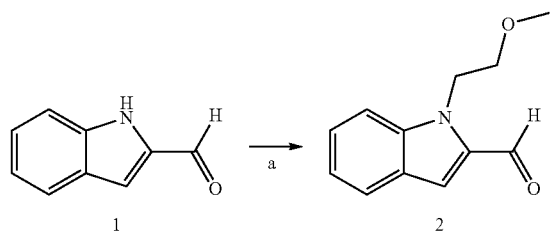

To the stirred solution of 1H-indole-2-carbaldehyde (1, 0.80 g, 5.5 mmol) in N, N-dimethylformamide (20 mL), cesium carbonate (5.36 g, 90.5 mmol) and 1-bromo-2-methoxyethane (0.62 mL, 6.7 mmol) were added at room temperature. The reaction mixture was stirred at 60° C. for 1 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexanes as eluent, to afford the 1-(2-methoxyethyl)-1H-indole-2-carbaldehyde as pale yellow oil. Yield: 3.0 g (42%). $^1$HNMR (400 MHz, DMSO-$d_6$) δ (ppm): 9.89 (s, 1H), 7.75 (d, J=7.9 Hz, 1H), 7.63 (d, J=8.5 Hz, 1H), 7.47 (s, 1H), 7.39 (t, J=7.2 Hz, 1H), 7.15 (t, J=7.5 Hz, 1H), 4.70 (t, J=5.44 Hz, 2H), 3.61 (t, J=5.3 Hz, 2H), 3.15 (s, 3H).

Synthesis of 1-(cyclopropylmethyl)-6-methoxy-1H-indole-2-carbaldehyde (Intermediate for Example-23)

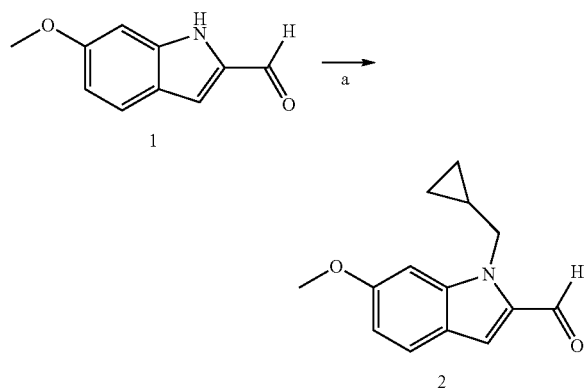

To the stirred solution of 6-methoxy-1H-indole-2-carbaldehyde (1, 2.0 g, 11.4 mmol) in N, N-dimethylformamide (20 mL), cesium carbonate (11.14 g, 34.3 mmol) and (bromomethyl)cyclopropane (1.41 mL, 13.7 mmol) were added at room temperature. The reaction mixture was stirred at room temperature for 2 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexanes as eluent, to afford the 1-(cyclopropylmethyl)-6-methoxy-1H-indole-2-carbaldehyde as pale yellow oil. Yield: 0.80 g (31%), MS (ESI) 229.13; m/z found 230.1 $[M+H]^{+1}$.

Synthesis of 1-(cyclopropylmethyl)-5-methoxy-1H-indole-2-carbaldehyde (Intermediate for Example-60)

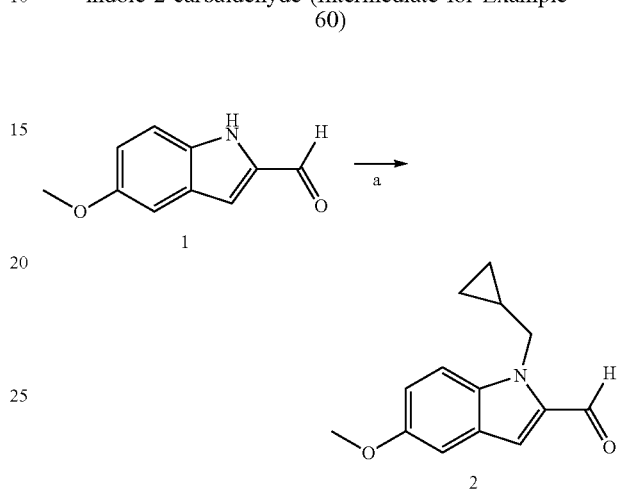

To the stirred solution of 6-methoxy-1H-indole-2-carbaldehyde (1, 2.0 g, 11.4 mmol) in N, N-dimethylformamide (20 mL), cesium carbonate (11.14 g, 34.3 mmol) and (bromomethyl)cyclopropane (1.41 mL, 13.7 mmol) were added at room temperature. The reaction mixture was stirred at room temperature for 2 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexanes as eluent, to afford the 1-(cyclopropylmethyl)-5-methoxy-1H-indole-2-carbaldehyde as pale yellow oil. Yield: 0.79 g (30%), MS (ESI) 229.13; m/z found 230.1 $[M+H]^{+1}$.

Synthesis of 6-methoxy-1-(2-methoxyethyl)-1H-indole-2-carbaldehyde (Intermediate for Example-21)

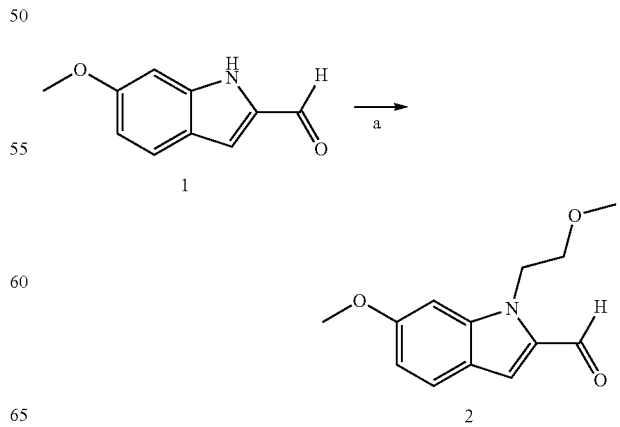

To the stirred solution of 6-methoxy-1H-indole-2-carbaldehyde (1, 0.80 g, 4.57 mmol) in N, N-dimethylformamide (3 mL), cesium carbonate (4.4 g, 13.7 mmol) and 1-bromo-2-methoxyethane (0.51 mL, 5.48 mmol) were added at room temperature. The reaction mixture was stirred at 60° C. for 16 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by combiFlash using 12 g RediSep and 20% ethyl acetate in hexane as eluent to afford the 6-methoxy-1-(2-methoxyethyl)-1H-indole-2-carbaldehyde as off white semi solid. Yield: 0.60 g, 60%, MS (ESI): 235; m/z found 234.10 $[M-1]^{-1}$.

Synthesis of 1-(2-fluorobenzyl)-1H-indole-2-carbaldehyde (Intermediate for Example-70)

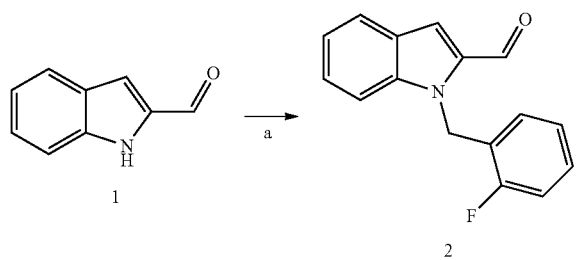 [SMILES: O=Cc1cc2ccccc2[nH]1 ; O=Cc1cc2ccccc2n1Cc1ccccc1F]

To a solution of 1H-indole-2-carbaldehyde (1, 2.0 g, 13.7 mmol) in N, N-dimethylformamide (15 mL), potassium carbonate (5.6 g, 41.1 mmol) and 1-(bromomethyl)-2-fluorobenzene (3.1 g, 16.5 mmol) were added at room temperature. The reaction mixture was stirred at room temperature for 4 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford 1-(2-fluorobenzyl)-1H-indole-2-carbaldehyde as yellow solid.

Synthesis of 1-(pyridin-4-ylmethyl)-1H-indole-2-carbaldehyde (Intermediate for Example-11 and 71)

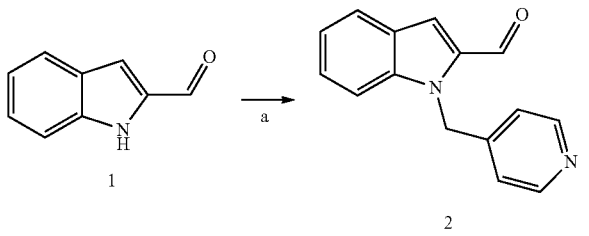 [SMILES: O=Cc1cc2ccccc2[nH]1 ; O=Cc1cc2ccccc2n1Cc1ccncc1]

To a solution of 1H-indole-2-carbaldehyde (1, 1.50 g, 10.3 mmol) in N, N-dimethylformamide (40 mL), potassium carbonate (4.2 g, 31.0 mmol) and 4-(bromomethyl)pyridine hydrobromide (3.1 g, 12.4 mmol) were added at room temperature. The reaction mixture was stirred at 60° C. for 4 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(pyridin-4-ylmethyl)-1H-indole-2-carbaldehyde as yellow oil. Yield: 1.0 g (40%). MS (ESI) 236.01; m/z found 2.37.12.1 $[M+H]^{+1}$.

Synthesis of 1-(pyrazin-2-ylmethyl)-1H-indole-2-carbaldehyde) (Intermediate for Example-25)

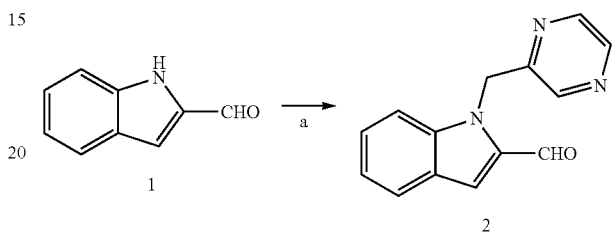

To the stirred solution of 1H-indole-2-carbaldehyde (1, 1.0 g, 6.81 mmol) in N, N-dimethylformamide (20.0 mL), cesium carbonate (11.2 g, 34.4 mmol) and 2-(chloromethyl)pyrazine (1.0 g, 8.27 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(pyrazin-2-ylmethyl)-1H-indole-2-carbaldehyde as yellow solid (3a). Yield: 0.80 g (48%). MS (ESI): 237.26, m/z found 238.12 $[M+H]^{+1}$.

Synthesis of 1-(cyclopropylmethyl)-6-fluoro-1H-indole-2-carbaldehyde (Intermediate for Example-28)

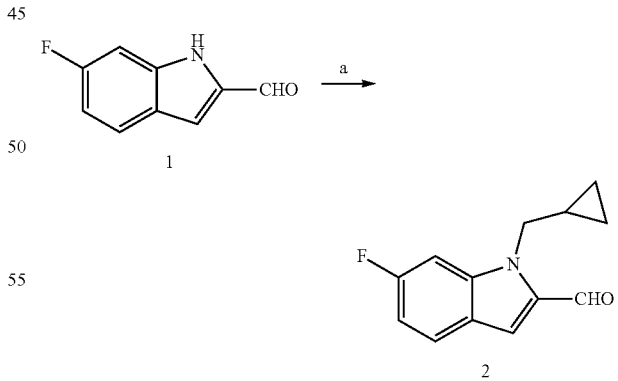

To the stirred solution of 6-fluoro-1H-indole-2-carbaldehyde (1, 1.5 g, 9.2 mmol) in N, N-dimethylformamide (30.0 mL), cesium carbonate (8.9 g, 27.6 mmol) and (bromomethyl)cyclopropane (1.47 g, 11.2 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(cyclopropylmethyl)-6-fluoro-1H-indole-2-carbaldehyde as yellow solid. Yield: 1.5 g (75%). MS (ESI): 217.24, m/z found 218.34 [M+H]$^{+1}$.

Synthesis of 1-(pyrimidin-5-ylmethyl)-1H-indole-2-carbaldehyde (Intermediate for Example-29)

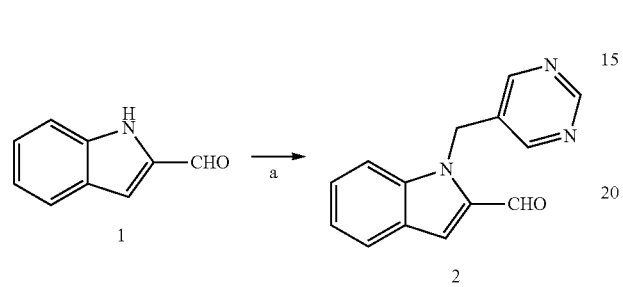

To the stirred solution of 1H-indole-2-carbaldehyde (1, 1.20 g, 8.27 mmol) in N, N-dimethylformamide (20.0 mL), cesium carbonate (8.08 g, 24.01 mmol) and 5-(chloromethyl)pyrimidine (1.0 g, 8.27 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(pyrimidin-5-ylmethyl)-1H-indole-2-carbaldehyde as brown solid. Yield: 1.60 g (81%). MS (ESI): 237.26, m/z found 238.32 [M+H]$^{+1}$.

Synthesis of 1-(pyridazin-3-ylmethyl)-1H-indole-2-carbaldehyde (Intermediate for Example-30)

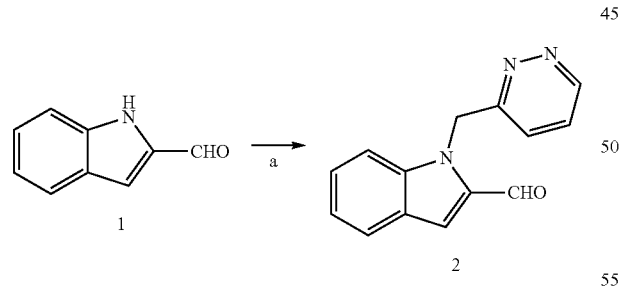

To the stirred solution of 1H-indole-2-carbaldehyde (1, 1.0 g, 6.81 mmol) in N, N-dimethylformamide (10.0 mL), cesium carbonate (6.7 g, 20.01 mmol) and 3-(chloromethyl)pyridazine (1.0 g, 7.10 mmol) were added at room temperature. The reaction mixture was stirred at room temperature for 3 h. After completion of the reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(pyridazin-3-ylmethyl)-1H-indole-2-carbaldehyde as brown solid (3a). Yield: 1.40 g (Crude). MS (ESI): 237.26, m/z found 238.42 [M+H]$^{+1}$.

Synthesis of 1-((tetrahydro-2H-pyran-4-yl)methyl)-1H-indole-2-carbaldehyde) (Intermediate for Example-40)

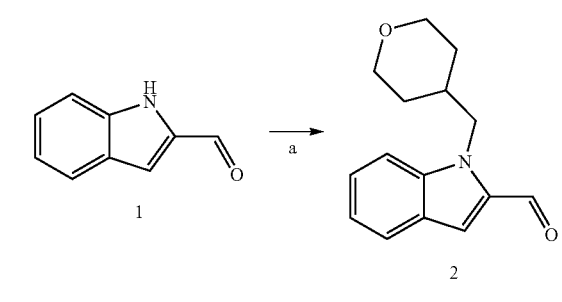 [SMILES: O=Cc1cc2ccccc2[nH]1 ; O=Cc1cc2ccccc2n1CC1CCOCC1]

To the stirred solution of 1H-indole-2-carbaldehyde (1, 1.0 g, 6.89 mmol) in N, N-dimethylformamide (10 mL), cesium carbonate (6.70 g, 20.68 mmol) and 4-(bromomethyl)tetrahydro-2H-pyran (1.48 g, 8.27 mmol) were added at room temperature. The reaction mixture was stirred at room temperature for 1 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 5% ethyl acetate in hexane as eluent to afford 1-((tetrahydro-2H-pyran-4-yl)methyl)-1H-indole-2-carbaldehyde as white solid). Yield: 0.80 g (48%). MS (ESI); 243.13 m/z found: 244.17[M+H]$^{+1}$.

Synthesis of 1-(cyclobutylmethyl)-1H-indole-2-carbaldehyde (Intermediate for Example-41)

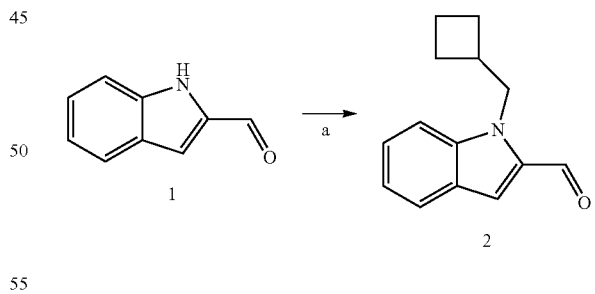

To the stirred solution of 1H-indole-2-carbaldehyde (1, 0.50 g, 3.44 mmol) in N, N-dimethylformamide (10 mL), cesium carbonate (3.3 g, 10.34 mmol) and cyclobutylmethyl methanesulfonate (2b, 0.84 g, 5.17 mmol) were added at room temperature. The reaction mixture was stirred at 100° C. for 1 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 5% ethyl acetate in hexane as eluent to afford 1-(cyclobutylmethyl)-1H-indole- 2-carbaldehyde as oily liquid (3a). Yield: 0.650 g (88%). MS (ESI); 213.12 m/z found no ionization.

¹HNMR (400 MHz, DMSO-d6): δ 9.89 (s, 1H), 7.75 (d, J=8.0 Hz, 1H), 7.67 (d, J=8.4 Hz, 1H), 7.46 (s, 1H), 7.40 (t, J=7.2 Hz, 1H), 7.14 (t, J=7.2 Hz, 1H), 4.60 (d, J=6.8 Hz, 2H), 2.72 (t, J=6.4 Hz, 1H), 1.87-1.71 (m, 6H).

Synthesis of Methyl 2-(2-formyl-1H-indol-1-yl) acetate Intermediate for (Example-42)

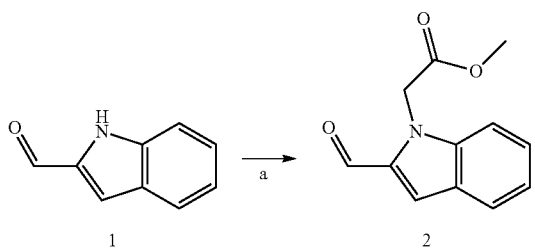 [SMILES: O=Cc1cc2ccccc2[nH]1 ; COC(=O)Cn1c(C=O)cc2ccccc21]

To the stirred solution of 1H-indole-2-carbaldehyde (1, 1.5 g, 10.3 mmol) in N, N-dimethylformamide (40.0 mL), cesium carbonate (10.0 g, 30.9 mmol) and methyl 2-chloroacetate (2a, 1.35 g, 12.4 mmol) were added at room temperature. The reaction mixture was stirred at room temperature for 1 h. After completion of reaction, the reaction mixture was diluted with water and extracted with ethyl acetate (100 mL×2). The combined organic extracts were washed with brine, dried over anhydrous sodium sulfate, filtered and concentrated under reduced pressure. The crude was purified by CombiFlash using 40 g RediSep and 5% ethyl acetate in hexane as eluent to afford methyl 2-(2-formyl-1H-indol-1-yl)acetate (3a) as yellow oil. Yield: 1.2 g (53%). MS (ESI): 217.04, m/z found 218.18 [M+H]$^{+1}$.

Synthesis of tert-butyl 4-((2-formyl-1H-indol-1-yl) methyl)piperidine-1-carboxylate (Intermediate for Example-43)

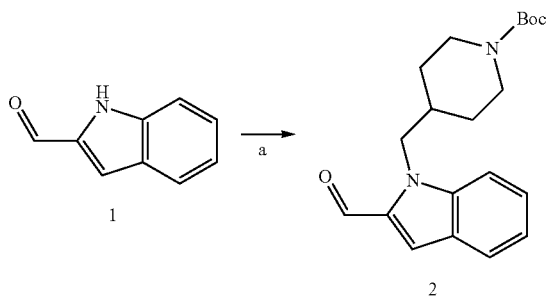 [SMILES: O=Cc1cc2ccccc2[nH]1 ; CC(C)(C)OC(=O)N1CCC(Cn2c(C=O)cc3ccccc32)CC1]

To the stirred solution of 1H-indole-2-carbaldehyde (1, 1.0 g, 6.81 mmol) in N, N-dimethylformamide (10 mL), cesium carbonate (6.72 g, 20.0 mmol) and tert-butyl 4-(bromomethyl)piperidine-1-carboxylate (2.29 g, 8.11 mmol) were added at room temperature. The reaction mixture was stirred at room temperature for 3 h. After completion of reaction, reaction mixture was diluted with water and extracted with ethyl acetate (50 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford the tert-butyl 4-((2-formyl-1H-indol-1-yl)methyl)piperidine-1-carboxylate as yellow solid. Yield: 2.0 g (86%). MS (ESI): found no ionization.

¹HNMR (400 MHz, DMSO-d₆) δ (ppm): 9.89 (s, 1H), 7.77-7.76 (m, 1H), 7.70-7.68 (m, 1H), 7.49 (s, 1H), 7.40-7.38 (m, 1H), 7.17-7.14 (m, 1H), 4.44 (d, J=7.41 Hz, 2H), 3.89 (s, 2H), 1.99-1.89 (m, 1H), 1.37 (s, 13H) 1.18-1.13 (m, 2H).

Synthesis of 1-((1-methylpiperidin-4-yl)methyl)-1H-indole-2-carbaldehyde (Intermediate for Example-45)

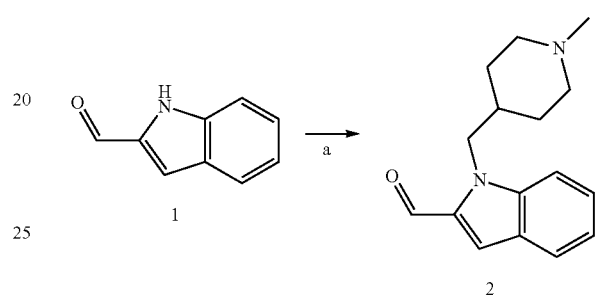

To the stirred solution of 1H-indole-2-carbaldehyde (1, 1.0 g, 6.81 mmol) in N, N-dimethylformamide (10 mL), cesium carbonate (6.72 g, 20.0 mmol) and tert-butyl 4 4-(bromomethyl)-1-methylpiperidine (2.2 g, 8 mmol) were added at room temperature. The reaction mixture was stirred at room temperature for 3 h. After completion of reaction, reaction mixture was diluted with water and extracted with ethyl acetate (50 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford the 1-((1-methylpiperidin-4-yl)methyl)-1H-indole-2-carbaldehyde as solid. Yield: 2.2 g (85%).

Synthesis of 1-(oxetan-3-ylmethyl)-1H-indole-2-carbaldehyde (Intermediate for Example-44)

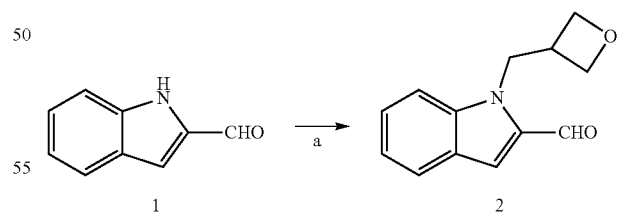

To the stirred solution of 1H-indole-2-carbaldehyde (1, 0.700 g, 4.82 mmol) in N, N-dimethylformamide (10.0 mL), cesium carbonate (4.7 g, 14.48 mmol) and (3-(chloromethyl) oxetane (0.562 g, 5.31 mmol) were added at room temperature. The reaction mixture was stirred at room temperature for 16 h. After completion of reaction, the reaction mixture was diluted with water and extracted with ethyl acetate (10 mL×2). The combined organic extracts were washed with brine, dried over anhydrous sodium sulfate, filtered and concentrated under reduced pressure. The crude was purified by CombiFlash using 12 g RediSep and 30% ethyl acetate in hexane as eluent to afford 1-(oxetan-3-ylmethyl)-1H-indole-2-carbaldehyde as yellow solid. Yield: 0.380 g (63%). MS (ESI): 215.09, m/z found 216.18 [M+H]$^{+1}$.

Synthesis of 6-fluoro-1-(2-methoxyethyl)-1H-indole-2-carbaldehyde (Intermediate for Example-52)

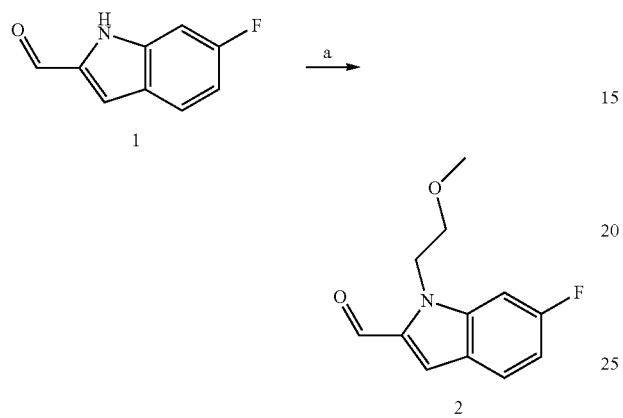

To the stirred solution of 6-fluoro-1H-indole-2-carbaldehyde (1, 0.90 g, 5.5 mmol) in N, N-dimethylformamide (20 mL), potassium carbonate (5.38 g, 16.5 mmol) and 1-bromo-2-methoxyethane (0.61 mL, 6.62 mmol) were added at room temperature. The reaction mixture was stirred at room temperature for 3 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexanes as eluent, to afford the 6-fluoro-1-(2-methoxyethyl)-1H-indole-2-carbaldehyde as sticky solid. Yield: 0.60 g (60%); MS (ESI) 221.09; m/z found 222.10 [M+H]$^{+1}$.

Synthesis of 1-((3-fluoropyridin-2-yl)methyl)-6-methoxy-1H-indole-2-carbaldehyde (Intermediate for Example-26)

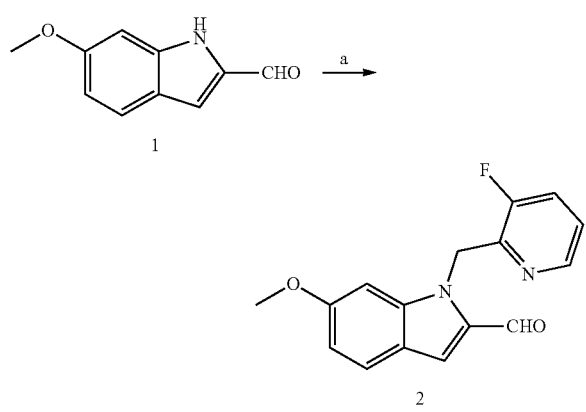

To the stirred solution of 6-methoxy-1H-indole-2-carbaldehyde (1, 0.50 g, 2.85 mmol) in N, N-dimethylformamide (10.0 mL), cesium carbonate (2.7 g, 8.57 mmol) and 2-(chloromethyl)-3-fluoropyridine hydrochloride (0.452 g, 3.14 mmol) were added at room temperature. The reaction mixture was stirred at 60° C. about 2 h. After completion of reaction, the reaction mixture was diluted with water and extracted with ethyl acetate (10 mL×2). The combined organic extracts were washed with brine, dried over anhydrous sodium sulfate, filtered and concentrated under reduced pressure. The crude was purified by CombiFlash using 12 g RediSep and 30% ethyl acetate in hexane as eluent to afford 1-((3-fluoropyridin-2-yl)methyl)-6-methoxy-1H-indole-2-carbaldehyde as solid Yield: 0.63 g (79%). MS (ESI): 284.10, m/z found 285.19 [M+H]$^{+1}$.

Synthesis of 1-((3-fluoropyridin-2-yl)methyl)-6-methoxy-1H-indole-2-carbaldehyde (Intermediate for Example-33)

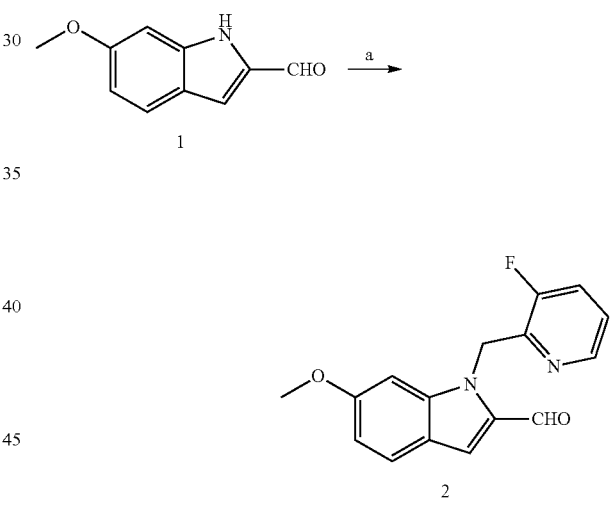

To the stirred solution of 6-methoxy-1H-indole-2-carbaldehyde (1, 0.50 g, 2.85 mmol) in N, N-dimethylformamide (10.0 mL), cesium carbonate (2.7 g, 8.57 mmol) and 2-(chloromethyl)-3-fluoropyridine hydrochloride (0.45 g, 3.14 mmol) were added at room temperature. The reaction mixture was stirred at 60° C. about 2 h. After completion of reaction, the reaction mixture was diluted with water and extracted with ethyl acetate (10 mL×2). The combined organic extracts were washed with brine, dried over anhydrous sodium sulfate, filtered and concentrated under reduced pressure. The crude was purified by CombiFlash using 12 g RediSep and 30% ethyl acetate in hexane as eluent to afford 1-((3-fluoropyridin-2-yl)methyl)-6-methoxy-1H-indole-2-carbaldehyde as yellow solid Yield: 0.66 g (81%). MS (ESI): 284.10, m/z found 285.19 [M+H]$^{+1}$.

Synthesis of 7-chloro-1-((3-fluoropyridin-2-yl)methyl)-1H-indole-2carbaldehyde (Intermediate for Example-34)

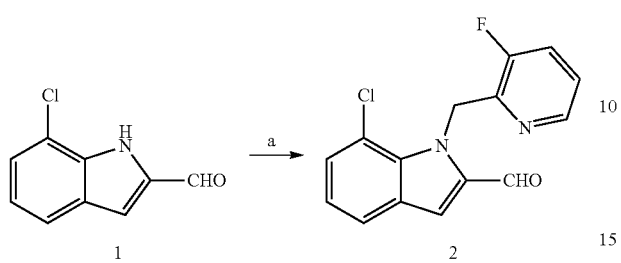

To the stirred solution of 7-chloro-1H-indole-2-carbaldehyde (1, 0.4 g, 2.23 mmol) in N, N-dimethylformamide (14.0 mL), cesium carbonate (2.1 g, 6.68 mmol) and 2-(chloromethyl)-3-fluoropyridine (0.39 g, 2.67 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford 7-chloro-1-((3-fluoropyridin-2-yl)methyl)-1H-indole-2-carbaldehyde as yellow oil. Yield: 0.30 g (46%). MS (ESI): 288.0, m/z found 289.01 [M+H]$^{+1}$.

Synthesis of 6-fluoro-1-((3-fluoropyridin-2-yl)methyl)-1H-indole-2-carbaldehyde (Intermediate for Example-35)

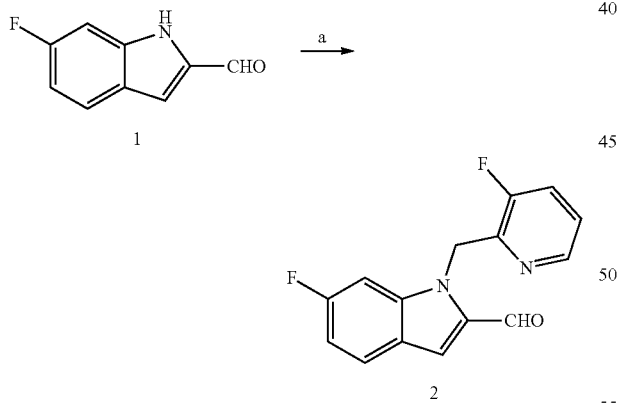

To the stirred solution of 6-fluoro-1H-indole-2-carbaldehyde (1, 0.5 g, 3.06 mmol) in N, N-dimethylformamide (6.0 mL), cesium carbonate (2.99 g, 9.2 mmol) and 2-(chloromethyl)-3-fluoropyridine hydrochloride (0.53 g, 3.6 mmol) were added at room temperature. The reaction mixture was stirred at room temperature for 3 h. After completion of reaction, the reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 5% ethyl acetate in hexane as eluent to afford 6-fluoro-1-((3-fluoropyridin-2-yl)methyl)-1H-indole-2-carbaldehyde as yellow solid. Yield: 0.72 g (86%). MS (ESI): 272.12, m/z found no ionization. $^{1}$HNMR (400 MHz, DMSO-d6): δ 9.80 (s, 1H), 8.15 (d, J=4.5 Hz, 1H), 7.85-7.82 (m, 1H), 7.73 (t, J=9.1 Hz, 1H), 7.54 (s, 1H), 7.50 (d, J=10.6 Hz, 1H), 7.35-7.28 (m, 1H), 7.05-7.02 (m, 1H), 5.97 (s, 2H).

Synthesis of 1-(2,2-difluoroethyl)-1H-indole-2-carbaldehyde (Intermediate for Example-47)

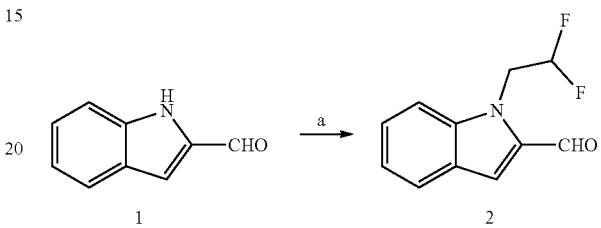

To the stirred solution of 1H-indole-2-carbaldehyde (1, 1.0 g, 6.81 mmol) in N, N-dimethylformamide (10.0 mL), cesium carbonate (6.7 g, 20.01 mmol) and 2-bromo-1,1-difluoroethane (1.78 mL, 20.6 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(2,2-difluoroethyl)-1H-indole-2-carbaldehyde as brown solid. Yield: 0.91 g (63%). MS (ESI): 209.26, m/z found no ionization. $^{1}$HNMR (400 MHz, DMSO-d6): δ 9.98 (s, 1H), 7.82 (d, J=8.1 Hz, 1H), 7.79 (d, J=7.9 Hz, 1H), 7.57 (s, 1H), 7.45 (t, J=8.0 Hz, 1H), 7.20 (t, J=7.6 Hz, 1H), 6.33 (t, J=54.3 Hz, 1H), 5.09-5.01 (m, 2H).

Synthesis of 5-fluoro-1-(2-methoxyethyl)-1H-indole-2-carbaldehyde (Intermediate for Example-48)

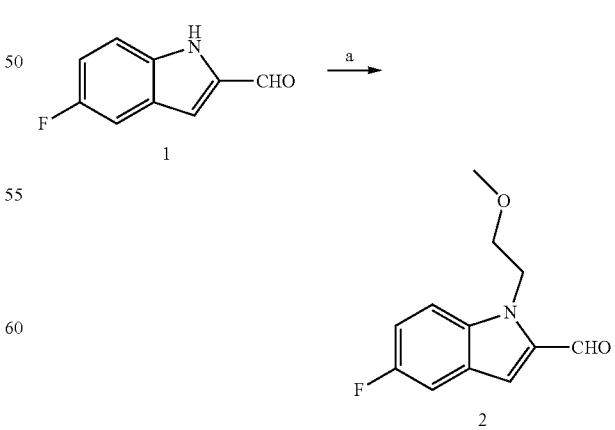

To the stirred solution of 5-fluoro-1H-indole-2-carbaldehyde (1, 0.5 g, 3.06 mmol) in N, N-dimethylformamide (20.0 mL), cesium carbonate (3.0 g, 9.18 mmol) and 1-bromo-2-methoxyethane (2a, 0.34 mL, 3.68 mmol) were added at room temperature. The reaction mixture was stirred at room temperature for 2 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford 5-fluoro-1-(2-methoxyethyl)-1H-indole-2-carbaldehyde as brown oil. Yield: 0.58 g (85%), MS (ESI) 221.0; m/z found 221.95 [M+H]$^{+1}$.

Synthesis of 6-fluoro-1-(4-fluorobenzyl)-1H-indole-2-carbaldehyde (Intermediate for Example-49)

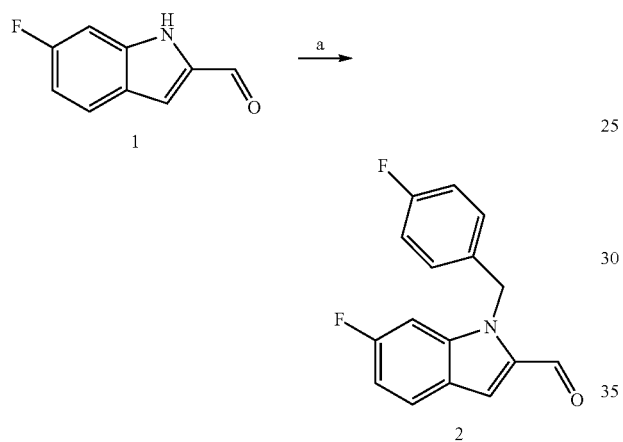

To the stirred solution of 6-fluoro-1H-indole-2-carbaldehyde (1, 1.00 g, 6.13 mmol) in N, N-dimethylformamide (10 mL), cesium carbonate (5.98 g, 18.4 mmol) and 1-(bromomethyl)-4-fluorobenzene (1.38 g, 7.36 mmol) were added at room temperature. The reaction mixture was stirred at room temperature for 1 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 5% ethyl acetate in hexane as eluent to afford 6-fluoro-1-(4-fluorobenzyl)-1H-indole-2-carbaldehyde as off white solid. Yield: 1.20 g (75%). MS (ESI); 271.08 m/z found: 272.19.

Synthesis of 5-bromo-1-(cyclopropylmethyl)-1H-indole-2-carbaldehyde (Intermediate for Example-67)

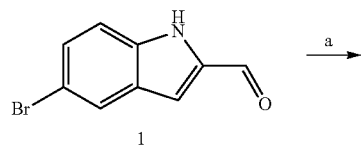

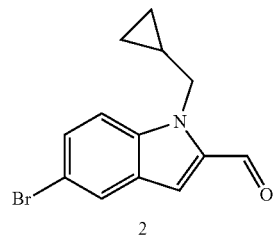

To the stirred solution of 5-bromo-1H-indole-2-carbaldehyde (1, 5 g, 32.9 mmol) in N, N-dimethylformamide (60 mL), cesium carbonate (29.5 g, 90.5 mmol) and (bromomethyl)cyclopropane (4.8 mL, 36.2 mmol) were added at room temperature. The reaction mixture was stirred at room temperature for 3 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by combi flash using 12 g Redisep and 20% ethyl acetate in hexane to afford the 5-bromo-1-(cyclopropylmethyl)-1H-indole-2-carbaldehyde as solid. Yield: 3.5 g (55%). MS (ESI): 278.06; m/z found 279.19.

Synthesis of 1-(cyclopropylmethyl)-7-chloro-1H-indole-2-carbaldehyde (Intermediate for Example-57)

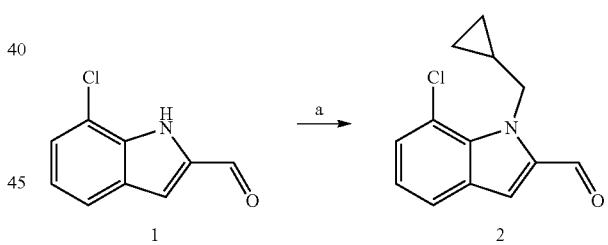

To the stirred solution of 7-chloro-1H-indole-2-carbaldehyde (1, 5.4 g, 30.9 mmol) in N, N-dimethylformamide (60 mL), cesium carbonate (29.5 g, 90.5 mmol) and (bromomethyl)cyclopropane (4.8 mL, 36.2 mmol) were added at room temperature. The reaction mixture was stirred at room temperature for 3 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by combi flash using 12 g Redisep and 20% ethyl acetate in hexane to afford the 1-(cyclopropylmethyl)-7-chloro-1H-indole-2-carbaldehyde as sticky solid. Yield: 3.0 g (42%). $^{1}$HNMR (400 MHz, DMSO-d6): δ (ppm): 9.92 (s, 1H), 7.80 (d, J=8.0 Hz, 1H), 7.62 (s, 1H) 7.47 (d, J=8.0 Hz, 1H), 7.16 (t, J=7.6 Hz, 1H), 4.80 (d, J=6.92 Hz, 2H), 1.26 (m, 1H), 0.42-0.34 (m, 4H). MS (ESI): 233.06; m/z found 234.19.

Synthesis of 7-chloro-1-(4-methoxybenzyl)-1H-indole-2-carbaldehyde (Intermediate for Example-39)

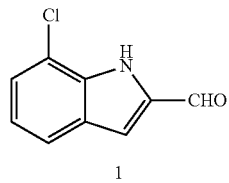

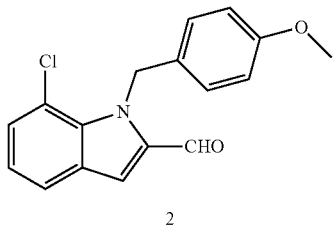

To the stirred solution of 7-chloro-1H-indole-2-carbaldehyde, 0.5 g, 2.78 mmol) in N, N-dimethylformamide (10.0 mL), cesium carbonate (2.7 g, 8.35 mmol) and 1-(chloromethyl)-4-methoxybenzene (0.52 g, 3.34 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 7-chloro-1-(4-methoxybenzyl)-1H-indole-2-carbaldehyde as yellow oil. Yield: 0.40 g (47%). MS (ESI): 299.0, m/z found 300.19 $[M+H]^{+1}$.

Synthesis of 5-fluoro-1-(4-methoxybenzyl)-1H-indole-2-carbaldehyde (Intermediate for Example-46)

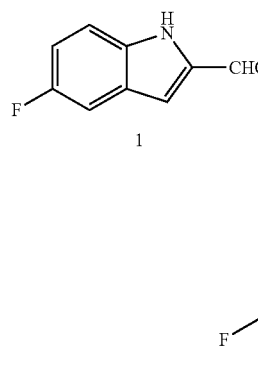

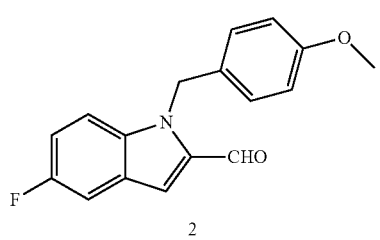

To the stirred solution of 5-fluoro-1H-indole-2-carbaldehyde (1, 0.5 g, 3.06 mmol) in N, N-dimethylformamide (20.0 mL), cesium carbonate (3.0 g, 9.18 mmol) and 1-(chloromethyl)-4-(methoxymethyl)benzene (0.72 mL, 3.68 mmol) were added at room temperature. The reaction mixture was stirred at room temperature for 2 h. After completion of reaction, reaction mixture was diluted with water and extracted with ethyl acetate (25 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford 5-fluoro-1-(4-methoxybenzyl)-1H-indole-2-carbaldehyde as yellow oil. Yield: 0.52 g (60%). MS (ESI): 283.06; m/z found no ionization. $^{1}$HNMR (400 MHz, DMSO-d6): δ 9.95 (s, 1H), 7.74 (d, J=6.28 Hz, 1H), 7.70 (d, J=4.28 Hz, 1H), 7.52 (s, 1H), 7.30-7.27 (m, 1H), 7.08 (d, J=13.5 Hz, 2H), 6.82 (d, J=8.7 Hz, 2H), 5.76 (s, 2H), 3.67 (s, 3H).

Synthesis of 6-fluoro-1-(4-methoxybenzyl)-1H-indole-2-carbaldehyde (Intermediate for Example-50)

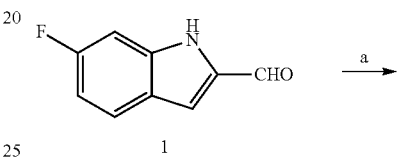

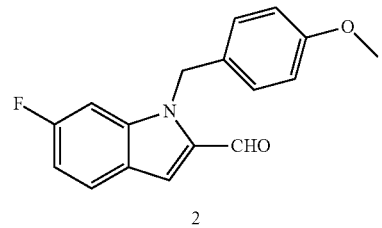

To the stirred solution of 6-fluoro-1H-indole-2-carbaldehyde (0.5 g, 3.06 mmol) in N, N-dimethylformamide (20.0 mL), cesium carbonate (3.0 g, 9.18 mmol) and 1-bromo-2-methoxyethane (0.34 mL, 3.68 mmol) were added at room temperature. The reaction mixture was stirred at room temperature for 2 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford 6-fluoro-1-(4-methoxybenzyl)-1H-indole-2-carbaldehyde as brown oil. Yield: 0.51 g (58%), MS (ESI) 283.1; m/z found 284.22 $[M+H]^{+1}$.

Synthesis of 1-(4-fluorobenzyl)-6-methoxy-1H-indole-2-carbaldehyde (Intermediate for Example-51)

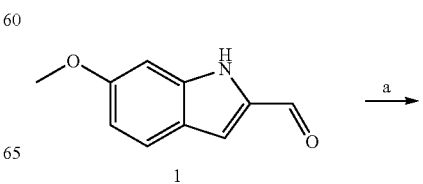

Synthesis of 7-chloro-1-isobutyl-1H-indole-2-carbaldehyde (Intermediate for Example-55)

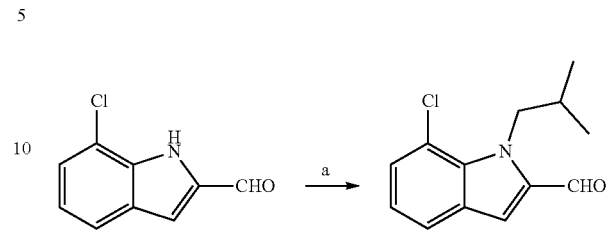

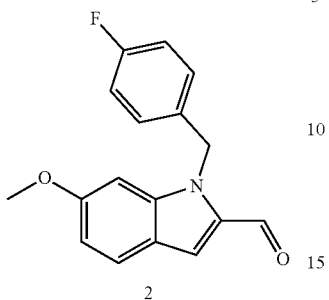

To the stirred solution of 6-methoxy-1H-indole-2-carbaldehyde (, 0.70 g, 5.5 mmol) in N, N-dimethylformamide (10 mL), cesium carbonate (5.31 g, 16.3 mmol) and 1-(bromomethyl)-4-fluorobenzene (1.22 g, 5.6 mmol) were added at room temperature. The reaction mixture was stirred at room temperature for 1 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 5% ethyl acetate in hexane as eluent to afford 1-(4-fluorobenzyl)-6-methoxy-1H-indole-2-carbaldehyde as yellow solid. Yield: 1.0 g (90%). MS (ESI); 283.1 m/z found: 284.18.

To the stirred solution of 7-chloro-1H-indole-2-carbaldehyde (0.7 g, 3.90 mmol) in N, N-dimethylformamide (20.0 mL), cesium carbonate (3.8 g, 11.69 mmol) and 1-bromo-2-methylpropane (0.53 g, 3.90 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 5% ethyl acetate in hexane as eluent to afford 7-chloro-1-isobutyl-1H-indole-2-carbaldehyde as yellow oil. Yield: 0.50 g (54%). MS (ESI): 235.71, m/z found 236.62 [M+H]$^{+1}$.

Synthesis of 2-(chloromethyl)-4-methylthiazole (Intermediate for Example-59)

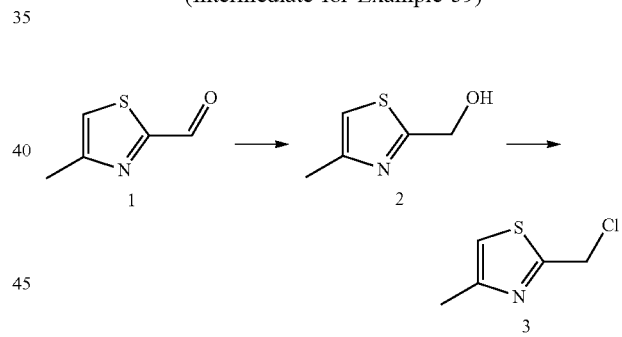

Synthesis of 7-chloro-1-(2,2-difluoroethyl)-1H-indole-2-carbaldehyde (Intermediate for Example-56)

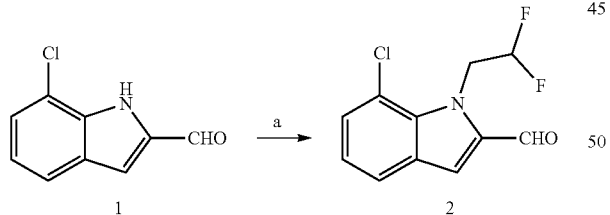

Step A: (4-methylthiazol-2-yl)methanol

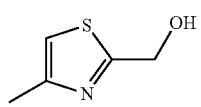

To the stirred solution of 7-chloro-1H-indole-2-carbaldehyde (0.9 g, 5.0 mmol) in N, N-dimethylformamide (20.0 mL), cesium carbonate (4.9 g, 15 mmol) and 2-bromo-1,1-difluoroethane (0.868 g, 6.0 mmol) were added at room temperature. The reaction mixture was stirred at room temperature for 3 h. After completion of reaction, the reaction mixture was diluted with water and extracted with ethyl acetate (30 mL×2). The combined organic extracts were washed with brine, dried over anhydrous sodium sulfate, filtered and concentrated to afford 7-chloro-1-(2,2-difluoroethyl)-1H-indole-2-carbaldehyde. Yield: 1.46 g (Crude). MS (ESI): 243.03, m/z found 244.00[M+H]$^{+1}$.

To the stirred solution of 4-methylthiazole-2-carbaldehyde (1, 1.0 g, 7 mmol) in MeOH (30 mL) at 0° C., was added sodium borohydrate (0.52 g, 14 mmol) lot wise. The reaction mixture was stirred at room temperature for 2 h. The reaction mixture was diluted with water (15 mL) and extracted with EtOAc (2×25 mL). Organic layer was washed with brine (15 mL) solution, dried over anhydrous Na$_2$SO$_4$ and evaporated. The crude residue was purified by gradient column chromatography using 40-60% EtOAc in Hexane to afford the product as pale yellow gummy. (0.9 g, 90%, Yield). MS (ESI): mass calcd. for $C_5H_7NOS$, 129.02; m/z found 130.1 (M+H)$^+$.

Step B: 2-(chloromethyl)-4-methylthiazole

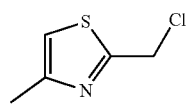

To a stirred solution of (4-methylthiazol-2-yl)methanol (2, 0.9 g, 6.97 mmol) in DCM (5 mL), was added $SOCl_2$ (0.83 mL, 11 mmol) drop wise at 0° C. and the reaction mixture was stirred at room temperature for 1 h. The reaction mixture was neutralized using cold $NaHCO_3$ (5 mL) solution and extracted with DCM (2×25 mL). Organic layer was washed with brine (5 mL) solution, dried over anhydrous $Na_2SO_4$ and evaporated to afford the product as yellow oil. (1 g). MS (ESI): mass calcd. for $C_5H_6ClNS$, 146.99; m/z found 148.1 (M+H)$^+$.

Synthesis of 7-chloro-1-(cyclobutylmethyl)-1H-indole-2-carbaldehyde (Intermediate for Example-53)

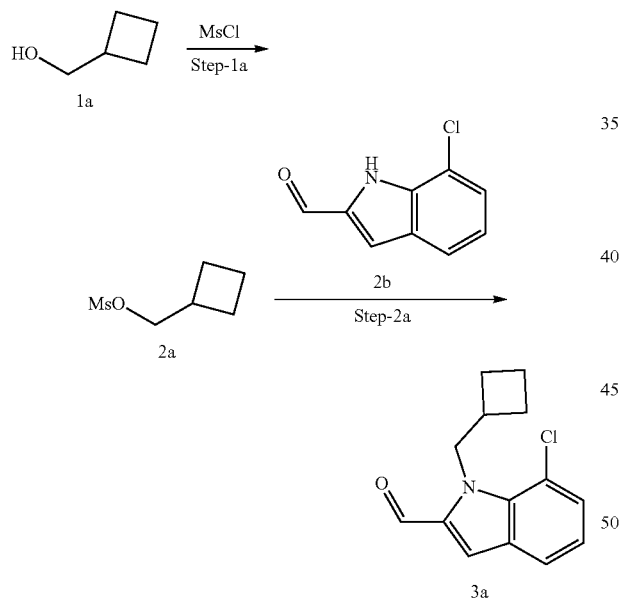

Step-1a: Preparation of Cyclobutylmethyl Methanesulfonate (2a)

To the stirred solution of cyclobutylmethanol (1a, 2.00 g, 23.2 mmol) in dichloromethane (20 mL), triethylamine (6.50 mL, 46.5 mmol) and N,N-dimethylaminopyridine (0.28 g, 2.3 mmol) were added at room temperature, mesyl chloride (2.27 mL, 27.9 mmol) was added at 0° C. The reaction mixture was stirred at room temperature for 3 h. After completion of reaction, reaction mixture was diluted with water and extracted with dichloromethane (20 mL×2). The combined organic extracts were washed with brine, dried over anhydrous sodium sulfate, filtered and concentrated under reduced pressure. The crude was purified by CombiFlash using 12 g Redisep and 10% ethyl acetate in hexanes as eluent, to afford the cyclobutylmethyl methanesulfonate as colorless oil (2a). Yield: 2.50 g (66%); MS (ESI) 164.05; m/z found no ionization. $^1$HNMR (400 MHz, DMSO-d6): δ (ppm): 4.16 (d, J=6.76 Hz, 2H), 3.16 (s, 3H), 2.67-2.60 (m, 1H), 2.05-1.98 (m, 2H), 1.94-1.76 (m, 4H).

Step-2a: Synthesis of 7-chloro-1-(cyclobutylmethyl)-1H-indole-2-carbaldehyde (3a)

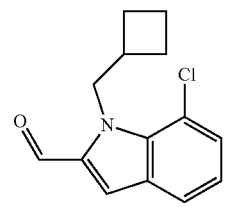 [SMILES: O=Cc1cc2cccc(Cl)c2n1CC1CCC1]

To the stirred solution of 7-chloro-1H-indole-2-carbaldehyde (2b, 0.90 g, 5.0 mmol) in N, N-dimethylformamide (10 mL), cesium carbonate (4.90 g, 15.1 mmol) and cyclobutylmethyl methanesulfonate (2a, 0.98 g, 6.0 mmol) were added at room temperature. The reaction mixture was stirred at 60° C. for 3 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g Redisep and 20% ethyl acetate in hexanes as eluent, to afford the 7-chloro-1-(cyclobutylmethyl)-1H-indole-2-carbaldehyde as pale yellow sticky solid (3a). Yield: 0.32 g (26%); MS (ESI) 247.08; m/z found 248.10 [M+H]$^{+1}$.

Synthesis of 1-(cyclopropylmethyl)-6-vinyl-1H-indole-2-carbaldehyde (Intermediate for Example-61)

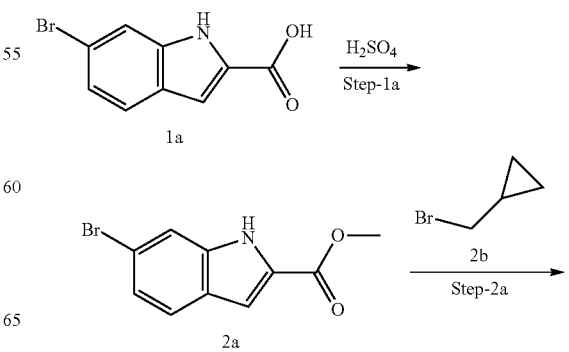

-continued

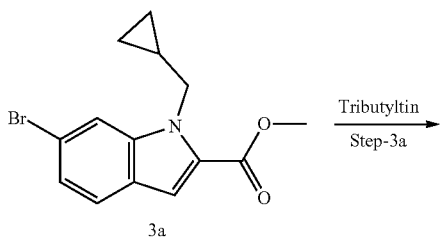

3a

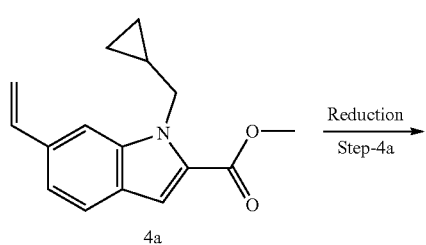

4a

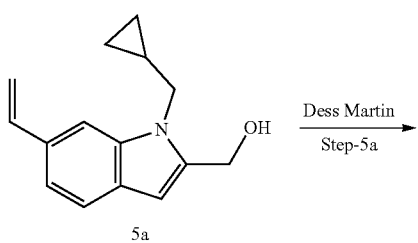

5a

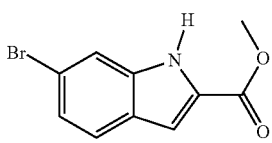

6a

Step-1a Preparation of methyl-6-bromo-1H-indole-2-carboxylate (2a)

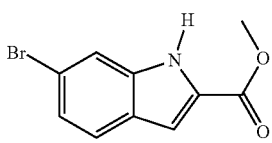

To the stirred solution of 6-bromo-1H-indole-2-carboxylic acid (1a, 5.0 g, 20.83 mmol) in methanol (50.0 mL), sulphuric acid (9 mL, 1.8 vol) was added at 0° C. The reaction mixture was stirred at 80° C. for 12 h. After completion of reaction, the reaction mixture was quenched with ice and precipitated solid was filtered and washed with water (100 mL×2). The compound obtained was dried under vacuum. The crude was purified by CombiFlash using 40 g RediSep and 10% ethyl acetate in hexane as eluent to afford methyl-6-bromo-1H-indole-2-carboxylate as white solid (2a). Yield: 4.5 g (86%). MS (ESI): 252.99 m/z found 253.99 [M+H]$^{+1}$.

Step-2a: Preparation of Methyl 6-bromo-1-(cyclopropylmethyl)-1H-indole-2-carboxylate (3a)

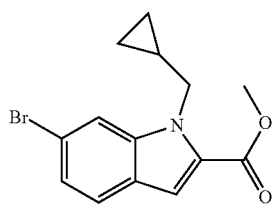 [SMILES: COC(=O)c1cc2ccc(Br)cc2n1CC1CC1]

To the stirred solution of 1H-indole-2-carbaldehyde (2a, 4.5 g, 17.85 mmol) in N, N-dimethylformamide (40 mL), cesium carbonate (17.4 g, 53.27 mmol) and (bromomethyl)cyclopropane (2b, 2.8 g, 21.42 mmol) were added at room temperature. The reaction mixture was stirred at room temperature for 2 h. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford methyl-6-bromo-1-(cyclopropylmethyl)-1H-indole-2-carboxylate as white solid (3a). Yield: 4.0 g (74%). MS (ESI): 307.18, m/z found 308.04 [M+H]$^{+1}$.

Step-3a: Preparation of methyl-1-(cyclopropylmethyl)-6-vinyl-1H-indole-2-carboxylate (4a)

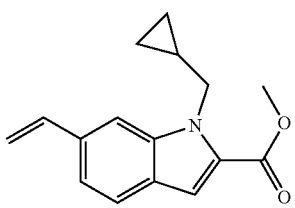 [SMILES: C=Cc1ccc2cc(C(=O)OC)n(CC3CC3)c2c1]

To the stirred solution of methyl-6-bromo-1-(cyclopropylmethyl)-1H-indole-2-carboxylate (3a, 4.0 g, 13.02 mmol) in N, N-dimethylformamide (40.0 mL), lithium chloride (0.656 g, 15.63 mmol) and tributyl vinyl tin (4.9 g, 15.63 mmol) were added at room temperature. Argon was purged for 15 min, tetrakis(triphenylphosphine) palladium (0) (0.75 g, 0.65 mmol) was added at room temperature. The reaction mixture was stirred at 90° C. for 4 h. After completion of reaction, the reaction mixture was diluted with water and extracted with ethyl acetate (40 mL×2). The combined organic extracts were washed with brine, dried over anhydrous sodium sulfate, filtered and concentrated under reduced pressure. The crude was purified by CombiFlash using 40 g RediSep and 5%-10% ethyl acetate in hexane as eluent to afford methyl 1-(cyclopropylmethyl)-6-vinyl-1H-indole-2-carboxylate as brown solid (4a). Yield: 3.1 g (92%). MS (ESI): 255.13, m/z found 256.11 [M+H]$^{+1}$.

Step-4a: Preparation of (1-(cyclopropylmethyl)-6-vinyl-1H-indol-2-yl) Methanol (5a)

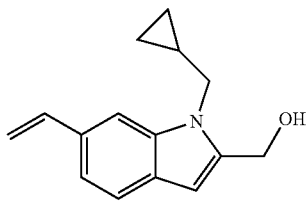 [SMILES: C=Cc1ccc2cc(CO)n(CC3CC3)c2c1]

To the stirred solution of methyl-1-(cyclopropylmethyl)-6-vinyl-1H-indole-2-carboxylate (4a, 2.7 g, 10.5 mmol) in tetrahydrofuran (30.0 mL), 1.0 M lithium aluminum hydrate in tetrahydrofuran (20 mL, 21.0 mmol) were added at 0° C. The reaction mixture was stirred at room temperature for 2 h. After completion of reaction, the reaction mixture was diluted with ammonium chloride and extracted with ethyl acetate (30 mL×2). The combined organic extracts were washed with brine, dried over anhydrous sodium sulfate, filtered and concentrated under reduced pressure. The crude was purified by CombiFlash using 12.0 g Redisep and 20% ethyl acetate in hexane as eluent to afford (1-(cyclopropylmethyl)-6-vinyl-1H-indol-2-yl)methanol as white solid (5a). Yield: 2.0 g (83%). MS (ESI): 227.13, m/z found 228.13 $[M+H]^{+1}$.

Step-5a: preparation of 1-(cyclopropylmethyl)-6-vinyl-1H-indole-2-carbaldehyde

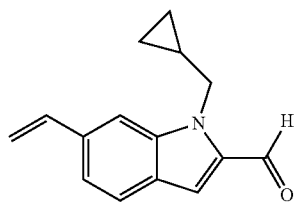 [SMILES: C=Cc1ccc2cc(C=O)n(CC3CC3)c2c1]

To the stirred solution of (1-(cyclopropylmethyl)-6-vinyl-1H-indol-2-yl)methanol (2.0 g, 8.73 mmol) in dichloromethane (20.0 mL), Dess Martin periodinane (4.4 g, 10.48 mmol) were added at room temperature. The reaction mixture was stirred at room temperature for 4 h. After completion of reaction, the reaction mixture was diluted with water and extracted with dichloromethane (20 mL×2). The combined organic extracts were washed with brine, dried over anhydrous sodium sulfate, filtered and concentrated under reduced pressure. The crude was purified by CombiFlash using 12 g RediSep and 30% ethyl acetate in hexane as eluent to afford 1-(cyclopropylmethyl)-6-vinyl-1H-indole-2-carbaldehyde as white solid (6a). Yield: 1.1 g (55%). MS (ESI): 225.12, m/z found 226.12 $[M+H]^{+1}$.

Synthesis of 5,6-difluoro-1-(2-methoxyethyl)-1H-indole-2-carbaldehyde (Intermediate for Example-54)

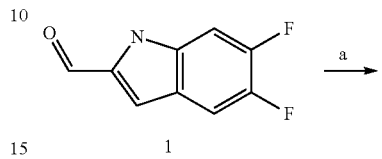

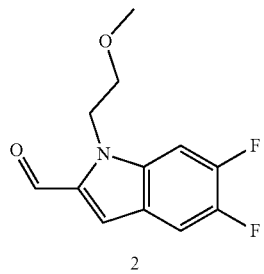

To the stirred solution of 5,6-difluoro-1H-indole-2-carbaldehyde (1, 0.50 g, 2.76 mmol) in N, N-dimethylformamide (10 mL), cesium carbonate (2.69 g, 8.28 mmol) and 1-bromo-2-methoxyethane (0.32 mL, 3.31 mmol) were added at room temperature. The reaction mixture was stirred at 60° C. for 3 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 5,6-difluoro-1-(2-methoxyethyl)-1H-indole-2-carbaldehyde as yellow solid. Yield: 0.66 g (45%). MS (ESI); 239.08 m/z found 240.04 $[M+H]^{+1}$.

Synthesis of 4-(chloromethyl)-3-fluoropyridine hydrochloride (Intermediate for Example-24)

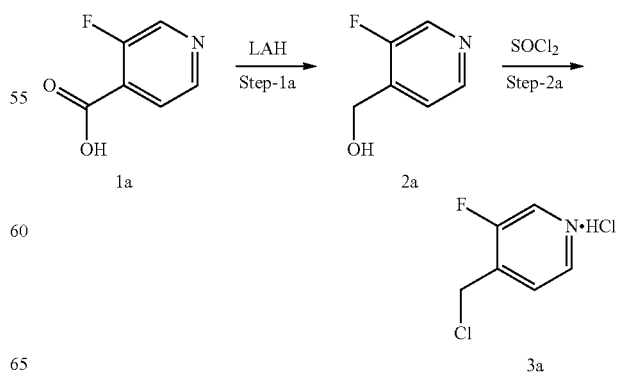

Step-1a: Preparation of (3-fluoropyridin-4-yl)methanol (2a)

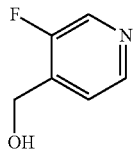

To a solution of 3-fluoroisonicotinic acid (1a, 2.0 g, 14.2 mmol) in tetrahydrofuran (20 mL), Lithium aluminium hydride (1M in tetrahydrofuran), (12.0 mL, 21.3 mmol) was added drop wise over 10 min at 0° C. and reaction mixture was stirred for 2 h at 0° C. After completion of reaction, 40% potassium hydroxide solution was (60 mL) was added to reaction mixture. The solid precipitated was filtered off and washed with diethyl ether. The crude was purified by CombiFlash using 12 g RediSep and 20% ethyl acetate in hexane as eluent to afford (3-fluoropyridin-4-yl) methanol (2a) as off white solid. Yield: 0.50 g (28%). MS (ESI): 127.04; m/z found, 128.01 [M+H]$^{+1}$.

Step 2a: Preparation of 4-(chloromethyl)-3-fluoropyridine Hydrochloride (3a)

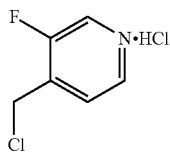

To a stirred solution of (3-fluoropyridin-4-yl)methanol (2a, 0.70 g, 5.51 mmol) in N,N-dichloromethane (5.0 mL), at 0° C., was added thionyl chloride (1.00 g, 13.78 mmol), the reaction mixture was then stirred at room temperature for 1 h. After completion of reaction dichloromethane was removed under reduced pressure and crude obtained was washed with diethyl ether and dried to afford 4-(chloromethyl)-3-fluoropyridine hydrochloride 3a as light brown solid. Yield: 1.0 g (90%). MS (ESI): 180.99; m/z found, 182.02[M+H]$^+$.

Synthesis of 1-(pyrimidin-2-ylmethyl)-1H-indole-2-carbaldehyde (Intermediate for Example-27)

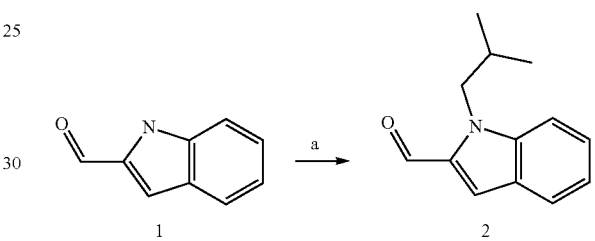

To the stirred solution of 1H-indole-2-carbaldehyde (1, 0.70 g, 4.82 mmol) in N, N-dimethylformamide (10 mL), cesium carbonate (7.8 g, 24.1 mmol) and 2-(chloromethyl) pyrimidine (0.98 g, 7.24 mmol) were added at room temperature. The reaction mixture was stirred at 60° C. for 3 h. After completion of reaction, reaction mixture was cooled to room temperature, diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-(pyrimidin-2-ylmethyl)-1H-indole-2-carbaldehyde as brown crystalline solid. Yield: 1.30 g (81%). MS (ESI): 237.09; m/z found 238.14 [M+H]$^{+1}$.

$^1$HNMR (400 MHz, DMSO-d6): δ 9.87 (s, 1H), 8.68 (d, J=4.8 Hz, 2H), 7.80 (d, J=8.0 Hz, 1H) 7.55 (d, J=5.84 Hz, 2H), 7.36 (d, J=4.72 Hz, 2H), 7.16 (t, J=7.36 Hz, 1H), 6.0 (s, 2H).

Synthesis of 1-isobutyl-1H-indole-2-carbaldehyde (Intermediate for Example-31)

To the stirred solution of 1H-indole-2-carbaldehyde (1, 0.70 g, 4.82 mmol) in N, N-dimethylformamide (10 mL), cesium carbonate (7.8 g, 24.1 mmol) and (1-bromo-2-methylpropane (0.98 g, 7.24 mmol) were added at room temperature. The reaction mixture was stirred at 60° C. for 3 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 10% ethyl acetate in hexane as eluent to afford 1-isobutyl-1H-indole-2-carbaldehyde as oily liquid. Yield: 0.80 g (82%). MS (ESI); 201.12 m/z found 202.30 (M+H)$^+$.

$^1$HNMR (400 MHz, DMSO-d6): δ 9.89 (s, 1H), 7.77 (d, J=8.0 Hz, 1H), 7.64 (d, J=8.44 Hz, 1H), 7.48 (s, 1H), 7.39 (t, J=7.5 Hz, 1H), 7.15 (t, J=7.4 Hz, 1H), 4.37 (d, J=7.4 Hz, 2H), 2.11-2.04 (m, 1H), 0.81 ((d, J=6.64 Hz, 6H).

Synthesis of 1-(2-methoxyethyl)-1H-indole-2-carbaldehyde (Intermediate for Example-22)

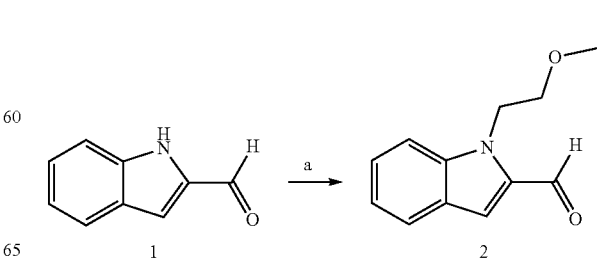

To the stirred solution of 1H-indole-2-carbaldehyde (1, 1.0 g, 6.0 mmol) in N, N-dimethylformamide (6.0 mL), cesium carbonate (6.6 g, 20.6 mmol) and 1-bromo-2-methoxyethane (0.76 mL, 8.0 mmol) were added at room temperature. The reaction mixture was stirred at 60° C. for 1.5 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford the 1-(2-methoxyethyl)-1H-indole-2-carbaldehyde as light yellow solid. Yield: 0.9 g (64%). MS (ESI): 203; m/z found no ionization.

$^1$HNMR (400 MHz, DMSO-d$_6$) δ (ppm): 9.89 (s, 1H), 7.75 (d, J=8.4 Hz, 1H), 7.63 (d, J=8.8 Hz, 1H) 7.47 (s, 1H), 7.39 (t, J=7.6 Hz, 1H), 7.15 (t, J=7.6 Hz, 1H), 4.70 (t, J=5.6 Hz, 2H), 3.61 (t, J=5.2 Hz, 2H), 3.17 (s, 3H).

Synthesis of 7-chloro-1-(2-methoxyethyl)-1H-indole-2-carbaldehyde (Intermediate for Example-36)

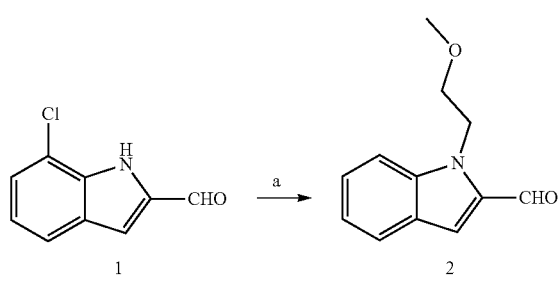

To the stirred solution of 7-chloro-1H-indole-2-carbaldehyde (1, 0.5 g, 2.79 mmol) in N, N-dimethylformamide (15 mL), cesium carbonate (2.7 g, 8.37 mmol) and 1-bromo-2-methoxyethane (0.31 mL, 3.35 mmol) were added at room temperature. The reaction mixture was stirred at room temperature for 3 h. After completion of reaction, the reaction mixture was diluted with water and extracted with ethyl acetate (50 mL×2). The combined organic extracts were washed with brine, dried over anhydrous sodium sulfate, filtered and concentrated under reduced pressure. The crude was purified by CombiFlash using 12 g RediSep and 20% ethyl acetate in hexane as eluent to afford 7-chloro-1-(2-methoxyethyl)-1H-indole-2-carbaldehyde as yellow oil. Yield: 0.34 g (52%). MS (ESI): 237.06; m/z found no ionization.

$^1$HNMR (400 MHz, DMSO-d6): δ (ppm): 9.93 (s, 1H), 7.77 (d, J=8.0 Hz, 1H), 7.56 (s, 1H) 7.45 (d, J=7.5 Hz, 1H), 7.15 (t, J=7.8 Hz, 1H), 5.13 (t, J=5.9 Hz, 2H), 3.62 (t, J=5.9 Hz, 2H), 3.16 (s, 3H).

Synthesis of 1-(4-(methoxymethyl)benzyl)-1H-indole-2-carbaldehyde (Intermediate for Example-37)

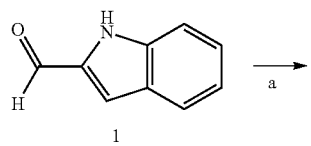

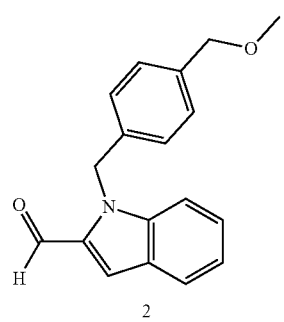

To the stirred solution of 1H-indole-2-carbaldehyde (1, 1.0 g, 6.0 mmol) in N, N-dimethylformamide (5.0 mL), cesium carbonate (0.58 g, 1.79 mmol) and (41-(bromomethyl)-4-(methoxymethyl)benzene (0.14 g, 0.72 mmol) were added at room temperature. The reaction mixture was stirred at room temperature for 3 h. After completion of reaction, reaction mixture was diluted with water and extracted with ethyl acetate (20 mL×2). The combined organic extracts were washed with brine, dried over anhydrous sodium sulfate, filtered and concentrated under reduced pressure. The crude was purified by CombiFlash using 12 g RediSep and 5% methanol in dichloromethane as eluent to afford the 1-(4-(methoxymethyl)benzyl)-1H-indole-2-carbaldehyde.

Synthesis of 1-(cyclopropylmethyl)-5,6-difluoro-1H-indole-2-carbaldehyde (Intermediate for Example-32 & 771

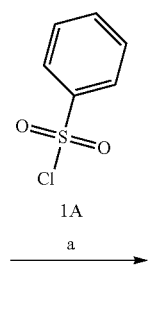

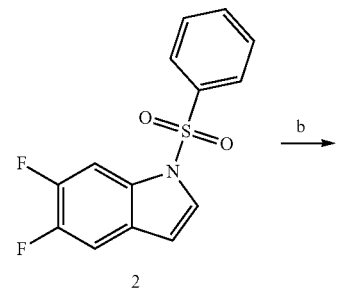

-continued

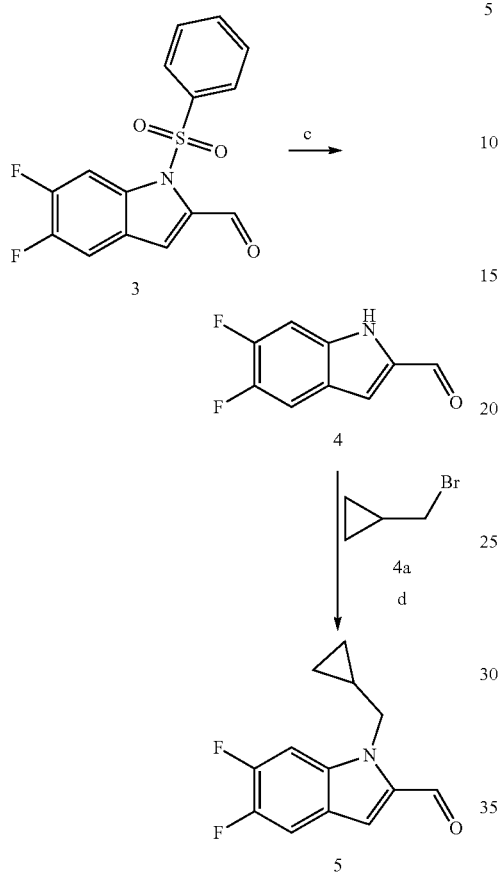

Step 1a: Preparation of 5,6-Difluoro-1-(phenylsulfonyl)-1H-indole (2)

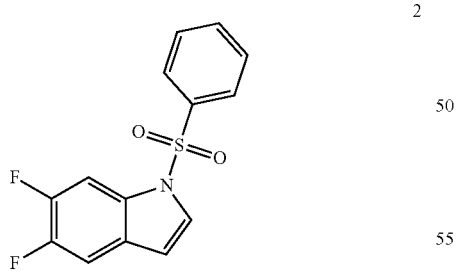

To a solution of sodium hydride (0.26 g, 13 mmol) in DMF (10 mL) was added solution of 5,6-difluoro-1H-indole (1, 0.52 g, 13 mmol) in DMF at 0° C., drop wise over 15 min. Followed by addition of solution of benzenesulfonyl chloride in DMF (1.4 g, 13 mmol) at 0° C. and stirred for 2 h at room temperature under $N_2$ atmosphere. To the reaction mixture was added ice cold water (50 mL), then filtered off the precipitate and washed with ice cold water to obtain brown solid. (1 g, 26% Yield). MS (ESI) m/z 293.0 (M+H)$^+$.

Step 2b: Preparation of 5,6-Difluoro-1-(phenylsulfonyl)-1H-indole-2-carbaldehyde (3)

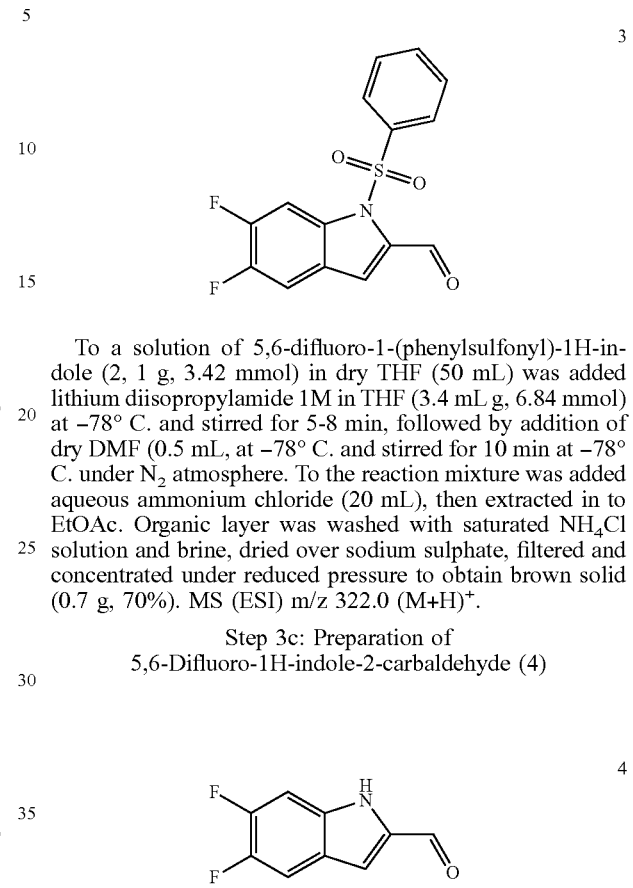

To a solution of 5,6-difluoro-1-(phenylsulfonyl)-1H-indole (2, 1 g, 3.42 mmol) in dry THF (50 mL) was added lithium diisopropylamide 1M in THF (3.4 mL g, 6.84 mmol) at −78° C. and stirred for 5-8 min, followed by addition of dry DMF (0.5 mL, at −78° C. and stirred for 10 min at −78° C. under $N_2$ atmosphere. To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain brown solid (0.7 g, 70%). MS (ESI) m/z 322.0 (M+H)$^+$.

Step 3c: Preparation of 5,6-Difluoro-1H-indole-2-carbaldehyde (4)

To the stirred solution of 5,6-Difluoro-1-(phenylsulfonyl)-1H-indole-2-carbaldehyde (3, 0.8 g, 2.49 mmol) in THF (50 mL), was added TBAF (1M in THF) (9.15 mL, 12.45 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford the 5-fluoro-1H-indole-2-carbaldehyde as sticky solid (0.4 g, 88% Yield) MS (ESI): Mass calcd. for $C_9H_5F_2NO$, 181.145; m/z found, 182 (M+H)$^+$.

Step 4d: Preparation of 1-(cyclopropylmethyl)-5,6-difluoro-1H-indole-2-carbaldehyde (5)

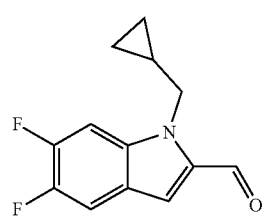

To the stirred solution of 5,6-difluoro-1H-indole-2-carbaldehyde (4, 0.3 g, 1.65 mmol) in DMF (20 mL), were added potassium carbonate (0.68 g, 4.97 mmol) and (bromomethyl)cyclopropane (4a, 0.16 mL, 1.82 mmol) at room temperature. The reaction mixture was stirred at room temperature for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(cyclopropylmethyl)-5,6-difluoro-1H-indole-2-carbaldehyde as off white solid (0.2 g, 48% Yield). $^1$HNMR (400 MHz, DMSO-d$_6$) δ (ppm): 9.86 (s, 1H), 7.90-7.78 (m, 2H), 7.48 (s, 1H), 4.42 (d, J=6.8 Hz, 2H), 1.20 (bs, 1H), 0.39-0.35 (m, 4H), MS (ESI): Mass calcd. for $C_{13}H_{11}F_2NO$, 235.23; m/z found, 236.1 [M+H]$^+$.

Synthesis of 1-(cyclopropylmethyl)-4-fluoro-1H-indole-2-carbaldehyde (Intermediate for Example-80)

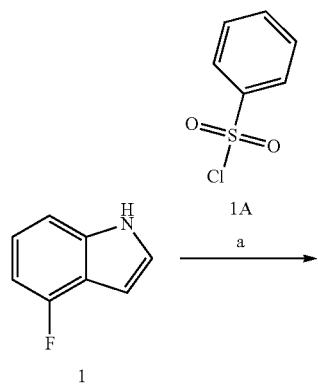

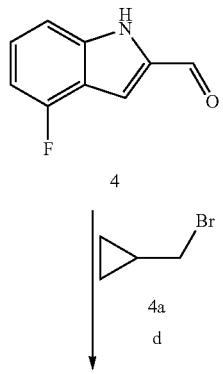

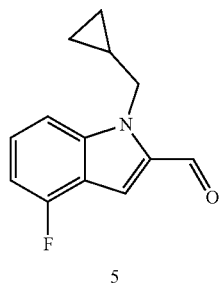

Step 1: Preparation of 4-fluoro-1-(phenylsulfonyl)-1H-indole (2)

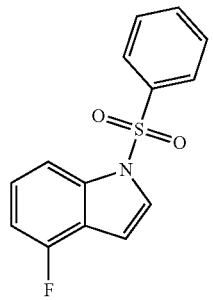

To a solution of sodium hydride (0.88 g, 22.2 mmol) in DMF (50 mL) was added solution of 4-fluoro-1H-indole (1, 3.0 g, 22.2 mmol) in DMF at 0° C., dropwise over 15 min. Benzenesulfonyl chloride in DMF (2.86 mL, 22.2 mmol) was added at 0° C. and stirred for 2 h at room temperature under N$_2$ atmosphere. To the reaction mixture was added ice cold water (50 mL), then filtered off the precipitate and washed with ice cold water to obtain white solid. (7.0 g—crude).

Step 2: Preparation of 4-fluoro-1-(phenylsulfonyl)-1H-indole-2-carbaldehyde (3)

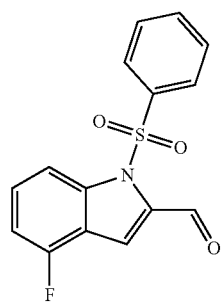

3

To a solution of 4-fluoro-1-(phenylsulfonyl)-1H-indole (2, 7.0 g, 22.0 mmol) in dry THF (60 mL) was added lithium diisopropylamide 2M in THF (10.9 mL, 22.0 mmol) at −78° C. and stirred for 5-8 min, followed by addition of dry DMF (2.5 mL, 33.0 mmol) at −78° C. and stirred for 10 min at −78° C. under $N_2$ atmosphere. To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain red liquid (6.80 g, 88.31%).

Step 3: Preparation of 4-fluoro-1H-indole-2-carbaldehyde (4)

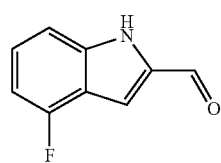

4

To a solution of 4-fluoro-1-(phenylsulfonyl)-1H-indole-2-carbaldehyde (4, 3.0 g, 9.9 mmol) in dry THF (20 mL) was added tetrabutyl ammonium fluoride 1M in THF (14.8 mL) and the reaction mixture was stirred for about 12 h under room temperature. The reaction mixture was quenched with water and, then extracted with ethyl acetate (50 mL×3). Combined organic extracts were washed with brine, dried over sodium sulfate, filtered and evaporated to get crude product. Crude residue was purified by gradient column chromatography using 5-10% ethyl acetate in hexane to get the product as yellow solid. (Yield: 99%, 1.6 g). MS (ESI): Mass calcd. for $C_9H_6FNO$, 163.04; m/z found 164 (M+H)$^+$.

Step-4: Preparation of 1-(cyclopropylmethyl)-4-fluoro-1H-indole-2-carbaldehyde

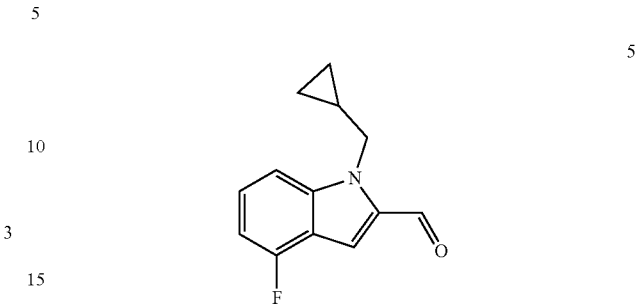

5

To a stirred solution of 4-fluoro-1H-indole-2-carbaldehyde (4, 1.6 g, 9.877 mmol) in DMF (10 mL), was added potassium carbonate (6.8 g, 49.38 mmol) followed by (bromomethyl)cyclopropane (6, 1.4 mL, 10.65 mmol) and the reaction mixture was stirred at room temperature for 12 h. The reaction mixture was quenched with water, extracted with ethyl acetate (30 mL×2). Combined organic extracts were washed with brine, dried over sodium sulfate, filtered and evaporated to get crude product. Crude residue was purified by gradient column chromatography using 5-10% ethyl acetate in hexane to get the product as brown liquid. (Yield: 47.6%, 1 g). $^1$HNMR (400 MHz, DMSO-$d_6$): δ 9.90 (s, 1H), 7.55-7.50 (m, 2H), 7.40-7.35 (m, 1H), 6.95-6.90 (m, 1H), 4.46 (d, J=8 Hz, 2H), 1.22-1.21 (m, 1H), 0.42-0.36 (m, 4H). MS (ESI): Mass calcd. for $C_{13}H_{12}FNO$, 217.24; m/z found, 218 [M+H]$^+$.

Synthesis of 7-chloro-1-(cyclopropylmethyl)-6-fluoro-1H-indole-2-carbaldehyde (Intermediate for Example-87)

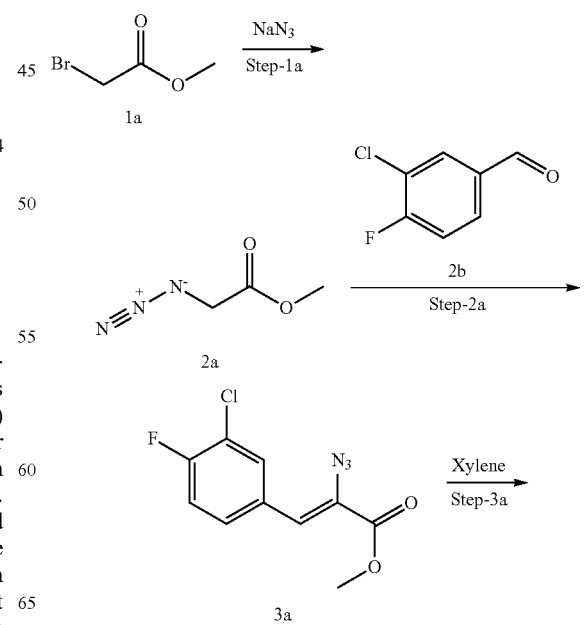

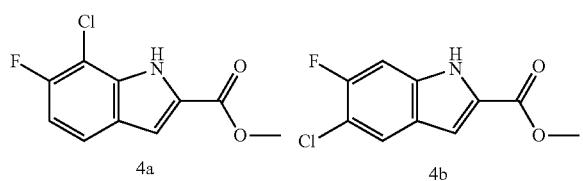

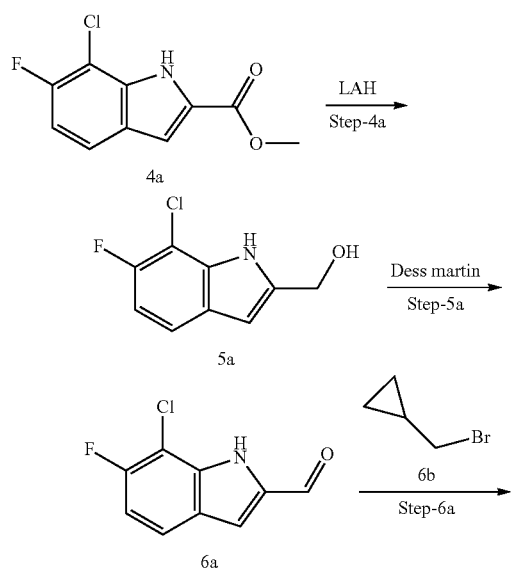

Step-2a: Synthesis of Methyl (Z)-2-azido-3-(3-chloro-4-fluorophenyl)acrylate (3a)

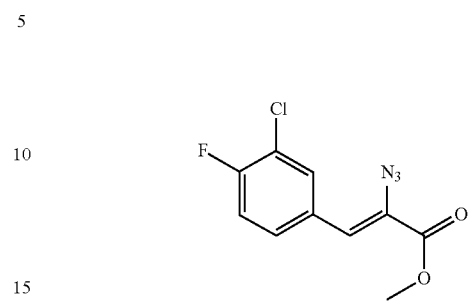

To a stirred solution of methanol (25 mL), sodium metal (1.09 g, 47.46 mmol) was added at room temperature and allowed to stir at room temperature for 10 min. Methyl-2-azidoacetate (2a, 2.50 g, 15.80 mmol) and 3-chloro-4-fluorobenzaldehyde (2b, 6.10 g, 53.70 mmol) solution in methanol (5.0 mL) were added at −15° C. The reaction mixture was stirred at −15° C. for 4 h. After completion of reaction, the reaction mixture was neutralized with 1 N Hydrogen chloride at 0° C. up to pH ~7. The precipitated solid was filtered, washed with water (10 mL×2). The compound obtained was dried under vacuum to afford methyl (Z)-2-azido-3-(3-chloro-4-fluorophenyl)acrylate (3a) as light yellow solid. Yield: 1.8 g (45%). MS (ESI): 255.02, m/z found 256.25 [M+H]$^{+1}$.

Step-3a: Synthesis of methyl-7-chloro-6-fluoro-1H-indole-2-carboxylate (4a)

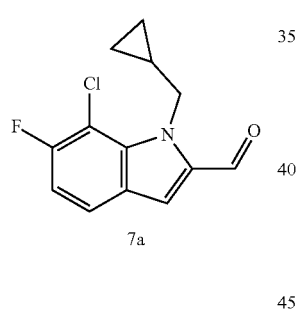

4a

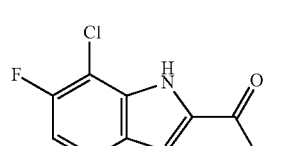

4b

Step-1a: Synthesis of methyl-2-azidoacetate (2a)

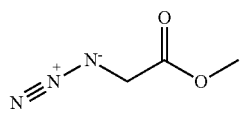

To a stirred solution of methyl-2-bromoacetate (1a, 20.0 g, 131.5 mmol) in N, N-dimethylformamide (40.0 mL), sodium azide (10.2 g, 157.8 mmol) was added at 0° C. The reaction mixture was stirred at room temperature for 16 h. After completion of reaction, the reaction mixture was diluted with water and extracted with ethyl acetate (100 mL×2). The combined organic extracts were washed with brine, dried over anhydrous sodium sulfate, filtered and concentrated under reduced pressure to afford methyl 2-azidoacetate as oily liquid (2a). Yield: 11.2 g (74%). ELSD MS (ESI): 115.04, m/z found 116.10 [M+H]$^{+1}$.

The stirred solution of methyl (Z)-2-azido-3-(3-chloro-4-fluorophenyl)acrylate (3a, 1.80 g, 7.05 mmol) in p-xylene (80.0 mL) was refluxed at 140° C. for 2 h. After completion of reaction, the reaction mixture was concentrated under reduced pressure. The resulting crude was purified by CombiFlash using 40.0 g RediSep column. Desired methyl-7-chloro-6-fluoro-1H-indole-2-carboxylate (4a) was obtained at 2% ethyl acetate in hexanes and methyl 5-chloro-6-fluoro-1H-indole-2-carboxylate (4b) was obtained at 5% ethyl acetate in hexanes. Desired fraction was concentrated to afford methyl-7-chloro-6-fluoro-1H-indole-2-carboxylate (4a) as light brown solid. Yield: 1.1 g (Crude). MS (ESI): 227.01, m/z found 228.01 [M+H]$^{+1}$.

Step-4a: Synthesis of (7-chloro-6-fluoro-1H-indol-2-yl)methanol (5a)

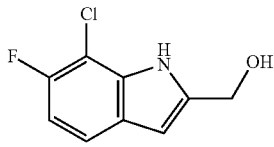 [SMILES: OCc1cc2ccc(F)c(Cl)c2[nH]1]

To a stirred solution of methyl-7-chloro-6-fluoro-1H-indole-2-carboxylate (4a, 1.0 g, 4.4 mmol) in tetrahydrofuran (20.0 mL), 1.0 M lithium aluminum hydrate in tetrahydrofuran (8.8 ml, 8.80 mmol) was added at 0° C. The reaction mixture was stirred at room temperature for 2 h. After completion of reaction, the reaction mixture was diluted with ammonium chloride and extracted with ethyl acetate (30 mL×2). The combined organic extracts were washed with brine, dried over anhydrous sodium sulfate, filtered and concentrated under reduced pressure. The crude was purified by CombiFlash using 40 g RediSep column and 20% ethyl acetate in hexane as eluent to afford (7-chloro-6-fluoro-1H-indol-2-yl)methanol as sticky solid (5a). Yield: 8.24 g (91%). MS (ESI): 199.02, m/z found 200.05 [M+H]$^{+1}$.

Step-5a: Synthesis of 7-chloro-6-fluoro-1H-indole-2-carbaldehyde (6a)

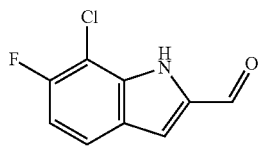 [SMILES: O=Cc1cc2ccc(F)c(Cl)c2[nH]1]

To a stirred solution of (7-chloro-6-fluoro-1H-indol-2-yl)methanol (5a, 0.80 g, 4.00 mmol) in dichloromethane (30.0 mL), Dess Martin periodinane (3.4 g, 8.00 mmol) were added at room temperature. The reaction mixture was stirred at room temperature for 4 h. After completion of reaction, the reaction mixture was diluted with water and extracted with dichloromethane (20 mL×2). The combined organic extracts were washed with brine, dried over anhydrous sodium sulfate, filtered and concentrated under reduced pressure. The crude was purified by CombiFlash using 12.0 g RediSep column and 2-5% ethyl acetate in hexane as eluent to afford 7-chloro-6-fluoro-1H-indole-2-carbaldehyde as white solid (6a). Yield: 0.63 g (75%). MS (ESI): 197.0, m/z found 198.12 [M+H]$^{+1}$.

Step-6a: Synthesis of 7-chloro-1-(cyclopropylmethyl)-6-fluoro-1H-indole-2-carbaldehyde (7a)

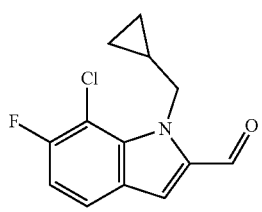

To a stirred solution of 7-chloro-6-fluoro-1H-indole-2-carbaldehyde (6a, 0.30 g, 1.52 mmol) in N, N-dimethylformamide (15.0 mL), cesium carbonate (1.40 g, 4.56 mmol) and (bromomethyl)cyclopropane (6b, 0.29 mL, 3.04 mmol) were added at room temperature. The reaction mixture was stirred at 60° C. for 30 min. After completion of reaction, the reaction mixture was diluted with water and extracted with ethyl acetate (30 mL×2). The combined organic extracts were washed with brine, dried over anhydrous sodium sulfate, filtered and concentrated under reduced pressure. The crude was purified by CombiFlash using 12.0 g RediSep column and 10% ethyl acetate in hexane as eluent to afford 7-chloro-1-(cyclopropylmethyl)-6-fluoro-1H-indole-2-carbaldehyde as sticky solid (7a). Yield: 0.33 g (88%). MS (ESI): 251.05, m/z found 252.25 [M+H]$^{+1}$.

Synthesis of 7-chloro-1-(pyrimidin-5-ylmethyl)-1H-indole-2-carbaldehyde (Intermediate for Example-88)

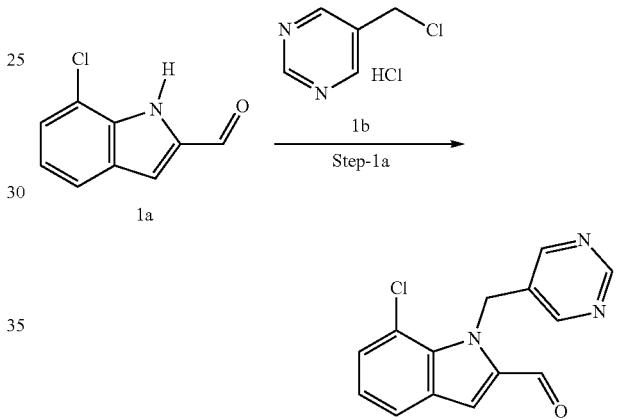

To a stirred solution of 7-chloro-1H-indole-2-carbaldehyde (1a, 0.500 g, 2.79 mmol) in N, N-dimethylformamide (10.0 mL), cesium carbonate (2.7 g, 8.37 mmol) and 5-(chloromethyl) pyrimidine hydrochloride (1b, 0.429 g, 3.34 mmol) were added at room temperature. The reaction mixture was stirred at room temperature about 16 h. After completion of reaction, the reaction mixture was diluted with water and extracted with ethyl acetate (10 mL×2). The combined organic extracts were washed with brine, dried over anhydrous sodium sulfate, filtered and concentrated under reduced pressure. The crude was purified by CombiFlash using 12.0 g RediSep and 30% ethyl acetate in hexane as eluent to afford 7-chloro-1-(pyrimidin-5-ylmethyl)-1H-indole-2-carbaldehyde as yellow solid (2a). Yield: 0.260 g (34%). MS (ESI): 271.10, m/z found 272.19 [M+H]$^{+1}$.

Biological Assays:
FP Binding Assay

Binding of compounds with PAD4 enzyme was detected by FP assay. PAD4 enzyme was diluted to 1 uM in assay buffer (100 mM HEPES, 50 mM NaCl, 1 mM DTT, 5% Glycerol and 1 mM CHAPS) and added to wells containing various concentration of compounds or DMSO vehicle (1%) in a 384 well black plate. 10 nM of fluorescein labelled probe (JPAD-00085) was added to the plate. Assay plate was incubated for 60 minutes at room temperature before measuring FP reading at FP module (λex 485/λem 535 nm) on Pherastar. $IC_{50}$ was calculated using XL-fit software model 205. (Ref: *Nat Chem Biol.* 2015 March; 11(3):189-91).

Ammonia Release Biochemical Assay

Citrullination assay was detected via ammonia release. PAD4 enzyme was diluted to 120 nM in assay buffer (100 mM HEPES, 50 mM NaCl, 2 mM DDT, 0.6 mg/mL BSA, pH 7.4) added to wells containing various concentration of compound or DMSO vehicle (1% final) in black 384 well plate. Following a 60-min preincubation at room temperature, the reaction was initiated by the addition of substrate (1.5 mM BAEE in 200 mM HEPES, 50 mM NaCl, 350 uM CaCl2, 2 mM, pH 7.4). The reaction was stopped after 60 min by addition of stop/detection buffer containing 50 mM EDTA, 2.6 mM of o-phthaladehyde and 2.6 mM DTT. Assay was incubated at room temperature for 90 min before measuring fluorescence's (λex 405/λem 460 nm) on Tecan reader. $IC_{50}$ was calculated using XL-fit software model 205. (Ref: *Nat Chem Biol.* 2015 March; 11(3):189-91).

Anti-PAD4 Activity:

Table 1, below, shows the activity of selected compounds of this disclosure in the PAD4 assays described above. Compounds having an activity designated as "A" provided $IC_{50} \leq 1$ uM; compounds having an activity designated as "B" provided $IC_{50}$ 1-10 uM; and compounds having an activity designated as "C" provided $IC_{50} \geq 10$ uM.

TABLE 1

| | PAD4 enzymatic activity | |
|---|---|---|
| Example No. | NH3 release; PAD4 $IC_{50}$ (uM) | FP PAD4 $IC_{50}$ (uM) |
| 1 | A | B |
| 2 | B | nd |
| 3 | B | nd |
| 4 | C | C |
| 5 | B | B |
| 6 | B | nd |
| 7 | B | nd |
| 8 | A | A |
| 9 | A | A |
| 10 | A | A |
| 11 | A | A |
| 12 | A | A |
| 13 | A | B |
| 14 | B | A |
| 15 | A | B |
| 16 | A | B |
| 17 | A | B |
| 18 | A | B |
| 19 | A | A |
| 20 | A | nd |
| 21 | A | nd |
| 22 | A | nd |
| 23 | A | nd |
| 24 | A | nd |
| 25 | A | nd |
| 26 | A | nd |
| 27 | A | nd |
| 28 | A | nd |
| 29 | B | nd |
| 30 | B | nd |
| 31 | A | nd |
| 32 | A | nd |
| 33 | A | nd |
| 34 | A | nd |
| 35 | A | nd |
| 36 | A | nd |
| 37 | A | nd |
| 38 | C | nd |
| 39 | A | nd |
| 40 | B | nd |
| 41 | A | nd |
| 42 | C | nd |
| 43 | C | nd |
| 44 | B | nd |
| 45 | C | nd |
| 46 | A | nd |
| 47 | A | nd |
| 48 | A | nd |
| 49 | A | nd |
| 50 | A | nd |
| 51 | A | nd |
| 52 | B | nd |
| 53 | A | nd |
| 54 | B | nd |
| 55 | A | nd |
| 56 | A | nd |
| 57 | A | nd |
| 58 | B | nd |
| 59 | A | nd |
| 60 | A | nd |
| 61 | A | nd |
| 62 | C | nd |
| 63 | A | A |
| 64 | A | A |
| 65 | A | A |
| 66 | A | B |
| 67 | A | nd |
| 68 | B | nd |
| 69 | A | nd |
| 70 | A | nd |
| 71 | A | nd |
| 72 | A | A |
| 73 | A | A |
| 74 | A | nd |
| 75 | A | nd |
| 76 | A | B |
| 77 | A | A |
| 78 | A | nd |
| 79 | B | nd |
| 80 | B | nd |
| 81 | C | nd |
| 82 | B | nd |
| 83 | B | nd |
| 84 | A | nd |
| 85 | A | nd |
| 86 | A | nd |
| 87 | A | nd |
| 88 | B | nd | nd = not determined

Table 1 illustrates that most of the compounds (from Examples 1-88) were found to be active against the PAD4 enzyme when evaluated through both Ammonia Release Biochemical and FP Binding assays. The $IC_{50}$ values display the efficacy of the compounds in inhibiting the PAD4 enzyme activity. $IC_{50}$ value indicates how much of a particular drug or a compound is needed to inhibit a given biological process or component of a process such as an enzyme. A low value of $IC_{50}$ denotes high inhibition efficacy of the test compound (Examples 1-88 as described herein). However, in the above Table 1, high efficacy is denoted by "A", "B", and "C", wherein "A" having least value of $IC_{50}$ and thus most effective.

The Ammonia Release Biochemical assay showed that 62 out of 88 compounds showed an $IC_{50}$ value of ≤1 μM denoted by "A". These 62 compounds were Examples-1, 8-13, 15-28, 31-37, 39, 41, 46-51, 53, 55-57, 59-61, 63-67, 69-78, and 84-88.

On the other hand, the FP Binding assay showed 13 out of 23 tested compounds to be actively inhibiting PAD4 enzyme activity. The individual examples being Examples-8-12, 14, 19, 63-65, 72, 73, and 77 respectively.

Therefore, it may be inferred that Examples-1, 8-13, 15-28, 31-37, 39, 41, 46-51, 53, 55-57, 59-61, 63-67, 69-78, and 84-87 are identified, and could be developed, as potential drugs for alleviating PAD4 enzyme activity and thus treating PAD4 mediated disorders.

What is claimed is:

1. A compound of Formula (I)

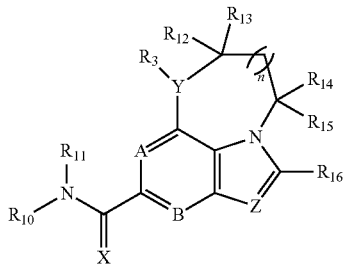

Formula (I)

or stereoisomers and pharmaceutically acceptable salts thereof,
wherein
X is selected from O or S;
Y is O;
Z is N;
A is $CR_1$;
B is $CR_2$;
n is 0;
$R_1$ and $R_2$ are independently selected from the group consisting of hydrogen and $C_{1-6}$ alkyl;
$R_3$ is absent;
$R_{10}$ and $R_{11}$ are taken together to form a 5-10 membered monocyclic or bicyclic saturated or unsaturated heterocyclic ring,
wherein,
the 5-10 membered monocyclic or bicyclic saturated or unsaturated heterocyclic ring is optionally substituted with the substituents selected from the group consisting of amino, $C_{1-6}$ alkylamino, and —NHC(O)CH=CHCH$_2$N(CH$_3$)$_2$;
$R_{12}$, $R_{13}$, $R_{14}$, and $R_{15}$ are independently selected from the group consisting of hydrogen or $C_{1-6}$ alkyl;
$R_{16}$ is 5-10 membered monocyclic or bicyclic heteroaryl with 1-5 heteroatoms selected from N, S or O,
wherein,
5-10 membered monocyclic or bicyclic heteroaryl is optionally substituted with 1-5 substituents selected from the group consisting of halogen, $C_{1-6}$ alkyl, $C_{1-6}$ alkoxy, $C_{1-6}$ haloalkyl, $C_{1-6}$ alkyl-$C_6$ aryl, $C_{2-6}$ alkenyl-$C_6$ aryl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{1-6}$ alkyl-$C_6$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, and —COOH.

2. The compound of Formula (T) as claimed in claim 1, their stereoisomers and pharmaceutically acceptable salts thereof, wherein
X is selected from O or S;
Y is O;
Z is N;
A is $CR_1$;
B is $CR_2$;
n is 0;
$R_1$ and $R_2$ are independently selected from the group consisting of hydrogen and $C_{1-6}$ alkyl;
$R_3$ is absent:
$R_{10}$ and $R_{11}$ are taken together to form a 5-10 membered monocyclic or bicyclic saturated or unsaturated heterocyclic ring,
wherein,
the 5-10 membered monocyclic or bicyclic saturated or unsaturated heterocyclic ring is optionally substituted with the substituents selected from the group consisting of amino, $C_{1-4}$ alkylamino, and NHC(O)CH=CHCH$_2$N(CH$_3$)$_2$;
$R_{12}$, $R_{13}$, $R_{14}$, and $R_{15}$ are independently selected from the group consisting of hydrogen or $C_{1-6}$ alkyl;
$R_{16}$ is 5-10 membered monocyclic or bicyclic heteroaryl with 1-5 heteroatoms selected from N, S or O,
Wherein,
5-10 membered monocyclic or bicyclic heteroalkyl is optionally substituted with 1-5 substituents selected from the group consisting of halogen, $C_{1-6}$ alkyl, $C_{1-6}$ alkoxy, $C_{1-6}$ haloalkyl, $C_{1-6}$ alkyl-$C_6$ aryl, $C_{2-6}$ alkenyl-$C_6$ aryl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{1-6}$ alkyl-$C_6$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, and —COOH.

3. The compound of Formula (I) as claimed in claim 1, their stereoisomers and pharmaceutically acceptable salts thereof, wherein
X is O or S;
Y is O;
Z is N;
A is $CR_1$;
B is $CR_2$;
n is 0;
$R_1$ and $R_2$ are independently selected from hydrogen;
$R_3$ is absent;
$R_{10}$ and $R_{11}$ are taken together to form a 5-6 membered monocyclic saturated heterocyclic ring,
wherein,
the 5-6 membered monocyclic saturated heterocyclic ring is optionally substituted with the substituents selected from amino, —NHC(O)CH=CHCH$_2$N(CH$_3$)$_2$, or $C_{1-6}$ alkylamino;
$R_{12}$, $R_{13}$, $R_{14}$, and $R_{15}$ are independently selected from hydrogen or $C_{1-6}$alkyl;
$R_{16}$ is 5-10 membered bicyclic heteroaryl with 1-2 heteroatoms selected from N or S,
wherein,
5-10 membered bicyclic heteroaryl is optionally substituted with 1-3 substituents selected from the group consisting of halogen, $C_{1-6}$ alkyl, $C_{1-6}$ alkoxy, $C_{1-6}$ haloalkyl, $C_{1-6}$ alkyl-$C_6$ aryl, $C_{2-6}$ alkenyl-$C_6$ aryl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{1-6}$ alkyl-$C_6$ aryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —CH$_2$OH, and —COOH.

4. The compound as claimed in claim 1, having Formula (II)

Formula (II)

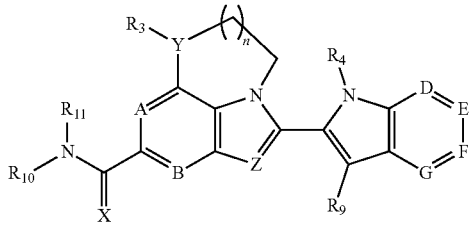

or stereoisomers and pharmaceutically acceptable salts, wherein

X is selected from O or S;
Y is O;
Z is N;
A is $CR_1$;
B is $CR_2$;
D is selected from N or $CR_5$;
E is selected from N or $CR_6$;
F is selected from N or $CR_7$;
G is selected from N or $CR_8$;
n is 1;
$R_1$ and $R_2$ are independently selected from the group consisting of hydrogen and $C_{1-6}$ alkyl;
$R_5$, $R_6$, $R_7$, $R_8$, and $R_9$ are independently selected from the group consisting of hydrogen, halogen, $C_{1-6}$ alkyl, $C_{1-6}$ alkoxy, $C_{1-6}$ haloalkyl, $C_{2-6}$ alkenyl-$C_6$ aryl, and $C_{1-6}$ heteroaryl, wherein,
$C_{1-6}$ alkoxy is optionally substituted with one or more of the groups selected from hydrogen, $C_{1-6}$ alkyl, $C_{1-6}$ alkoxy, and hydroxyl;
$R_3$ is absent;
$R_4$ is selected from the group consisting of hydrogen, $C_{1-6}$ alkyl, $C_{1-6}$ haloalkyl, $C_{1-6}$ alkoxy, $C_{1-6}$ alkyl-$C_6$ aryl, $C_{1-6}$ heterocyclyl, $C_{1-6}$ heteroaryl, and $C_{1-6}$ alkyl-$C_{1-6}$ heterocyclyl, wherein $C_{1-6}$ alkyl, $C_{1-6}$ alkoxy, $C_{1-6}$ alkyl-$C_6$ aryl, $C_{1-6}$ alkyl-$C_{1-6}$ heterocyclyl, $C_{1-6}$ heteroaryl, and $C_{1-6}$ alkyl-$C_{1-6}$ heteroaryl, is optionally substituted with one or more groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, and —COOH;
$R_{10}$ and $R_{11}$ are taken together to form a 5-10 membered monocyclic or bicyclic saturated or unsaturated heterocyclic ring, wherein,
the 5-10 membered monocyclic or bicyclic saturated or unsaturated heterocyclic ring is optionally substituted with the substituents selected from the group consisting of amino, $C_{1-6}$ alkylamino, and —NHC(O)CH=$CHCH_2N(CH_3)_2$.

5. The compound as claimed in claim 1, having Formula (III)

Formula (III)

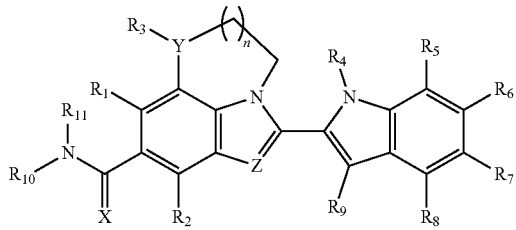

or stereoisomers and pharmaceutically acceptable salts,
Wherein,
X is selected from O or S;
Y is O;
Z is N;
n is 1;
$R_1$ and $R_2$ are independently selected #mom the group consisting of hydrogen and $C_{1-6}$ alkyl;
$R_5$, $R_6$, $R_7$, $R_8$, and $R_9$ are independently selected from the group consisting of hydrogen, halogen, $C_{1-6}$ alkyl, $C_{1-6}$ alkoxy, $C_{1-6}$ haloalkyl, $C_{2-6}$ alkenyl-$C_6$ aryl, and $C_{1-6}$ heteroaryl, wherein
$C_{1-6}$ alkoxy is optionally substituted with one or more of the groups selected from hydrogen, $C_{1-6}$ alkyl, $C_{1-6}$ alkoxy, and hydroxyl;
$R_3$ is absent;
$R_4$ is selected from the group consisting of hydrogen, $C_{1-6}$ alkyl, $C_{1-6}$ haloalkyl, $C_{1-6}$ alkoxy, $C_{1-6}$ alkyl-$C_6$ aryl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{1-6}$ alkyl-$C_6$ aryl, $C_{1-6}$alkyl-$C_{1-6}$ heterocyclyl, $C_{1-6}$ heteroaryl, and $C_{1-6}$ alkyl-$C_{1-6}$ heteroaryl, is optionally substituted with one or more groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, and —COOH;
$R_{10}$ and $R_{11}$ are taken together to form a 5-10 membered monocyclic or bicyclic saturated or unsaturated heterocyclic ring, wherein,
the 5-10 membered monocyclic or bicyclic saturated or unsaturated heterocyclic ring is optionally substituted with the substituents selected from the group consisting of amino, $C_{1-6}$ alkylamino, and —NHC(O)CH=$CHCH_2N(CH_3)_2$.

6. A compound, its stereoisomers, or pharmaceutically acceptable salts thereof, wherein the compound is selected from the group consisting of:

(R)-(3-aminopiperidin-1-yl)(2-(1-(cyclopropylmethyl)-1H-indol-2-yl)-3,4-dihydro-5-oxa-1,2a-diazaacenaphthylen-7-yl)methanone (1), (R)-(3-aminopyrrolidin-1-yl)(2-(1-(cyclopropylmethyl)-1H-indol-2-yl)-3,4-dihydro-5-oxa-1,2a-diazaacenaphthylen-7-yl)methanone (2), (R)-(3-aminopiperidin-1-yl)(2-(1-ethyl-1H-indol-2-yl)-3,4-dihydro-5-oxa-1,2a-diazaacenaphthylen-7-yl)methanone (3), (2-(aminomethyl)piperidin-1-yl)(2-(1-(cyclopropylmethyl)-1H-indol-2-yl)-3,4-dihydro-5-oxa-1,2a-diazaacenaphthylen-7-methanone (4), (R)-(3-aminopiperidin-1-yl)(2-(1-ethyl-1H-pyrrolo[2,3-b]pyridin-2-yl)-3,4-dihydro-5-oxa-1,2a-diazaacenaphthylen-7-yl)methanone (5), (R)-(3-aminopiperidin-1-yl)(2-(1-(cyclopropylmethyl)-7-methyl-1H-indol-2-yl)-3,4-dihydro-5-oxa-1,2a-diazaacenaphthylen-7-yl)methanone (8), (R)-(3-aminopiperidin-1-yl)(2-(1-(cyclopropylmethyl)-5-fluoro-1H-indol-2-yl)-3,4-dihydro-5-oxa-1,2a-diazaacenaphthylen-7-yl)methanone (9), (R)-(3-aminopiperidin-1-yl)(2-(1-(pyridin-4-ylmethyl)-1H-indol-2-yl)-3,4-dihydro-5-oxa-1,2a-diazaacenaphthylen-7-yl)methanone (10), (R)-(3-aminopiperidin-1-yl)(2-(1-(pyridin-2-ylmethyl)-1H-indol-2-yl)-3,4-dihydro-5-oxa-1,2a-diazaacenaphthylen-7-yl)methanone (11), (R)-(3-aminopiperidin-1-yl)(2-(3-ethylbenzo[b]thiophen-2-yl)-3,4-dihydro-5-oxa-1,2a-diazaacenaphthylen-7-yl)methanone (12), (R)-(3-aminopiperidin-1-yl)(2-(1-(4-chlorobenzyl)-1H-indol-2-yl)-3,4-dihydro-5-oxa-1,2a-diazaacenaphthylen-7-yl)methanone (13), (R)-(3-aminopiperidin-1-yl)(2-(1-(2-fluorobenzyl)-1H-indol-2-yl)-3,4-dihydro-5-oxa-1,2a-diazaacenaphthylen-7-yl)methanone (14), (R)-(3-aminopiperidin-1-yl)(2-(1-(4-fluorobenzyl)-1H-indol-2-yl)-3,4-dihydro-5 oxa-1,2a-diazaacenaphthylen-7-yl)methanone (15), (R)-(3-aminopiperidin-1-yl)(2-(1-(pyridin-3-ylmethyl)-1H-indol-2-yl)-3,4-dihydro-5-oxa-1,2a-diazaacenaphthylen-7-yl)methanone (16), (R)-(3-aminopiperidin-1-yl)(2-(1-(cyclopropylmethyl)-5,6-dimethoxy-1H-indol-hydro-5-oxa-1,2a-diazaacenaphthylen-7-yl)methanone (17), (R)-(3-aminopiperidin-1-yl)(2-(1-benzyl-1H-indol-2-yl)-3,4-dihydro-5-oxa-1,2a-diazaacenaphthylen-7-yl)methanone (18), (R)-(3-aminopiperidin-1-yl)(2-(1-(4-methoxybenzyl-1H-indol-2-yl)-3,4-dihydro-5-oxa-1,2a-diazaacenaphthylen-7-yl)methanone (19), (R)-(3-aminopiperidin-1-yl)(2-(1-(2-methoxyethyl-1H-indol-2-yl)-3,4-dihydro-5-oxa-1,2a-diazaacenaphthylen-7-yl)methanone (20), (R)-(3-aminopiperidin-1-yl)(2-(6-methoxy-1-(2-methoxyethyl)-1H-indol-2-yl)-3,4-dihydro-5-oxa-1,2a-diazaacenaphthylen-7-yl)methanone (21), (R)-(3-aminopiperidin-1-yl)(2-(1-(2-hydroxyethyl)-1H-indol-2-yl)-3,4-dihydro-5-oxa-1,2a-diazaacenaphthylen-7-yl)methanone (22), (R)-(3-aminopiperidin-1-yl)(2-(1-(cyclopropylmethyl)-6-methoxy-1H-indol-2-yl)-3,4-dihydro-5-oxa-1,2a-diazaacenaphthylen-7-yl)methanone (23), (R)-(3-aminopiperidin-1-yl)(2-(1-(3-fluoropyridin-4-yl)methyl)-1H-indol-2-yl)-3,4-dihydro-5-oxa-1,2a-diazaacenaphthylen-7-yl)methanone (24), (R)-(3-aminopiperidin-1-yl)(2-(1-(pyrazin-2-ylmethyl)-1H-indol-2-yl1)-3,4-dihydro-5-oxa-1,2a-diazaacenaphthylen-7-yl)methanone (25), (R)-(3-aminopiperidin-1-yl)(2-(1-((3-fluoropyridin-2-yl)methyl)-1H-indol-2-yl)-3,4-dihydro-5-oxa-1,2a-diazaacenaphthylen-7-yl)methanone (26), (R)-(3-aminopiperidin-1-yl)(2-(1-(pyrimidin-2-ylmethyl-1H-indol-2-yl)-3,4-dihydro-5-oxa-1,2a-diazaacenaphthylen-7-yl)methanone (27), (R)-(3-aminopiperidin-1-yl)(2-(1-(cyclopropylmethyl)-6-fluoro-1H-indol-2-yl)-3,4-dihydro-5-oxa-1,2a-diazaacenaphthylen-7-yl)methanone (28), (R)-(3-aminopiperidin-1-yl)(2-(1-pyrimidin-5-ylmethyl)-1H-indol-2-yl)-3,4-dihydro-5-oxa-1,2a-diazaacenaphthylen-7-yl)methanone (29), (R)-(3-aminopiperidin-1-yl)(2-(1-(pyridazin-3-ylmethyl)-1H-indol-2-yl)-3,4-dihydro-5-oxa-1,2a-diazaacenaphthylen-7-yl)methanone (30), (R)-(3-aminopiperidin-1-yl)(2-(1-isobutyl-1H-indol-2-yl)-3,4-dihydro-5-oxa-1,2a-diazaacenaphthylen-7-yl)methanone (31), (R)-(3-aminopiperidin-1-yl)(2-(1-(cyclopropylmethyl)-5,6-difluoro-1H-indol-2-yl)-3,4-dihydro-5-oxa-1,2a-diazaacenaphthylen-7-yl)methanone (32), (R)-(3-aminopiperidin-1-yl)(2-(1-(3-fluoropyridin-2-yl)methyl)-6-methoxy-1H-hydro-5-oxa-1,2a-diazaacenaphthylen-7-yl)methanone (33), (R)-(3-aminopiperidin-1-yl)(2-(7-chloro-1-((3-fluoropyridin-2-yl)methyl)-1H-indol-2-yl)-3,4-dihydro-5-oxa-1,2a-diazaacenaphthylen-7-yl)methanone (34), (R)-(11)-(3-aminopiperidin-1-yl)(2-(6-fluoro-14(3-fluoropyridin-2-yl)methyl)-1H-hydro-5-oxa-1,2a-diazaacenaphthylen-7-yl)methanone (35), (R)-(3-aminopiperidin-1-yl)(2-(7-chloro-1-(2-methoxyethyl)-1H-indol-2-yl)-3,4-dihydro-5-oxa-1,2a-diazaacenaphthylen-7-yl)methanone (36), (R)-(11)-(3-aminopiperidin-1-yl)(2-(1-(4-hydroxymethyl)benzyl)-1H-indol-2-yl)-3,4-dihydro-5-oxa-1,2a-diazaacenaphthylen-7-yl)methanone (37), (R,E)-N-(1-(2-(1-(cyclopropylmethyl)-1H-indol-2-yl)-3,4-dihydro-5-oxa-1,2a-diazaacenaphthylen-7-carbonyl)piperidin-3-yl)-4-(dimethylamino)but-2-enamide (38), (R)-(3-aminopiperidin-1-yl)(2-(7-chloro-1-(4-methoxybenzyl)-1H-indol-2-yl)-3,4-dihydro-5-oxa-1,2a-diazaacenaphthylen-7-yl)methanone (39), (R)-(3-aminopiperidin-1-yl)(2-(1-((tetrahydro-2H-pyran-4-yl)methyl)-1H-indol-2-yl)-3,4-dihydro-5-oxa-1,2a-diazaacenaphthylen-7-yl)methanone (40), (R)-(3-aminopiperidin-1-yl)(2-(1-(cyclobutyl ethyl)-1H-indol-2-yl)-3,4-dihydro-5-oxa-1,2a-diazaacenaphthylen-7-yl)methanone (41), (R)-2-(2-(7-(3-aminopiperidine-1-carbonyl)-3,4-dihydro-5-ox diazaacenaphthylen-2-yl)-1H-indol-1-yl)acetic acid (42), (R)-(3-aminopiperidin-1-yl)(2-(1-(piperidin-4-ylmethyl)-1H-indol-2-yl)-3,4-dihydro-5-oxa-1,2a-diazaacenaphthylen-7-yl)methanone (43), (11)-(3-aminopiperidin-1-yl)(2-(1-(oxetan-3-ylmethyl)-1H-indol-2-yl)-3,4-dihydro-5-oxa-1,2a-diazaacenaphthylen-7-yl)methanone (44), (R)-(3-aminopiperidin-1-yl)(2-(1-((1-methylpiperidin-4-yl)methyl)-1H-indol-2-yl)-3,4-dihydro-5-oxa-1,2a-diazaacenaphthylen-7-yl)methanone (45), (R)-(3-aminopiperidin-1-yl)(2-(5-fluoro-1-(4-methoxybenzyl)-1H-indol-2-yl)-3,4-dihydro-5-oxa-1,2a-diazaacenaphthylen-7-yl)methanone (46), (R)-(3-aminopiperidin-1-yl)(2-(1-(2,2-difluoroethyl)-1H-indol-2-yl)-3,4-dihydro-5-oxa-1,2a-diazaacenaphthylen-7-yl)methanone (47), (R)-(3-aminopiperidin-1-yl)(2-(5-fluoro-1-(2-methoxyethyl)-1H-indol-2-yl)-3,4-dihydro-5-oxa-1,2a-diazaacenaphthylen-7-yl)methanone (48), (R)-(3-aminopiperidin-1-yl)(2-(6-fluoro-1-(4-fluorobenzyl)-1H-indol-2-yl)-3,4-dihydro-5-oxa-1,2a-diazaacenaphthylen-7-yl)methanone (49), (R)-(3-aminopiperidin-1-yl)(2-(6-fluoro-1-(4-methoxybenzyl)-1H-indol-2-yl)-3,4-dihydro-5-oxa-1,2a-diazaacenaphthylen-7-yl)methanone (50), (R)-(3-aminopiperidin-1-yl)(2-(1-(4-fluorobenzyl)-6-methoxy-1H-indol-2-yl)-3,4-dihydro-5-oxa-1,2a-diazaacenaphthylen-7-yl)methanone (51), (R)-(3-aminopiperidin-1-yl)(2-(6-fluoro-1-(2-methoxyethyl)-1H-indol-2-yl)-3,4-dihydro-5-oxa-1,2a-diazaacenaphthylen-7-yl)methanone (52), (R)-(3-aminopiperidin-1-yl)(2-(7-chloro-1-(cyclobutylmethyl)-1H-indol-2-yl)-3,4-dihydro-5-oxa-1,2a-diazaacenaphthylen-7-yl)methanone (53), (R)-(3-aminopiperidin-1-yl)(2-(5,6-difluoro-1-(2-methoxyethyl)-1H-indol-2-yl)-3,4-dihydro-5-oxa-1,2a-diazaacenaphthylen-7-yl)methanone (54), (R)-(3-aminopiperidin-1-yl)(2-(7-chloro-1-isobutyl-1H-indol-2-371)-3 oxa-1,2a-diazaacenaphthylen-7-yl)methanone (55), (R)-(3-aminopiperidin-1-yl)(2-(7-chloro-1-(2,2-difluoroethyl)-H-indol-2-yl)-3,4-dihydro-5-oxa-1,2a-diazaacenaphthylen-7-yl)methanone (56), (R)-(3-aminopiperidin-1-yl)(2-(7-chloro-1-(cyclopropyl-methyl)-1H-indol-2-yl)-3,4-dihydro-5-oxa-1,2a-diaz-aacenaphthylen-7-yl)methanone (57), (R,E)-(3-aminopiperid 1-yl)(2-(1-(cyclopropylmethyl)-5-styryl-1H-indol-2-yl)-3,4-dihydro-5-oxa-1,2a-diaz-aacenaphthylen-7-yl)methanone (58), (R)-(3-aminopiperidin-1-yl)(2-(1-((4-methylthiazol-2-yl)methyl-1H-indol-2-yl)-3,4-dihydro-5-oxa-1,2a-diaz-aacenaphthylen-7-yl)methanone (59), (R)-(3-aminopiperidin-1-yl)(2-(1-(cyclopropylmethyl)-5-methoxy-1H-indol-2-yl)-3,4-dihydro-5-oxa-1,2a-diaz-aacenaphthylen-7-yl)methanone (60), (R)-(3-aminopiperidin-1-yl)(2-(1-(cyclopropylmethyl)-6-(hydroxymethyl)-1H-indol-2-yl)-3,4-dihydro-5-oxa-1,2a-diazaacenaphthylen-7-yl)methanone (61), (R)-(3-aminopiperidin-1-yl)(2-(1-(cyclopropylmethyl)-1H-indol-2-yl)-3,3-dimethyl-3,4-dihydro-5-oxa-1,2a-diazaacenaphthylen-7-yl)methanone (62), (R)-(3-aminopiperidin-1-yl)(2-(7-chloro-1-(cyclopropyl-methyl)-6-fluoro-1H-indol-2-yl)-3,4-dihydro-5-oxa-1,2a-diazaacenaphthylen-7-yl)methanone (87), and (R)-(3-aminopiperidin-1-yl)(2-(7-chloro-1-(pyrimidin-5-ylmethyl)-1H-indol-2-yl)-3,4-dihydro-5-oxa-1,2a-diazaacenaphthylen-7-yl)methanone (88).

7. A process of preparation of compounds of Formula a) as claimed in claim 1, its stereoisomers and pharmaceutically acceptable salts thereof, the process comprising reacting Formula (IV) and $R_{16}C(O)H$

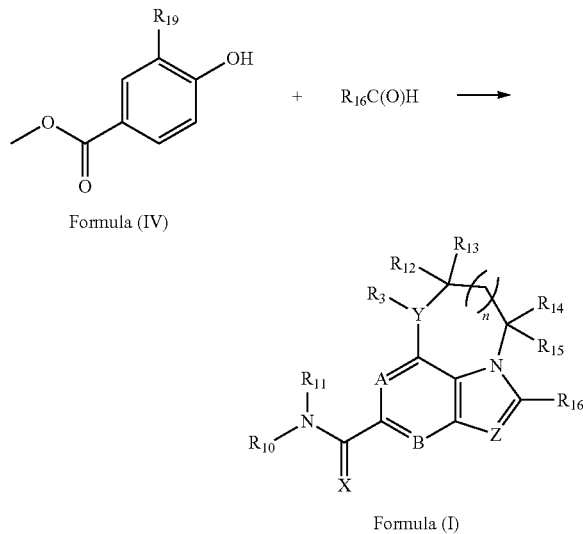

wherein, $R_{19}$ of Formula (IV) is selected from nitro, and $C_{1-6}$ alkoxy: $R_{16}$ of $R_{16}C(O)H$ is selected from the group consisting of 5-10 membered monocyclic or bicyclic heteroaryl with 1-5 heteroatoms selected from N, S or O, wherein, 5-10 membered monocyclic or bicyclic heteroaryl are optionally substituted with 1-5 substituents selected from the group consisting of halogen, $C_{1-6}$ alkyl, $C_{1-6}$ alkoxy, $C_{1-6}$ haloalkyl, $C_{1-6}$ alkyl-$C_6$ aryl, $C_{2-6}$ alkenyl-$C_6$ aryl, $C_{1-6}$alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{1-6}$ alkyl-$C_6$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, and —COOH; X of Formula (I) is selected from O or S; Y is O; Z is N; A is $CR_1$; B is $CR_2$; n is 0; $R_1$ and $R_2$ are independently selected from the group consisting of hydrogen or $C_{1-6}$ alkyl; $R_3$ is absent; $R_{10}$ and $R_{11}$ are taken together to form a 5-10 membered monocyclic or bicyclic saturated or unsaturated heterocyclic ring, wherein the 5-10 membered monocyclic or bicyclic saturated or unsaturated heterocyclic ring is optionally substituted with the substituents selected from the group consisting of amino, $C_{1-6}$ alkylamino, and —NHC(O)CH=CHCH$_2$N(CH$_3$)$_2$; $R_{12}$, $R_{13}$, $R_{14}$, and $R_{15}$ are independently selected from the group consisting of hydrogen and $C_{1-6}$ alkyl; $R_{16}$ is 5-10 membered monocyclic or bicyclic heteroaryl with 1-5 heteroatoms selected from N, S or O, Wherein 5-10 membered monocyclic or bicyclic heteroaryl are optionally substituted with 1-5 substituents selected from the group consisting of halogen, $C_{1-6}$ alkyl, $C_{1-6}$ alkoxy $C_{1-6}$ haloalkyl, $C_{1-6}$ alkyl-$C_6$ aryl, $C_{2-6}$ alkenyl-$C_6$ aryl, $C_{1-6}$ alkyl-$C_{1-6}$ heterocyclyl, $C_{1-6}$ heteroaryl, and $C_{1-6}$ alkyl-$C_{1-6}$ heteroaryl, wherein $C_{1-6}$ alkyl, $C_{1-6}$ alkoxy, $C_{1-6}$ alkyl-$C_6$ aryl, $C_{1-6}$ heteroaryl, $C_{1-6}$ alkyl-$C_{1-6}$ heteroaryl, and $C_{1-6}$ alkyl-$C_{1-6}$ heterocyclyl is optionally substituted with one or more of the groups selected from hydrogen, $C_{1-6}$ alkyl, $C_{1-6}$ alkoxy, $C_{3-8}$ cycloalkyl, $C_{1-6}$ heteroaryl, halogen, hydroxyl, —$CH_2OH$, and —COOH.

8. A pharmaceutical composition comprising the compound of Formula (I) or a pharmaceutically acceptable salt thereof as claimed in claim 1 together with a pharmaceutically acceptable carrier.

9. The pharmaceutical composition as claimed in claim 8, wherein the composition is in the form selected from the group consisting of a tablet, capsule, powder, syrup, solution, aerosol, and suspension.

10. A method for the treatment of rheumatoid arthritis caused by PAD4 said method comprising administering the compound of Formula (I) or a pharmaceutically acceptable salt thereof as claimed in claim 1.

11. A method for the treatment of rheumatoid arthritis caused by PAD4, said method comprising administering the pharmaceutical composition as claimed in claim 8.

12. The compound, its stereoisomers, or pharmaceutically acceptable salts thereof as claimed in claim 8, wherein the pharmaceutically acceptable salt is a trifluoracetic acid salt, and the compound is selected from (R)-(3-aminopiperidin-1-yl)(2-(1-(4-(hydroxymethyl)benzyl)-1H-indol-2-yl)-3,4-dihydro-5-oxa-1,2a-diaz-aacenaphthylen-7-yl)methanone (37); and (R,E)-N-(1-(2-(1-(cyclopropylmethyl)-1H-indol-2-yl)-3,4-dihydro-5-oxa-1,2a-diazaacenaphthylen-7-carbonyl)piperidin-3-yl)-4-(dimethylamino)but-2-enamide (38).

* * * * *